United States Patent
Yang et al.

(10) Patent No.: US 10,934,264 B2
(45) Date of Patent: *Mar. 2, 2021

(54) AMYLOID TARGETING AGENTS AND METHODS OF USING THE SAME

(71) Applicants: THE REGENTS OF THE UNIVERSITY OF CALIFORNIA, Oakland, CA (US); Amydis, Inc., San Diego, CA (US)

(72) Inventors: Jerry Yang, La Jolla, CA (US); Emmanuel A. Theodorakis, San Diego, CA (US); Stella Sarraf, Beverly Hills, CA (US)

(73) Assignees: The Regents of the University of California, Oakland, CA (US); Amydis, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/439,505

(22) Filed: Jun. 12, 2019

(65) Prior Publication Data

US 2020/0123118 A1    Apr. 23, 2020

Related U.S. Application Data

(63) Continuation of application No. 15/969,328, filed on May 2, 2018, now Pat. No. 10,370,345, which is a
(Continued)

(51) Int. Cl.
| | |
|---|---|
| *C07D 295/155* | (2006.01) |
| *C07D 401/14* | (2006.01) |
| *C07D 333/22* | (2006.01) |
| *C07D 401/04* | (2006.01) |
| *C07D 405/04* | (2006.01) |
| *C07D 405/10* | (2006.01) |
| *C07D 407/10* | (2006.01) |
| *C07D 409/10* | (2006.01) |
| *C07D 409/14* | (2006.01) |
| *C07D 241/04* | (2006.01) |
| *C07D 413/10* | (2006.01) |
| *C07D 413/12* | (2006.01) |
| *C07D 265/30* | (2006.01) |
| *C07D 211/06* | (2006.01) |

(Continued)

(52) U.S. Cl.
CPC ........ *C07D 295/155* (2013.01); *A61B 5/0075* (2013.01); *A61P 25/28* (2018.01); *C07C 255/42* (2013.01); *C07C 255/58* (2013.01); *C07C 255/59* (2013.01); *C07C 311/35* (2013.01); *C07D 211/06* (2013.01); *C07D 213/57* (2013.01); *C07D 213/85* (2013.01); *C07D 241/04* (2013.01); *C07D 265/30* (2013.01); *C07D 295/04* (2013.01); *C07D 307/52* (2013.01); *C07D 333/22* (2013.01); *C07D 401/04* (2013.01); *C07D 401/14* (2013.01); *C07D 405/04* (2013.01); *C07D 405/10* (2013.01); *C07D 407/10* (2013.01); *C07D 409/04* (2013.01); *C07D 409/10* (2013.01); *C07D 409/14* (2013.01); *C07D 413/10* (2013.01); *C07D 413/12* (2013.01); *C07H 13/04* (2013.01); *C07H 19/056* (2013.01); *A61B 5/4082* (2013.01); *A61B 5/4088* (2013.01)

(58) Field of Classification Search
CPC .............. C07D 295/155; C07D 407/10; C07D 413/12; C07D 265/30; C07D 405/04; C07D 409/04; C07D 213/57; C07D 213/85; C07D 333/22; C07D 409/14; C07D 295/04; C07D 401/14; C07D 405/10; C07D 413/10; C07D 401/04; C07D 409/10; C07D 241/04; C07D 307/52; C07D 211/06; C07D 295/13; C07H 13/04; C07H 19/056; C07H 13/00; C07C 255/59; C07C 311/35; C07C 255/42; C07C 255/58; C07C 255/43; A61B 5/0075; A61B 5/4082; A61B 5/4088; A61P 25/28

See application file for complete search history.

(56) References Cited

U.S. PATENT DOCUMENTS

| | | |
|---|---|---|
| 5,043,013 A | 8/1991 | Kluger et al. |
| 6,048,662 A | 4/2000 | Bruhnke et al. |

(Continued)

FOREIGN PATENT DOCUMENTS

| | | |
|---|---|---|
| EP | 1431280 A1 | 6/2004 |
| JP | 2008-013446 A | 1/2008 |

(Continued)

OTHER PUBLICATIONS

Mircheva, K., "Properties of β-carotene and retinoic acid in mixed monolayers with dipalmitoylphosphatidylcholine (DPPC) and Solutol." Colloids and Surfaces A: Physicochemical and Engineering Aspects 460 (2014): 209-218.*

(Continued)

*Primary Examiner* — John M Mauro
(74) *Attorney, Agent, or Firm* — Mintz, Levin, Cohn, Ferris, Glovsky and Popeo, P.C.

(57) ABSTRACT

Provided herein is the design and synthesis of novel molecular rotor fluorophores useful for detection of amyloid or amyloid like proteins. The fluorophores are designed to exhibit enhanced fluorescence emission upon associating with amyloid or amyloid like proteins as compared to unbound compound. Also disclosed herein are methods for treating diseases associated with amyloid or amyloid like proteins.

20 Claims, 27 Drawing Sheets

Related U.S. Application Data continuation of application No. 14/915,883, filed as application No. PCT/US2015/021512 on Mar. 19, 2015, now Pat. No. 10,005,745.

(60) Provisional application No. 61/955,366, filed on Mar. 19, 2014.

(51) Int. Cl.

| | | |
|---|---|---|
| *C07D 295/04* | (2006.01) | |
| *C07D 213/57* | (2006.01) | |
| *C07D 307/52* | (2006.01) | |
| *A61P 25/28* | (2006.01) | |
| *A61B 5/00* | (2006.01) | |
| *C07H 13/04* | (2006.01) | |
| *C07C 255/58* | (2006.01) | |
| *C07C 255/42* | (2006.01) | |
| *C07C 255/59* | (2006.01) | |
| *C07D 213/85* | (2006.01) | |
| *C07D 409/04* | (2006.01) | |
| *C07H 19/056* | (2006.01) | |
| *C07C 311/35* | (2006.01) | |

(56) References Cited

U.S. PATENT DOCUMENTS

| | | | |
|---|---|---|---|
| 1,000,574 A1 | 6/2018 | Yang et al. | |
| 1,037,034 A1 | 8/2019 | Mauro et al. | |
| 2006/0115516 A1 | 6/2006 | Pearson et al. | |
| 2012/0302603 A1 | 11/2012 | Yang et al. | |
| 2016/0326126 A1 | 11/2016 | Yang et al. | |
| 2017/0248616 A1 | 8/2017 | Sarraf | |
| 2018/0327373 A1 | 11/2018 | Yang et al. | |

FOREIGN PATENT DOCUMENTS

| | | |
|---|---|---|
| JP | 2013-534171 A | 2/2013 |
| WO | WO-2005/040337 | 5/2005 |
| WO | WO-2006/057824 | 6/2006 |
| WO | WO-2008/016682 | 2/2008 |
| WO | WO-2011/072257 | 6/2011 |
| WO | WO-2015/143185 | 9/2015 |

OTHER PUBLICATIONS

Ash, M., "Handbook of Pharmaceutical Additives. Endicott, NY: Synapse Information Resources." (2007) p. 673.*
Antonsen, K.P., "Water structure of PEG solutions by differential scanning calorimetry measurements." Poly (ethylene glycol) chemistry. Springer, Boston, MA, 1992. 15-28.*
Berge et al., Pharmaceutical Salts. Journal of Pharmaceutical Sciences 66(1):1-19 (Jan. 1977).
Buhimschi et al., Protein misfolding, congophilia, oligomerization, and defective amyloid processing in preeclampsia. Sci. Transl. Med. 6(425):245ra92; pp. 1-15 (Jul. 16, 2014).
Cai, Radioligand Development for PET Imaging of [beta]-Amyloid (A[beta])-Current Status. Current Medical Chemistry, 14(1):19-52 (Jan. 1, 2007).
Cao et al., Amino Naphthalenyl-2-Cyano-Acrylate (ANCA) Probes Fluorescently Discriminate between Amyloid-[beta] and Prion Plaques in Brain. Journal of the American Chemical Society, 134 (42):17338-17341 (2012).
Carey, Organic Chemistry, 6th Edition, McGraw Hill Chapter 1, pp. 1-9, 2006.
Carré et al., Fluorescent Molecular Rotors with Specific Hydrophilic Functions: Glucosamine and Inositol Derivatives. Journal of Fluorescence 8(1): 53-57 (Feb. 16, 1998).
CAS Registry No. 478016-48-7, located at <https://stneasy.cas.org/tmp/20171006/1240090-1942032854-200/479739346.html> last visited Oct. 6, 2017, 1 page.
CAS Registry No. 811462-20-1, located at <https://stneasy.cas.org/tmp/20171006/1240090-1942032854-200/33392095.html> last visited Oct. 6, 2017, 1 page.
CAS Registry No. 862649-67-0, located at <https://stneasy.cas.org/tmp/20171006/1240090-1942032854-200/740546802.html> last visited Oct. 6, 2017, 1 page.
CAS Registry No. 888490-95-7, located at <https://stneasy.cas.org/tmp/20171006/1240090-1942032854-200/490202741.html> last visited Oct. 6, 2017, 1 pag.
Chang et al., ANCA: A Family of Fluorescent Probes that Bind and Stain Amyloid Plaques in Human Tissue. ACS Chemical Neuroscience 2(5): 249-255 (May 18, 2011).
Furumoto et al., Recent advances in the development of amyloid imaging agents. Current Topics in Medicinal Chemistry, 7(18):1773-1789 (Jan. 1, 2007).
Geoffroy-Chapotot et al., Three Dimensional Fluorescence Microscopy of Endothelial Cells Labeled with Coumarins. Journal of Fluorescence 10(2): 203-207 (Jan. 12, 2000).
International Application No. PCT/US2015/021512 International Search Report and Written Opinion dated Aug. 15, 2015.
International Application No. PCT/US2015/049825 International Preliminary Report on Patentability dated Mar. 14, 2017.
International Application No. PCT/US2015/049825 International Search Report and Written Opinion dated Mar. 23, 2017.
International Preliminary Report on Patentability for International Application No. PCT/US2015/021512 dated Sep. 20, 2016, 9 pages.
Knowles et al., The amyloid state and its association with protein misfolding cases. Nature Reviews Molecular Cell Biology, 15(6):384-396 (Jun. 2014).
Maruyama et al., Imaging of Tau pathology in a tauopathy mouse model and in Alzheimer patients compared to normal controls. Neuron, 79:1094-1108 (Sep. 18, 2013).
Maruyama et al., Imaging of Tau pathology in a tauopathy mouse model and in Alzheimer patients compared to normal controls. Neuron, 79 Supplemental Information, 37 pages (Sep. 18, 2013).
Mathis et al., Synthesis and evaluation of 11C-labeled 6-substituted 2-arylbenzothiazoles as amyloid imaging agents. Journal of Medicinal Chemistry, 46(19):2740-2754 (Jun. 19, 2003).
Moda et al., Prion in the Urine of Patients with Variant Creutzfeldt-Jakob Disease, New England Journal of Medicine, 371(6):530-539 (Aug. 7, 2014).
Nelson, "Correlation of Alzheimer Disease Neuropathologic Changes with Cognitive Status: A Review of the Literature", J. Neuropathol Exp Neurol 71(5):362-381, 2012.
Nokazi et al., Medicinal Chemistry, 1995, $1^{st}$ Ed. pp. 98-99.
Silva et al., Prion-like aggregation of mutant p53 in cancer, Trends in Biochemical Sciences, 39(6):260-267 (2014).
STN-RN1013518-60-9, 2-Propenamide, 2-cyano-N-(2-rnethoxyethyl)-3-[2-(4-morpholinyl)-3-quinolinyl) entered Apr. 10, 2008. (1 page).
STN-RN1164496-51-8, 2-Propenamide, 2-cyano-N-(2-methoxyethyl)-3-[5-(4-morpholinyl)-2-furanyl], entered Jul. 19, 2009. (1 page).
STN-RN347334-29-6, 2-Propenamide, 2-cyano-3-[4-(dimethylamino)phenyl]-N-(2-methoxyethyl), entered Jul. 22, 2001. (1 page).
STN-RN364768-44-5, 2-Propenamide, 2-cyano-N-(2-methoxyethyl)-3-[5-(4-morpholinyl)-2-furanyl], entered Oct. 26, 2001. (1 page).
STN-RN365234-08-8, 2-Propenarnide, 3-[3-bromo-4-(dimethylamino)phenyl]-2-cyano-N-(2-methoxyethyl), entered Oct. 29, 2001. (1 page).
STN-RN365550-20-5, 2-Propenamide, 2-cyano-N-(2-methoxyethyl)-3-[5-(1-piperidinyl)-2-furanyl], entered Oct. 31, 2001. (1 page).
STN-RN444317-74-2, 2-Propenamide, 2-cyano-3-[4-(diethylamino)-2-methoxwhenyl]-N-(2-methoxyethyl), entered Aug. 20, 2002. (1 page).
STN-RN473875-91-1, 2-Propenamide, 2-cyano-3-[4-(diethylamino)-2-hydroxphenyl]-N-(2-methoxyethyl), entered Nov. 19, 2002. (1 page).
STN-RN474401-13-3, 2-Propenamide, 2-cyano-3-[4-(diethylamino)phenyl]-N-(2-methoxyethyl], entered Nov. 25, 2002. (1 page).
STN-RN478016-48-7, 2-Propenamide, 2-cyano-N-(2-methoxyethyl)-3-[4-(4-morpholinyl)phenyl], entered Jan. 3, 2003. (1 page).

(56) References Cited

OTHER PUBLICATIONS

STN-RN478016-72-7, 2-Propenamide, 2-cyano-3-[4-(diphenylamino)phenyl]-N-(2-methoxyethyl), entered Jan. 3, 2003. (1 page).
STN-RN502908-83-0, 2-Propenamide, 2-cyano-N-(2-methoxyethyl)-3-[2-(4-morpholinyl)-4-phenyl-5-thiazolyl], entered Apr. 14, 2003. (1 page).
STN-RN568557-51-7, 2-Propenamide, 2-cyano-N-(2-methoxyethyl)-3-(5-(4-morpholinyl)-2-thienyl, entered Aug. 18, 2003. (1 page).
STN-RN775314-93-7, 2-Propenamide, 3-[5-chloro-2-(dimethylamino)-1-(4-fluorophenyl)-IH-imidazol-4-yl)-2-cyano-N-(2-methoxyethyl), entered Nov. 5, 2004. (1 page).
STN-RN811462-20-1, 2-Propenamide, 2-cyano-N-(2-methoxyethyl)-3-[2-methoxy-4-(4-morpholinyl)phenyl], entered Jan. 11, 2005. (1 page).
STN-RN862649-67-0, 2-Propenamide, 2-cyano-N-(2-methoxyethyl)-3-[4-(1-piperidinyl)phenyl], entered Sep. 8, 2005. (1 page).
STN-478016-52-3, 2-Propenamide, 2-cyano-3-[4-[ethyl(phenylmethyl)amino]phenyl]-N-(2-methoxyethyl)—entered Jan. 3, 2003. (1 page).
Sutharsan et al., Rational Design of Amyloid Binding Agents Based on the Molecular Rotor Motif. ChemMedChem 5(1): 56-60 (Jan. 2010).
Teiten et al., Specific Fluorescent Tracers. Imaging and Applications for Photodynamic Therapy. C. R. Biologies 325: 487-493 (2002).
U.S. Pharmacopeia Convention USP 30 (467) Residual Solvents. Table 2. Class 2 Residual Solvents. pp. 1-10. Published Mar. 23, 2007. Accessed Apr. 20, 2017.
Wermuth, The Practice of Medicinal Chemistry, Chapter 13, pp. 235-271.
Atsushi Kittaka, Drug discovery science, Medicinal chemistry, 2007, pp. 142-150.
Satoshi Shuto, Molecular theory of organic medicine, 2012, pp. 201-218.

* cited by examiner

Compound 1: HCl salt

AMYLOID TARGETING AGENTS AND METHODS OF USING THE SAME

CROSS-REFERENCE TO RELATED APPLICATIONS

This application is a continuation of U.S. application Ser. No. 15/969,328 filed May 2, 2018, issued as U.S. Pat. No. 10,370,345, which is a continuation of U.S. application Ser. No. 14/915,883 filed Mar. 1, 2016, issued as U.S. Pat. No. 10,005,745, which is a 371 of PCT/US2015/021512 filed Mar. 19, 2015, which claims priority to U.S. Application No. 61/955,366 filed Mar. 19, 2014, the disclosures of which are hereby incorporated by reference in their entirety and for all purposes.

BACKGROUND OF THE INVENTION

Amyloid plaque accumulation in the brain is the hallmark of many neurodegenerative disorders, including Alzheimer's disease (AD), Parkinson disease, Down's syndrome and Creutzfeldt-Jakob disease (CJD). Approaches to clinically diagnose and monitor the progression of these diseases include targeting of amyloid deposits with small-molecule imaging agents. Accordingly, fluorescence-based small molecule imaging of amyloids is a low cost, accessible, and non-radioactive technique for to detection of the amyloid deposits. Fluorescent compounds that maintain their brightness, spectroscopic properties, and specificity for binding amyloids in neuronal tissue, and exhibit superior chemical/hydrolytic stability in physiologically relevant solutions are disclosed herein. The enhanced stability of such compounds is useful in labeling amyloid deposits in living systems.

SUMMARY OF THE INVENTION

Disclosed herein is a compound of Formula I:

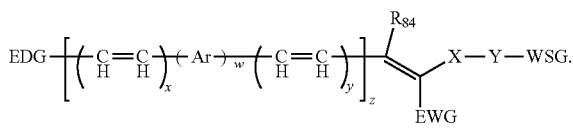

(Formula I)

In some aspects of formula I,

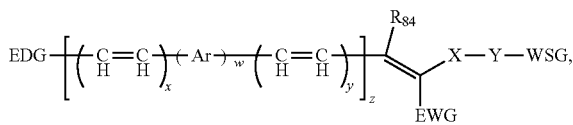

EDG is an electron donating group; each Ar is independently $C_1$-$C_{14}$ arylene or $C_1$-$C_{14}$ heteroarylene, each optionally substituted with one or more $R_1$; each $R_1$ is independently halogen, —$OR_2$, —$NR_3R_4$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_5$; $R_2$, $R_3$ and $R_4$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_5$; each $R_5$ is independently halogen, —$OR_6$, —$NR_7R_8$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_6$, $R_7$, $R_8$ and $R_{84}$ are independently hydrogen or $C_1$-$C_{10}$ alkyl; EWG is an electron withdrawing group; WSG is a water soluble group; X is C=O or $SO_2$; Y is NH, or S; each x is independently an integer from 0-10; each w is independently an integer from 1-5; each y is independently an integer from 0-10; and z is an integer from 1-10.

In some compounds of Formula I, the substituent $R_{84}$ is hydrogen or $C_1$-$C_{10}$ alkyl. In some compounds of Formula I, $R_{84}$ is hydrogen. In some compounds of Formula I, $R_{84}$ is methyl.

In some compounds of Formula I, the substituent EDG is any electron donating group, for example, EDG is $OR_9$, $NR_{10}R_{11}$, —$SR_{12}$, —$PR_{13}R_{14}$, —$NR_{15}C(O)R_{16}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{17}$; wherein each $R_{17}$ is independently halogen, —$OR_{18}$, —$NR_{19}R_{20}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_9$, $R_{10}$, $R_{11}$, $R_{12}$, $R_{13}$, $R_{14}$, $R_{15}$, $R_{16}$, $R_{18}$, $R_{19}$ and $R_{20}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{21}$ and wherein $R_{10}$ and $R_{11}$ are optionally joined together to form a heterocycloalkyl or heteroaryl optionally substituted with $R_{21}$; each of $R_{21}$ is independently halogen, —$OR_{22}$, —$NR_{23}R_{24}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{25}$; each of $R_{22}$, $R_{23}$ and $R_{24}$ is independently hydrogen or $C_1$-$C_{10}$ alkyl; and each $R_{25}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In some compounds of Formula I, the EDG is selected from a group consisting of

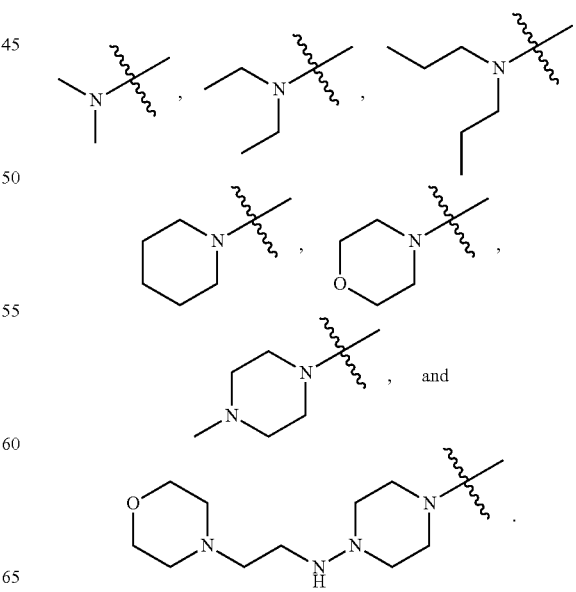

In some compounds of Formula I, the EDG is

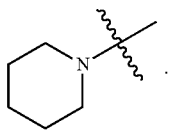

The substituent EWG in Formula I is any electron withdrawing group. In some compounds of Formula I, EWG is halogen, —CN, —NO$_2$, —SO$_3$H, —CR$_{26}$R$_{27}$R$_{28}$, COR$_{29}$, or COOR$_{30}$; wherein each R$_{26}$, R$_{27}$ and R$_{28}$ is independently hydrogen or halogen; R$_{29}$ is halogen, hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{31}$; R$_{30}$ is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{32}$; and each R$_{31}$ and R$_{32}$ is independently C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene.

In some compounds of Formula I, the EWG is selected from a group consisting of F, Cl, Br, —CH═O, NO$_2$, —CF$_3$, —CCl$_3$, —SO$_3$ and —CN. In some compounds of Formula I, the EWG is —CN.

The substituent WSG in Formula I is a water soluble group in some cases. In some compounds of Formula I, WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{33}$; wherein each R$_{33}$ is independently halogen, —OR$_{34}$, —NR$_{35}$R$_{36}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$;
each R$_{34}$, R$_{35}$ and R$_{36}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{37}$ is independently halogen, —OR$_{38}$, —NR$_{39}$R$_{40}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, —(C$_1$-C$_6$alkyl)(C$_1$-C$_{10}$heterocycloalkyl), C$_1$-C$_{10}$ arylene, or C$_1$-C$_{10}$ heteroarylene; and each of R$_{38}$, R$_{39}$ and R$_{40}$ is independently hydrogen or C$_1$-C$_{10}$ alkyl.

The substituent WSG in Formula I is a water soluble group in some cases. In some compounds of Formula I, WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{33}$; wherein each R$_{33}$ is independently halogen, —OR$_{34}$, —NR$_{35}$R$_{36}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$;
each R$_{34}$, R$_{35}$ and R$_{36}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{37}$ is independently halogen, —OR$_{38}$, —NR$_{39}$R$_{40}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene; and each of R$_{38}$, R$_{39}$ and R$_{40}$ is independently hydrogen or C$_1$-C$_{10}$ alkyl.

In some compounds of Formula I, WSG is

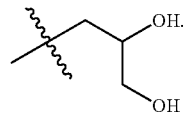 [SMILES: *CC(O)CO]

In some compounds of Formula I, WSG is polyethylene glycol, polypropylene glycol, co-polymer of polyethylene glycol and polypropylene glycol, or alkoxy derivatives thereof.

In some compounds of Formula I, WSG is

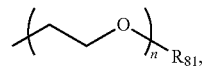

wherein n is an integer from 1-50 and R$_{81}$ is hydrogen, a C$_1$-C$_{10}$ alkyl, a C$_1$-C$_{10}$ alkenyl, or a C$_1$-C$_{10}$ alkynyl wherein each wherein the alkyl, alkenyl, or alkynyl is optionally substituted with one or more C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene. In some compounds of Formula I, R$_{81}$ is methyl or —CH$_2$—C≡CH.

In some compounds of Formula I, WSG is

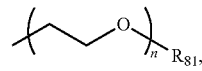

wherein n is an integer from 1-50 and R$_{81}$ is hydrogen or C$_1$-C$_{10}$ alkyl. In some compounds of Formula I, R$_{81}$ is methyl. In some compounds of Formula I, the variable n is an integer from 1-10. In some compounds of Formula I, n is 3 or 6.

In some compounds of Formula I, the WSG is

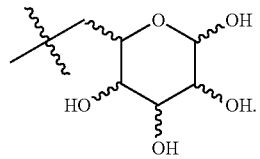 [SMILES: *CC1OC(O)C(O)C(O)C1O]

In some compounds of Formula I, WSG is

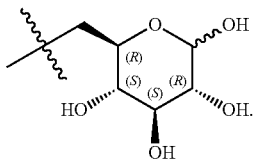

In some compounds of Formula I, WSG is

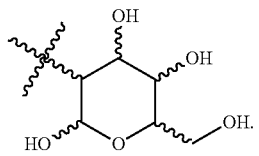

In some compounds of Formula I, WSG is

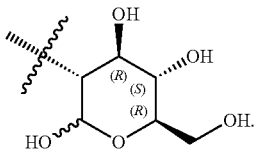

In some compounds of Formula I, WSG is —($C_1$-$C_{10}$ alkyl)-$R_{33}$—$R_{37}$. In some compounds of Formula I, WSG is —($C_1$-$C_{10}$ alkyl)-$R_{33}$—$R_{37}$ and $R_{33}$ is $C_1$-$C_{10}$ heteroarylene. In some compounds of Formula I, WSG is —($C_1$-$C_{10}$ alkyl)-$R_{33}$—$R_{37}$, $R_{33}$ is $C_1$-$C_{10}$ heteroarylene and $R_{37}$ is —($C_1$-$C_6$alkyl)($C_1$-$C_{10}$heterocycloalkyl). In some compounds of Formula I, WSG is WSG is —$CH_3$—$R_{33}$—$R_{37}$. In some compounds of Formula I, WSG is —$CH_3$—$R_{33}$—$R_{37}$ and $R_{33}$ is triazole. In some compounds of Formula I, WSG is —$CH_3$—$R_{33}$—$R_{37}$, $R_{33}$ is triazole, and $R_{37}$ is

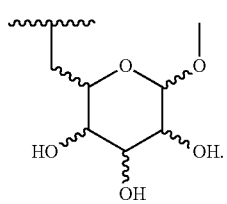

In some compounds of Formula I, WSG is

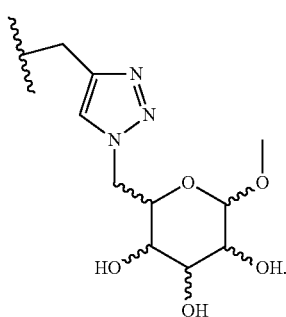 [SMILES: *Cc1cn(CC2OC(OC)C(O)C(O)C2O)nn1]

In some compounds of Formula I, WSG is —($C_1$-$C_{10}$ heteroalkyl)-$R_{33}$—$R_{37}$. In some compounds of Formula I, WSG is —($C_1$-$C_{10}$ heteroalkyl)-$R_{33}$—$R_{37}$ and $R_{33}$ is $C_1$-$C_{10}$ heteroarylene. In some compounds of Formula I, WSG is —($C_1$-$C_{10}$ heteroalkyl)-$R_{33}$—$R_{37}$ and $R_{33}$ is $C_1$-$C_{10}$ heteroarylene and $R_{37}$ is —($C_1$-$C_6$alkyl)($C_1$-$C_{10}$ heterocycloalkyl).

In some compounds of Formula I, WSG is and p is 1, 2, 3, 4, 5, or
In some compounds of Formula I, WSG is and p 3.
In some compounds of Formula I, WSG is and $R_{33}$ is triazole.
In some compounds of Formula I, WSG is $R_{33}$ is triazole, and $R_{37}$ is
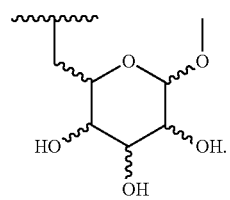 [SMILES: *CC1OC(OC)C(O)C(O)C1O]
In some compounds of Formula I, WSG is
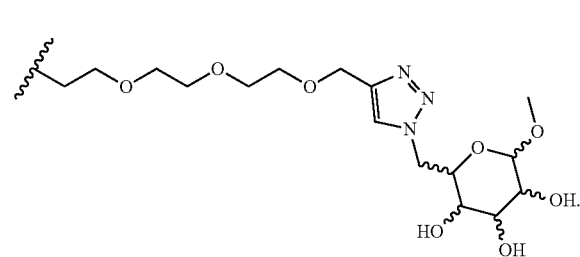 [SMILES: *CCOCCOCCOCc1cn(CC2OC(OC)C(O)C(O)C2O)nn1]
In some compounds of Formula I, WSG is
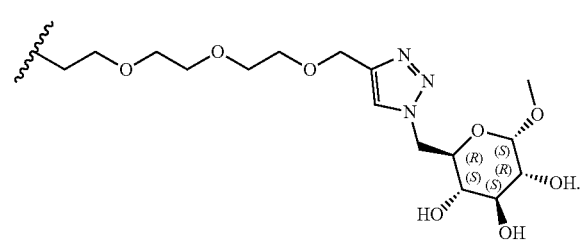
In some cases, the compounds of Formula I is of formula (Ic):
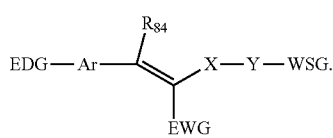
In some cases, the compounds of Formula I is of formula (Id):
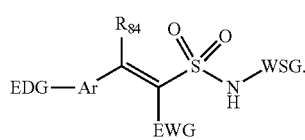
In some cases, the compounds of Formula I is of formula (Ie):
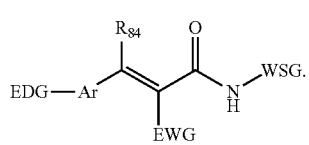
In some cases, the compound of Formula I is selected from a group consisting of:
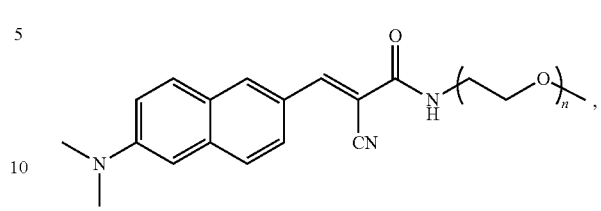
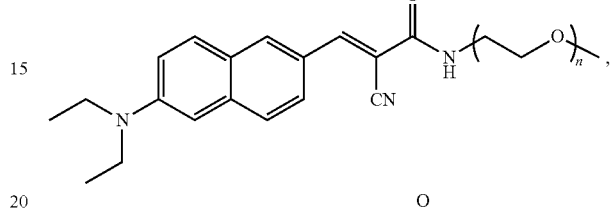

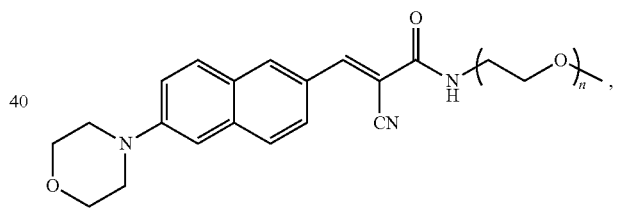
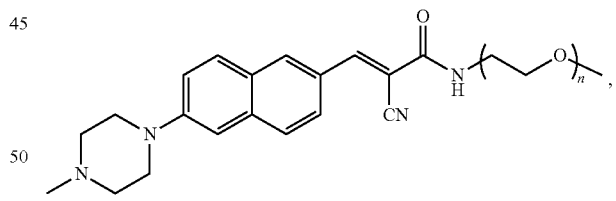
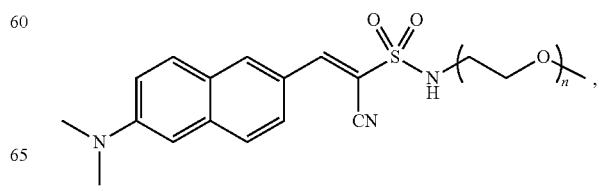

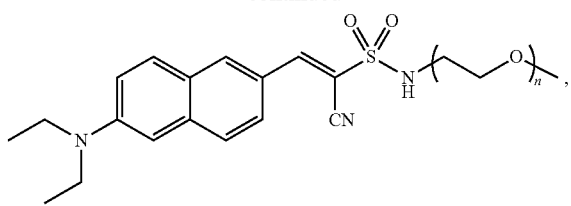
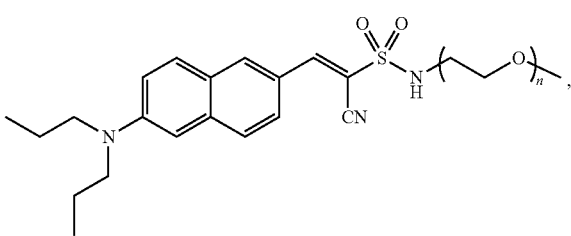
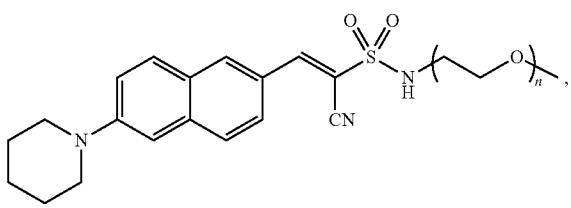
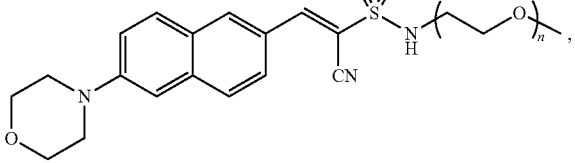
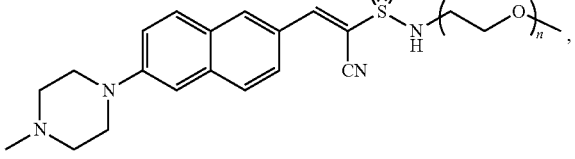
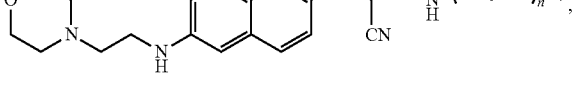
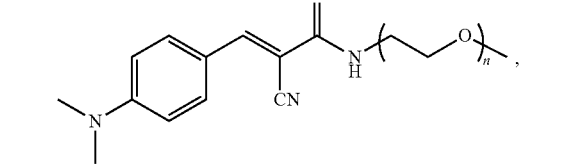
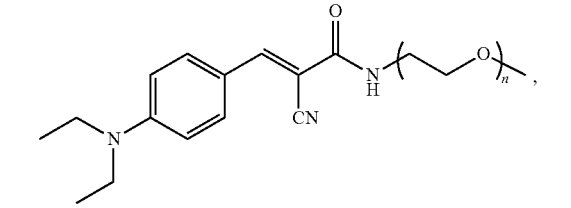
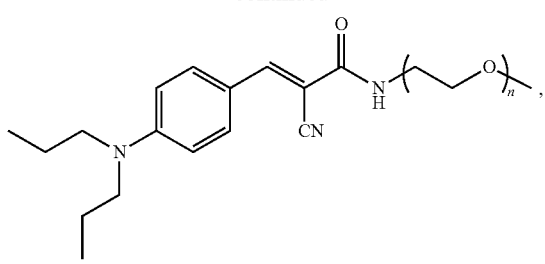
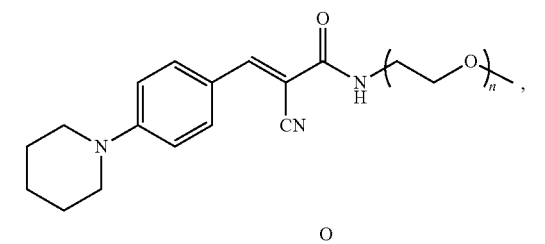
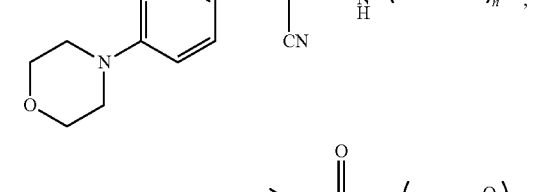

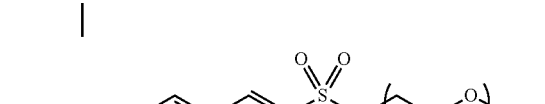
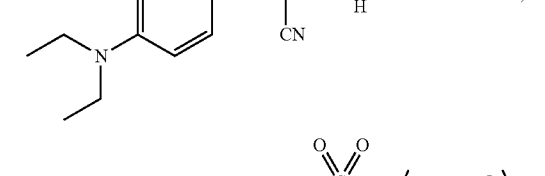
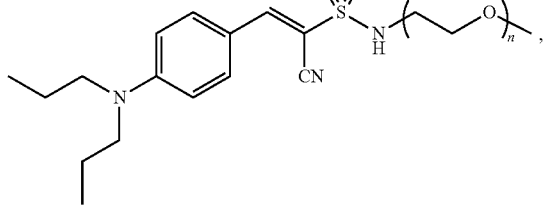

-continued
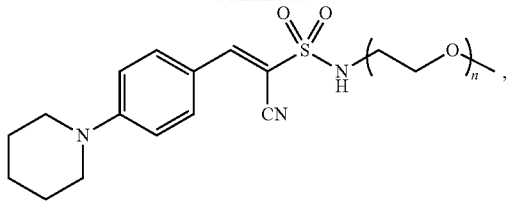
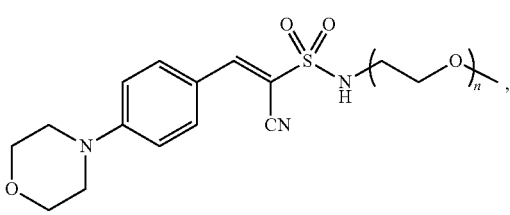
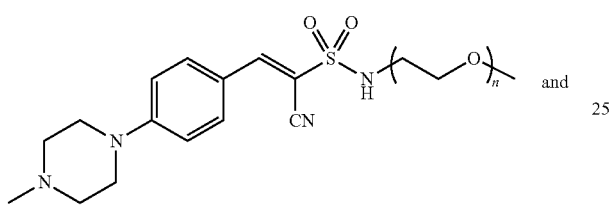
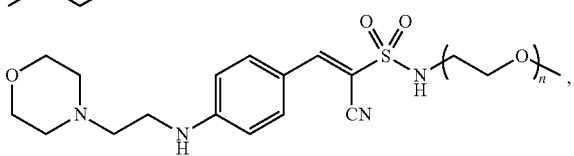
wherein n is an integer, for example an integer with value 1-10.
In some cases, the compound of Formula I is selected from:
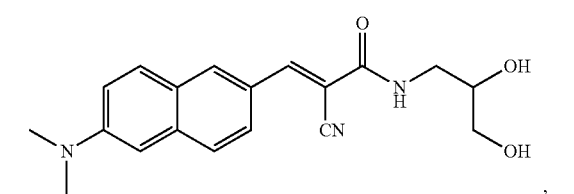
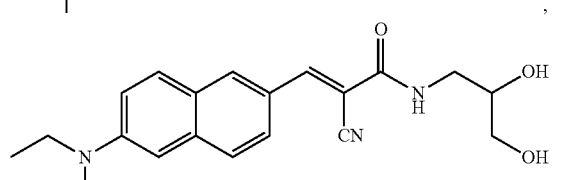
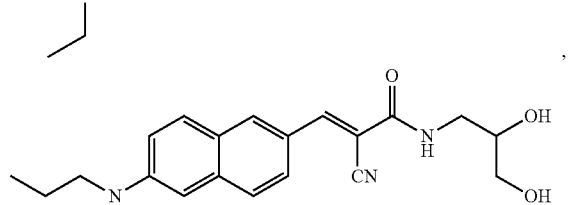
-continued
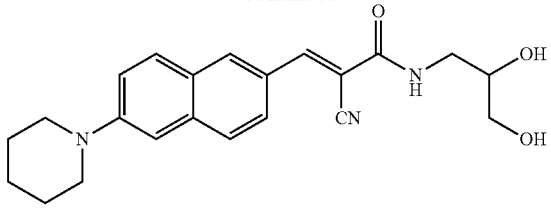
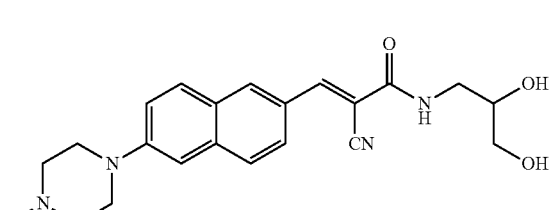

-continued
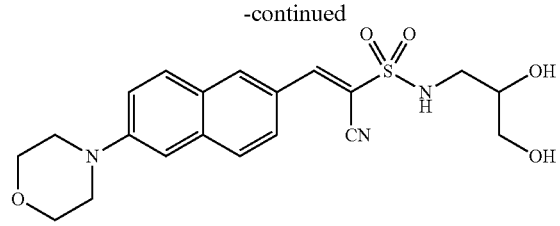
,
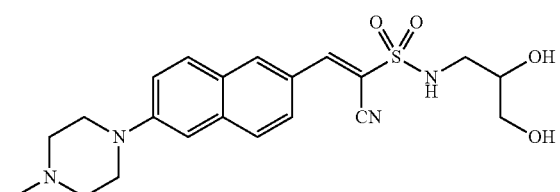
,
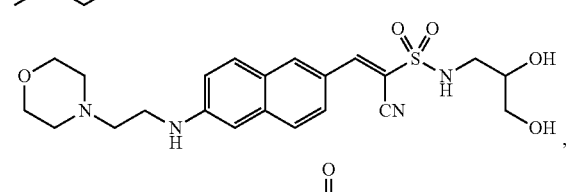
,
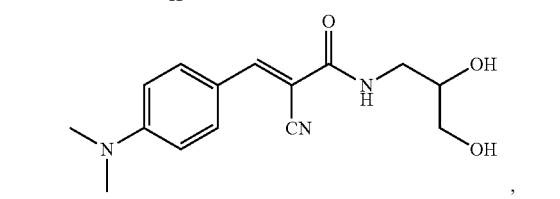
,
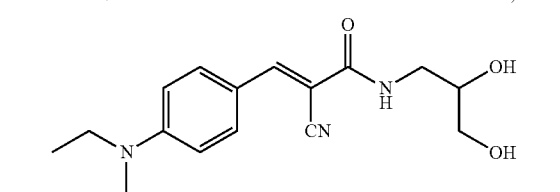
,
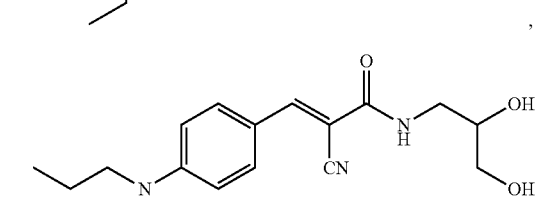
,
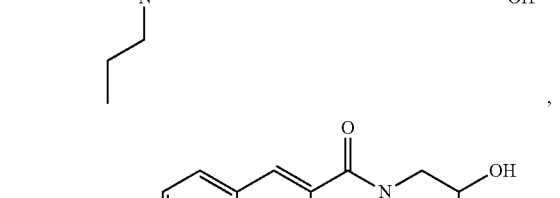
,
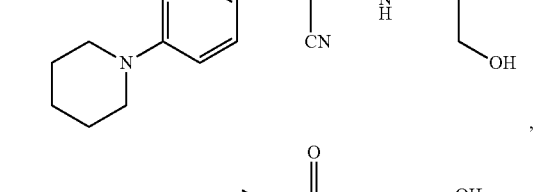
,
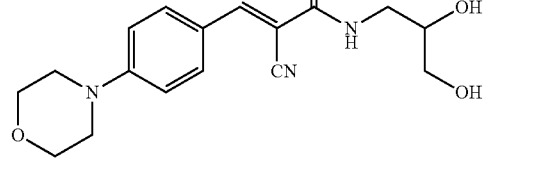
,
-continued
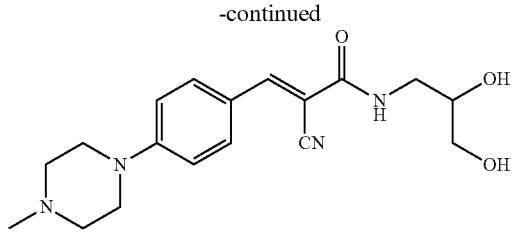
,
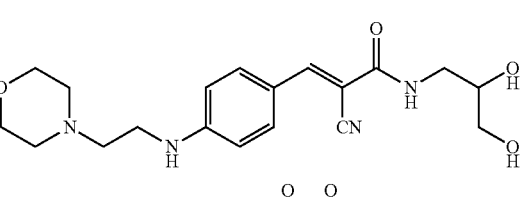
,
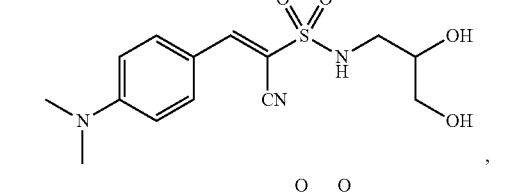
,
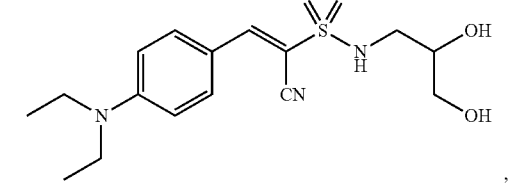
,
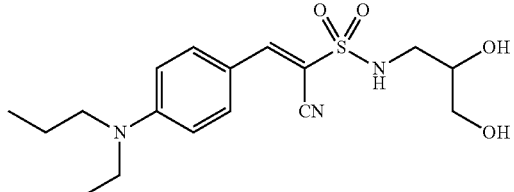
,
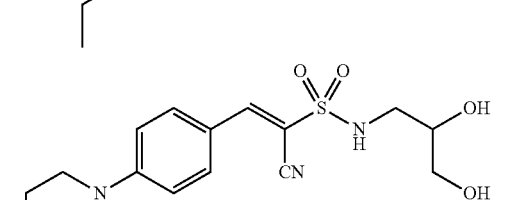
,
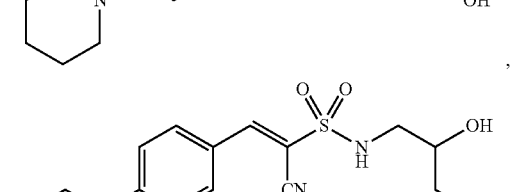
,
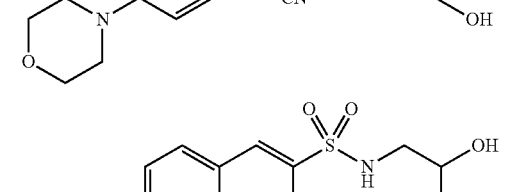
,
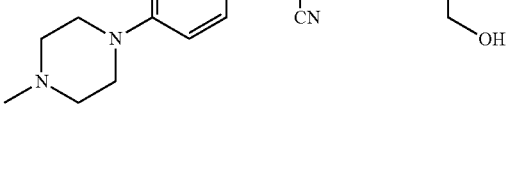
and -continued

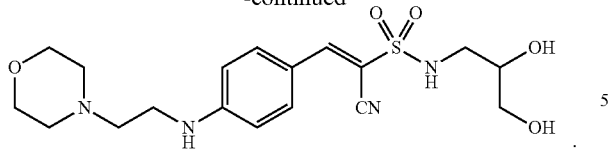

In some cases, the compound of Formula I is

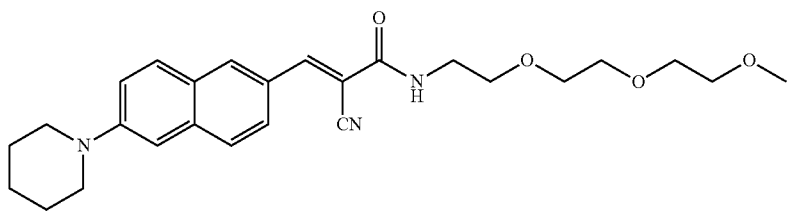

In some cases, the compound of Formula I is (E)-2-cyano-N-(2-(2-(2-methoxyethoxy)ethoxy)ethyl)-3-(6-(piperidin-1-yl)naphthalen-2-yl)acrylamide. In some cases, the compound of Formula I is (Z)-2-cyano-N-(2-(2-(2-methoxyethoxy)ethoxy)ethyl)-3-(6-(piperidin-1-yl)naphthalen-2-yl)acrylamide.

In some cases, the compound of Formula I is

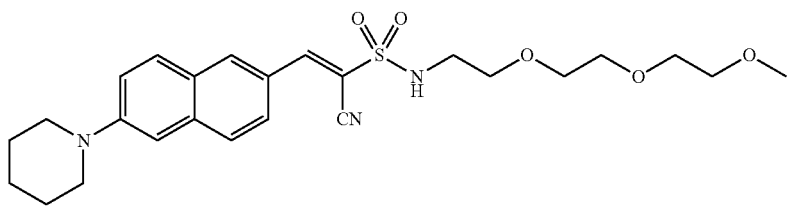

In some cases, the compound of Formula I is (E)-1-cyano-N-(2-(2-(2-methoxyethoxy)ethoxy)ethyl)-2-(6-(piperidin-1-yl)naphthalen-2-yl)ethenesulfonamide. In some cases, the compound of Formula I is (Z)-1-cyano-N-(2-(2-(2-methoxyethoxy)ethoxy)ethyl)-2-(6-(piperidin-1-yl)naphthalen-2-yl)ethenesulfonamide.

In some cases, the compound of Formula I is

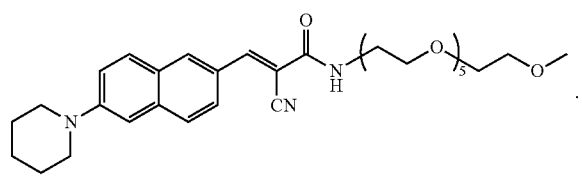

In some cases, the compound of Formula I is (E)-2-cyano-N-(2,5,8,11,14,17-hexaoxanonadecan-19-yl)-3-(6-(piperidin-1-yl)naphthalen-2-yl)acrylamide. In some cases, the compound of Formula I is (Z)-2-cyano-N-(2,5,8,11,14,17-hexaoxanonadecan-19-yl)-3-(6-(piperidin-1-yl)naphthalen-2-yl)acrylamide.

In some cases, the compound of Formula I is

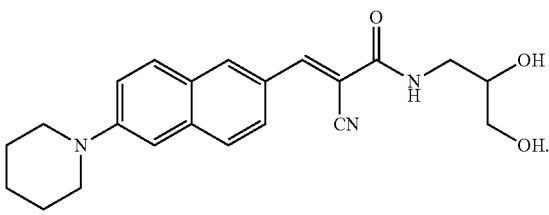 [SMILES: N#C/C(=C\c1ccc2cc(N3CCCCC3)ccc2c1)C(=O)NCC(O)CO]

In some cases, the compound of Formula I is (E)-2-cyano-N-(2,3-dihydroxypropyl)-3-(6-(piperidin-1-yl)naphthalen-2-yl)acrylamide. In some cases, the compound of Formula I is (Z)-2-cyano-N-(2,3-dihydroxypropyl)-3-(6-(piperidin-1-yl)naphthalen-2-yl)acrylamide.

In some cases, the compound of Formula I is

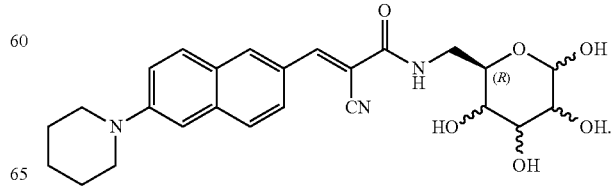

In some cases, the compound of Formula I is (R,E)-2-cyano-3-(6-(piperidin-1-yl)naphthalen-2-yl)-N-((3,4,5,6-tetrahydroxytetrahydro-2H-pyran-2-yl)methyl)acrylamide. In some cases, the compound of Formula I is (R,Z)-2-cyano-3-(6-(piperidin-1-yl)naphthalen-2-yl)-N-((3,4,5,6-tetrahydroxytetrahydro-2H-pyran-2-yl)methyl)acrylamide In some cases, the compound of Formula I is

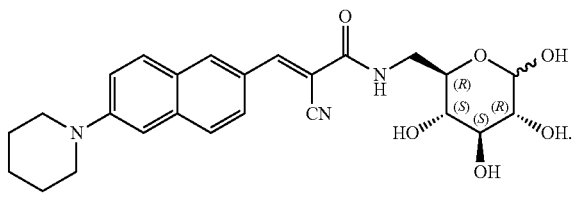

In some cases, the compound of Formula I is (E)-2-cyano-3-(6-(piperidin-1-yl)naphthalen-2-yl)-N-(((2R,3S,4S,5R)-3,4,5,6-tetrahydroxytetrahydro-2H-pyran-2-yl)methyl)acrylamide. In some cases, the compound of Formula I is (Z)-2-cyano-3-(6-(piperidin-1-yl)naphthalen-2-yl)-N-(((2R,3S,4S,5R)-3,4,5,6-tetrahydroxytetrahydro-2H-pyran-2-yl)methyl)acrylamide.

In some cases, the compound of Formula I is

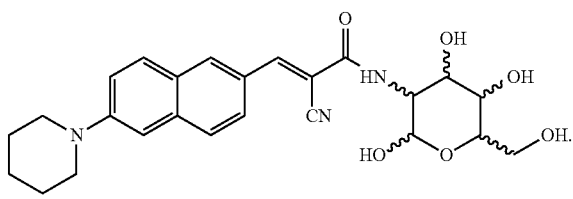 [SMILES: N#C/C(=C\c1ccc2cc(N3CCCCC3)ccc2c1)C(=O)NC1C(O)OC(CO)C(O)C1O]

In some cases, the compound of Formula I is (E)-2-cyano-3-(6-(piperidin-1-yl)naphthalen-2-yl)-N-(2,4,5-trihydroxy-6-(hydroxymethyl)tetrahydro-2H-pyran-3-yl)acrylamide. In some cases, the compound of Formula I is (Z)-2-cyano-3-(6-(piperidin-1-yl)naphthalen-2-yl)-N-(2,4,5-trihydroxy-6-(hydroxymethyl)tetrahydro-2H-pyran-3-yl)acrylamide.

In some cases, the compound of Formula I is

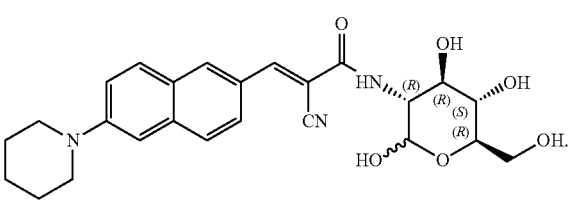

In some cases, the compound of Formula I is (E)-2-cyano-3-(6-(piperidin-1-yl)naphthalen-2-yl)-N-((3R,4R,5S,6R)-2,4,5-trihydroxy-6-(hydroxymethyl)tetrahydro-2H-pyran-3-yl)acrylamide. In some cases, the compound of Formula I is (Z)-2-cyano-3-(6-(piperidin-1-yl)naphthalen-2-yl)-N-((3R,4R,5S,6R)-2,4,5-trihydroxy-6-(hydroxymethyl)tetrahydro-2H-pyran-3-yl)acrylamide.

In some cases, the compound of Formula I is

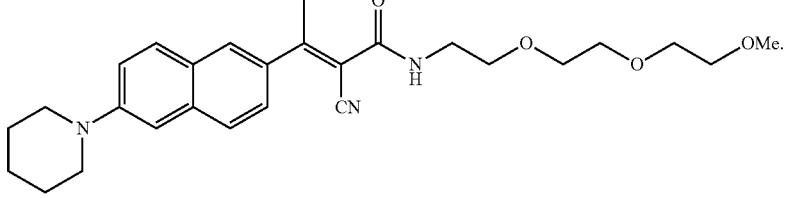

In some cases, the compound of Formula I is (E)-2-cyano-N-(2-(2-(2-methoxyethoxy)ethoxy)ethyl)-3-(6-(piperidin-1-yl)naphthalen-2-yl)but-2-enamide. In some cases, the compound of Formula I is (Z)-2-cyano-N-(2-(2-(2-methoxyethoxy)ethoxy)ethyl)-3-(6-(piperidin-1-yl)naphthalen-2-yl)but-2-enamide.

In some cases, the compound of Formula I is

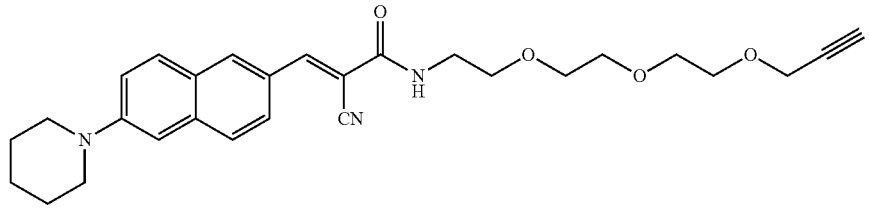

In some cases, the compound of Formula I is (E)-2-cyano-3-(6-(piperidin-1-yl)naphthalen-2-yl)-N-(2-(2-(2-(prop-2-ynyloxy)ethoxy)ethoxy)ethyl)acrylamide. In some cases, the compound of Formula I is (Z)-2-cyano-3-(6-(piperidin-1-yl)naphthalen-2-yl)-N-(2-(2-(2-(prop-2-ynyloxy)ethoxy)ethoxy)ethyl)acrylamide.

In some cases, the compound of Formula I is

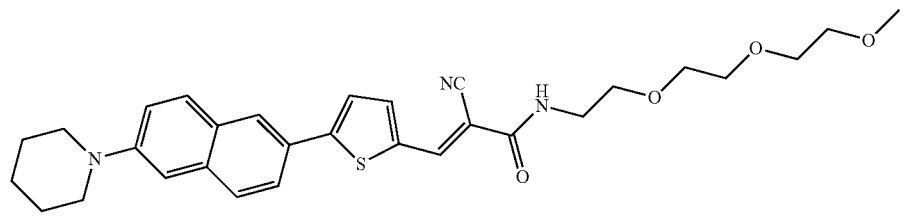

In some cases, the compound of Formula I is (E)-2-cyano-N-(2-(2-(2-methoxyethoxy)ethoxy)ethyl)-3-(5-(6-(piperidin-1-yl)naphthalen-2-yl)thiophen-2-yl)acrylamide. In some cases, the compound of Formula I is (Z)-2-cyano-N-(2-(2-(2-methoxyethoxy)ethoxy)ethyl)-3-(5-(6-(piperidin-1-yl)naphthalen-2-yl)thiophen-2-yl)acrylamide.

In some cases, the compound of Formula I is

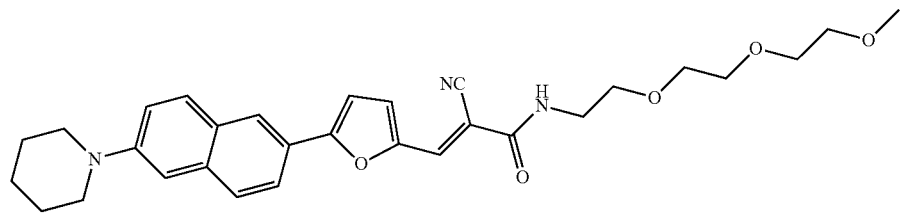

In some cases, the compound of Formula I is (E)-2-cyano-N-(2-(2-(2-methoxyethoxy)ethoxy)ethyl)-3-(5-(6-(piperidin-1-yl)naphthalen-2-yl)furan-2-yl)acrylamide. In some cases, the compound of Formula I is (Z)-2-cyano-N-(2-(2-(2-methoxyethoxy)ethoxy)ethyl)-3-(5-(6-(piperidin-1-yl)naphthalen-2-yl)furan-2-yl)acrylamide.

In some cases, the compound of Formula I is

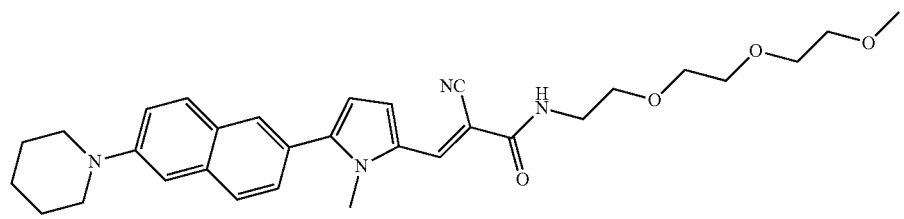

In some cases, the compound of Formula I is (E)-2-cyano-N-(2-(2-(2-methoxyethoxy)ethoxy)ethyl)-3-(1-methyl-5-(6-(piperidin-1-yl)naphthalen-2-yl)-1H-pyrrol-2-yl)acrylamide. In some cases, the compound of Formula I is (Z)-2-cyano-N-(2-(2-(2-methoxyethoxy)ethoxy)ethyl)-3-(1-methyl-5-(6-(piperidin-1-yl)naphthalen-2-yl)-1H-pyrrol-2-yl)acrylamide.

In some cases, the compound of Formula I is

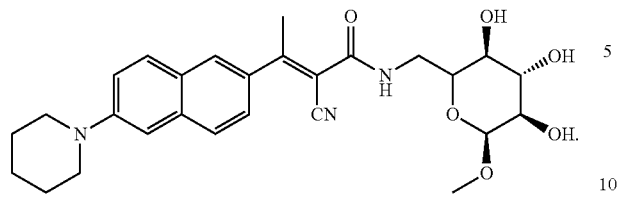

In some cases, the compound of Formula I is (E)-2-cyano-3-(6-(piperidin-1-yl)naphthalen-2-yl)-N-(((3 S,4S,5R,6S)-3,4,5-trihydroxy-6-m ethoxytetrahydro-2H-pyran-2-yl)methyl)but-2-enamide. In some cases, the compound of Formula I is (Z)-2-cyano-3-(6-(piperidin-1-yl)naphthalen-2-yl)-N-(((3 S,4S,5R,6S)-3,4,5-trihydroxy-6-methoxytetrahydro-2H-pyran-2-yl)methyl)but-2-enamide.

In some cases, the compound of Formula I is

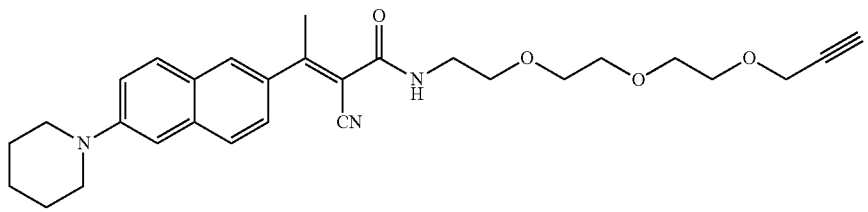

In some cases, the compound of Formula I is (E)-2-cyano-3-(6-(piperidin-1-yl)naphthalen-2-yl)-N-(2-(2-(2-(prop-2-ynyloxy)ethoxy)ethoxy)ethyl)but-2-enamide. In some cases, the compound of Formula I is (Z)-2-cyano-3-(6-(piperidin-1-yl)naphthalen-2-yl)-N-(2-(2-(2-(prop-2-ynyloxy)ethoxy)ethoxy)ethyl)but-2-enamide.

In some cases, the compound of Formula I is

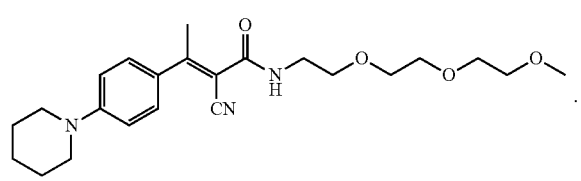 [SMILES: COCCOCCOCCNC(=O)/C(C#N)=C(\C)c1ccc(N2CCCCC2)cc1]

In some cases, the compound of Formula I is (E)-2-cyano-N-(2-(2-(2-methoxyethoxy)ethoxy)ethyl)-3-(4-(piperidin-1-yl)phenyl)but-2-enamide. In some cases, the compound of Formula I is (Z)-2-cyano-N-(2-(2-(2-methoxyethoxy)ethoxy)ethyl)-3-(4-(piperidin-1-yl)phenyl)but-2-enamide.

In some cases, the compound of Formula I is

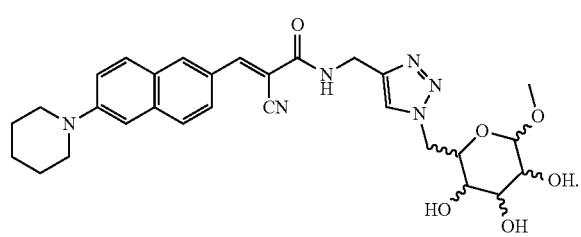 [SMILES: COC1OC(Cn2cc(CNC(=O)/C(C#N)=C/c3ccc4cc(N5CCCCC5)ccc4c3)nn2)C(O)C(O)C1O]

In some cases, the compound of Formula I is (E)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide. In some cases, the compound of Formula I is (Z)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide.

In some cases, the compound of Formula I is

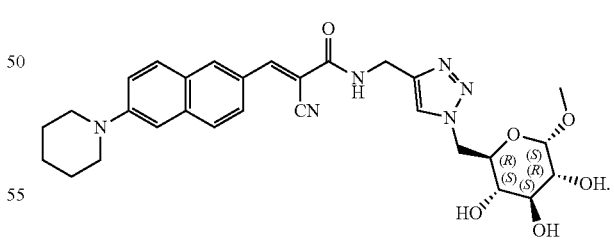

In some cases, the compound of Formula I is (E)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)acrylamide. In some cases, the compound of Formula I is (Z)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)acrylamide.

In some cases, the compound of Formula I is

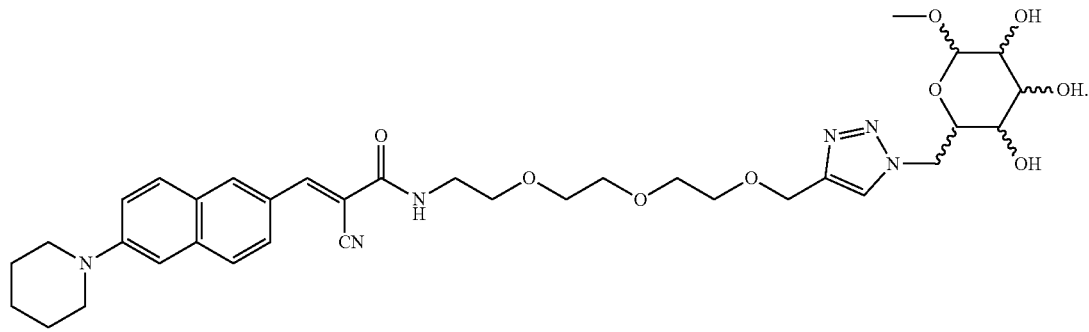 [SMILES: COC1OC(Cn2cc(COCCOCCOCCNC(=O)/C(C#N)=C/c3ccc4cc(N5CCCCC5)ccc4c3)nn2)C(O)C(O)C1O]

In some cases, the compound of Formula I is (E)-2-cyano-3-(6-(piperidin-1-yl)naphthalen-2-yl)-N-(2-(2-(2-((1-(((3,4,5-trihydroxy-6-methoxytetrahydro-2H-pyran-2-yl)methyl)-1H-1,2,3-triazol-4-yl)methoxy)ethoxy)ethoxy)ethyl)acrylamide. In some cases, the compound of Formula I is (Z)-2-cyano-3-(6-(piperidin-1-yl)naphthalen-2-yl)-N-(2-(2-(2-((1-(((3,4,5-trihydroxy-6-methoxytetrahydro-2H-pyran-2-yl)methyl)-1H-1,2,3-triazol-4-yl)methoxy)ethoxy)ethoxy)ethyl)acrylamide.

In some cases, the compound of Formula I is

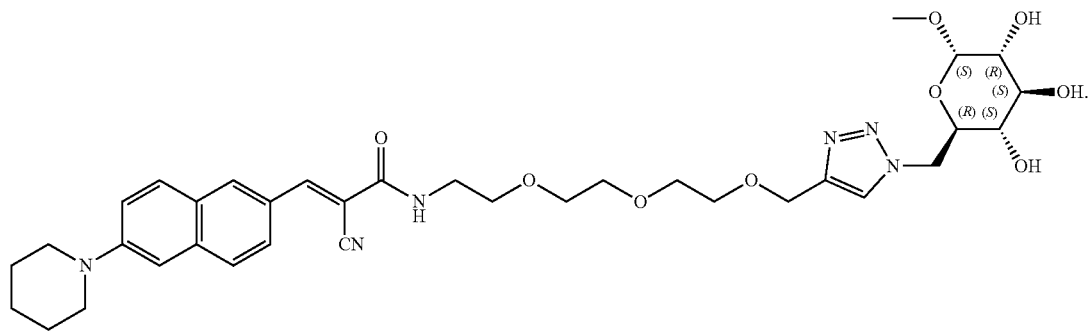

In some cases, the compound of Formula I is (E)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)acrylamide. In some cases, the compound of Formula I is (Z)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)acrylamide.

In some cases, the compound of Formula I is

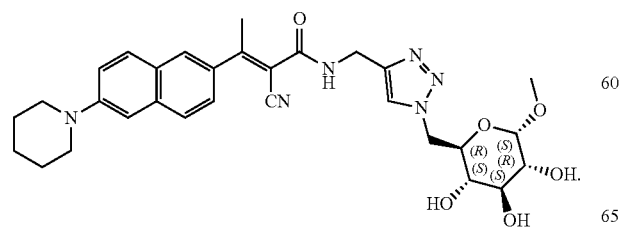

In some cases, the compound of Formula I is (E)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)but-2-enamide. In some cases, the compound of Formula I is (Z)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)but-2-enamide.

In some cases, the compound of Formula I is

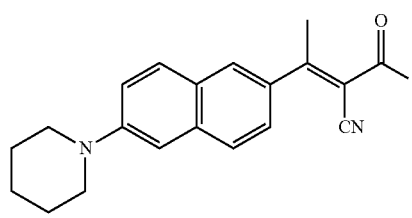

In some cases, the compound of Formula I is (E)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)but-2-enamide. In some cases, the compound of Formula I is (Z)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)but-2-enamide.

The disclosure provides a compound of Formula II (Formula II)

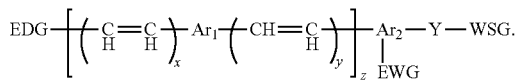

In some aspects of Formula II, EDG is an electron donating group; $Ar_2$ and each $Ar_1$ is independently $C_1$-$C_{14}$ arylene or $C_1$-$C_{14}$ heteroarylene, each optionally substituted with one more $R_{41}$; each $R_{41}$ is independently halogen, —CN, —$OR_{42}$, —$NR_{43}R_{44}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_{45}$; $R_{42}$, $R_{43}$ and $R_{44}$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{45}$; each $R_{45}$ is independently halogen, —$OR_{46}$, —$NR_{47}R_{48}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_{46}$, $R_{47}$ and $R_{48}$ are independently hydrogen or $C_1$-$C_{10}$ alkyl; EWG is an electron withdrawing group; Y is absent, O, NH, or S; WSG is hydrogen or a water soluble group; x is an integer from 0-10; y is an integer from 0-10; and z is an integer from 1-10.

The substituent EDG in Formula II is an electron donating group in some cases. In some compounds of Formula II, EDG is $OR_{49}$, $NR_{50}R_{51}$, —$SR_{52}$, —$PR_{53}R_{54}$, —$NR_{55}C(O)R_{56}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{57}$; wherein each $R_{57}$ is independently halogen, —$OR_{58}$, —$NR_{59}R_{60}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of

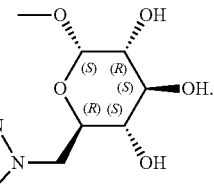

$R_{49}$, $R_{50}$, $R_{51}$, $R_{52}$, $R_{53}$, $R_{54}$, $R_{55}$, $R_{56}$, $R_{58}$, $R_{59}$ and $R_{60}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{61}$ and wherein $R_{50}$ and $R_{51}$ are optionally joined together to form a heterocycloalkyl or heteroaryl optionally substituted with $R_{61}$; each of $R_{61}$ is independently halogen, —$OR_{62}$, —$NR_{63}R_{64}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{65}$; each of $R_{62}$, $R_{63}$ and $R_{64}$ is independently hydrogen or $C_1$-$C_{10}$ alkyl; and each $R_{65}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In some compounds of formula II, EDG is selected from a group consisting of

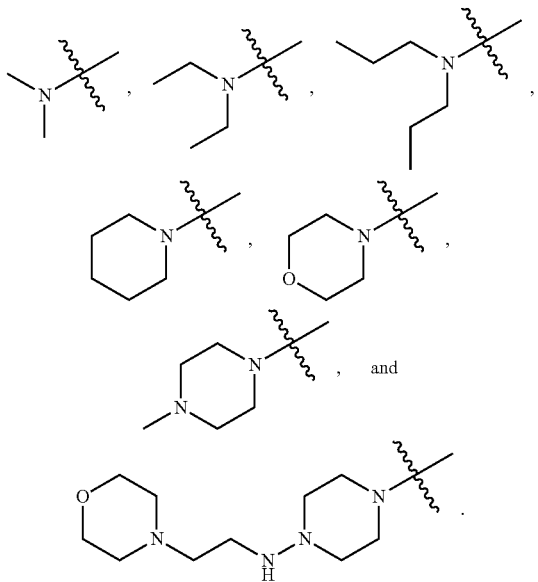

In some compounds of Formula II, EDG is

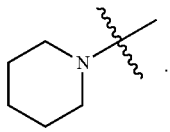

The substituent EWG in the Formula II is an electron withdrawing group in some aspects. In some compounds of Formula II, EWG is halogen, —CN, —NO$_2$, —SO$_3$H, —CR$_{66}$R$_{67}$R$_{68}$, COR$_{69}$, or COOR$_{70}$; wherein each R$_{66}$, R$_{67}$ and R$_{68}$ is independently hydrogen or halogen; R$_{69}$ is halogen, hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{71}$; R$_{70}$ is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{72}$; each R$_{71}$ and R$_{72}$ is independently C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene.

In some compounds of formula II, EWG is selected from a group consisting of F, Cl, Br, —CH=O, NO$_2$, —CF$_3$, —CCl$_3$, —SO$_3$ and —CN. In some compounds of Formula II, EWG is —CN.

In some compounds of Formula II, Y is absent, O, NH, or S. In some compounds of Formula II, Y is absent. In some compounds of Formula II, Y is O, NH, or S.

The substituent WSG in Formula II is a water soluble group in some cases. In some compounds of Formula II, WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{73}$; wherein each R$_{73}$ is independently halogen, —OR$_{74}$, —NR$_{75}$R$_{76}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{77}$; each R$_{74}$, R$_{75}$ and R$_{76}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{77}$; each R$_{37}$ is independently halogen, —OR$_{78}$, —NR$_{79}$R$_{80}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, —(C$_1$-C$_6$alkyl)(C$_1$-C$_{10}$ heterocycloalkyl), C$_1$-C$_{10}$ arylene, or C$_1$-C$_{10}$ heteroarylene; and each of R$_{78}$, R$_{79}$ and R$_{80}$ is independently hydrogen or C$_1$-C$_{10}$ alkyl.

The substituent WSG in Formula II is a water soluble group in some cases. In some compounds of Formula II, WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{73}$; wherein each R$_{73}$ is independently halogen, —OR$_{74}$, —NR$_{75}$R$_{76}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{77}$; each R$_{74}$, R$_{75}$ and R$_{76}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{77}$; each R$_{77}$ is independently halogen, —OR$_{78}$, —NR$_{79}$R$_{80}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene; and each of R$_{78}$, R$_{79}$ and R$_{80}$ is independently hydrogen or C$_1$-C$_{10}$ alkyl.

In some compounds of formula II, WSG is hydrogen. In some compounds of formula II, WSG is

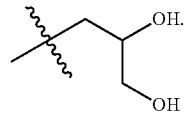 [SMILES: *CC(O)CO]

In some compounds of formula II, WSG is polyethylene glycol, polypropylene glycol, co-polymer of polyethylene glycol and polypropylene glycol, or alkoxy derivatives thereof. In some compounds of formula II, WSG is

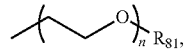

wherein n is an integer from 0-50 and R$_{81}$ is hydrogen, C$_1$-C$_{10}$ alkyl, a C$_1$-C$_{10}$ alkenyl, or a C$_1$-C$_{10}$ alkynyl wherein each wherein the alkyl, alkenyl, or alkynyl is optionally substituted with one or more C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene. In some compounds of Formula II, WSG is

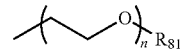

and R$_{81}$ is hydrogen. In some compounds of formula II, WSG is

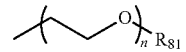

and R$_{81}$ is methyl. In some compounds of Formula II, WSG is

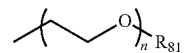

and R$_{81}$ is ethyl. In some compounds of Formula II, WSG is

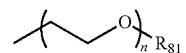

and R$_{81}$ is CH$_2$—C≡CH. In some compounds of Formula II, WSG is

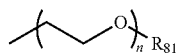

and the variable n is any integer of value 0-10. In some compounds of Formula II, WSG is

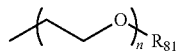

and n is 0, 3 or 6.

In some compounds of formula II, WSG is

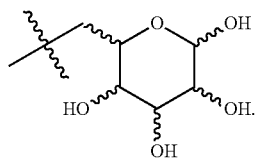 [SMILES: *CC1OC(O)C(O)C(O)C1O]

In some compounds of Formula II, WSG is

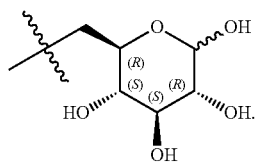

In some compounds of formula II, WSG is

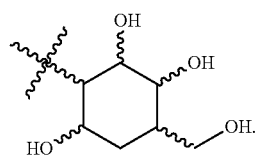

In some compounds of Formula II, WSG is

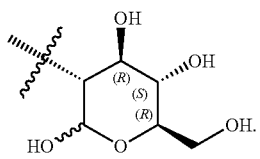

In some compounds of Formula II, WSG is —($C_1$-$C_{10}$ alkyl)-$R_{73}$—$R_{77}$. In some compounds of Formula II, WSG is —($C_1$-$C_{10}$ alkyl)-$R_{73}$—$R_{77}$ and $R_{73}$ is $C_1$-$C_{10}$ heteroarylene. In some compounds of Formula II, WSG is —($C_1$-$C_{10}$ alkyl)-$R_{73}$—$R_{77}$, $R_{73}$ is $C_1$-$C_{10}$ heteroarylene and $R_{77}$ is —($C_1$-$C_6$alkyl)($C_1$-$C_{10}$heterocycloalkyl). In some compounds of Formula II, WSG is WSG is —$CH_3$—$R_{73}$—$R_{77}$. In some compounds of Formula II, WSG is —$CH_3$—$R_{73}$—$R_{77}$ and $R_{73}$ is triazole. In some compounds of Formula II, WSG is —$CH_3$—$R_{73}$—$R_{77}$, $R_{73}$ is triazole, and $R_{77}$ is

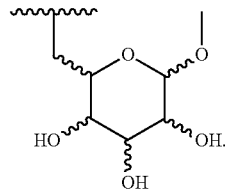 [SMILES: *CC1OC(OC)C(O)C(O)C1O]

In some compounds of Formula II, WSG is

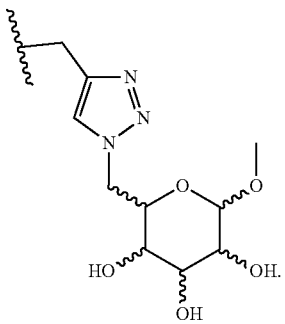 [SMILES: *Cc1cn(CC2OC(OC)C(O)C(O)C2O)nn1]

In some compounds of Formula II, WSG is

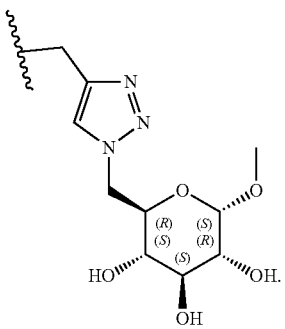

In some compounds of Formula II, WSG is —($C_1$-$C_{10}$ heteroalkyl)-$R_{73}$—$R_{77}$. In some compounds of Formula II, WSG is —($C_1$-$C_{10}$ heteroalkyl)-$R_{73}$—$R_{77}$ and $R_{73}$ is $C_1$-$C_{10}$ heteroarylene. In some compounds of Formula II, WSG is —($C_1$-$C_{10}$ heteroalkyl)-$R_{73}$—$R_{77}$ and $R_{73}$ is $C_1$-$C_{10}$ heteroarylene and $R_{77}$ is —($C_1$-$C_6$alkyl)($C_1$-$C_{10}$ heterocycloalkyl).

In some compounds of Formula II, WSG is

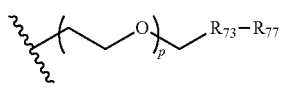

and p is 1, 2, 3, 4, 5, or 6. In some compounds of Formula II, p is greater than 6.

In some compounds of Formula II, WSG is

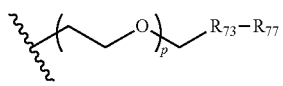

and p 3.

In some compounds of Formula II, WSG is

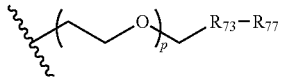

and R$_{73}$ is triazole.

In some compounds of Formula II, WSG is

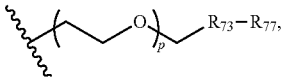

R$_{73}$ is triazole, and R$_{77}$ is

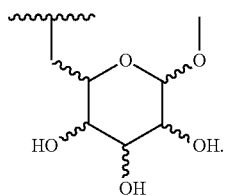 [SMILES: *CC1OC(OC)C(O)C(O)C1O]

In some compounds of Formula II, WSG is

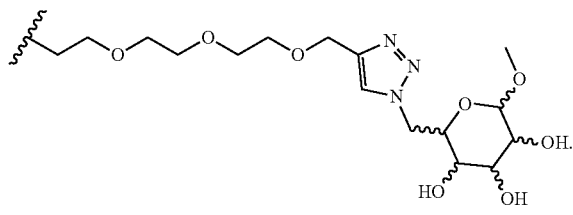 [SMILES: *CCOCCOCCOCc1cn(CC2OC(OC)C(O)C(O)C2O)nn1]

In some compounds of Formula II, WSG is

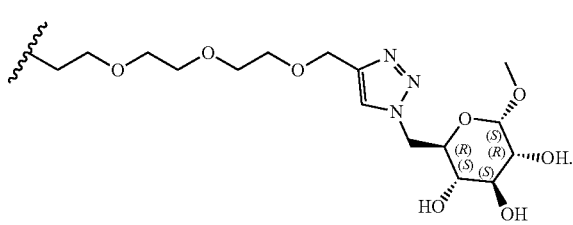

In some compounds of formula II, each of Ar$_1$ is independently a naphthylene or a phenylene.

In some compounds of Formula II, Ar$_2$ is a naphthylene, a phenylene, or a pyridyl.

In some compounds of Formula II, Ar$_2$ is a naphthylene or a phenylene.

In some compounds of Formula II, Ar$_2$ is a pyridyl.

In some cases, the compound of Formula II is selected from a group consisting of

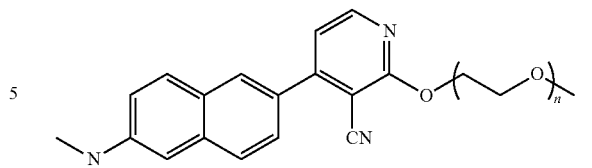

,

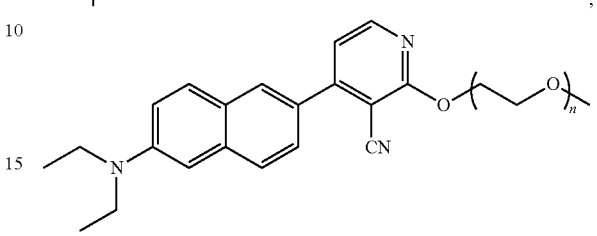

,

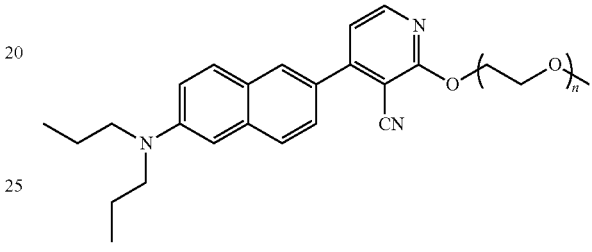

,

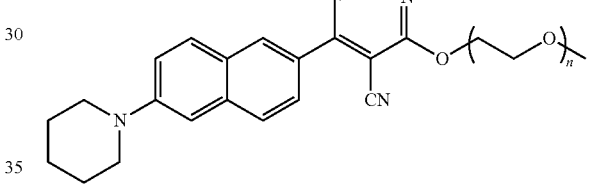

,

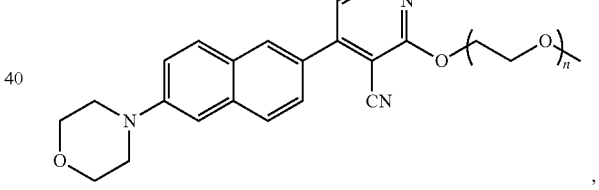

,

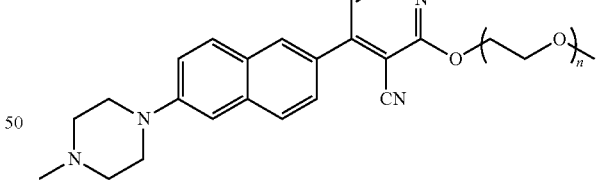

,

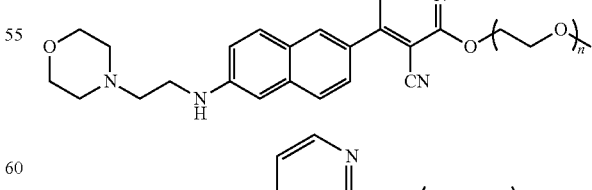

,

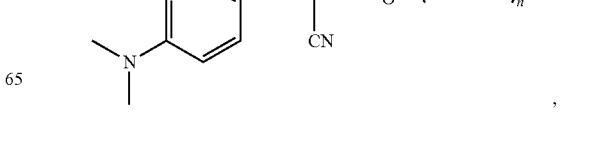

,

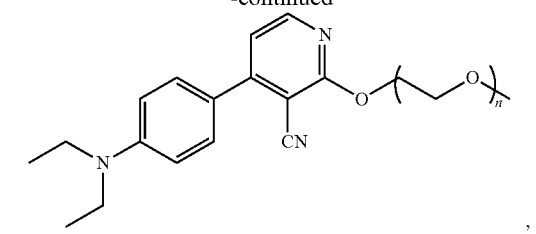
,
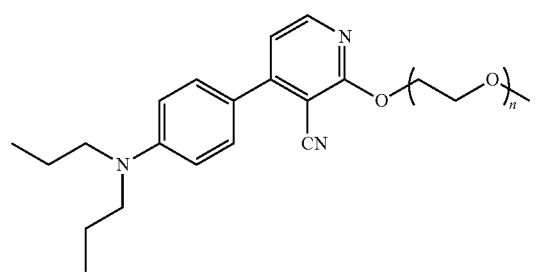
,
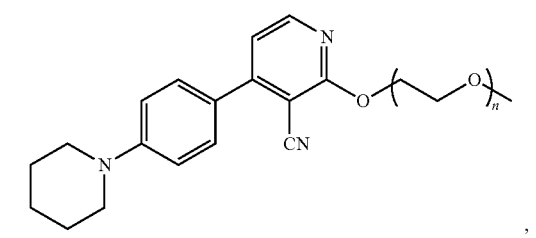
,
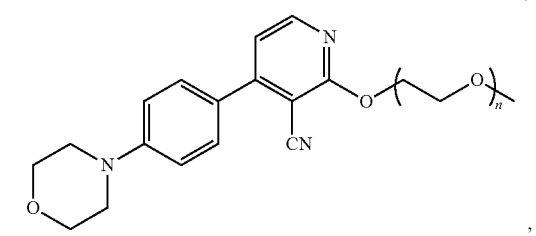
,
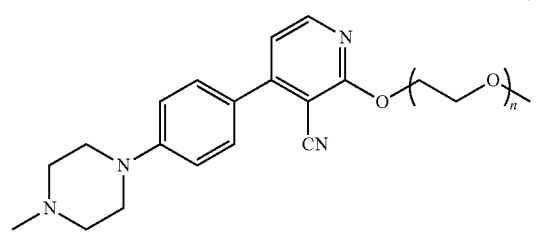
,
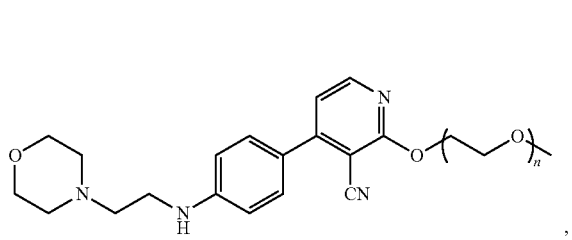
,
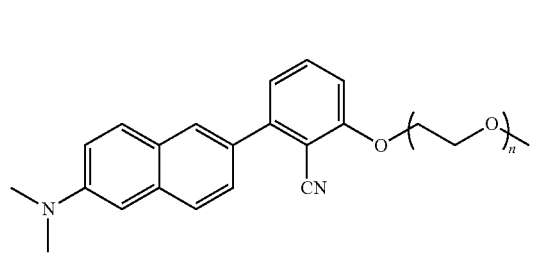
,
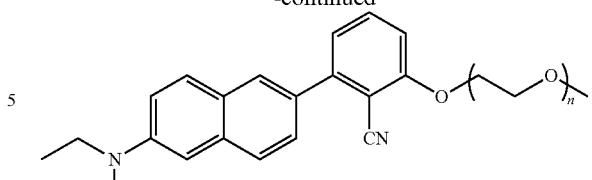
,
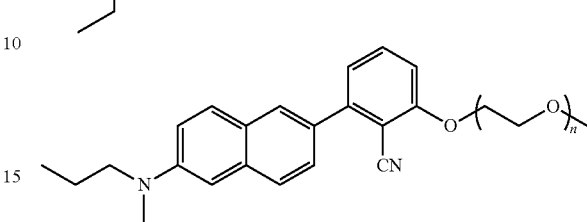
,
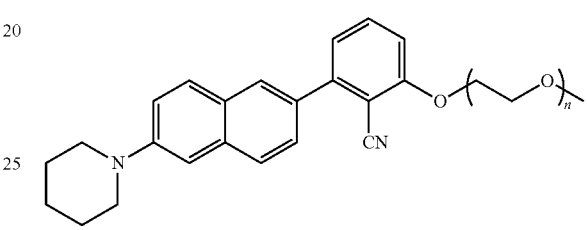
,
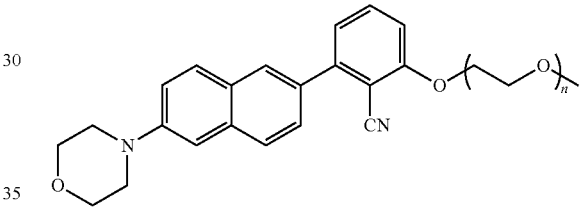
,
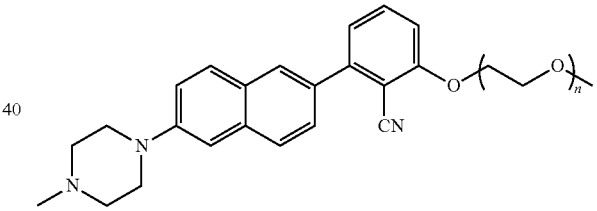
,
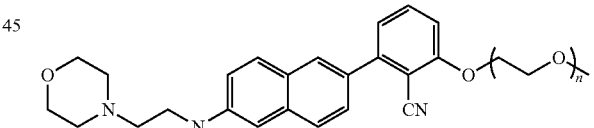
,
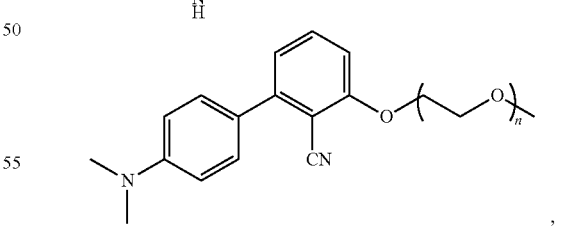
,
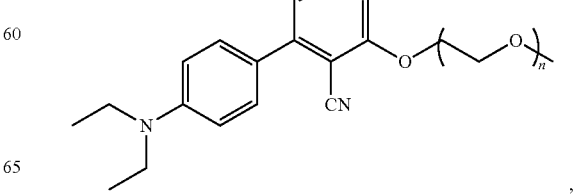
,

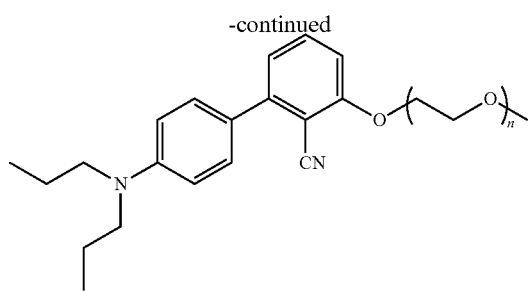
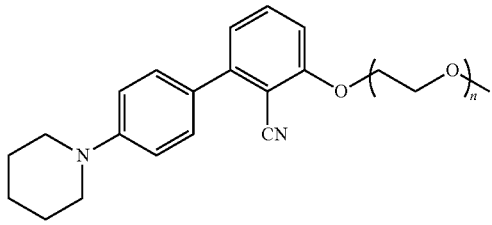
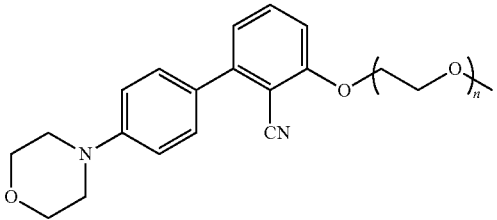
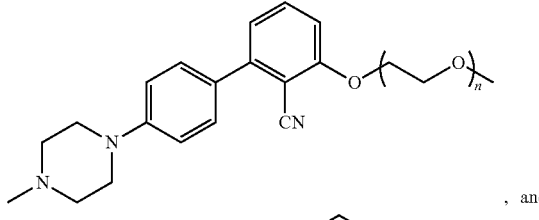
, and
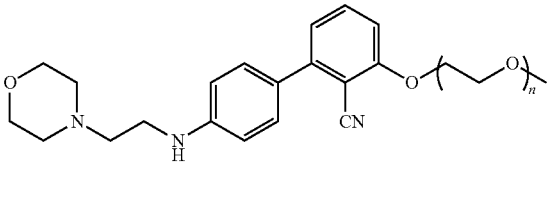
wherein n is an integer, such as an integer with value 0-10. In some cases n is greater than 10.
In some cases, the compound of Formula II is selected from a group consisting of
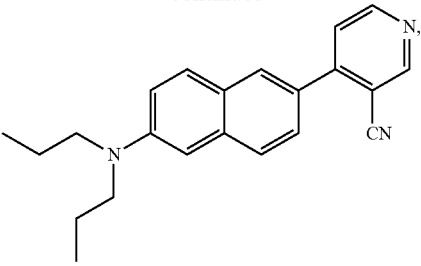
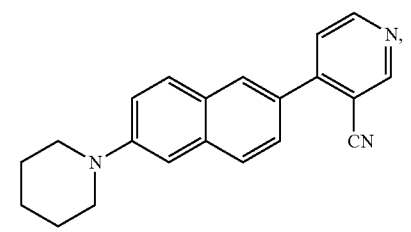
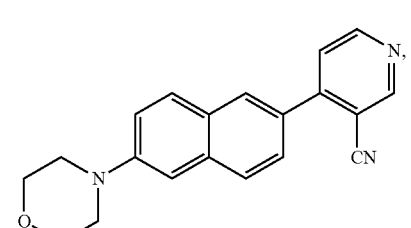
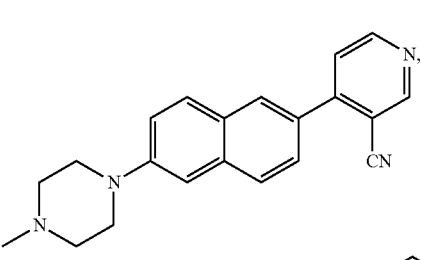
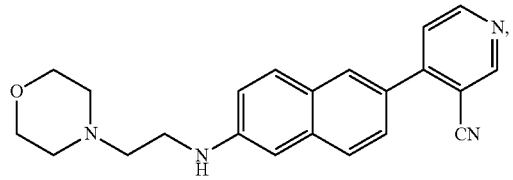
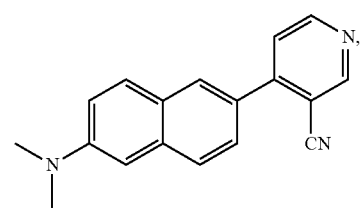
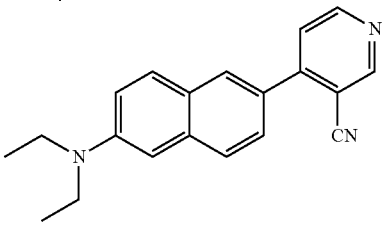
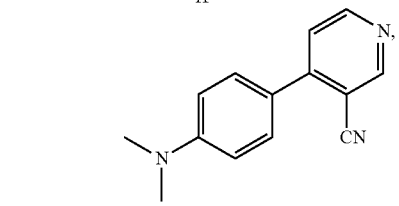
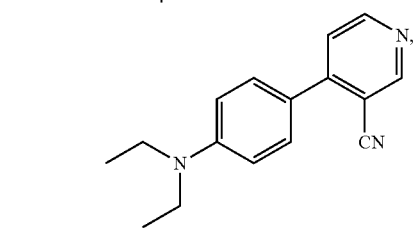

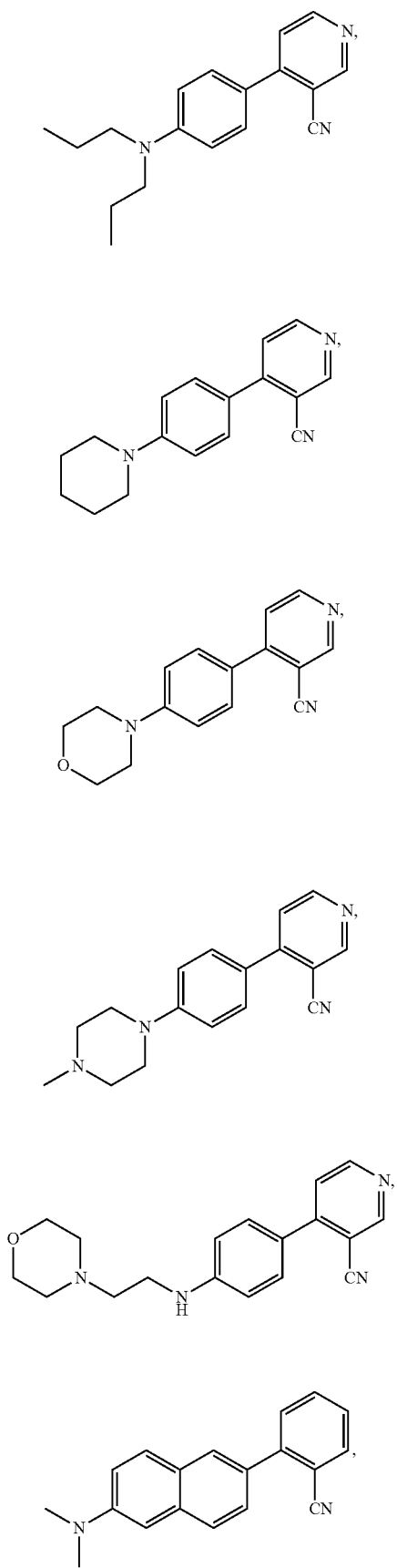
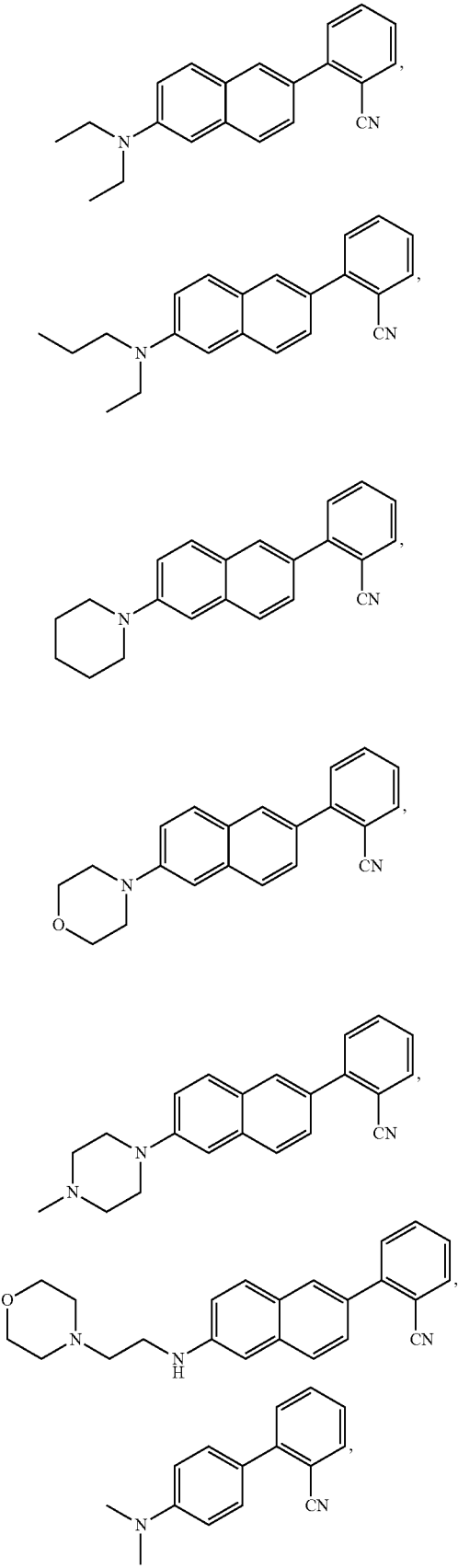

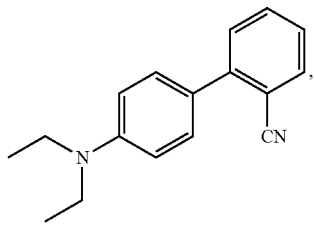
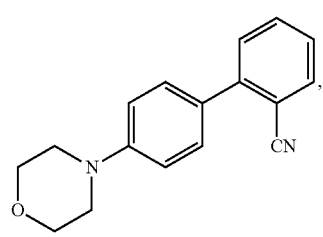
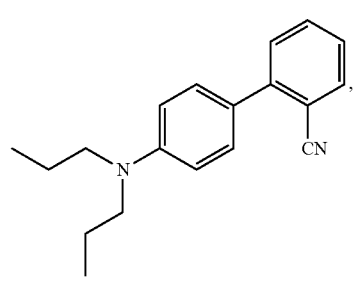
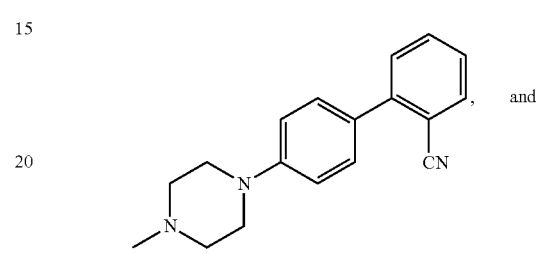
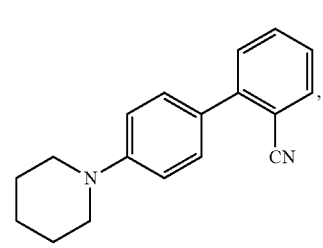
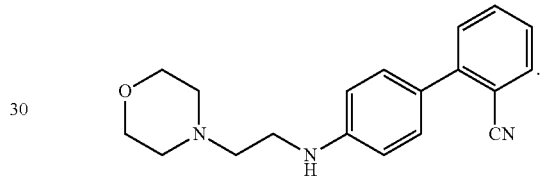
In some cases, the compound of Formula II is
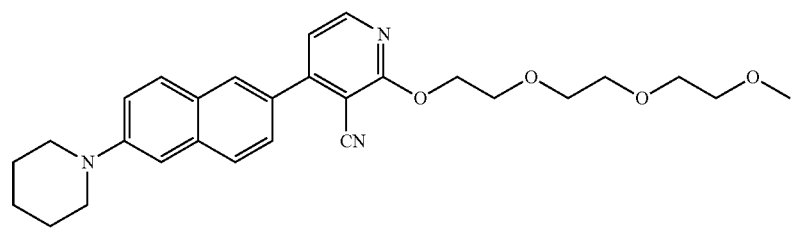

In some cases, the compound of Formula II is 2-(2-(2-(2-methoxyethoxy)ethoxy)ethoxy)-4-(6-(piperidin-1-yl)naphthalen-2-yl)nicotinonitrile.

In some cases, the compound of Formula II is

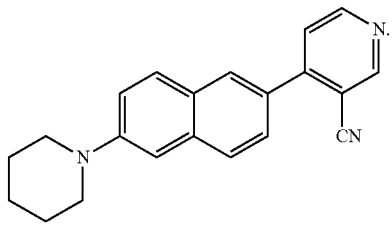 [SMILES: N#Cc1cnccc1-c1ccc2cc(N3CCCCC3)ccc2c1]

In some cases, the compound of Formula II is 4-(6-(piperidin-1-yl)naphthalen-2-yl)nicotinonitrile.

In some cases, the compound of Formula II is

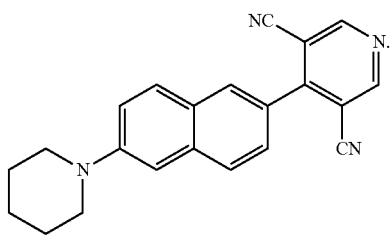 [SMILES: N#Cc1cncc(C#N)c1-c1ccc2cc(N3CCCCC3)ccc2c1]

In some cases, the compound of Formula II is 4-(6-(piperidin-1-yl)naphthalen-2-yl)pyridine-3,5-dicarbonitrile.

In some cases, the compound of Formula II is

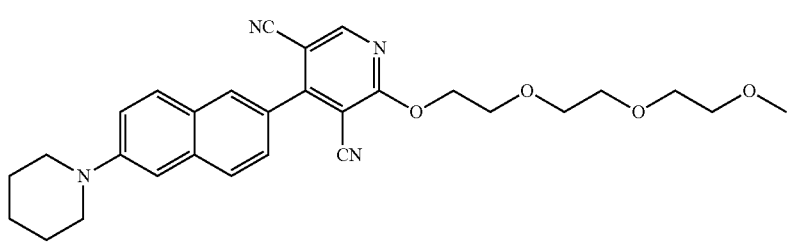

In some cases, the compound of Formula II is 2-(2-(2-(2-methoxyethoxy)ethoxy)ethoxy)-4-(6-(piperidin-1-yl)naphthalen-2-yl)pyridine-3,5-dicarbonitrile.

In some cases, the compound of Formula II is

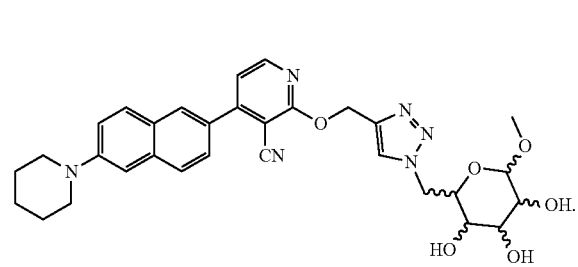 [SMILES: COC1OC(Cn2cc(COc3nccc(-c4ccc5cc(N6CCCCC6)ccc5c4)c3C#N)nn2)C(O)C(O)C1O]

In some cases, the compound of Formula II is 4-(6-(piperidin-1-yl)naphthalen-2-yl)-2-((1-((3,4,5-trihydroxy-6-methoxytetrahydro-2H-pyran-2-yl)methyl)-1H-1,2,3-triazol-4-yl)methoxy)nicotinonitrile.

In some cases, the compound of Formula II is

In some cases, the compound of Formula II is 4-(6-(piperidin-1-yl)naphthalen-2-yl)-2-((1-(((2R,3S,4S,5R,6S)-3,4,5-trihydroxy-6-methoxytetrahydro-2H-pyran-2-yl)methyl)-1H-1,2,3-triazol-4-yl)methoxy)nicotinonitrile.

In some cases, the compound of Formula II is

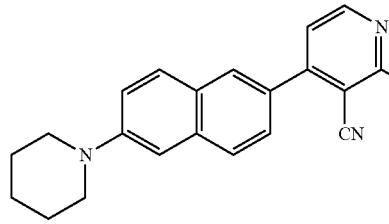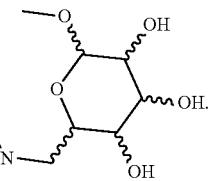

In some cases, the compound of Formula II is 4-(6-(piperidin-1-yl)naphthalen-2-yl)-2-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethoxy)nicotinonitrile.

In some cases, the compound of Formula II is

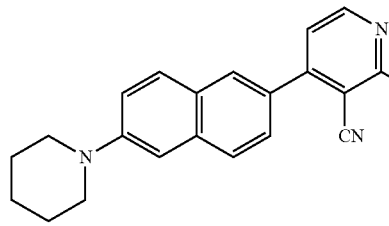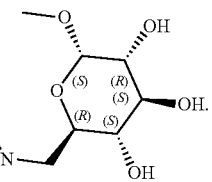

In some cases, the compound of Formula II is 4-(6-(piperidin-1-yl)naphthalen-2-yl)-2-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethylamino)nicotinonitrile.

In some embodiments, the disclosure provides a pharmaceutical composition comprising a compound of Formula I or Formula II or Formula I and Formula II. In some cases, the pharmaceutical composition further comprises any pharmaceutically acceptable additive, carrier or excipient. In some cases, the additive, carrier, or excipient is selected from a group consisting of ethanol, DMSO, polyethylene glycol, polypropylene glycol, aqueous acetate buffers, aqueous citrate buffers, aqueous phosphate buffers, aqueous carbonate buffers, cyclodextrins, corn oil, vitamin E, polysorbates, solutol and bile acids.

In some embodiments, the disclosure provides a composition comprising a compound according the disclosure (Formula I or II) and an amyloid or amyloid like protein. In some cases, the amyloid like protein is Aβ peptide, prion peptide, alpha-synuclein, or superoxide dismutase.

In some embodiments, the disclosure provides a method of detecting an amyloid or amyloid like protein. The method comprise contacting a compound according to Formula I or Formula II with a sample potentially comprising the amyloid or amyloid like protein, wherein in presence of an amyloid or amyloid like protein the compound forms a detectable complex, and detecting the formation of the detectable complex such that the presence or absence of the detectable complex correlates with the presence or absence of the amyloid or amyloid like protein. In some cases, the detection of the formation of the detectable complex is performed by measuring a signal generated by the detectable complex. In some cases, the signal is an electromagnetic signal, for example a fluorescence signal. In some cases, the amyloid or amyloid like protein is Aβ peptide, prion peptide, alpha-synuclein, or superoxide dismutase. In some cases, the amyloid or amyloid like protein is beta amyloid (1-42) (Aβ (1-42)). In some cases, detection is performed within about 1 sec, about 5 sec, about 1 min, about 10 min, about 30 min or about 60 min of the contacting of the compound of Formula I or Formula II with the sample. In some cases, detection is performed within about 1-5 minutes of the contacting of the compound of Formula I or Formula II.

In some embodiments, the disclosure provides a method of determining the presence or absence of one or more disease or condition in a subject. In some cases, the disease or condition is a disease or condition characterized by protein aggregation or protein misfolding. In some aspects the method comprises administering to the subject an effective amount of a compound according to Formula I or Formula II, or a pharmaceutical composition thereof, wherein in presence of the disease or condition the administered compound forms a detectable complex, and detecting the detectable complex such that presence or absence of detectable complex correlates with the presence or absence of the disease or condition. In some cases the disease or condition is amyloid based disease or condition characterized by accumulation of amyloid in the subject. In some cases, the disease or condition is accompanied by protein that produces amyloid like morphology. In some cases, the disease or condition is Alzheimer's disease (AD), Parkinson's disease, Huntington's disease, amyotrophic lateral sclerosis (ALS), Lewy body dementia (LBD), or Down's syndrome. In some cases, the disease of condition is Alzheimer's disease. In some cases, the disease or condition is a prion disease or condition, for example Creutzfeldt-Jakob disease (CJD). In some cases, administration is systemic or topical. In some cases, the compound is administered to the eye of the subject. In some cases, detection is performed within about 1 sec, about 5 sec, about 1 min, about 10 min, about 30 min or about 60 min of the administration of the compound of Formula I or Formula II to the subject. In some cases, the detection is within about 1-5 min of the administration of the compound of Formula I or Formula II to the subject. In some cases, detection of the formation of the detectable complex is performed by measuring a signal generated by the detectable complex. In some cases, the signal is an electromagnetic signal. In some cases, the signal is a fluorescence signal. In some cases, the effective amount of the compound corresponds to about 50-500 mg of compound per adult subject, such as 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg.

In some embodiments, the disclosure provides a method of treating or preventing a one or more disease or condition, in a subject. In some cases, the method comprises administering to a subject in need of treatment an effective amount of a compound according to Formula I or II or a pharmaceutical composition thereof. In some cases, the diseases or conditions is characterized by protein aggregate association or protein misfolding. In some cases, the disease or condition is an amyloid disease or condition. In some cases, non-limiting examples of diseases or conditions treated by the compounds of the disclosure include Alzheimer's disease (AD), Parkinson's disease, Huntington's disease, amyotrophic lateral sclerosis (ALS), Lewy body dementia (LBD), or Down's syndrome. In some cases, the disease or condition is Alzheimer's disease. In some cases, the disease or condition is a prion disease or condition, for example Creutzfeldt-Jakob disease. In some cases, the effective amount the compound correspond to about 50-500 mg.

In some embodiments, the disclosure provides a screening method. The method comprises administering to a subject an effective amount of a compound according to Formula I or Formula II or a pharmaceutical composition thereof, wherein in some cases, the administration of the compound according to Formula I or Formula II results in formation of a detectable complex. In some cases, the screening method further comprises measuring a signal generated by the compound of Formula I or Formula II administered to the subject, and/or by the detectable complex formed by compound of Formula I or Formula II. In some cases, the method comprises making a clinical decision based on the measured signal. In some cases, the signal is an electromagnetic signal. In some cases, the signal is fluorescence signal. In some cases, the administering is systemic or topical administration. In some cases, the administering is done to the eye of the subject.

In another aspect, the disclosure provides a kit comprising a compound according to Formula I or Formula II. In some cases, the kit further comprises instructions for using the compound for the purpose of binding to an amyloid or amyloid like protein to form a detectable complex, and detecting the formation of the detectable complex such that presence or absence of detectable complex correlates with the presence or absence of the amyloid or amyloid like protein. In some cases, the kit further comprises instructions for using the compound for binding to an amyloid or amyloid like protein to form a detectable complex, and detecting changes in abundance of the detectable complex over time such that the changes in the abundance of the detectable complex over time are correlated to changes in abundance of amyloid or amyloid like protein over time. In some cases, the kit further comprises instructions for correlating the changes in the abundance of the detectable complex to monitor progression of a disease. In some cases, the compound of Formula I or Formula II is contained in one or more containers as a sterile liquid formulation. In some cases, the compounds of Formula I or Formula II is contained in one or more container as a sterile freeze-dried formulation. In some cases, the container is a vial. In some cases, the vial is an amber vial. In some cases, the container is also be capable of protecting light sensitive compounds or formulation.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 22A Shows a Fluorescent image of a live prion-infected mouse dosed with Compound 1. FIG. 22B Shows Ex vivo image of the same retina (dissected and flat mounted) from the same eye shown in FIG. 22A.

DETAILED DESCRIPTION OF THE INVENTION

Figure 1A:
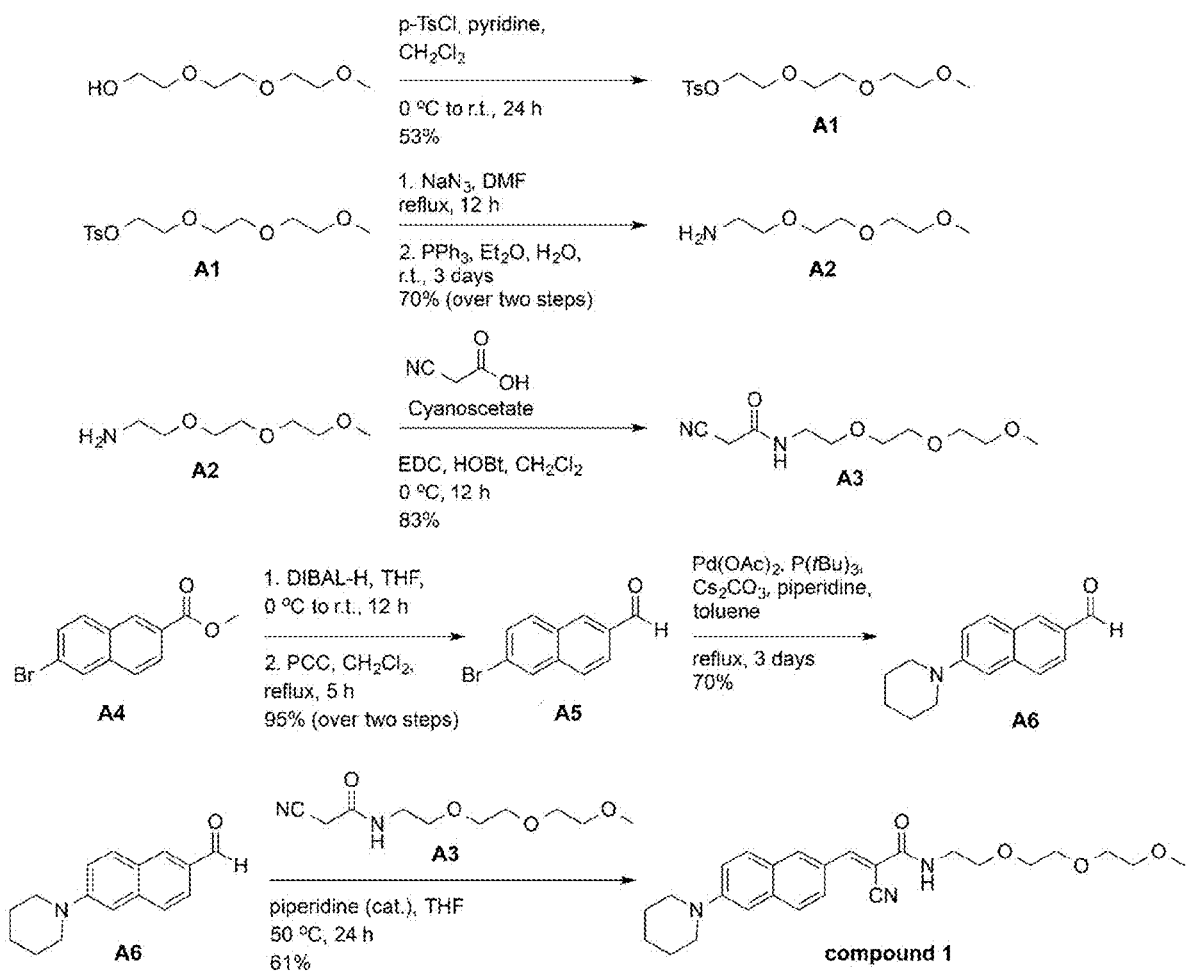
FIG. 1A Shows a synthetic strategy towards the synthesis of compound 1.
Figure 1B:
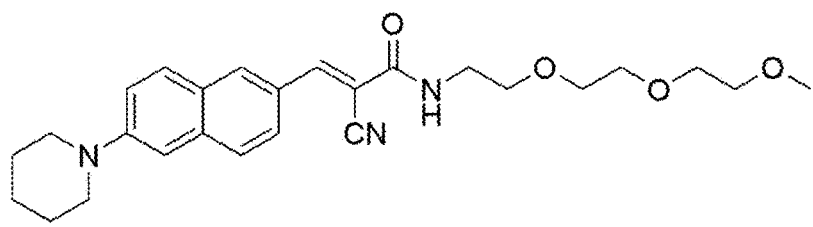
FIG. 1B Shows the structure of compound 1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, represent a straight (i.e. unbranched) or branched chain, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—O—CH$_2$—CH$_2$—O—CH$_3$, —CH$_2$—CH$_2$—O—CH$_2$—CH$_2$—O—CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—

OCH₃, —CH=CH—N(CH₃)—CH₃, O—CH₃, —O—CH₂—CH₃, and —CN. Two or more heteroatoms may also be consecutive.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, tetrahydropyran, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Examples of heterocycloalkyl include, but are not limited to glucose, mannose, allose, altrose, gulose, idose, galactose, and talose. Examples of heterocycloalkyl include, but are not limited to:

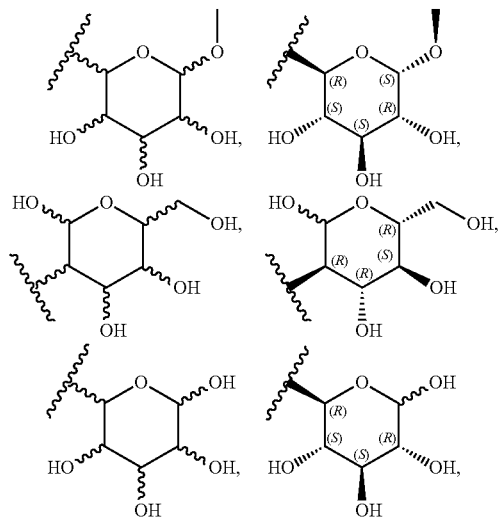

and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C₁-C₄)alkyl" is meant to include, but not be limited to, fluoromethyl, difluoromethyl, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together (i.e. a fused ring aryl) or linked covalently. A fused ring aryl refers to multiple rings fused together wherein at least one of the fused rings is an aryl ring.

The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e. multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, triazolyl, 1,2,3-triazolyl, 1,2,4-triazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

An "arylene" and a "heteroarylene," alone or as part of another substituent means a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

As used herein, the term "heteroatom" or "ring heteroatom" is meant to include oxygen (O), nitrogen (N), sulfur (S), phosphorus (P), and silicon (Si).

As used herein, the term "about" a number or range of numbers refers to that number or range of numbers plus or minus 10% of that number or that range of numbers minus 10% of the lowest listed member of the range and plus 10% of the highest listed member of the range.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

In some cases, the compounds of the present disclosure exist as salts, such as with pharmaceutically acceptable acids. The present disclosure contemplates such salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. In some cases, these salts are prepared, for example, by methods known to those skilled in the art.

The neutral forms of the compounds are preferably regenerated by contacting the salt with a base or acid and isolating the parent compound in the conventional manner. The parent form of the compound differs from the various salt forms in certain physical properties in some cases, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. In some cases, certain compounds of the present disclosure exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, tautomers, geometric isomers and individual isomers are encompassed within the scope of the present disclosure. In some embodiments, compounds which are known in the art to be too unstable to synthesize and/or isolate are excluded.

In some cases, the compounds of the present disclosure contain unnatural proportions of atomic isotopes at one or more of the atoms that constitute such compounds. In some cases, the compounds are radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and or causing remission of cancer.

An "effective amount" is an amount of a compound described herein sufficient to contribute to the treatment, prevention, or reduction of a symptom or symptoms of a disease, or to inhibit effects of an amyloid relative to the absence of the compound. In some cases, where recited in reference to a disease treatment, an "effective amount" is also referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. In some cases, the full prophylactic effect does not necessarily occur by administration of one dose, and occur only after administration of a series of doses. In some cases, a prophylactically effective amount is administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an osteoclast or leukocyte relative to the absence of the antagonist.

In some cases, diseases or conditions that are treated with the compounds of the present disclosure include diseases or conditions accompanied by protein that produces amyloid like morphology and disease or conditions associated with the formation of abnormal protein structures, protein aggregation, or protein misfolding. In some cases, an abnormal protein structure is a protein structure that arises when a protein or peptide refolds from the three-dimensional structure, which it generally adopts in healthy individuals, into a different three-dimensional structure, which is associated with a pathological condition. In some cases, diseases or conditions that are treated with the compounds of the present disclosure are diseases or conditions associated with amyloid or amyloid-like proteins. In some cases, such diseases are referred to as amyloid based diseases or conditions. Amyloid based diseases or conditions, include any disease or condition that is associated with amyloid or amyloid-like protein and is characterized, in part, by the buildup of extracellular deposits of amyloid or amyloid-like material. In the context of this disclosure, amyloid based diseases or conditions also include disease or conditions accompanied by protein that produces amyloid like morphology. These diseases include, but are not limited to, neurological disorders such as Alzheimer's disease (AD), Parkinson's disease, Huntington's disease, diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeldt Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidosis; the retina, including primary retinal degenerations and macular degeneration, in particular age-related macular degeneration; the optic nerve, including optic nerve drusen, optic neuropathy and optic neuritis; and the cornea, including lattice dystrophy.

The term "amyloid protein" is intended to denote a protein which is involved in the formation of fibrils, plaques and/or amyloid deposits, either by being part of the fibrils, plaques and/or deposits as such or by being part of the biosynthetic pathway leading to the formation of the fibrils, plaques and/or amyloid deposits. In the present context the term "protein" or is intended to mean both short peptides of from 2 to 10 amino acid residues, oligopeptides of from 11 to 100 amino acid residues, polypeptides of more than 100 amino acid residues, and full length proteins. The terms also encompass peptides having substantial similarity to amyloid proteins, such as, e.g., structural variants. In some cases, the proteins occur naturally or be synthetically constructed. The term amyloid protein or amyloid like protein also includes amyloidgenic proteins and proteins that produce amyloid like morphology.

The term "substantial similarity" means that two peptide sequences, when optimally aligned, share at least 50% sequence identity, or at least 60% sequence identity, or at least 70% sequence identity, or at least 80% sequence identity, or at least 90 percent sequence identity, or at least 95 percent sequence identity or more (e.g., 99% sequence identity). Preferably, residue positions, which are not identical, differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutarnine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. In some cases, residue positions, which are not identical are also composed of peptide analogs, including unnatural amino acids or derivatives of such. Analogs typically differ from naturally occurring peptides at one, two or a few positions, often by virtue of conservative substitutions. Some analogs also include unnatural amino acids or modifications of N or C terminal amino acids at one, two or a few positions. Examples of unnatural amino acids are D-amino acids, alpha,alpha-disubstituted amino acids, N-alkyl amino acids, lactic acid, 4-hydroxyproline, y-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega.-N-methylarginine, and isoaspartic acid.

Overview

In some cases, the disclosure provides novel compounds that are employed in the detection, diagnosis, treatment, and monitoring of diseases or conditions associated with protein aggregation or protein misfolding. In some cases, the compounds of the disclosure are also employed in the detection, diagnosis, treatment, and monitoring of amyloid based diseases or conditions. The disclosure further provides pharmaceutical compositions comprising these compounds and the use of these compounds for the preparation of medicaments for the treatment of such diseases or conditions.

The compounds of the disclosure are designed form a detectable complex in presence of an amyloid or amyloid-like protein. In some cases, the compounds disclosed herein are classified as molecular rotor fluorophores. The compounds comprise an electron rich donor moiety covalently connected to a conjugated pi system (for example, to an aromatic pi network) and in electronic conjugation to an electron poor acceptor moiety covalently connected elsewhere on the pi system. The compounds also comprise one or more single bonds between the donor and acceptor that can rotate freely under standard thermal control of the environment in the temperature range of interest. The rotation of the single bond allows the donor and acceptor to remain substantially decoupled in the absence of binding to a protein and thus the compounds exhibit poor fluorescence signal. However, in presence of an amyloid or amyloid-like protein these compounds may bind to amyloid or amyloid-like proteins. Accordingly, the rotatable single bonds may become essentially frozen and the electronic coupling between the donor and acceptor may be substantially enhanced. In some cases, it leads to a strong fluorescence signal upon irradiation with an appropriate wavelength of light. In some cases, the strong fluorescence enhancement of these compounds upon binding to amyloid or amyloid-like proteins compared to the free compound in solution results in excellent signal to noise ratio and make it possible to image amyloid or amyloid-like proteins with high sensitivity.

Also provided herein is a method for detecting an amyloid or amyloid-like protein. The method comprises contacting a compound of the disclosure or a pharmaceutical composition thereof with the sample potentially comprising the amyloid or amyloid-like protein, wherein in presence of an amyloid or amyloid-like protein the compound forms a detectable complex, and detecting the formation of the detectable complex such that the presence or absence of the detectable complex correlates with the presence or absence of the amyloid or amyloid like protein. In some cases, the detection of the detectable complex in the methods of the disclosure comprises illuminating the sample with light of an appropriate wavelength and detecting light received from the sample. In some cases, the wavelength of the illuminating light is varied and selected according to the fluorescence excitation and emission spectrum of the detectable complex. In some cases, the detectable complex has a fluorescent excitation peak in the range of 350-500 nm, and the fluorescence emission spectrum of the detectable complex in the range of 500-550 nm. In some cases, the illuminating light has a wavelength of 350-450 nm (example 400 nm). In some cases, amyloid or amyloid like protein or peptide is detected by the methods of the disclosure. In some cases, the method is used to detect the presence or absence of Aβ peptide, prion peptide, alpha-synuclein, or superoxide dismutase.

The disclosure also provides a method of determining the presence or absence of one or more disease or condition in a subject. The method comprises administering to the subject an effective amount of a compound of the disclosure or a pharmaceutical composition thereof, wherein in presence of the a disease or condition the administered compound forms a detectable complex, and detecting the formation of the detectable complex such that presence or absence of the detectable complex correlates with the presence or absence of the disease or condition. In some cases, the method includes comparing the amount of the detectable complex to a normal control value, wherein an increase in the amount of the detectable complex compared to a normal control value indicates that said patient is suffering from or is at risk of developing the disease or condition. Also provided herein is a method of treating, preventing or alleviating the symptoms of a disease or condition in a subject. The method comprises administering to a subject in need of treatment an effective amount of a compound of the disclosure or a pharmaceutical composition thereof. In some cases, the subject is a mammal. In one case, the subject is a primate (such as a human), canine, feline, ovine, bovine and the like.

In some cases, the disease or condition is a disease or condition characterized by protein aggregation or misfolding. In some cases, the disease or condition is also an amyloid based disease or condition. In some cases, the amyloid-based disease or condition is any disease or condition associated with the increased or decreased presence of amyloid or amyloid like proteins, such as the presence of amyloid plaques or other amyloid aggregates. In some cases, the disease is a neuronal disease. In some cases, the disease is a neurodegenerative diseases, in which amyloid-beta peptides, oligomers, fibrils, or plaques are implicated. In some cases, the disease is Alzheimer's disease, Parkinson's disease, Huntington's disease, amyotrophic lateral sclerosis (ALS), Lewy body dementia (LBD), or Down's syndrome. In some cases, the amyloid-based disease or condition also includes ocular diseases associated with pathological abnormalities/changes in the tissues of the visual system, particularly associated with amyloid-beta-related pathological abnormalities/changes in the tissues of the visual system, such as, for example, neuronal degradation. In some cases, pathological abnormalities occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidosis; the retina leading to primary retinal degeneration and macular degeneration; the optic nerve leading to optic nerve drusen, optic neuropathy and optic neuritis; and the cornea leading to lattice dystrophy.

In some cases, the compounds and the methods of the disclosure are also used to monitor minimal residual disease in a patient following treatment with a compound or a mixture according to the disclosure. In some cases, a sample or a specific body part or body area suspected to contain the amyloid antigen is contacted with a compound of the disclosure, and the compound is allowed to bind to the amyloid or amyloid like protein to form a detectable complex. In some cases, the formation of the detectable complex is detected and its presence or absence is correlated with the presence or absence of amyloid or amyloid like protein in the sample or specific body part or area. In some cases, the amount of said detectable complex is compared to a normal control value, wherein an increase in the amount of said detectable complex compared to a normal control value indicates that the patient may still be suffering from a minimal residual disease.

In some cases, the compounds and methods disclosed herein are useful for predicting responsiveness of a patient to a treatment. In some cases, a sample or a specific body part or body area suspected to contain the amyloid or amyloid like protein is brought into contact with a compound of the disclosure, such that in presence of the amyloid or amyloid like protein the compound binds to the amyloid or amyloid like protein to form a detectable complex. In some cases, the formation of the detectable complex is detected and the presence or absence of the detectable complex is correlated with the presence or absence of amyloid or amyloid like protein in the sample or specific body part or area. In some cases, the amount of the detectable complex before and after onset of the treatment is compared, such that a decrease in the amount of the detectable complex indicates that the patient is being responsive to the treatment.

Compounds

In one aspect the disclosure provides a compound of Formula I:

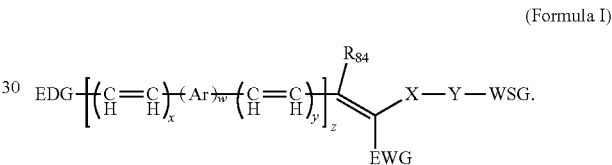

(Formula I)

An Ar in Formula I is independently $C_1$-$C_{14}$ arylene or $C_1$-$C_{14}$ heteroarylene, each optionally substituted with one or more RI; wherein each $R_1$ is independently halogen, —CN, —$OR_2$, —$NR_3R_4$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_5$; $R_2$, $R_3$ and $R_4$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_5$; each $R_5$ is independently halogen, —$OR_6$, —$NR_7R_8$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_6$, $R_7$ and $R_8$ are independently hydrogen or $C_1$-$C_{10}$ alkyl.

$R_{84}$ in Formula I is hydrogen or $C_1$-$C_{10}$ alkyl. In some compounds of Formula I, $R_{84}$ is hydrogen. In some compounds of Formula I, $R_{84}$ is $C_1$-$C_{10}$ alkyl. In some compounds of Formula I, $R_{84}$ is methyl, ethyl, propyl, butyl, pentyl, hexyl, heptyl, octyl, neptyl or decyl. In some compounds of Formula I, $R_{84}$ is methyl.

The substituent EDG in Formula I is an electron donor group, as known in the art. In some compounds of Formula I, EDG is any atom or functional group that is capable of donating some of its electron density into a conjugated pi system, thus making the pi system more nucleophilic. In some compounds of Formula I, the EDG is —$OR_9$, —$NR_{10}R_{11}$, —$SR_{12}$, —$PR_{13}R_{14}$, —$NR_{15}C(O)R_{16}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{17}$; wherein each $R_{17}$ is independently halogen, $-OR_{18}$, $-NR_{19}R_{20}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_9$, $R_{10}$, $R_{11}$, $R_{12}$, $R_{13}$, $R_{14}$, $R_{15}$, $R_{16}$, $R_{18}$, $R_{19}$ and $R_{20}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{21}$ and wherein $R_{10}$ and $R_{11}$ are optionally joined together to form a heterocycloalkyl or heteroaryl optionally substituted with $R_{21}$; each of $R_{21}$ is independently halogen, $-OR_{22}$, $-NR_{23}R_{24}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{25}$; each of $R_{22}$, $R_{23}$ and $R_{24}$ is independently hydrogen or $C_1$-$C_{10}$ alkyl; and each $R_{25}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In some compounds of Formula I, the EDG is selected from a group consisting of

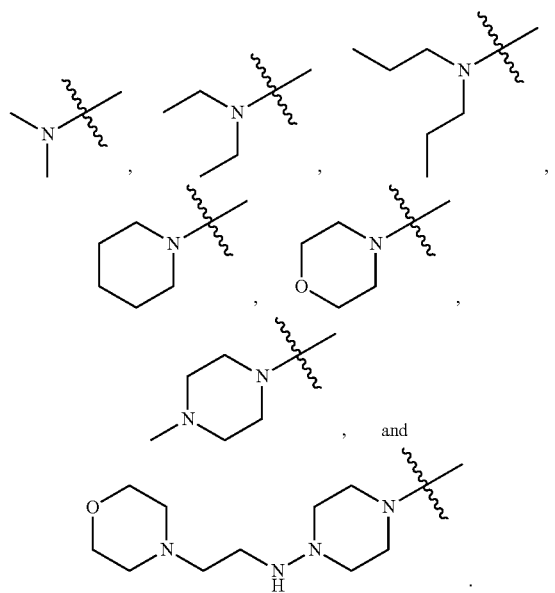

In some compounds of Formula I, the EDG is

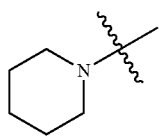

In some compounds of formula II, EDG is

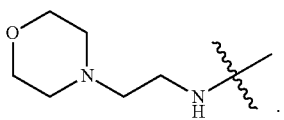 [SMILES: *NCCN1CCOCC1]

EWG is an electron withdrawing group. In some compounds of Formula I, the electron withdrawing group as used herein is any atom or group that is capable of drawing electron density from neighboring atoms towards itself, either by resonance or inductive effects. In some compounds of Formula I, EWG is selected from a group consisting of halogen, $-CN$, $-NO_2$, $-SO_3H$, $-CR_{26}R_{27}R_{28}$, $-COR_{29}$, or $-COOR_{30}$; wherein each $R_{26}$, $R_{27}$ and $R_{28}$ is independently hydrogen or halogen; $R_{29}$ is halogen, hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{31}$; $R_{30}$ is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{32}$; and each $R_{31}$ and $R_{32}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In some compounds of Formula I, the EWG is selected from a group consisting of $-F$, $-Cl$, $-Br$, $-CH=O$, $NO_2$, $-CF_3$, $-CCl_3$, $-SO_3$ and $-CN$. In some compounds of Formula I, the EWG is F, Cl, or Br. In some compounds of Formula I, the EWG is $-CN$.

WSG is a water soluble group. In some compounds of Formula I, the WSG group in Formula I serves to alter the solubility of the compounds of Formula I in an aqueous systems. In some compounds of Formula I, WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{33}$; wherein each $R_{33}$ is independently halogen, $-OR_{34}$, $-NR_{35}R_{36}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{37}$; each $R_{34}$, $R_{35}$ and $R_{36}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{37}$; each $R_{37}$ is independently halogen, $-OR_{38}$, $-NR_{39}R_{40}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $-(C_1$-$C_6$alkyl)($C_1$-$C_{10}$ heterocycloalkyl), $C_1$-$C_{10}$ arylene, or $C_1$-$C_{10}$ heteroarylene; and each of $R_{38}$, $R_{39}$ and $R_{40}$ is independently hydrogen or $C_1$-$C_{10}$ alkyl.

WSG is a water soluble group. The WSG group in Formula I serves to alter the solubility of the compounds of Formula I in an aqueous systems. In some compounds of Formula I, WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{33}$; wherein each $R_{33}$ is independently halogen, $-OR_{34}$, $-NR_{35}R_{36}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{37}$; each $R_{34}$, $R_{35}$ and $R_{36}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{37}$; each $R_{37}$ is independently halogen, —$OR_{38}$, —$NR_{39}R_{40}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; and each of $R_{38}$, $R_{39}$ and $R_{40}$ is independently hydrogen or $C_1$-$C_{10}$ alkyl.

In some compounds of Formula I, the WSG is

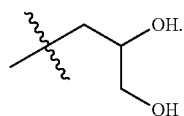 [SMILES: *CC(O)CO]

In some compounds of Formula I, WSG is polyethylene glycol, polypropylene glycol, co-polymer of polyethylene glycol and polypropylene glycol, or alkoxy derivatives thereof. In some compounds of Formula I, WSG is

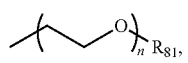

wherein n is an integer from 1-50 and $R_{81}$ is hydrogen, $C_1$-$C_{10}$ alkyl, a $C_1$-$C_{10}$ alkenyl, or a $C_1$-$C_{10}$ alkynyl wherein each wherein the alkyl, alkenyl, or alkynyl is optionally substituted with one or more $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene. In some compounds of Formula I, WSG is

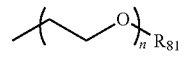

and $R_{81}$ is hydrogen. In some compounds of Formula I, WSG is

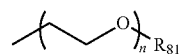

and $R_{81}$ is methyl. In some compounds of Formula I, WSG is

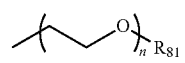

and $R_{81}$ is ethyl.

In some compounds of Formula I, WSG is

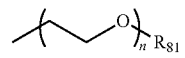

and $R_{81}$ is $CH_2$—C≡CH.

In some compounds of Formula I, WSG is

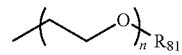

and n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some compounds of Formula I, WSG is

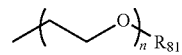

and n is an integer of value 1-10, 1-20, 1-30, 1-40, 1-50, 10-20, 10-30, 10-40, 10-50, 20-30, 20-40, 20-50, 30-40, 30-50, or 40-50.

In some compounds of Formula I, WSG is

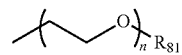

and n is 1, 2, 3, 4, 5, 6, 7, 8, 9, or 10. In some compounds of Formula I, WSG is

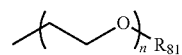

and n is 3 or 6.

In some compounds of Formula I, WSG is

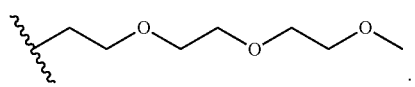 [SMILES: *CCOCCOCCOC]

In some compounds of Formula I, WSG is

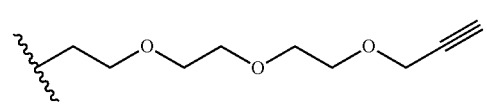

In some compounds of Formula I, the WSG is

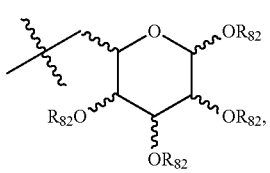

wherein each $R_{82}$ is hydrogen or $C_1$-$C_{10}$ alkyl.

In some compounds of Formula I, each $R_{82}$ is independently a hydrogen, methyl, ethyl, propyl, or butyl.

In some compounds of Formula I, the WSG is

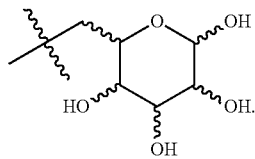 [SMILES: *CC1OC(O)C(O)C(O)C1O]

In some compounds of Formula I, the WSG is

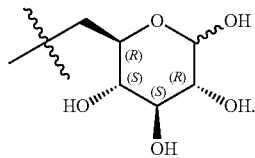

In some compounds of Formula I, the WSG is

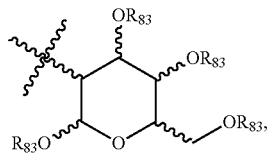

wherein each $R_{83}$ is hydrogen or $C_1$-$C_{10}$ alkyl. In some compounds of Formula I, each $R_{83}$ is independently a hydrogen, methyl, ethyl, propyl, or butyl.

In some compounds of Formula I the WSG is

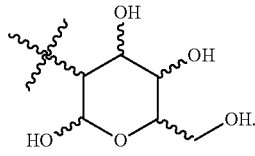

In some compound of Formula I the WSG is

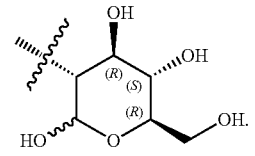

In some compounds of Formula I, WSG is —($C_1$-$C_{10}$ alkyl)-$R_{33}$—$R_{37}$. In some compounds of Formula I, WSG is —($C_1$-$C_{10}$ alkyl)-$R_{33}$—$R_{37}$ and $R_{33}$ is $C_1$-$C_{10}$ heteroarylene. In some compounds of Formula I, WSG is —($C_1$-$C_{10}$ alkyl)-$R_{33}$—$R_{37}$, $R_{33}$ is $C_1$-$C_{10}$ heteroarylene and $R_{37}$ is —($C_1$-$C_6$alkyl)($C_1$-$C_{10}$heterocycloalkyl).

In some compounds of Formula I, WSG is —$CH_3$—$R_{33}$—$R_{37}$.

In some compounds of Formula I, WSG is —$CH_3$—$R_{33}$—$R_{37}$ and $R_{33}$ is triazole, imidazole, or pyrrazole.

In some compounds of Formula I, WSG is —$CH_3$—$R_{33}$—$R_{37}$ and $R_{33}$ is triazole.

In some compounds of Formula I, WSG is $CH_3$—$R_{33}$—$R_{37}$ and $R_{33}$ is 1,2,4-triazole.

In some compounds of Formula I, WSG is —$CH_3$—$R_{33}$—$R_{37}$ and $R_{33}$ is 1,2,3-triazole.

In some compounds of Formula I, WSG is —$CH_3$—$R_{33}$—$R_{37}$, $R_{33}$ is 1,2,3-triazole and $R_{37}$ is —($C_1$-$C_6$alkyl)($C_1$-$C_{10}$heterocycloalkyl).

In some compounds of Formula I, WSG is —$CH_3$—$R_{33}$—$R_{37}$, $R_{33}$ is 1,2,3-triazole and $R_{37}$ is —($C_1$alkyl)($C_1$-$C_{10}$heterocycloalkyl).

In some compounds of Formula I, WSG is —$CH_3$—$R_{33}$—$R_{37}$, $R_{33}$ is 1,2,3-triazole, $R_{37}$ is —($C_1$alkyl)($C_1$-$C_{10}$heterocycloalkyl), and $C_1$-$C_{10}$heterocycloalkyl is a tetrahydropyran derivative.

In some compounds of Formula I, WSG is —$CH_3$—$R_{33}$—$R_{37}$, $R_{33}$ is 1,2,3-triazole, and $R_{37}$ is

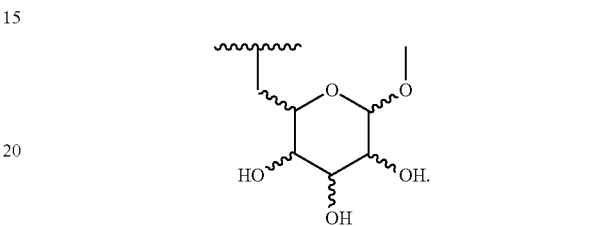

In some compounds of Formula I, WSG is

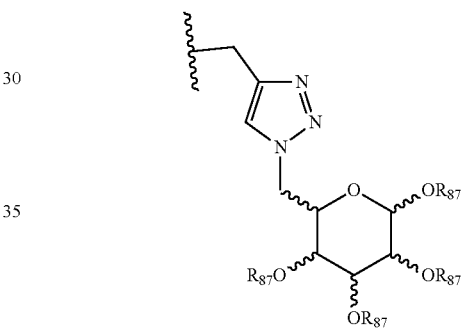

wherein each $R_{87}$ is hydrogen, $C_1$-$C_{10}$ alkyl, or —C(=O)$C_1$-$C_{10}$ alkyl. In some compounds of Formula I, each $R_{87}$ is independently a hydrogen, methyl, ethyl, propyl, butyl, acetate, propionate, or butyrate. In some compounds of Formula I, each $R_{87}$ is independently a hydrogen or methyl. In some compounds of Formula I, each $R_{87}$ is independently a methyl or acetate.

In some compounds of Formula I, WSG is

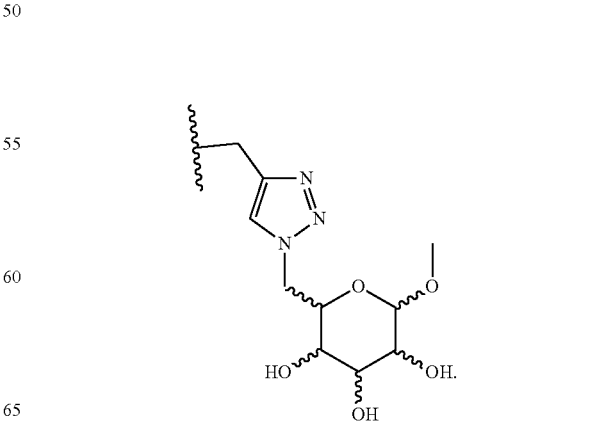

In some compounds of Formula I, WSG is

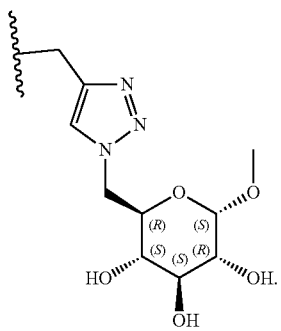

In some compounds of Formula I, WSG is —($C_1$-$C_{10}$ heteroalkyl)-$R_{33}$—$R_{37}$. In some compounds of Formula I, WSG is —($C_1$-$C_{10}$ heteroalkyl)-$R_{33}$—$R_{37}$ and $R_{33}$ is $C_1$-$C_{10}$ heteroarylene. In some compounds of Formula I, WSG is —($C_1$-$C_{10}$ heteroalkyl)-$R_{33}$—$R_{37}$ and $R_{33}$ is $C_1$-$C_{10}$ heteroarylene and $R^{37}$ is —($C_1$-$C_6$alkyl)($C_1$-$C_{10}$heterocycloalkyl).

In some compounds of Formula I, WSG is

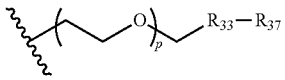

and p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some compounds of Formula I, p is an integer of value 1-10, 1-20, 1-30, 1-40, 1-50, 10-20, 10-30, 10-40, 10-50, 20-30, 20-40, 20-50, 30-40, 30-50, or 40-50.

In some compounds of Formula I, p is 1, 2, 3, 4, 5, 6, 7, 8, 9, or 10.

In some compounds of Formula I, p is 3 or 6.

In some compounds of Formula I, WSG is

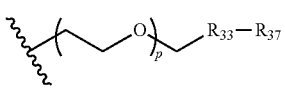

and p 3.

In some compounds of Formula I, WSG is

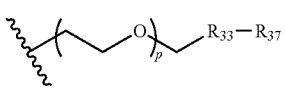

and $R_{33}$ is a $C_1$-$C_{10}$ heteroarylene.

In some compounds of Formula I, WSG is

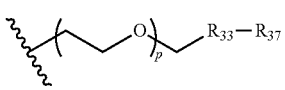

and $R_{33}$ is a $C_5$ heteroarylene.

In some compounds of Formula I, WSG is

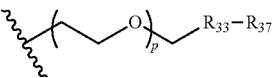

and $R_{33}$ is triazole, imidazole, or pyrrazole.

In some compounds of Formula I, WSG is

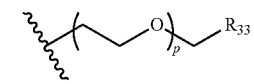

and $R_{33}$ is triazole.

In some compounds of Formula I, WSG is

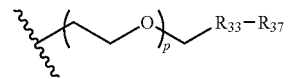

and $R_{33}$ is 1,2,4-triazole. In some compounds of Formula I, WSG is

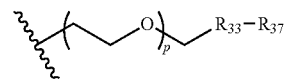

and $R_{33}$ is 1,2,3-triazole.

In some compounds of Formula I, WSG is

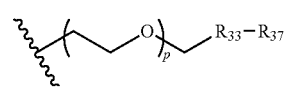

$R_{33}$ is 1,2,3-triazole, and p is 3.

In some compounds of Formula I, WSG is

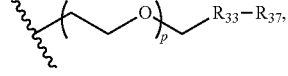

$R_{33}$ is 1,2,3-triazole and $R_{37}$ is —($C_1$-$C_6$alkyl)($C_1$-$C_{10}$heterocycloalkyl).

In some compounds of Formula I, WSG is

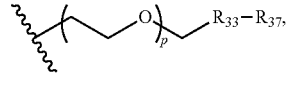

$R_{33}$ is 1,2,3-triazole and $R_{37}$ is —($C_1$alkyl)($C_1$-$C_{10}$heterocycloalkyl).

In some compounds of Formula I, WSG is

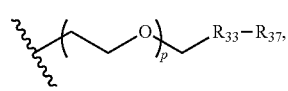

$R_{33}$ is 1,2,3-triazole, $R_{37}$ is a tetrahydropyran derivative.

In some compounds of Formula I, WSG is

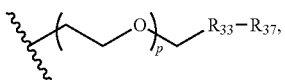

R$_{33}$ is 1,2,3-triazole, and R$_{37}$ is

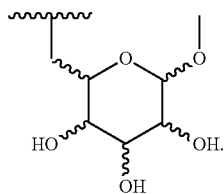 [SMILES: *CC1OC(OC)C(O)C(O)C1O]

In some compounds of Formula I, WSG is

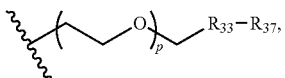

R$_{33}$ is 1,2,3-triazole, R$_{37}$ is

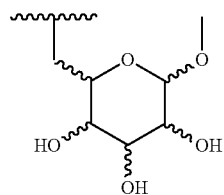 [SMILES: *CC1OC(OC)C(O)C(O)C1O]

and p is 3.

In some compounds of Formula I, WSG is

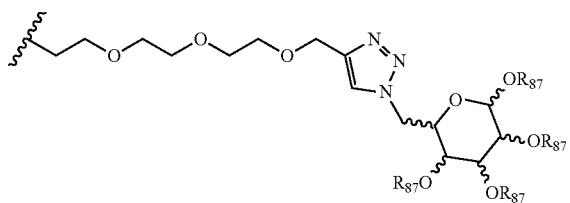

wherein each R$_{87}$ is hydrogen, C$_1$-C$_{10}$ alkyl, or —C(=O) C$_1$-C$_{10}$ alkyl. In some compounds of Formula I, each R$_{87}$ is independently a hydrogen, methyl, ethyl, propyl, butyl, acetate, propionate, or butyrate. In some compounds of Formula I, each R$_{87}$ is independently a hydrogen or methyl. In some compounds of Formula I, each R$_{87}$ is independently a methyl or acetate.

In some compounds of Formula I, WSG is

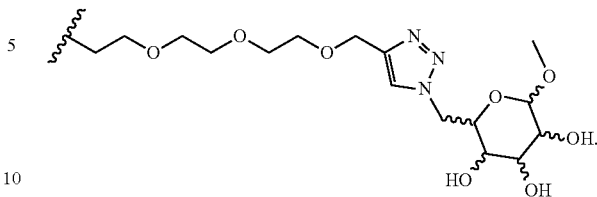

In some compounds of Formula I, WSG is

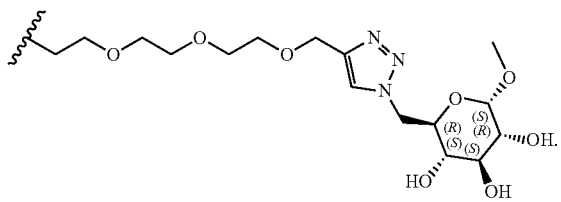

In some compounds of Formula I, X is C—O or SO$_2$. In some compounds of Formula I, X is C=O. In some compounds of Formula I, X is SO$_2$.

In some compounds of Formula I, Y is NH or S. In some compounds of Formula I, Y is NH. In some compounds of Formula I, Y is S.

The variable w in Formula I is an integer from 1-5. In some compounds of Formula I, w is 1. In some compounds of Formula I, w is 2. In some compounds of Formula I, w is 3. In some compounds of Formula I, w is 4. In some compounds of Formula I, w is 5.

The variable x in Formula I is an integer from 0-10. In some compounds of Formula I, x is 0. In some compounds of Formula I, x is 1. In some compounds of Formula I, x is 2. In some compounds of Formula I, x is 3. In some compounds of Formula I, x is 4. In some compounds of Formula I, x is 5. In some compounds of Formula I, x is 6. In some compounds of Formula I, x is 7. In some compounds of Formula I, x is 8. In some compounds of Formula I, x is 9. In some compounds of Formula I, x is 10.

The variable y in Formula I is an integer from 0-10. In some compounds of Formula I, y is 0. In some compounds of Formula I, y is 1. In some compounds of Formula I, y is 2. In some compounds of Formula I, y is 3. In some compounds of Formula I, y is 4. In some compounds of Formula I, y is 5. In some compounds of Formula I, y is 6. In some compounds of Formula I, y is 7. In some compounds of Formula I, y is 8. In some compounds of Formula I, y is 9. In some compounds of Formula I, y is 10.

The variable z in Formula I is an integer from 1-10. In some compounds of Formula I, z is 1. In some compounds of Formula I, z is 2. In some compounds of Formula I, z is 3. In some compounds of Formula I, z is 4. In some compounds of Formula I, z is 5. In some compounds of Formula I, z is 6. In some compounds of Formula I, z is 7. In some compounds of Formula I, z is 8. In some compounds of Formula I, z is 9. In some compounds of Formula I, z is 10.

In some compounds of Formula I, x is 0, w is 1, y is 0, z is 1, X is C=O, and Y is NH.

In some compounds of Formula I, x is 0, w is 1, y is 0, z is 1, X is SO$_2$, and Y is NH.

In some compounds of Formula I, x is 0, w is 2, y is 0, z is 1, X is C=O, and Y is NH.

In some compounds of Formula I, x is 0, w is 2, y is 0, z is 1, X is SO$_2$, and Y is NH.

In one aspect the disclosure provides a compound of Formula Ia:

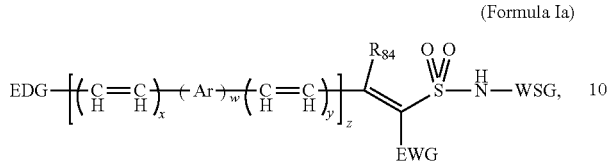
(Formula Ia)

wherein EDG, Ar, R$_{84}$, x, w, y, z, EWG, and WSG are defined as above for Formula I.

In one aspect the disclosure provides a compound of Formula Ib:

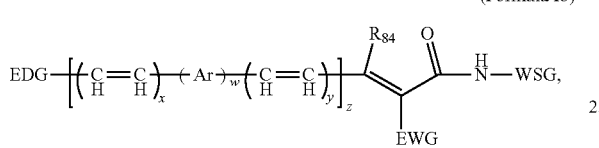
(Formula Ib)

wherein EDG, Ar, R$_{84}$, x, W, y, z, EWG, and WSG are defined above for Formula I.

In one aspect the disclosure provides a compound of Formula Ic:

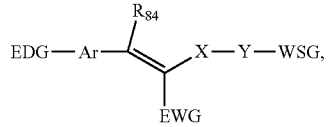
(Formula Ic)

wherein EDG, Ar, R$_{84}$, X, Y, EWG, and WSG are defined above for Formula I.

In one aspect the disclosure provides a compound of Formula Id:

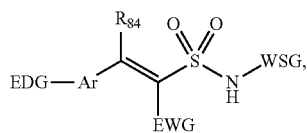
(Formula Id)

wherein EDG, R$_{84}$, Ar, EWG, and WSG are defined as above for Formula I.

In one aspect the disclosure provides a compound of Formula Ie:

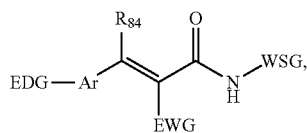
(Formula Ie)

wherein EDG, R$_{84}$, Ar, EWG, and WSG are defined as above for Formula I.

In some cases, the compound of Formula I is selected from a group consisting of

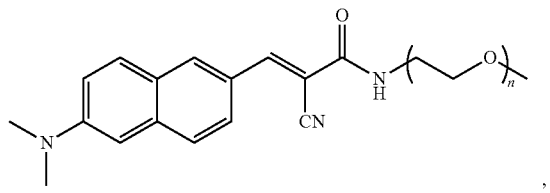
,

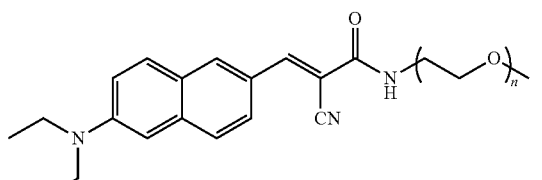
,

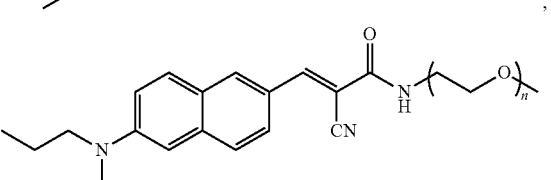
,

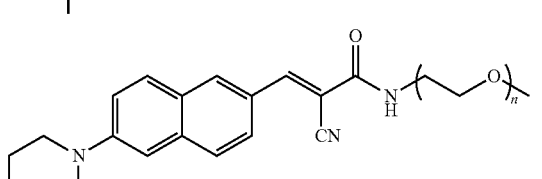
,

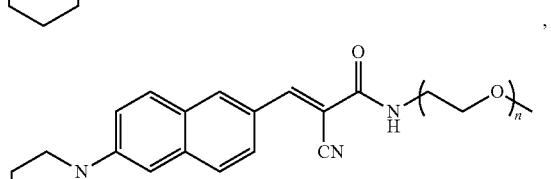
,

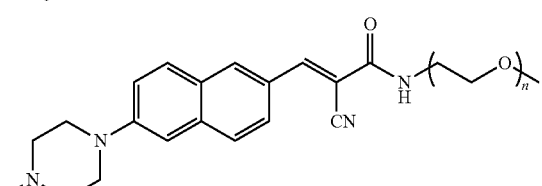
,

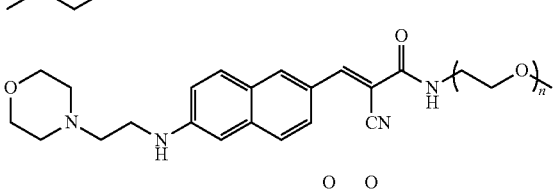
,

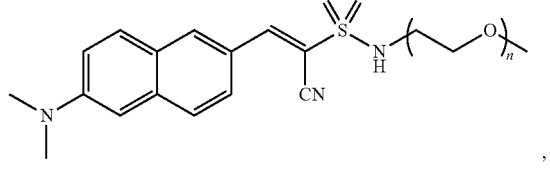
,

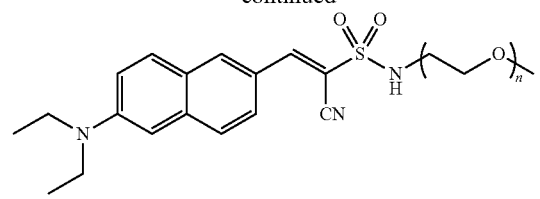
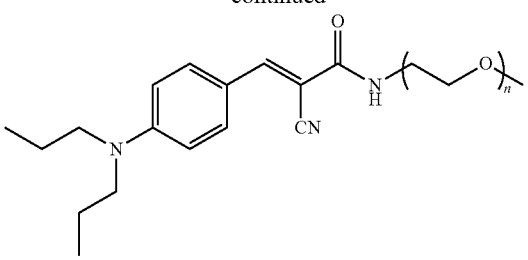
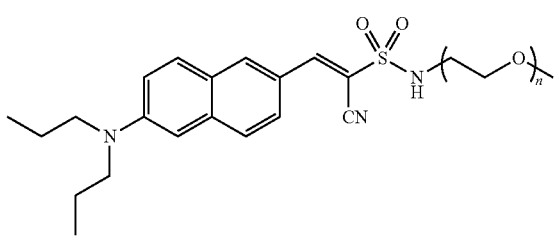
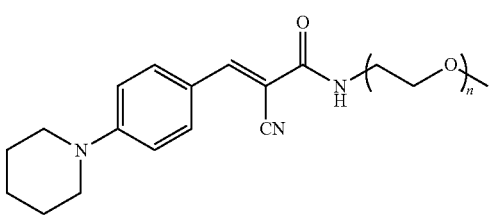
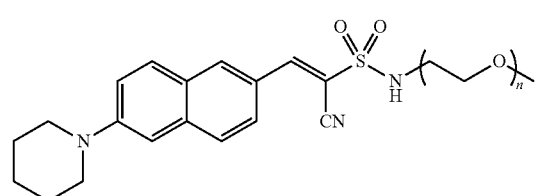
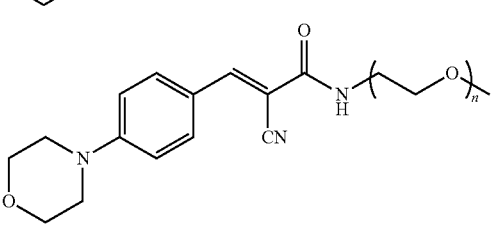
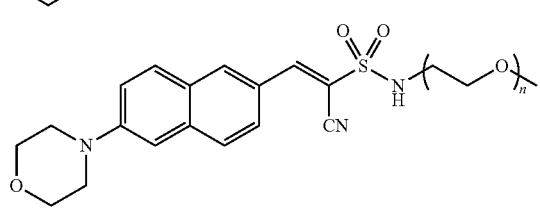
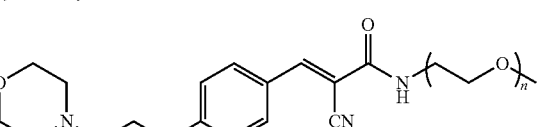
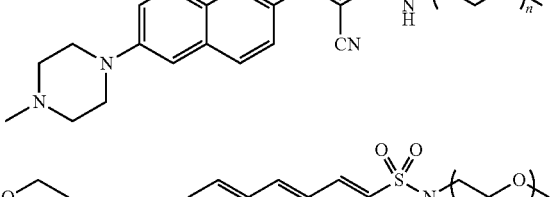
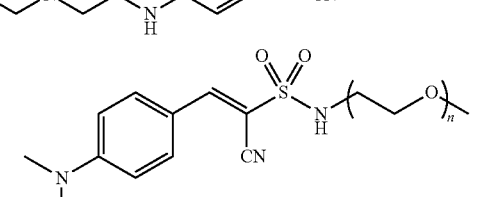
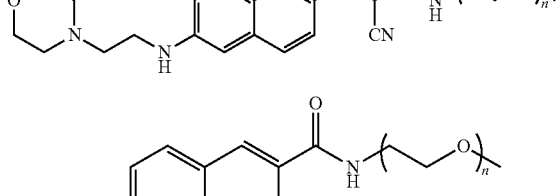
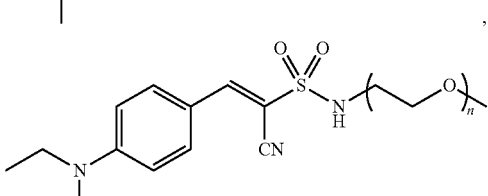
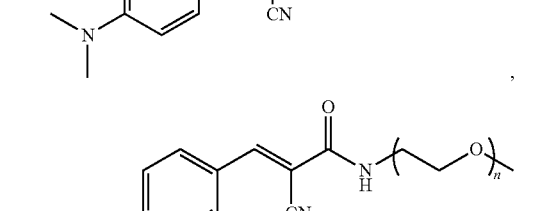
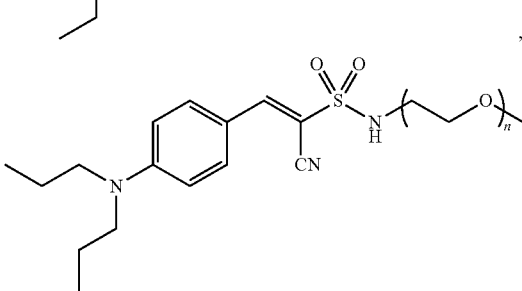

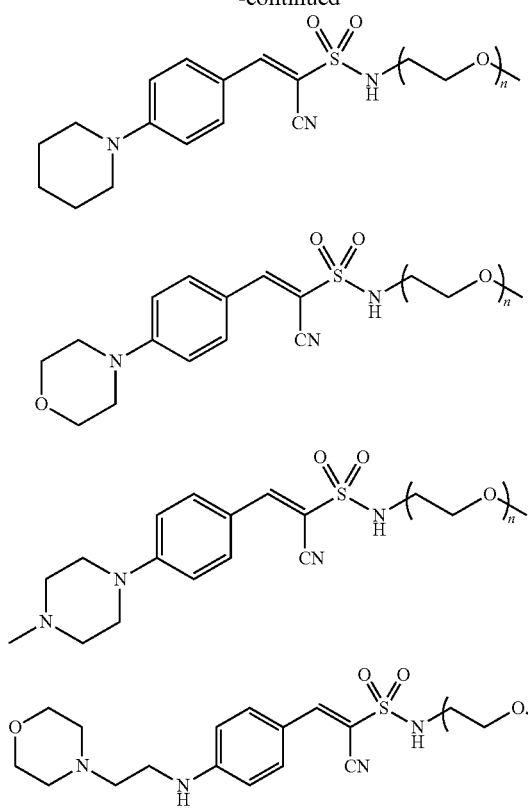
wherein n is an integer with value 1-50. In some cases, n is a integer of value 1-10, e.g. n is 1, 2, 3, 4, 5, 6, 7, 8, 9, or 10.
In other cases the compound of Formula I is selected from a group consisting of
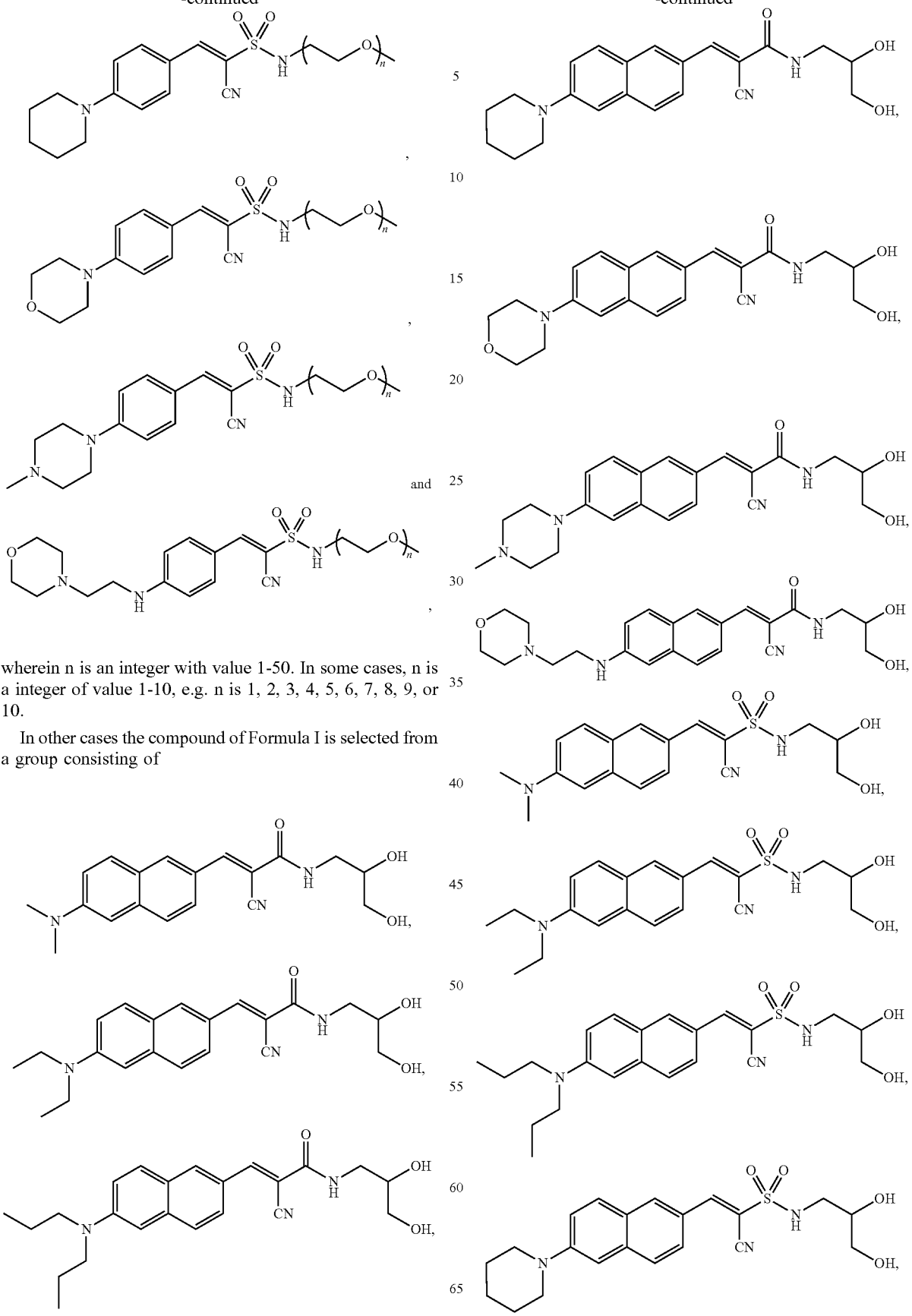

73
-continued
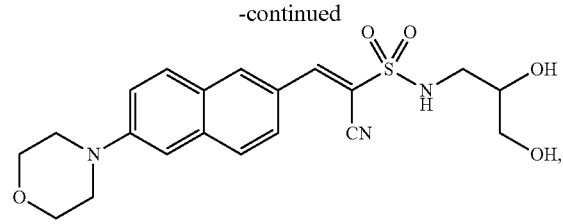
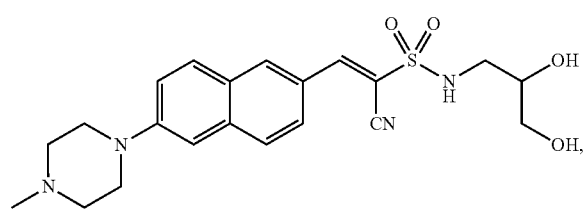
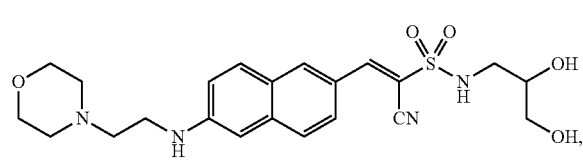
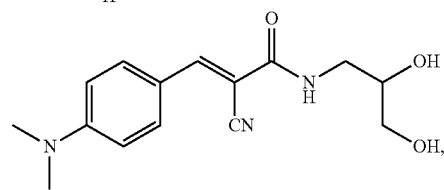
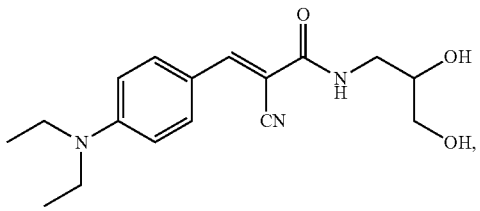
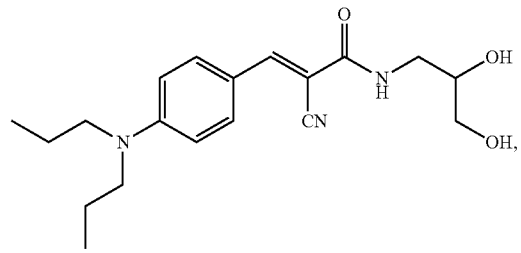
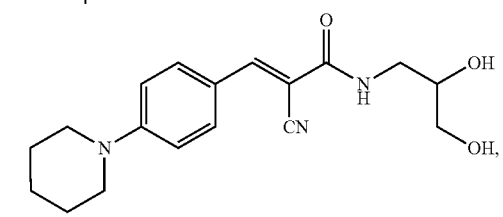
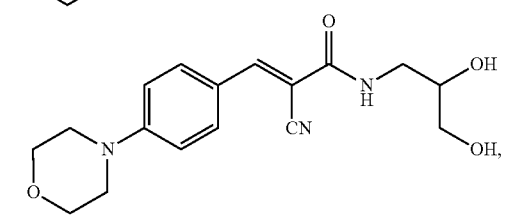
74
-continued
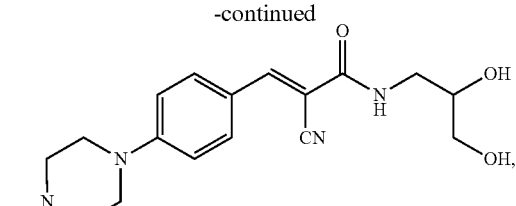
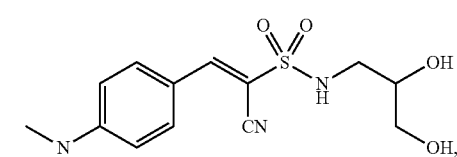
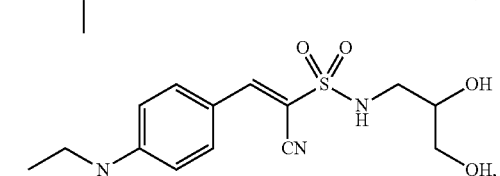
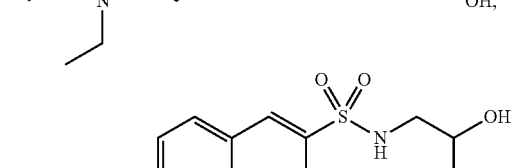
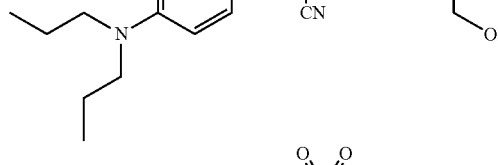
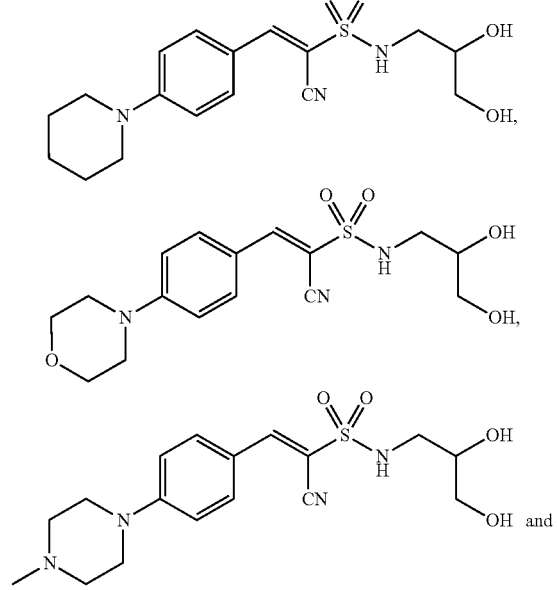
and

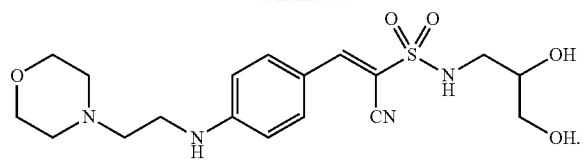
In other cases the compound of Formula I is selected from a group consisting of
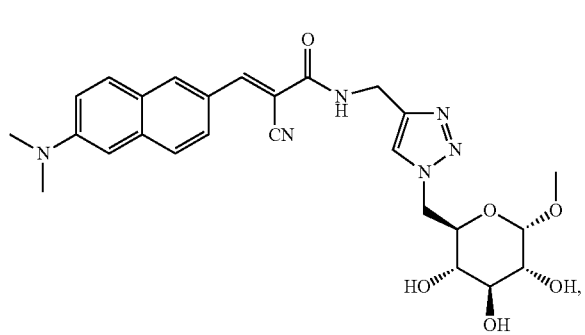
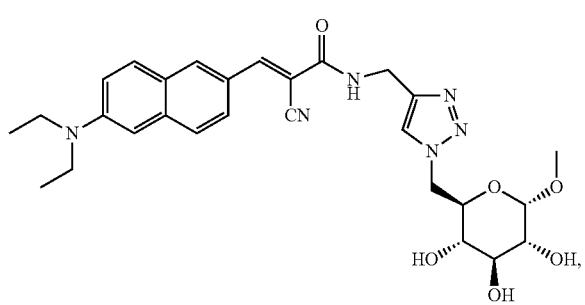
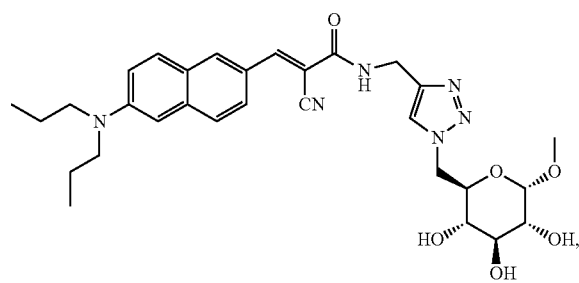
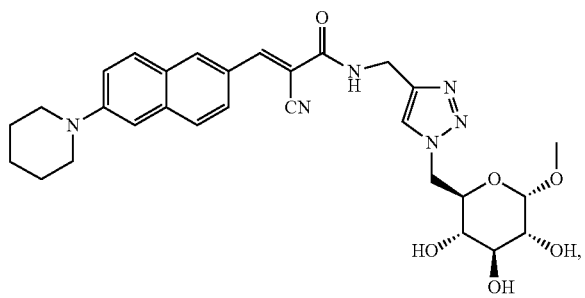
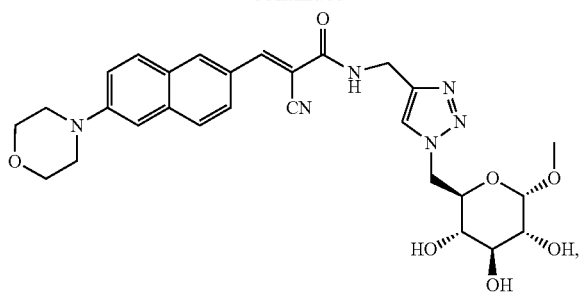
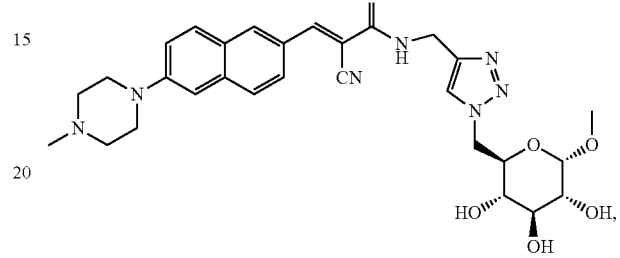
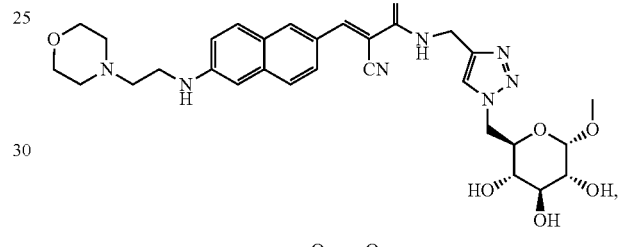
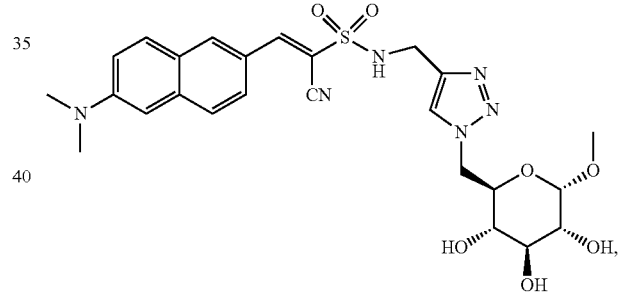
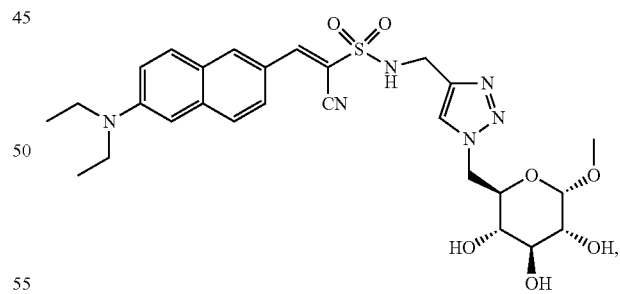
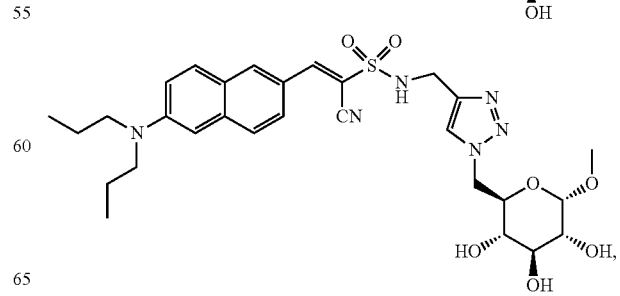

77
78
-continued
-continued
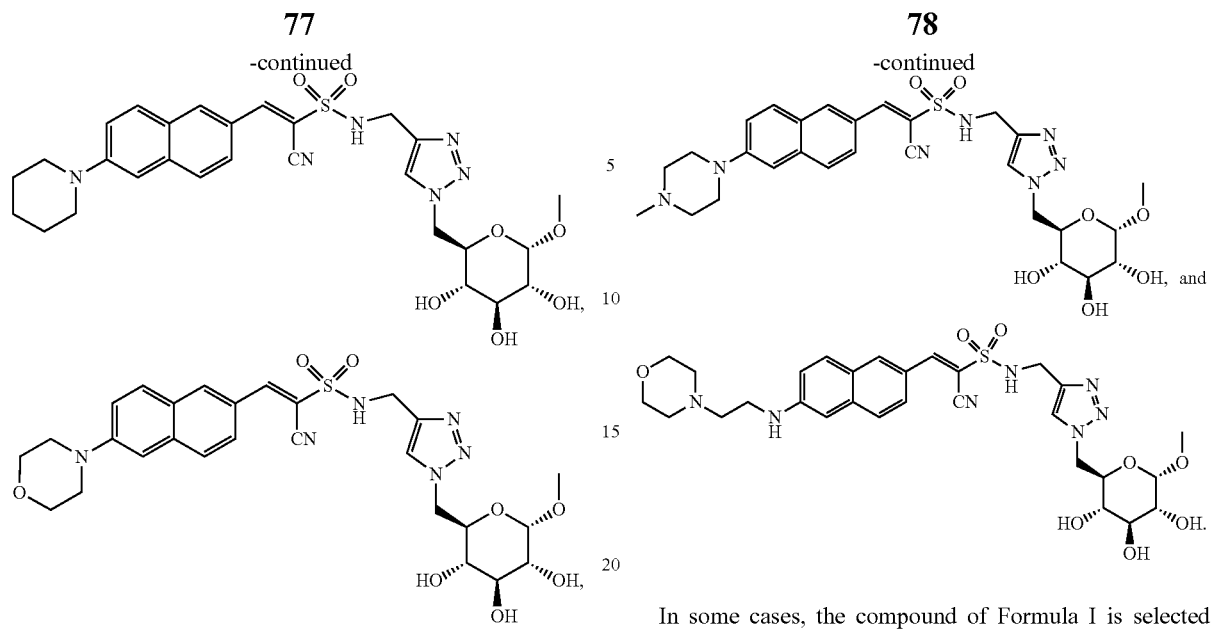
In some cases, the compound of Formula I is selected from a group consisting of
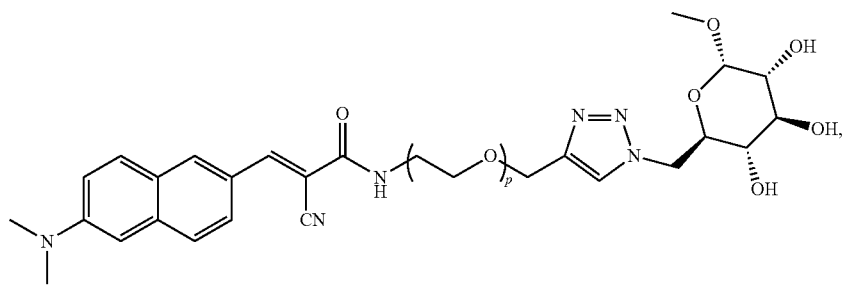
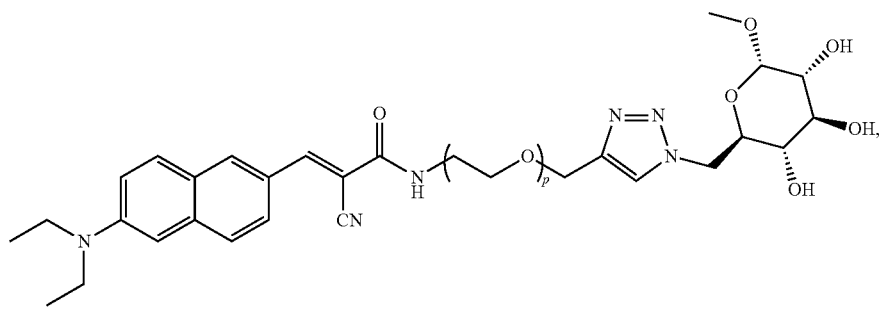
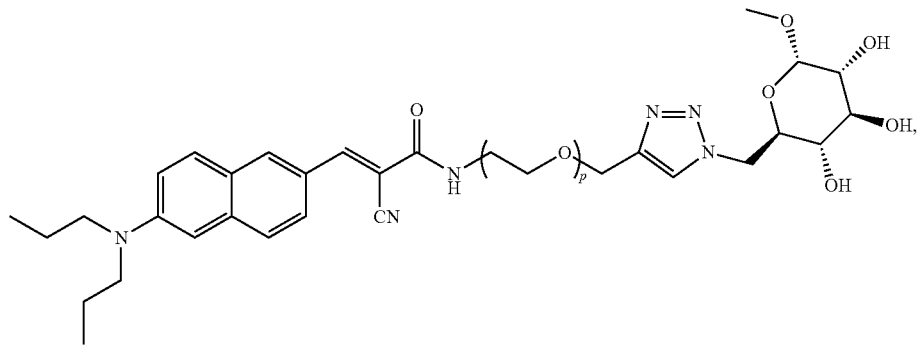

-continued
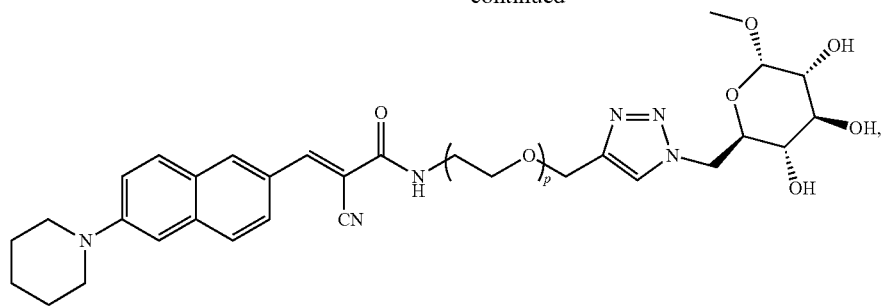
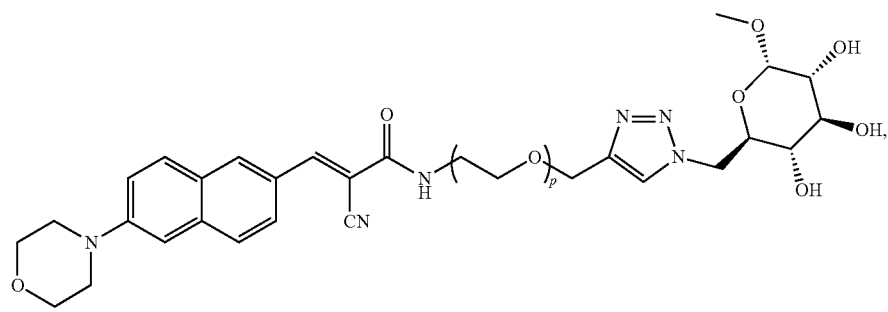
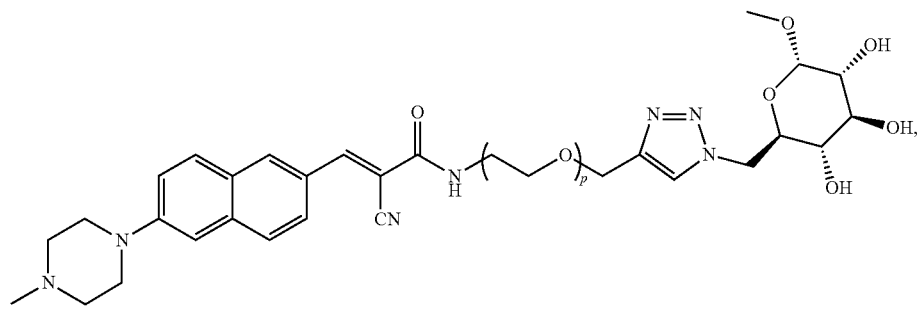
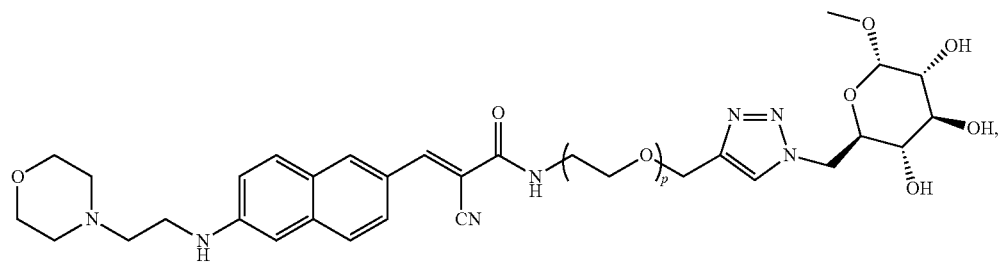
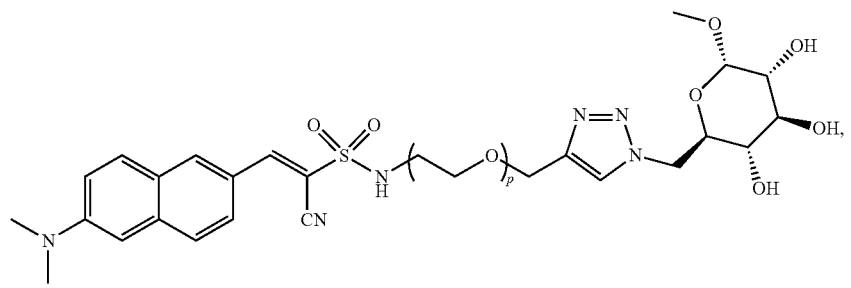

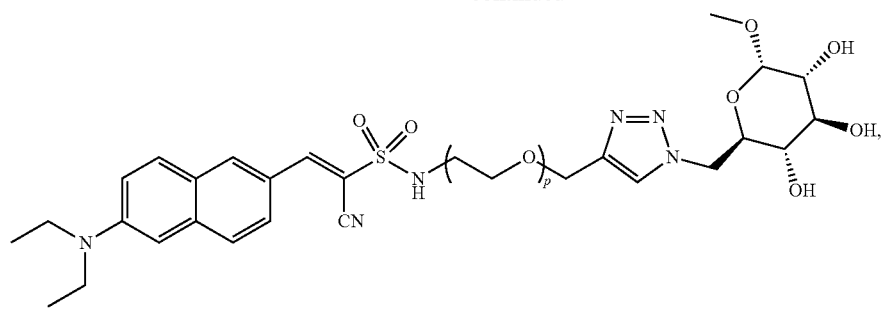
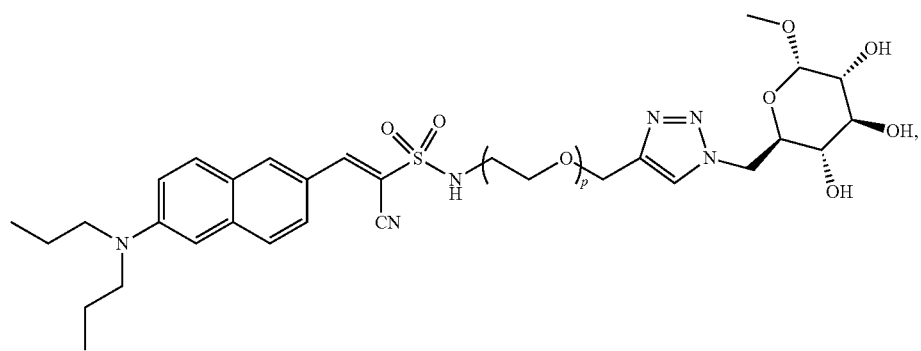
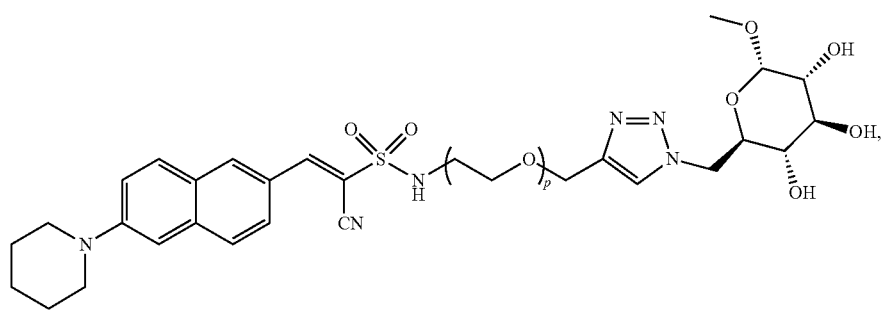
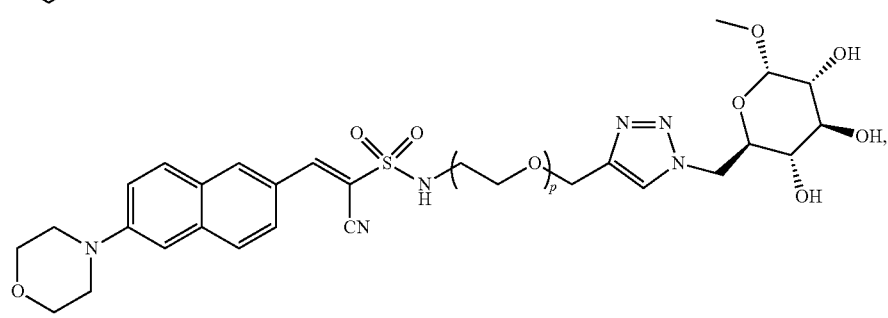
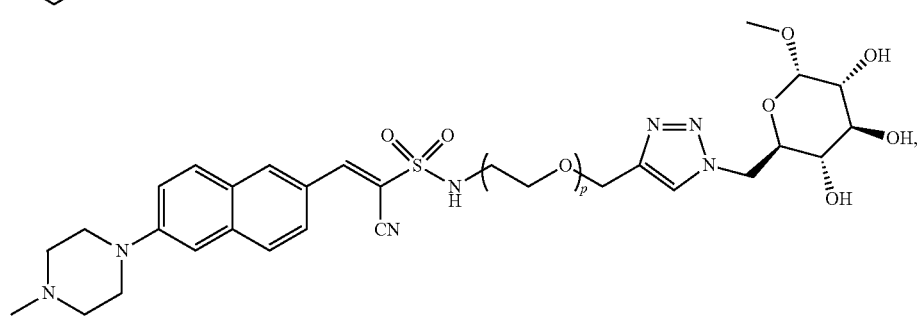

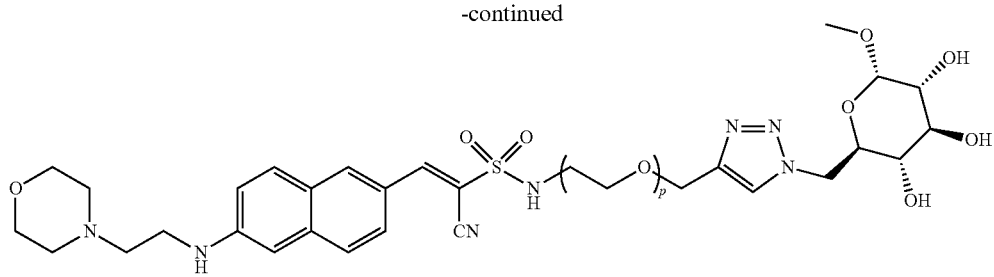
wherein p is an integer with value 1-50. In some cases, p is a integer of value 1-10, e.g. p is 1, 2, 3, 4, 5, 6, 7, 8, 9, or 10.
In some cases, the compound of Formula I is selected from a group consisting of
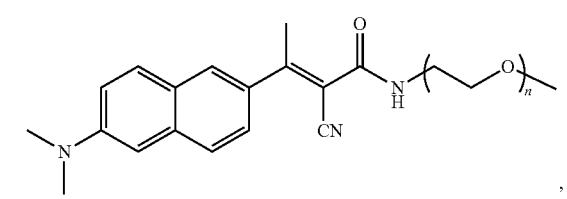
,
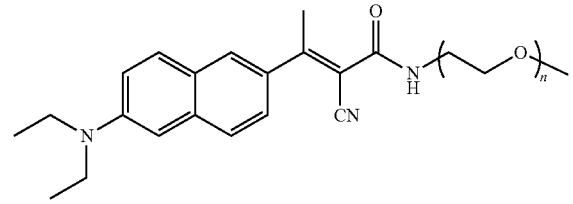
,
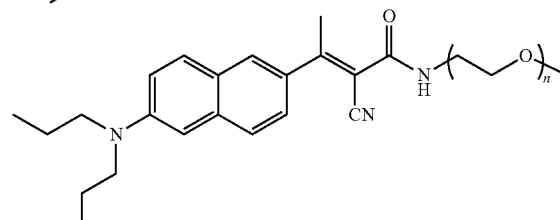
,
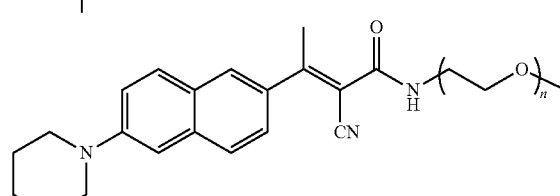
,
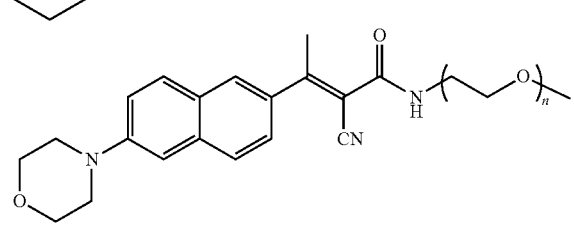
,
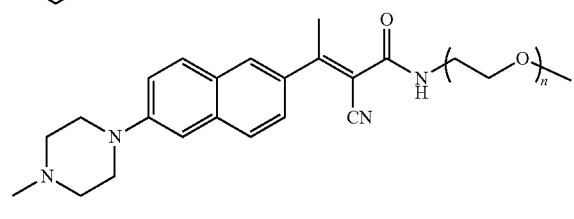
,
-continued
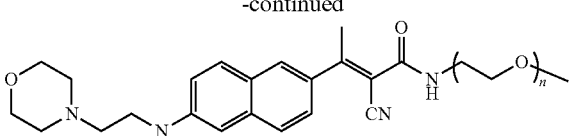
,
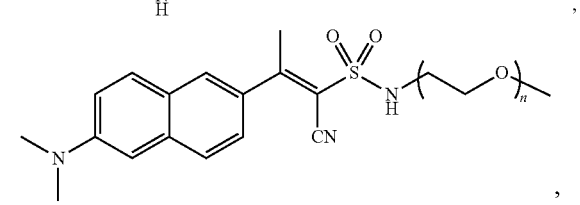
,
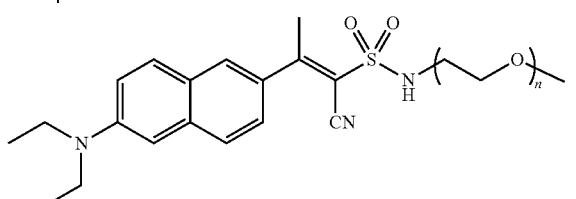
,
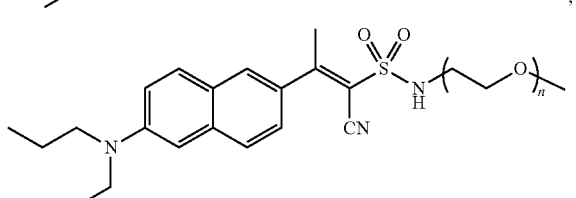
,
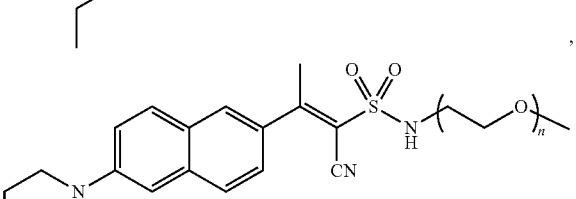
,
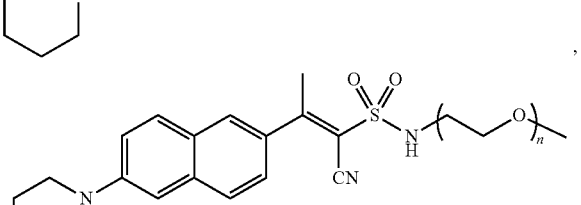
,
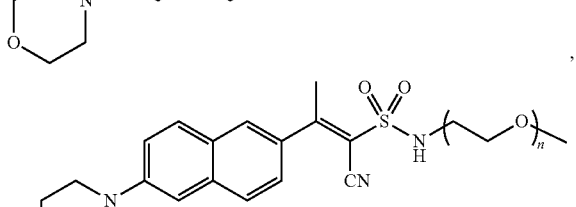
, -continued
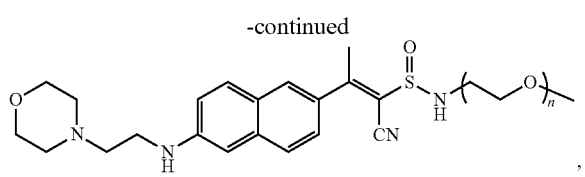
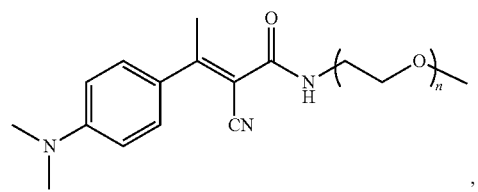
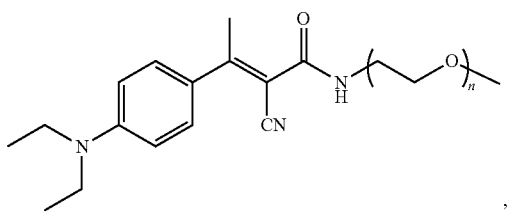
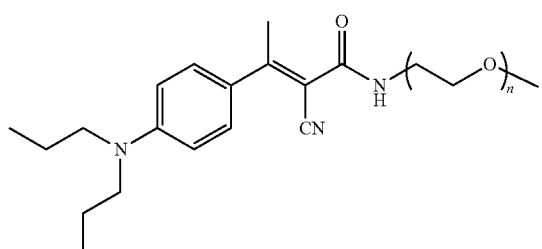
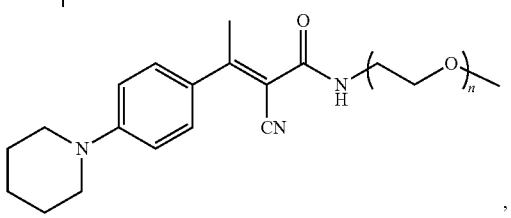
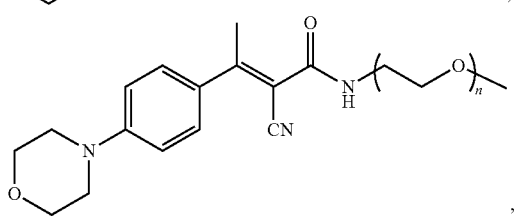
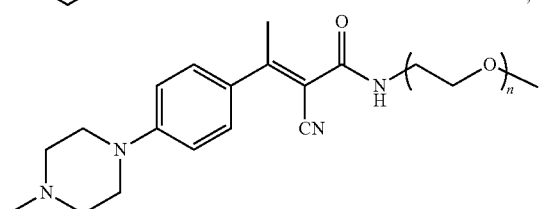
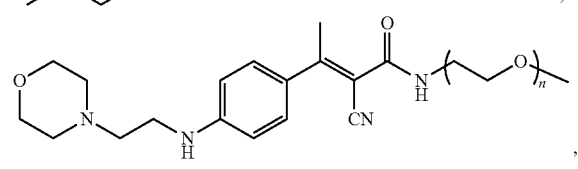
-continued
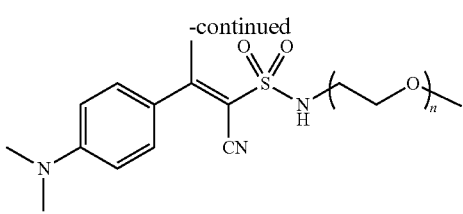
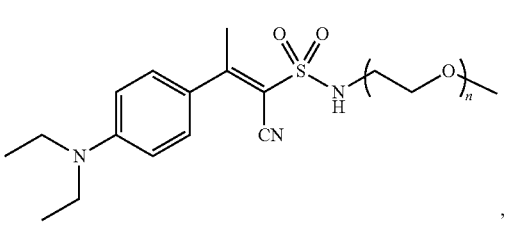
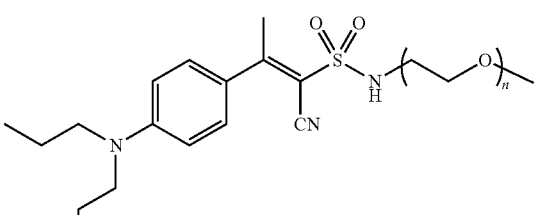
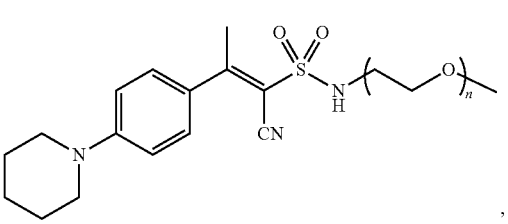
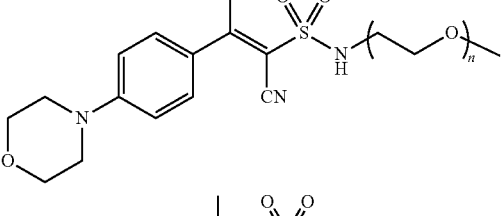
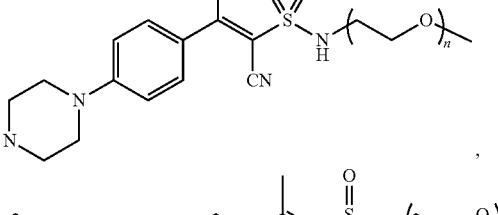
, and
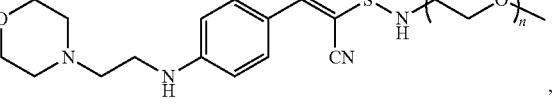
,
wherein n is an integer with value 1-50. In some cases, n is a integer of value 1-10, e.g. n is 1, 2, 3, 4, 5, 6, 7, 8, 9, or 10.
In other cases the compound of Formula I is selected from a group consisting of 87
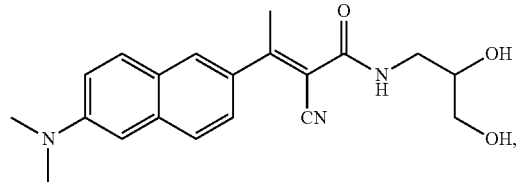
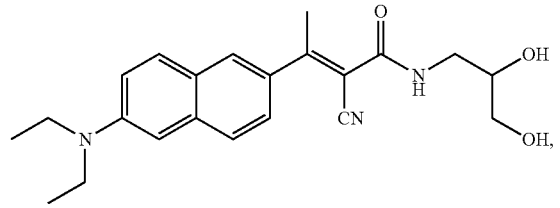
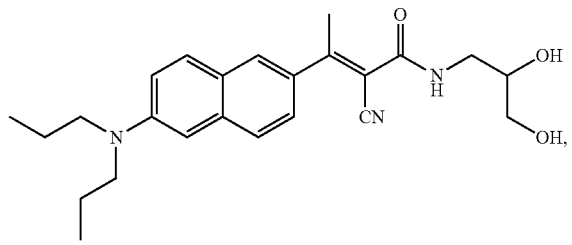
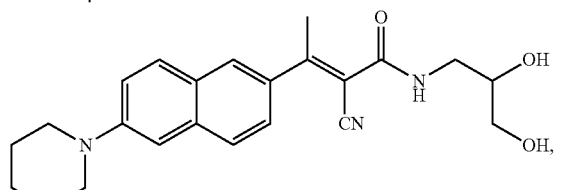
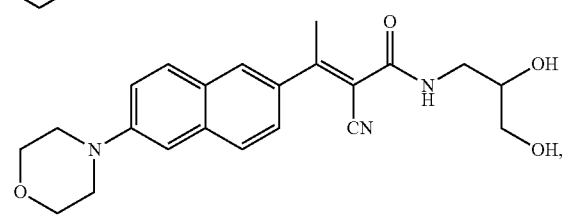
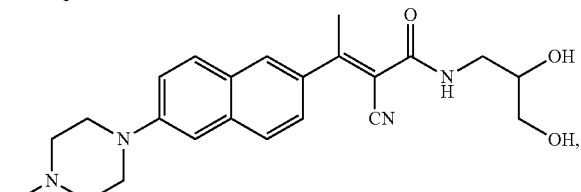
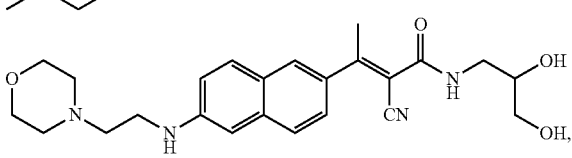
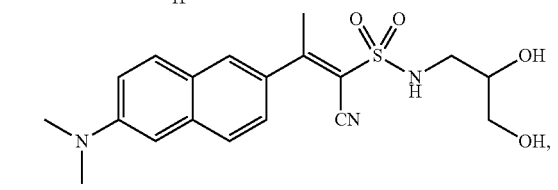
88
-continued
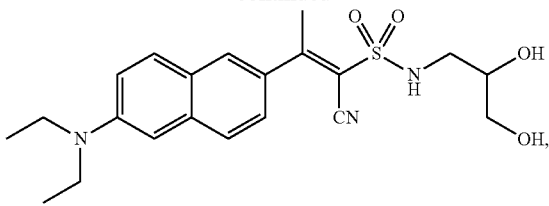
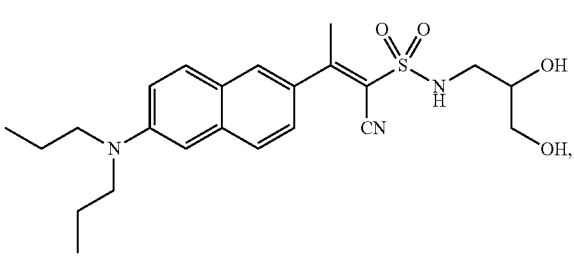
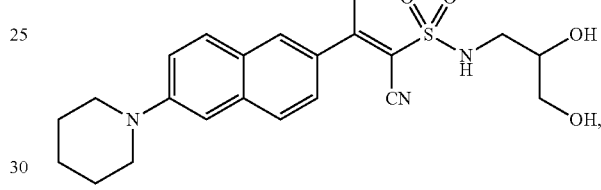
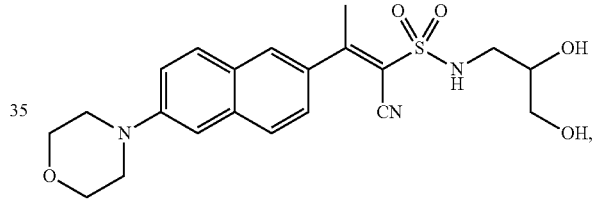
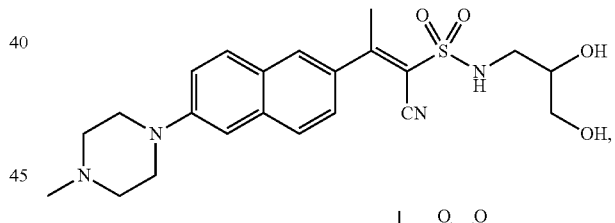
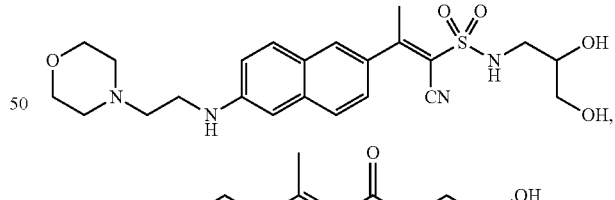
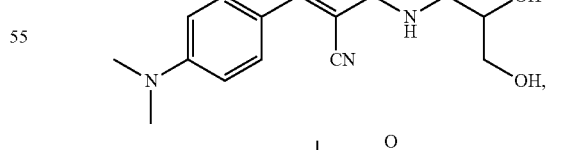
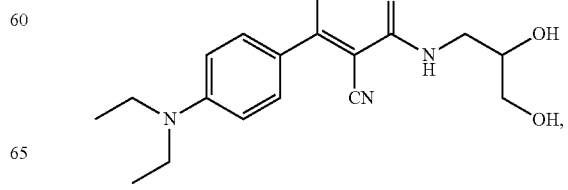

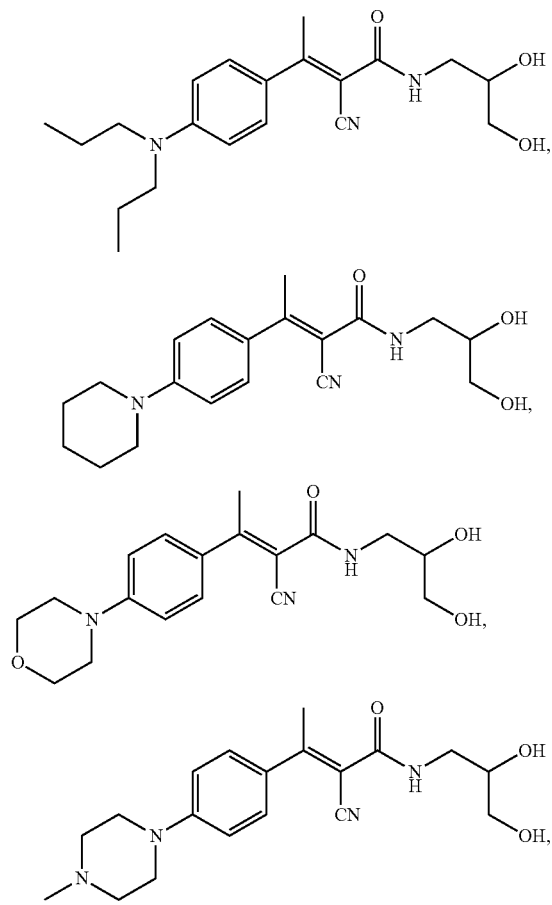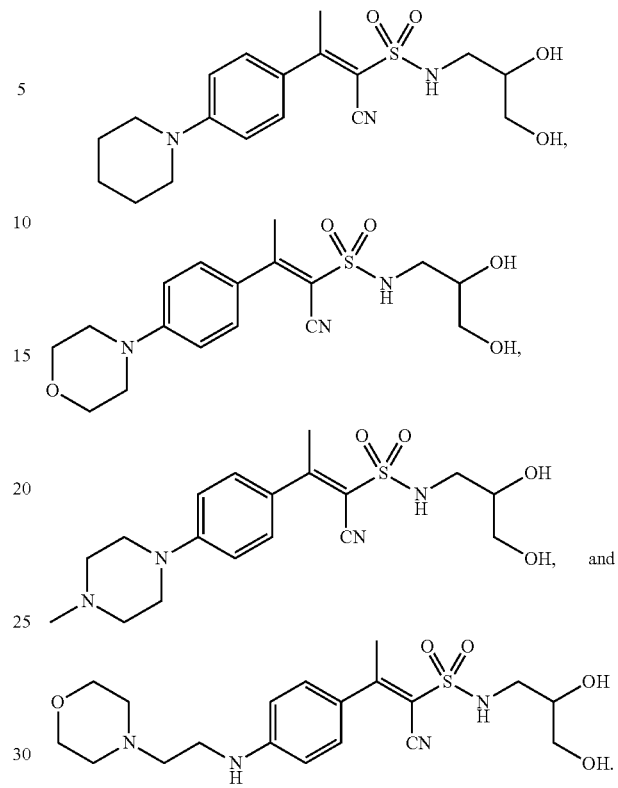
In some cases, the compound of Formula I is selected from a group consisting of
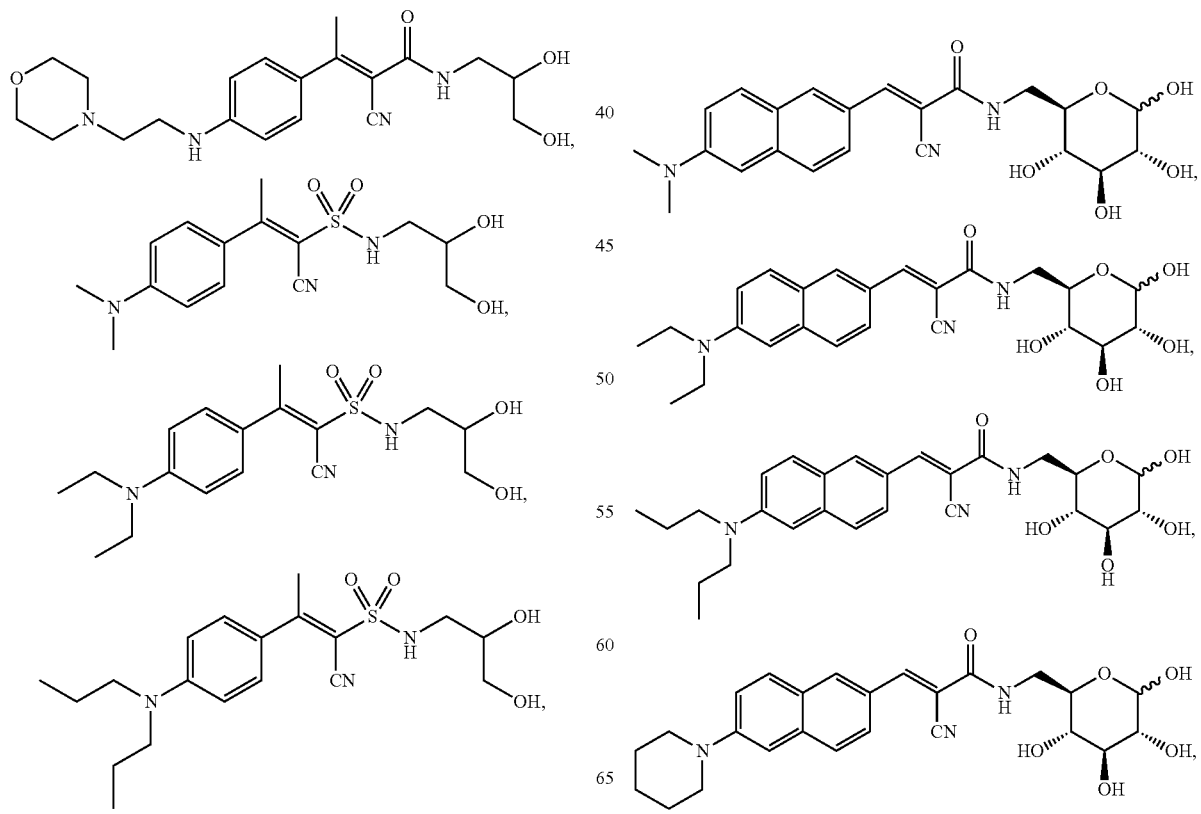

-continued

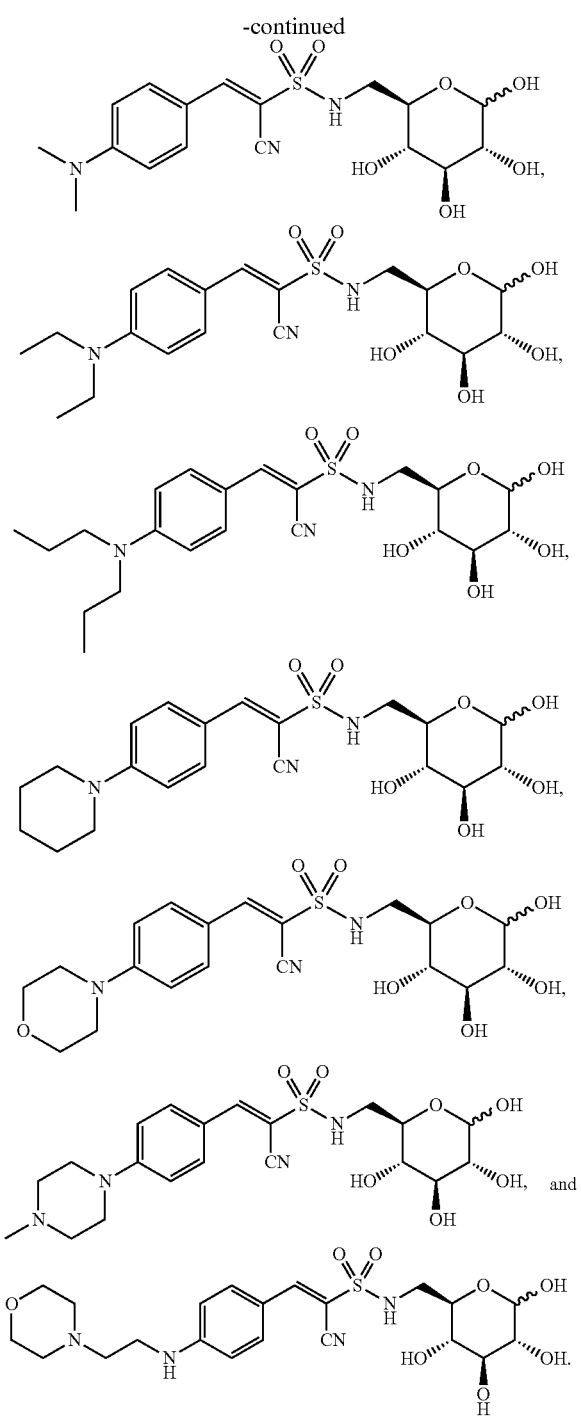
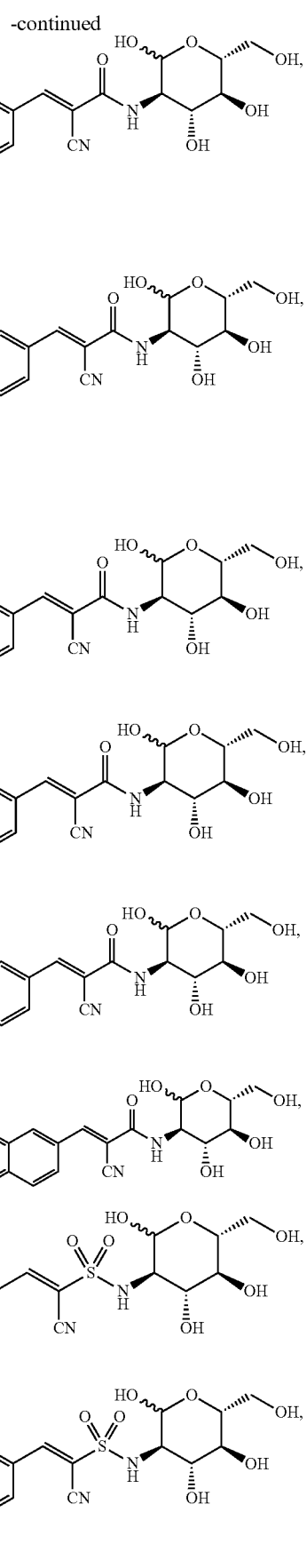
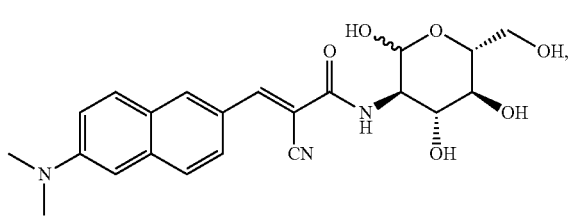
In other cases the compound of Formula I is selected from a group consisting of
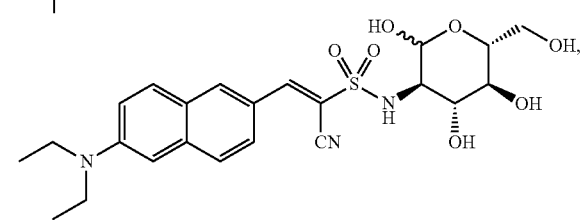

-continued
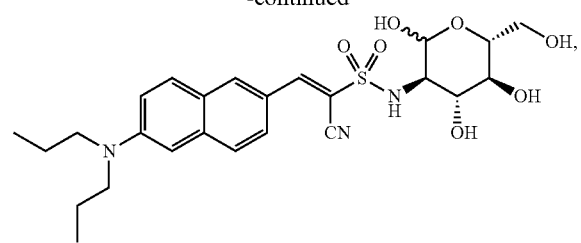
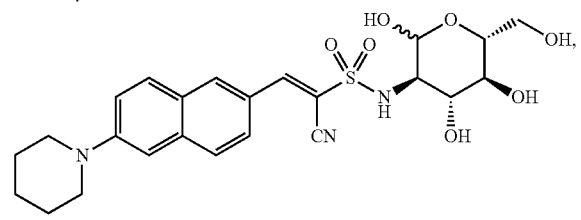
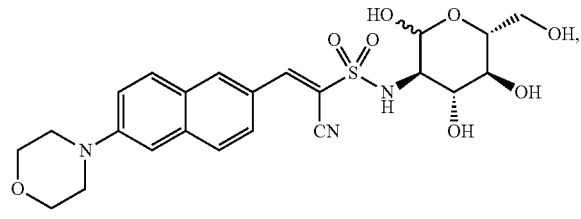
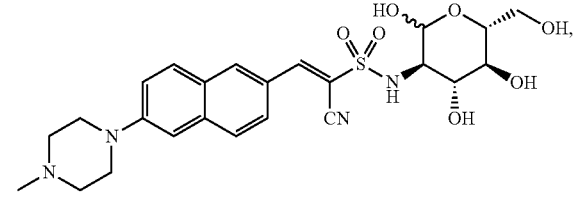
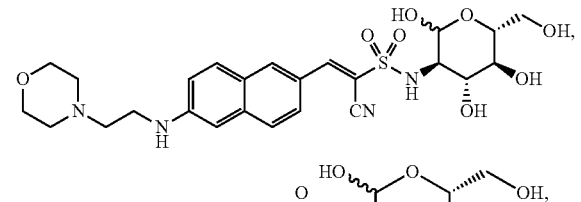
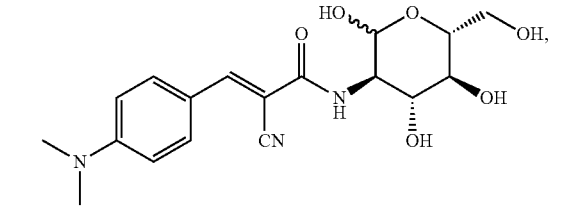
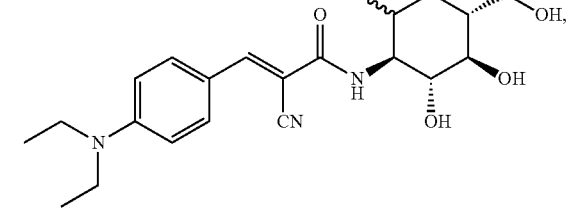
-continued
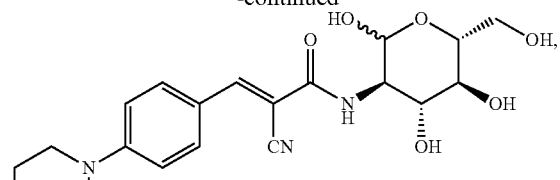
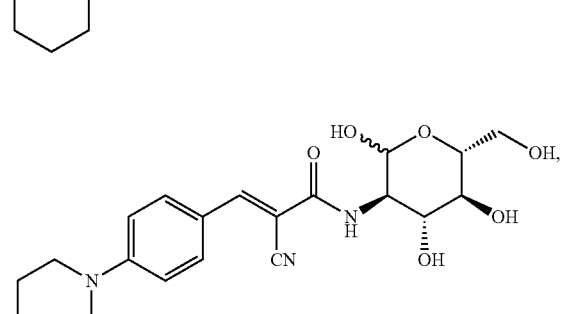
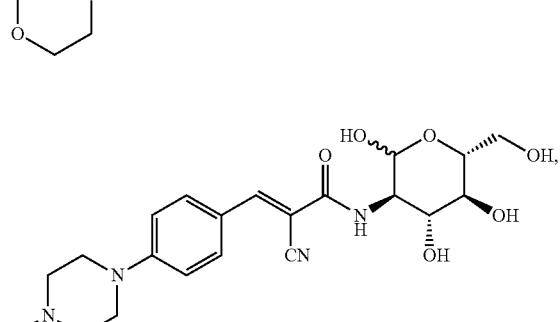
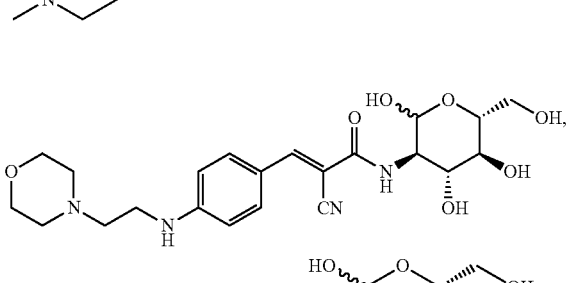
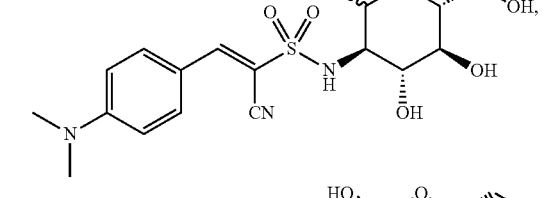
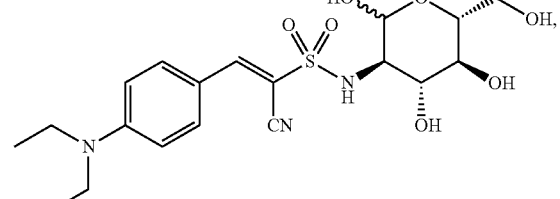
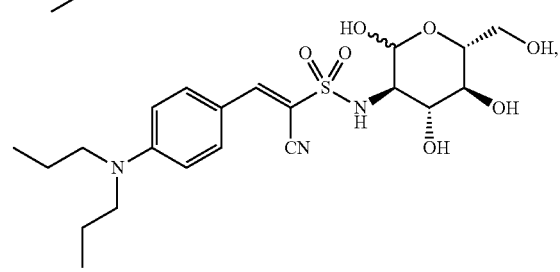

-continued
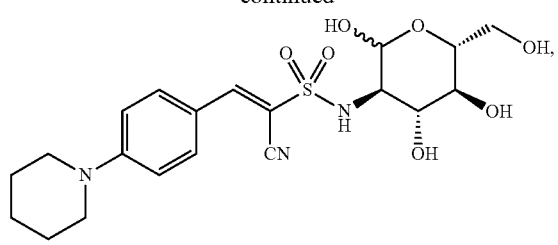
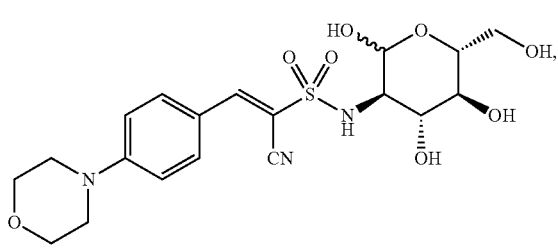
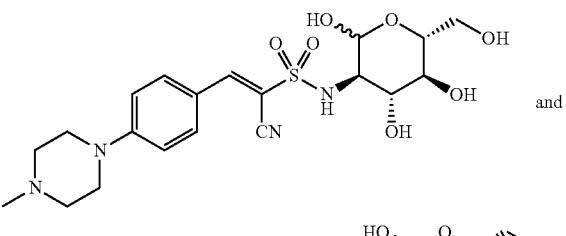
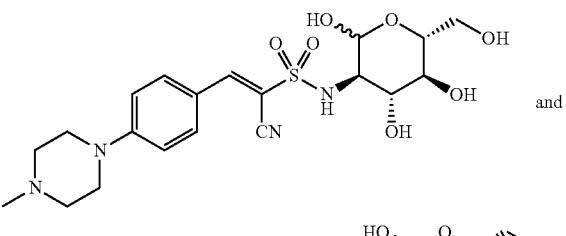
In some cases the compound of Formula I is selected from a group consisting of
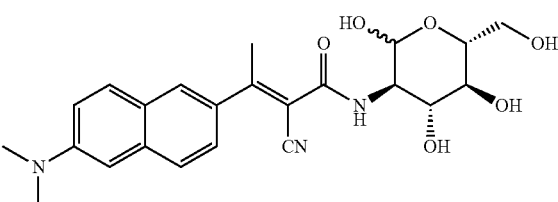
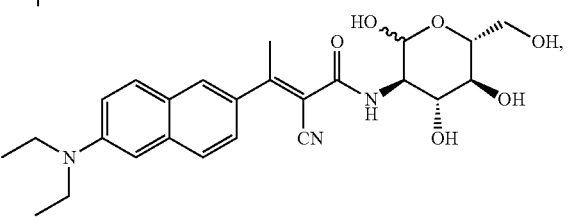
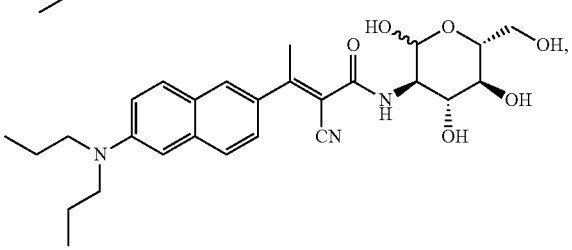
and
-continued
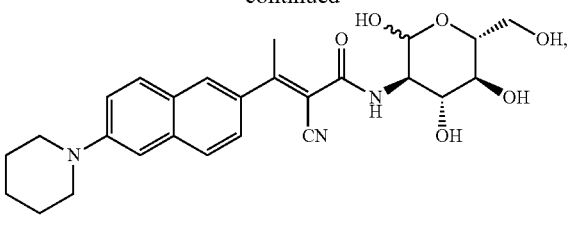
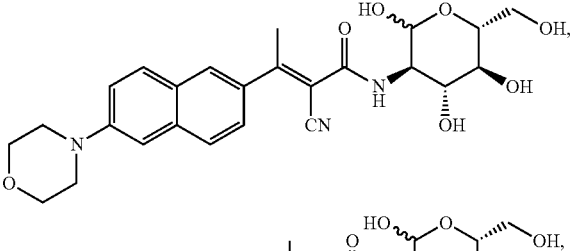
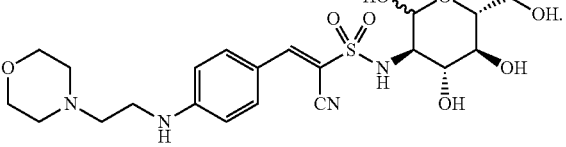
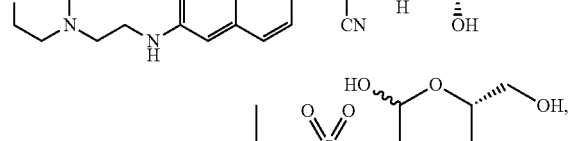
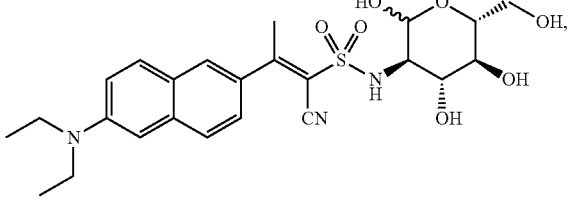
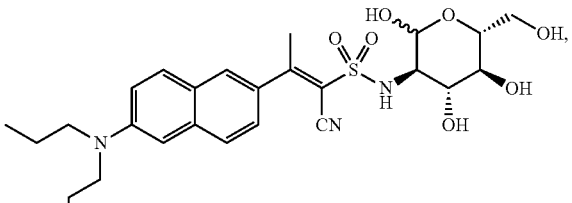
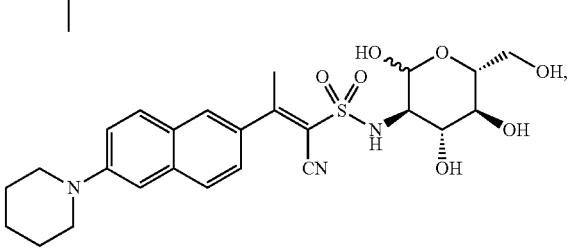

99
-continued

100
-continued

101
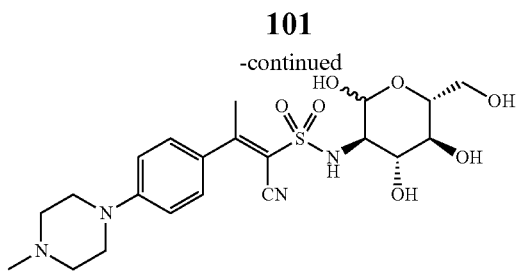
and
102
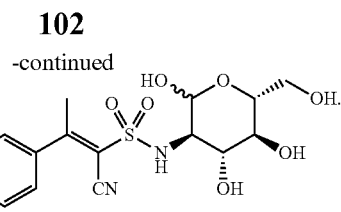
In some cases, the compound of Formula I is selected from a group consisting of
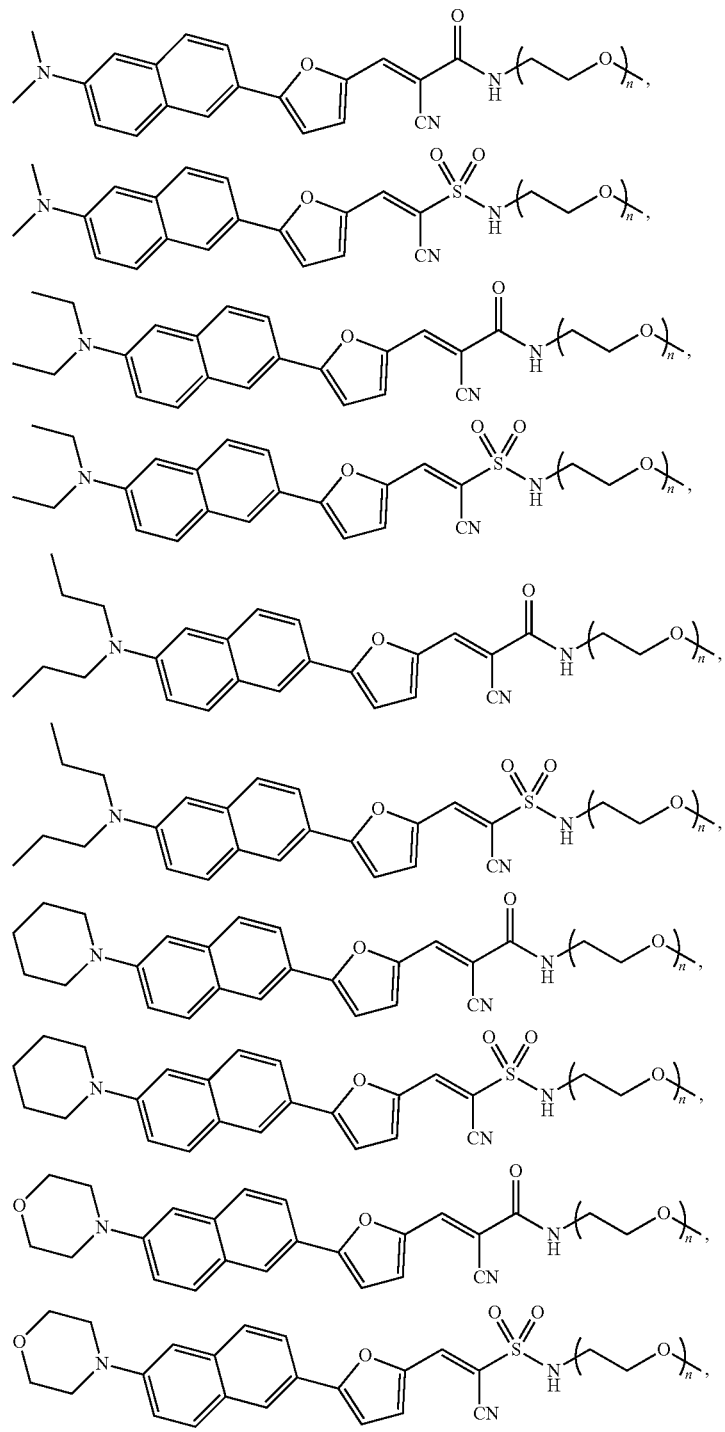

-continued
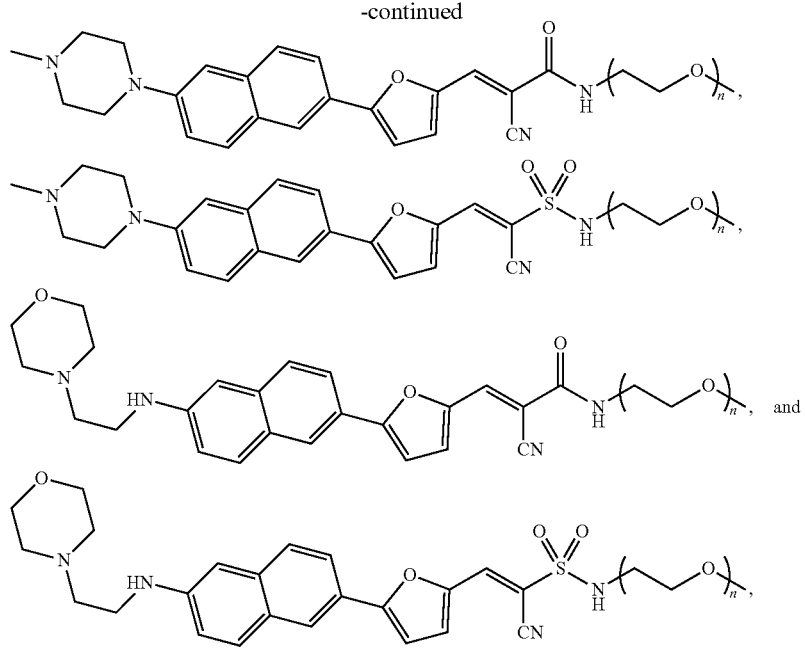
wherein n is an integer with value 1-50. In some cases, n is a integer of value 1-10, e.g. n is 1, 2, 3, 4, 5, 6, 7, 8, 9, or 10.
In some cases, the compound of Formula I is selected from a group consisting of
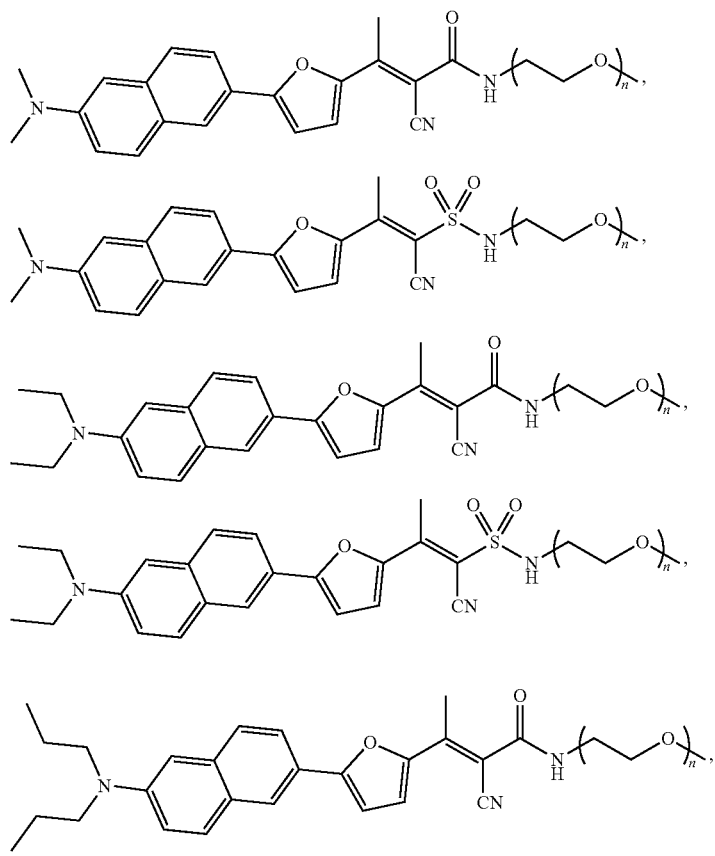

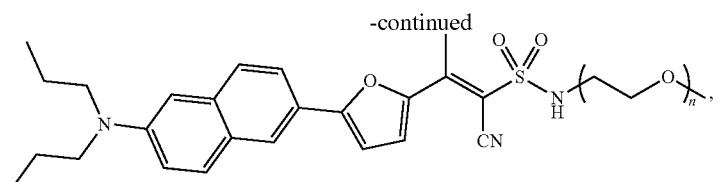
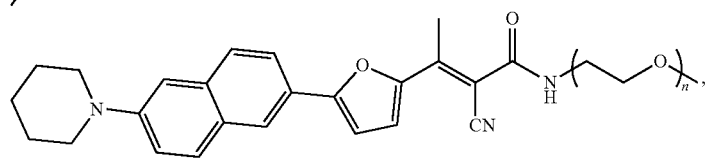
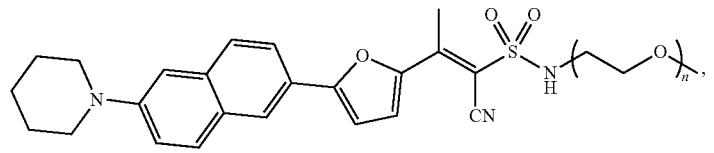
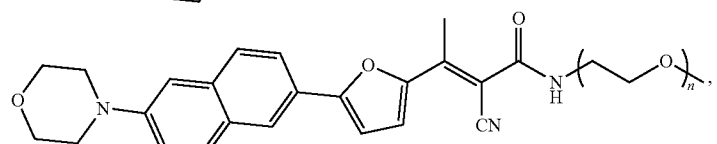
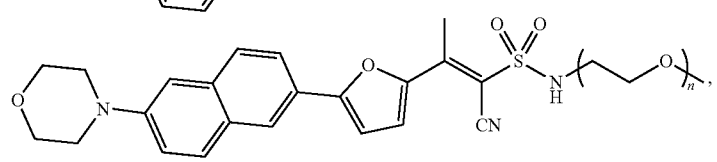
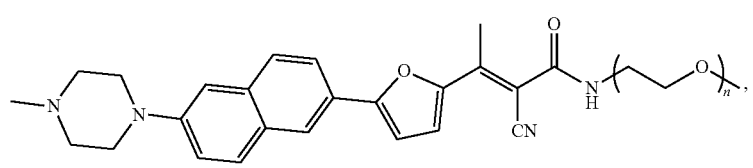
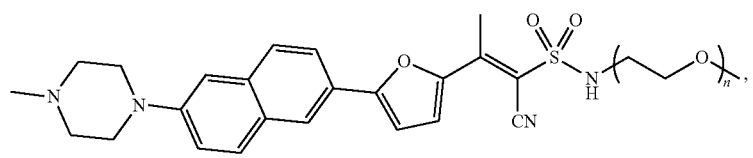
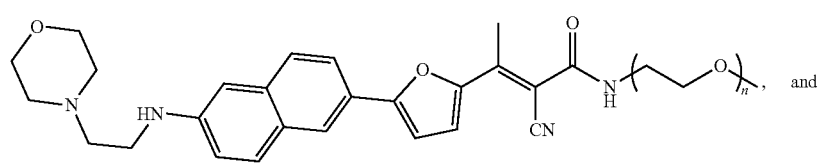, and
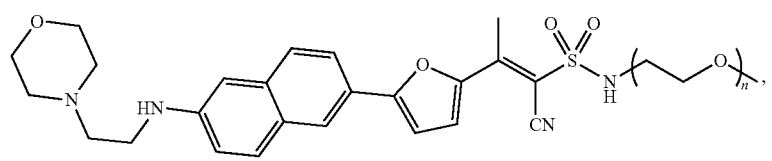
wherein n is an integer with value 1-50. In some cases, n is a integer of value 1-10, e.g. n is 1, 2, 3, 4, 5, 6, 7, 8, 9, or 10.

In some cases, the compound of Formula I is selected from a group consisting of
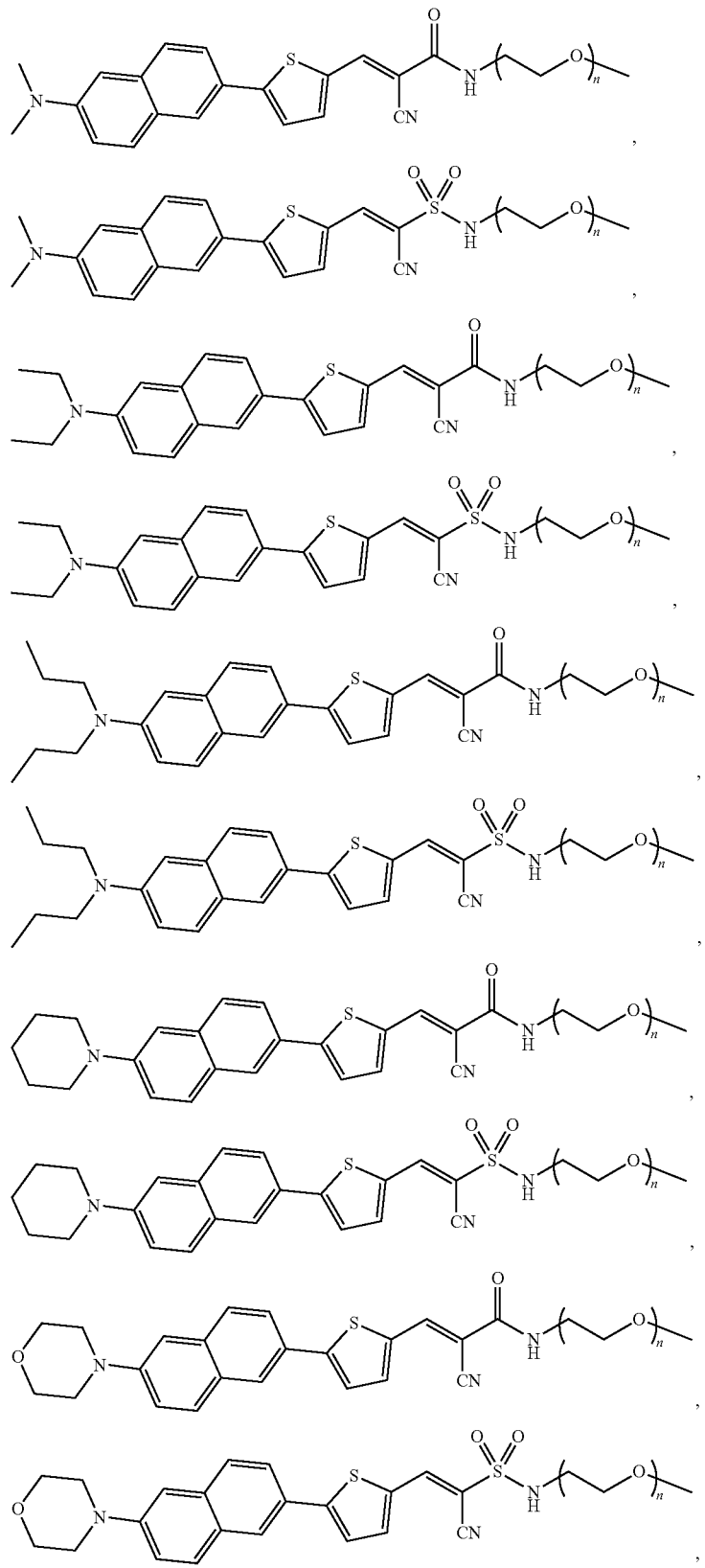

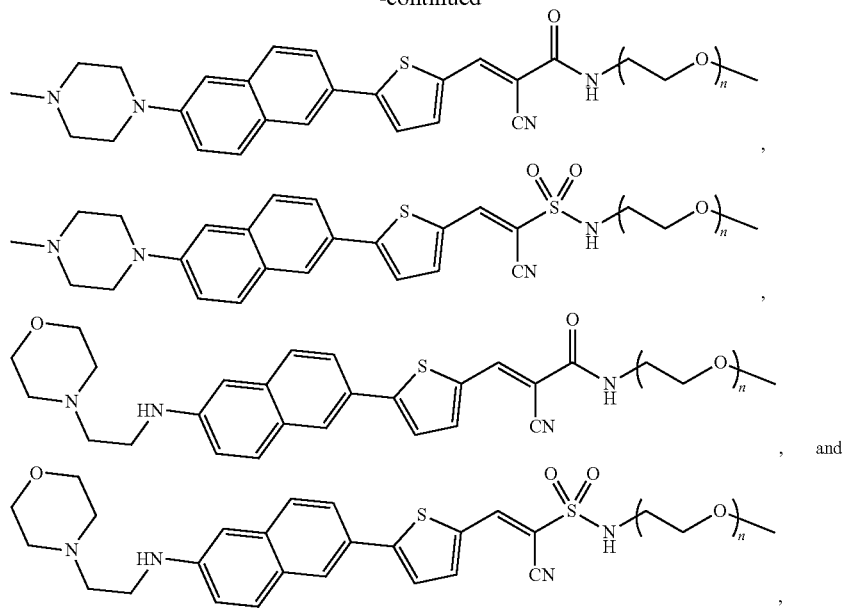
wherein n is an integer with value 1-50. In some cases, n is a integer of value 1-10, e.g. n is 1, 2, 3, 4, 5, 6, 7, 8, 9, or 10.
In some cases, the compound of Formula I is selected from a group consisting of
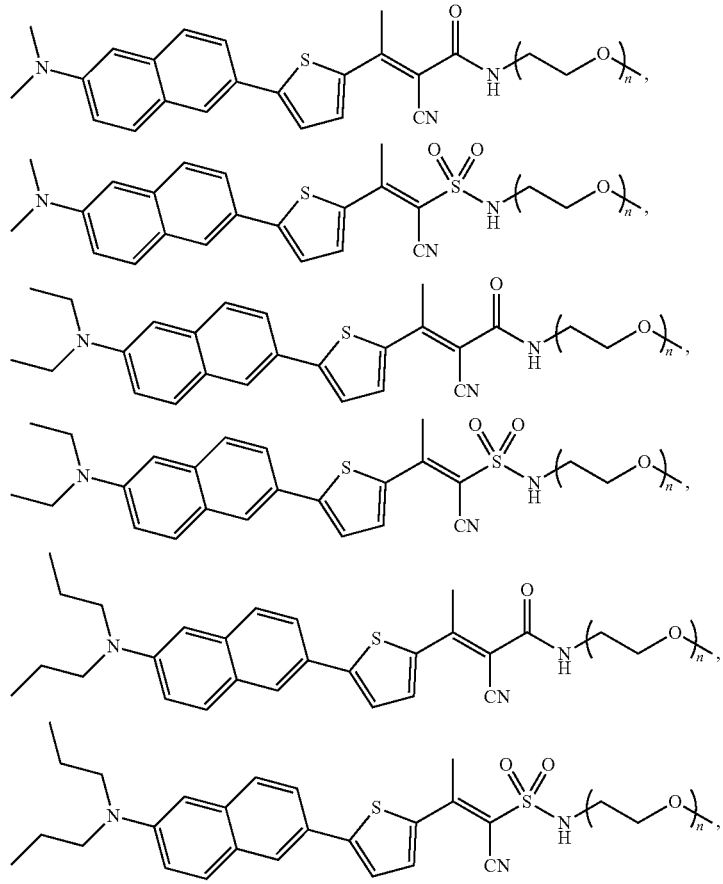

-continued
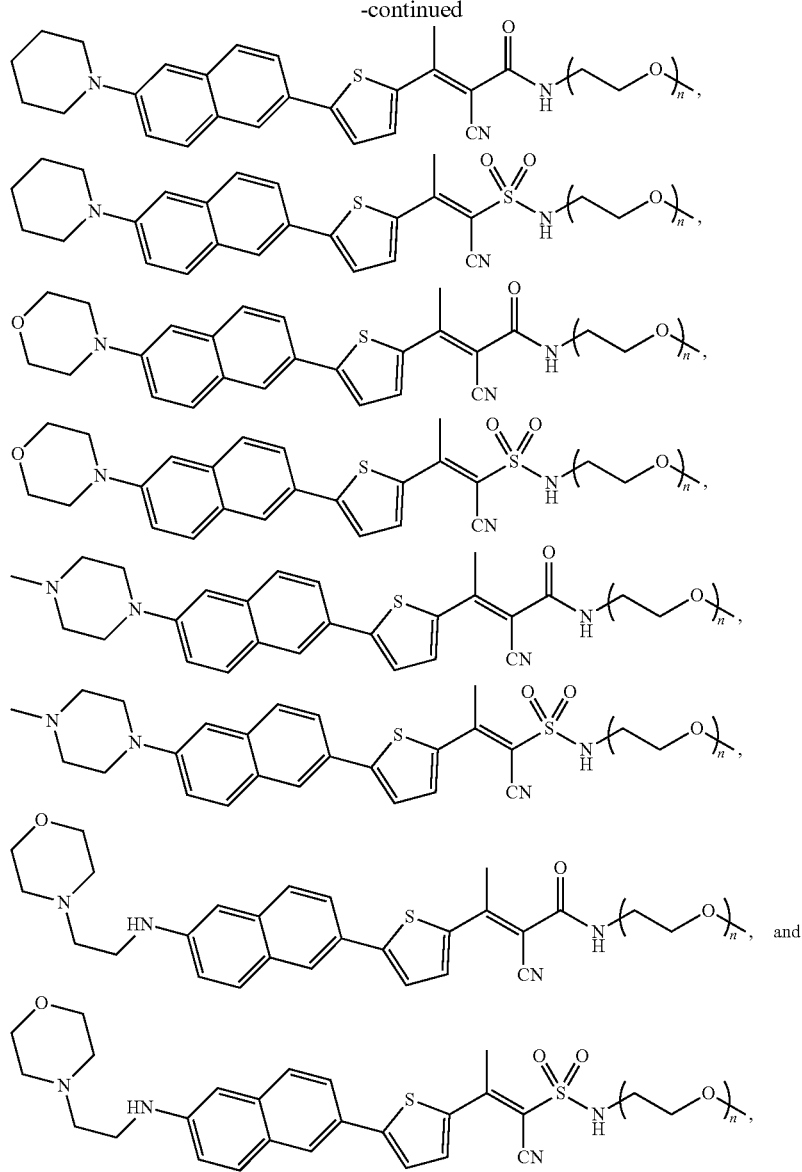
wherein n is an integer with value 1-50. In some cases, n is a integer of value 1-10, e.g. n is 1, 2, 3, 4, 5, 6, 7, 8, 9, or 10.
In some cases, the compound of Formula I is selected from a group consisting of
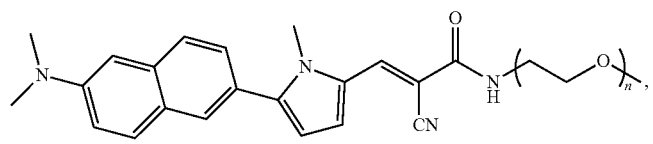
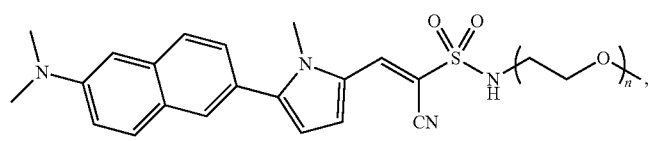

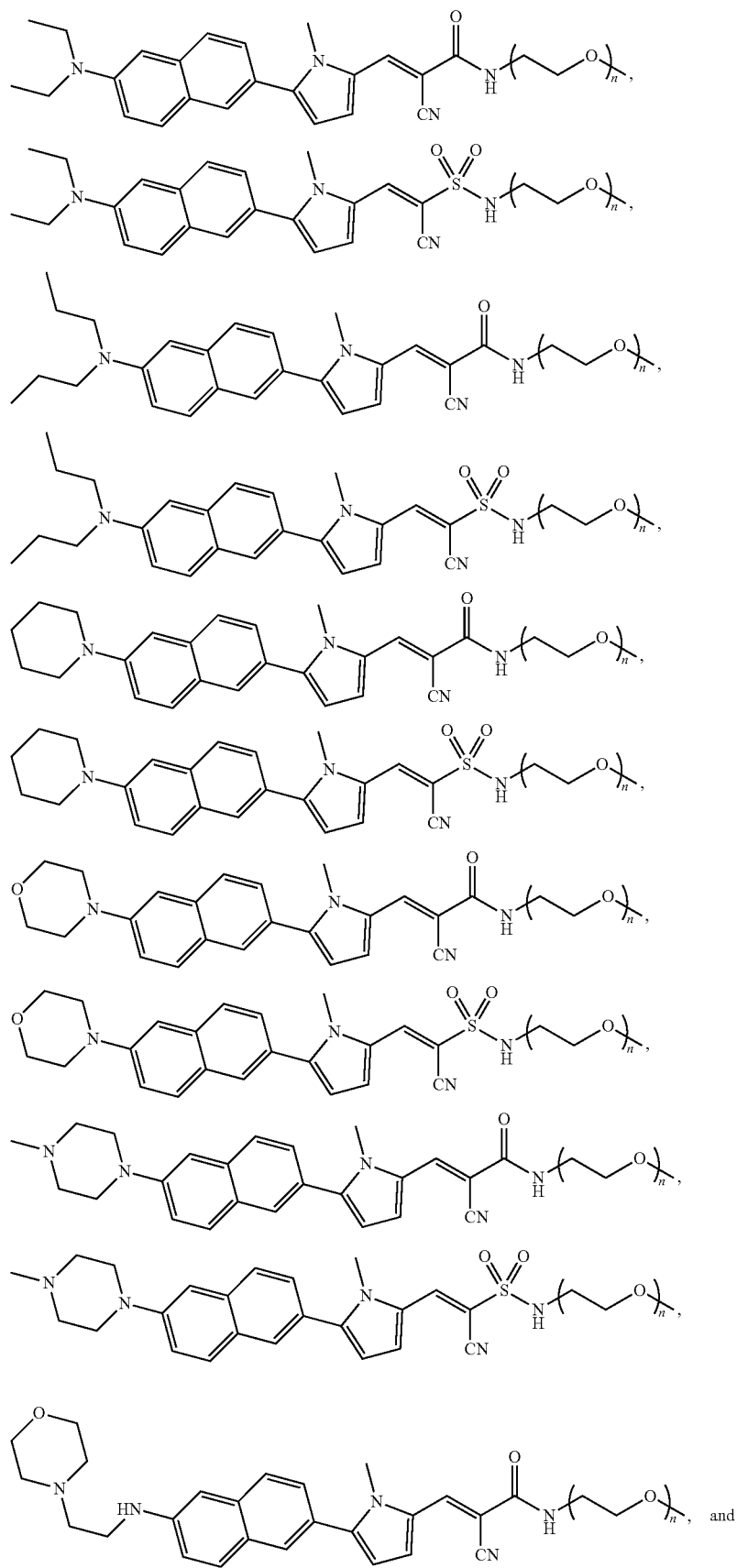

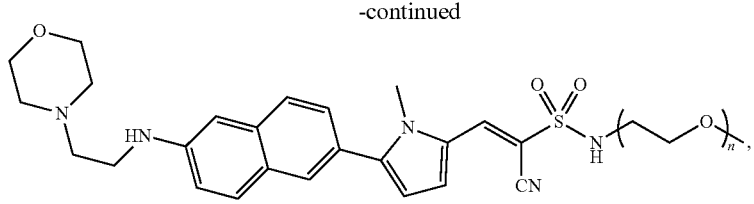
10
wherein n is an integer with value 1-50. In some cases, n is a integer of value 1-10, e.g. n is 1, 2, 3, 4, 5, 6, 7, 8, 9, or 10.
In some cases, the compound of Formula I is selected from a group consisting of
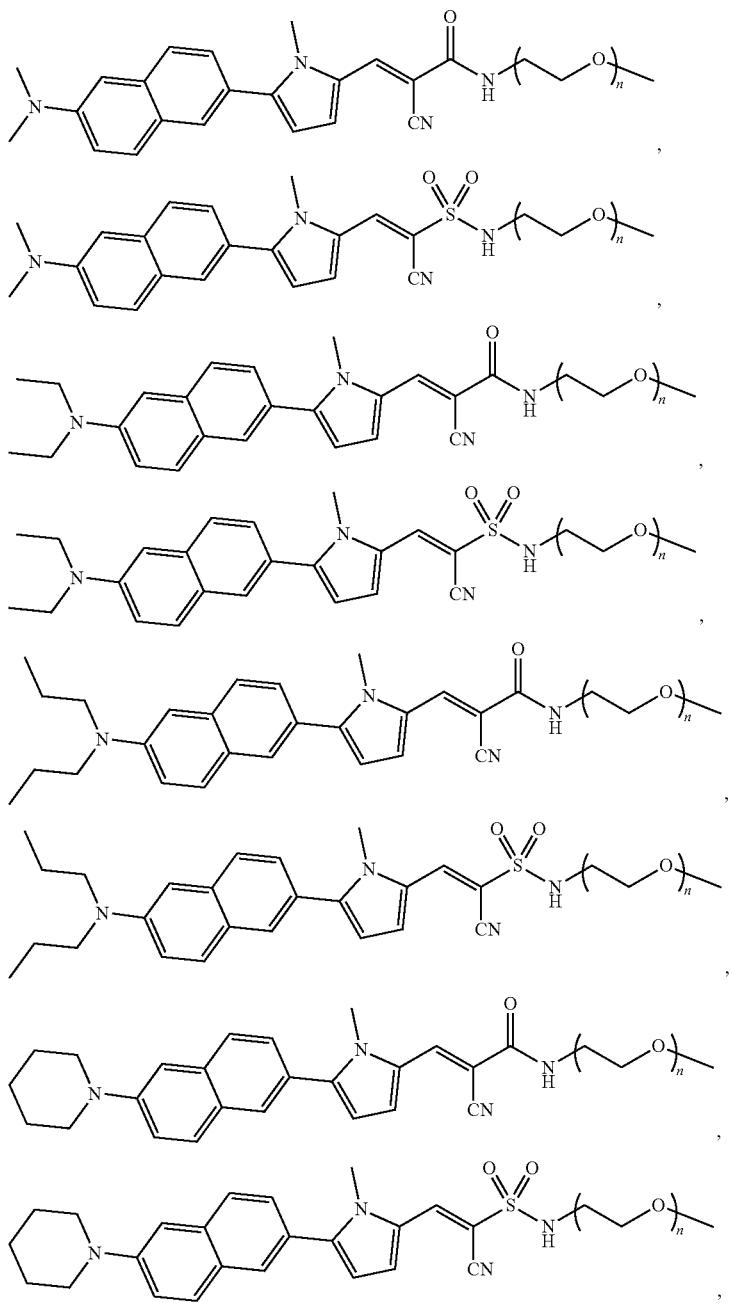

-continued
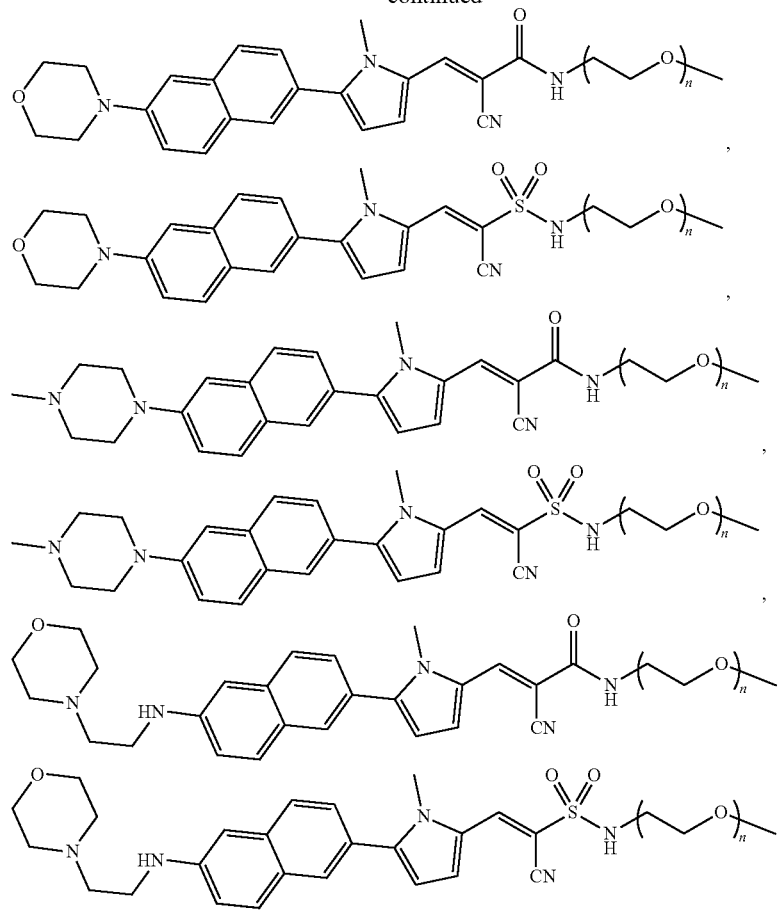
wherein n is an integer with value 1-50. In some cases, n is a integer of value 1-10, e.g. n is 1, 2, 3, 4, 5, 6, 7, 8, 9, or 10.
In some cases, the compound of Formula I is selected from a group consisting of
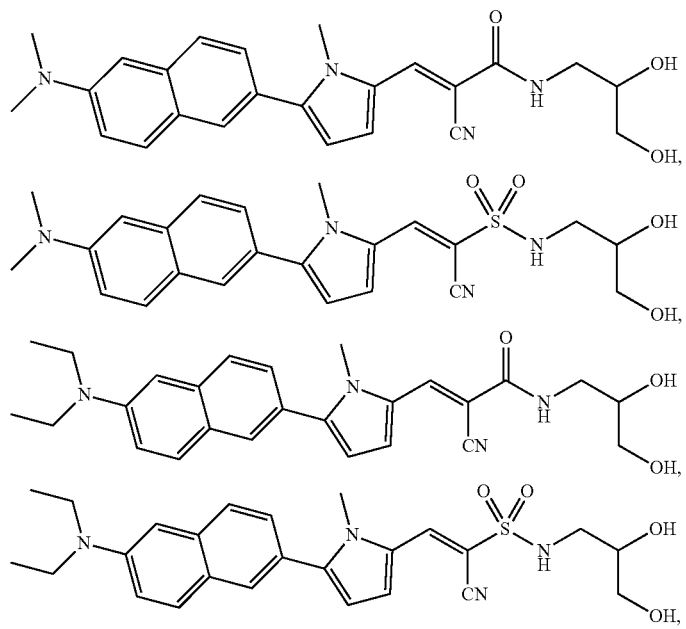

-continued
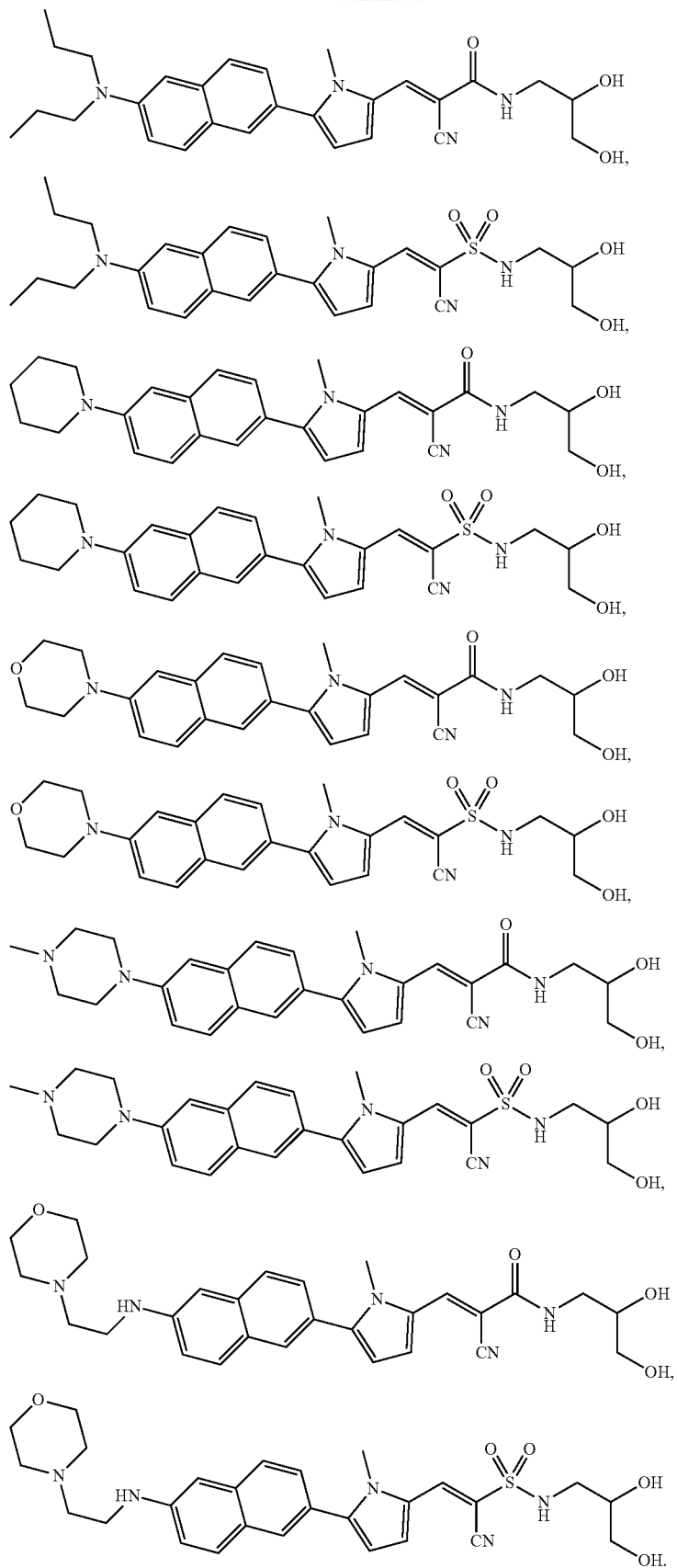

In some cases, the compound of Formula I is selected from a group consisting of
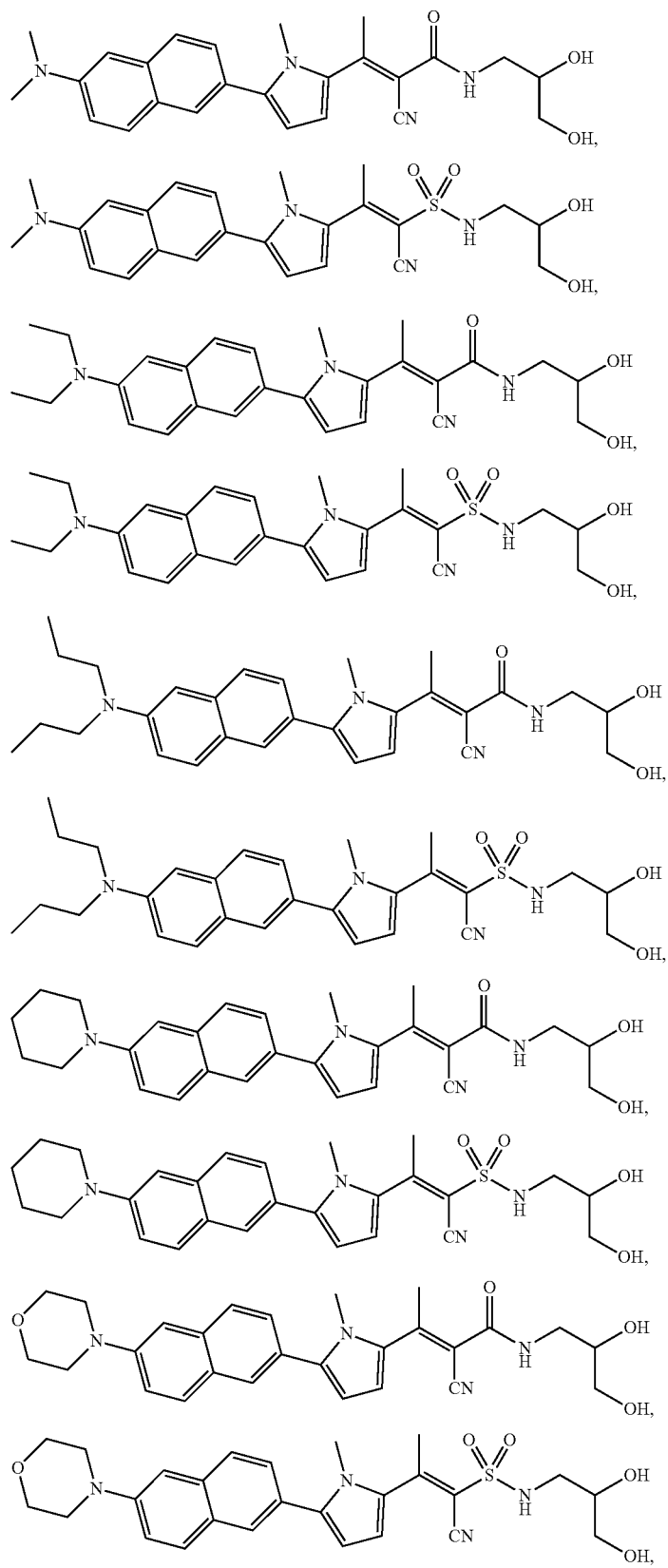

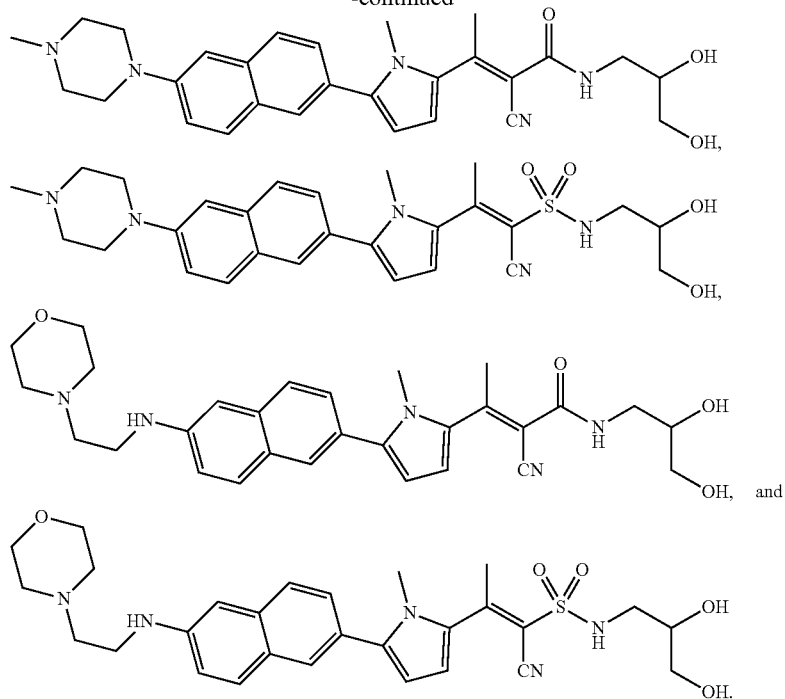
In some cases, the compound of Formula I is selected from a group consisting of
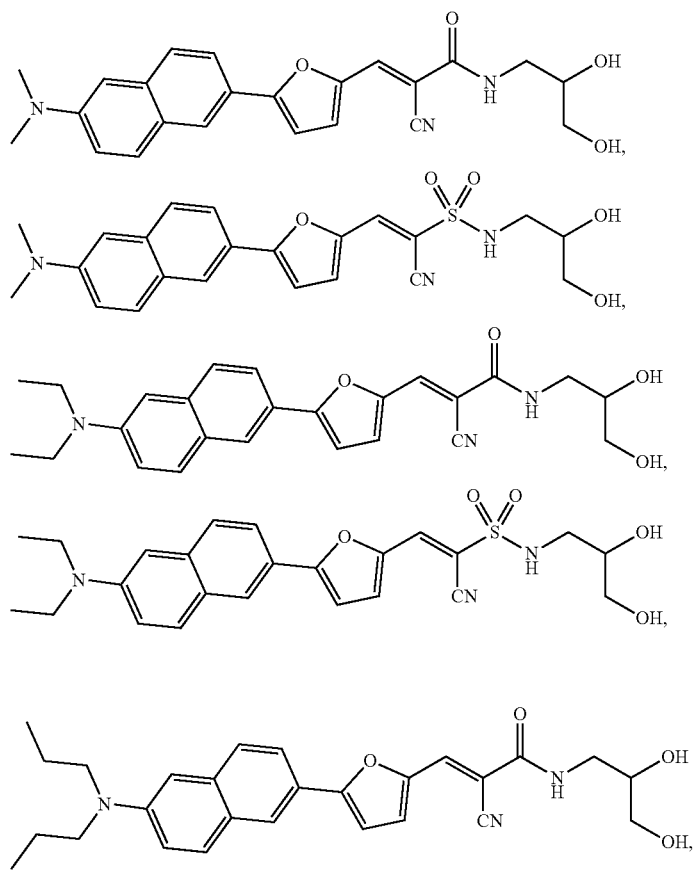

-continued
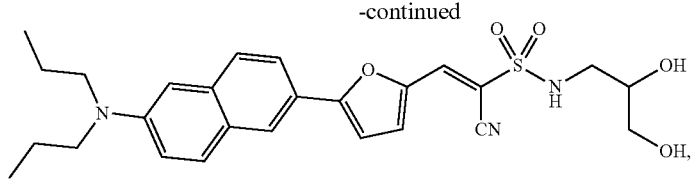
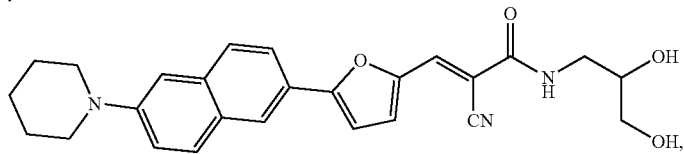
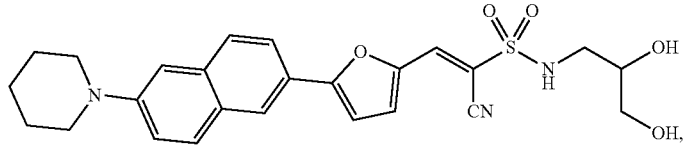
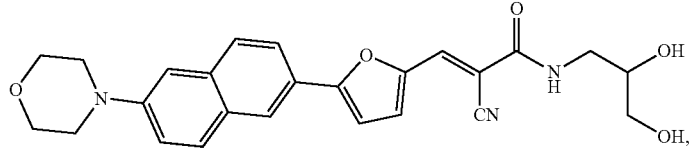
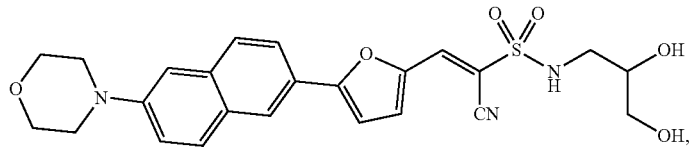
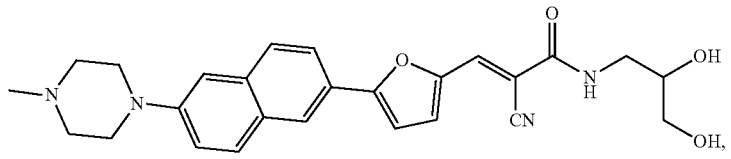
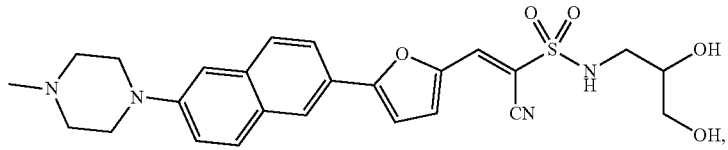
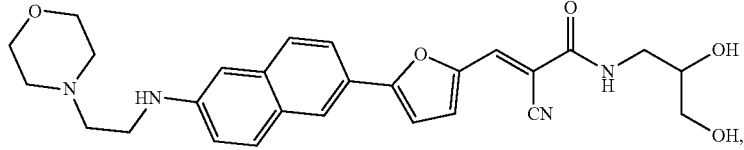
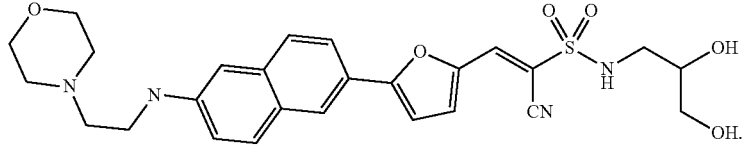
In some cases, the compound of Formula I is selected from a group consisting of
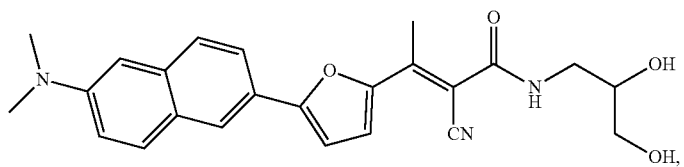

-continued
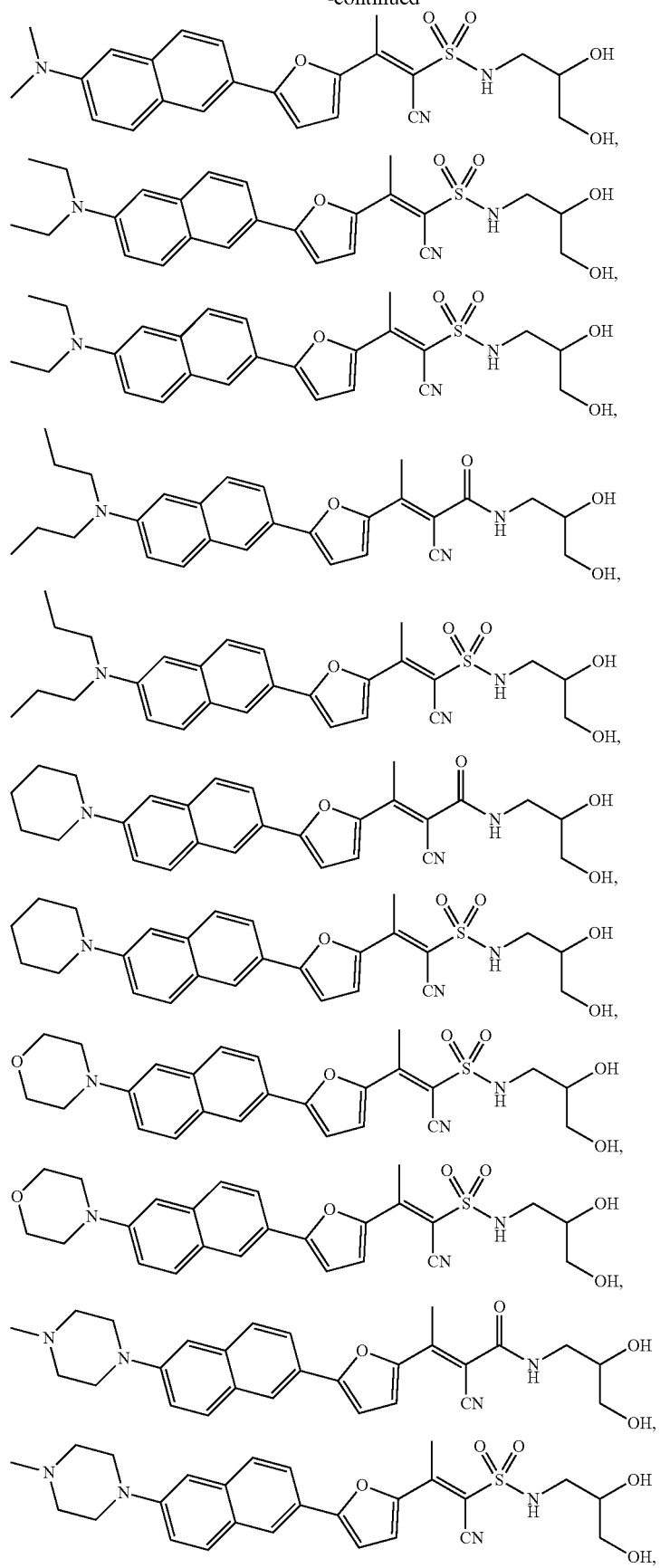

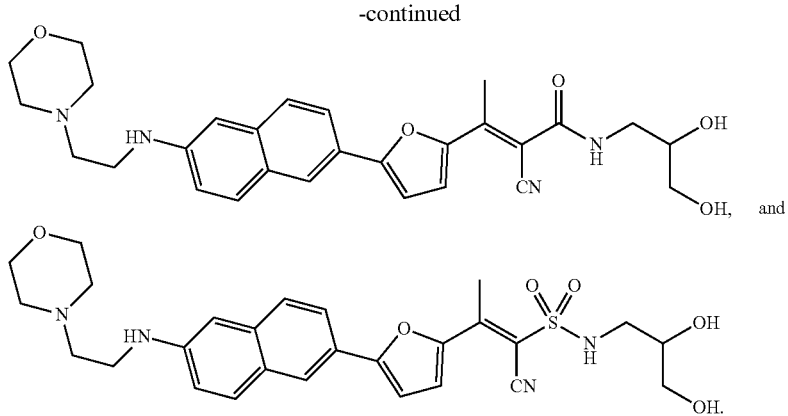
In some cases, the compound of Formula I is selected from a group consisting of
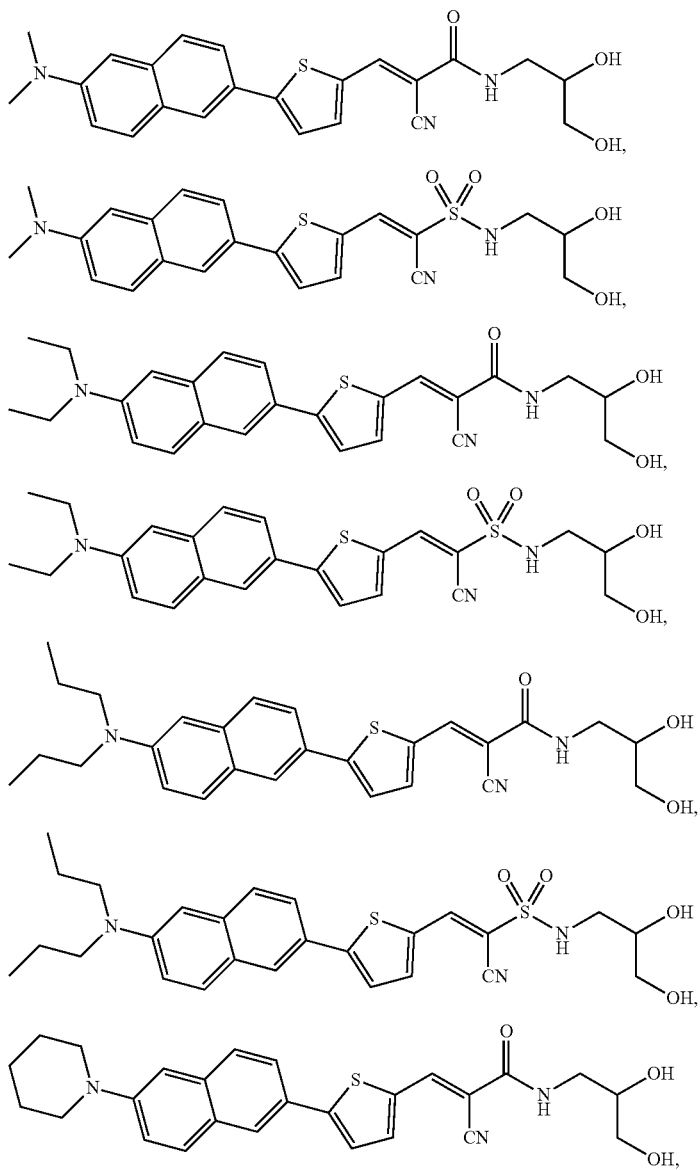

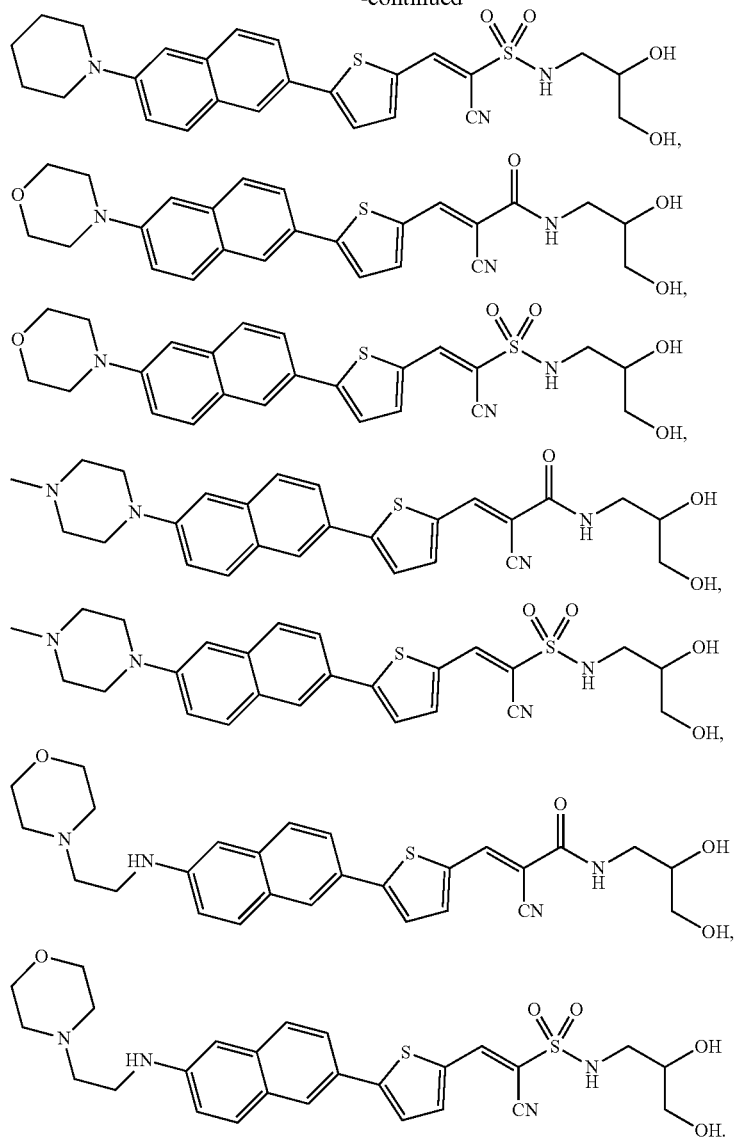
In some cases, the compound of Formula I is selected from a group consisting of
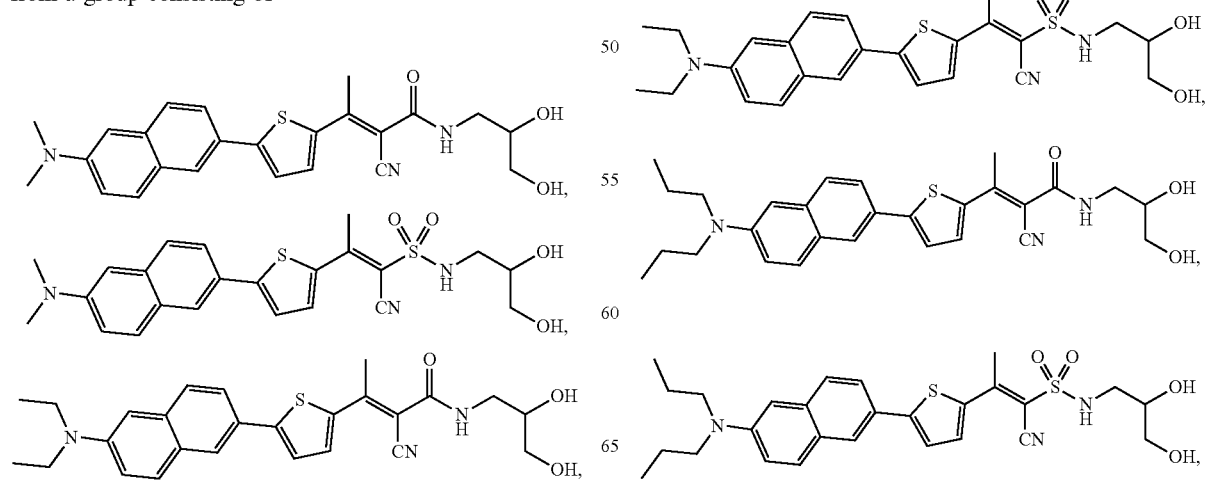

133
-continued
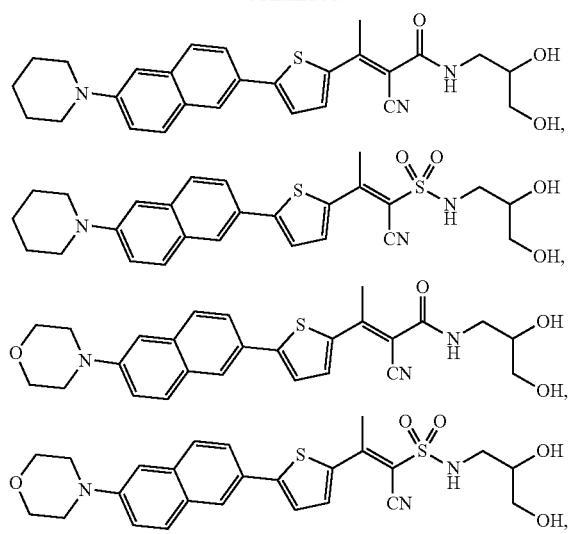
134
-continued
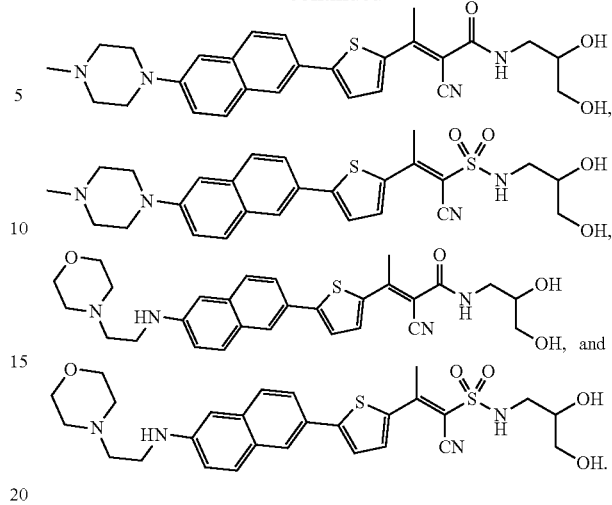
In some cases, the compound of Formula I is selected from a group consisting of
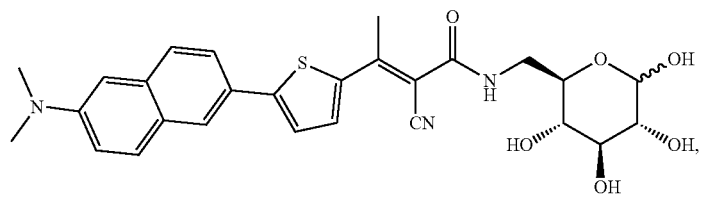
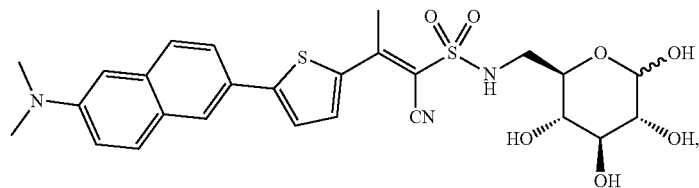
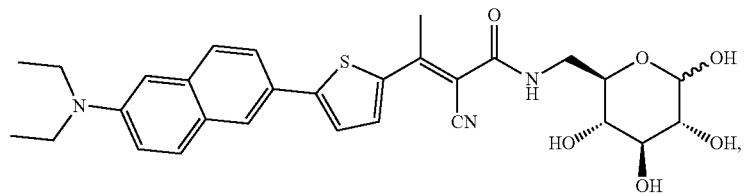
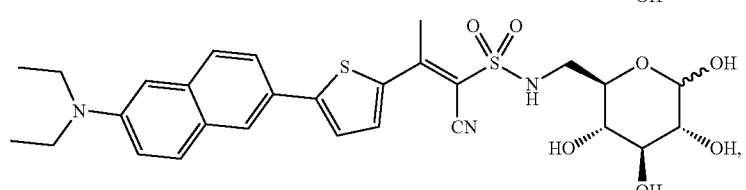
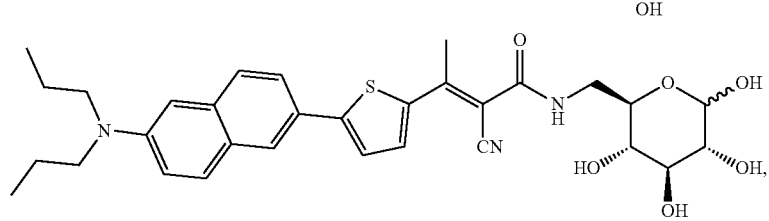

-continued
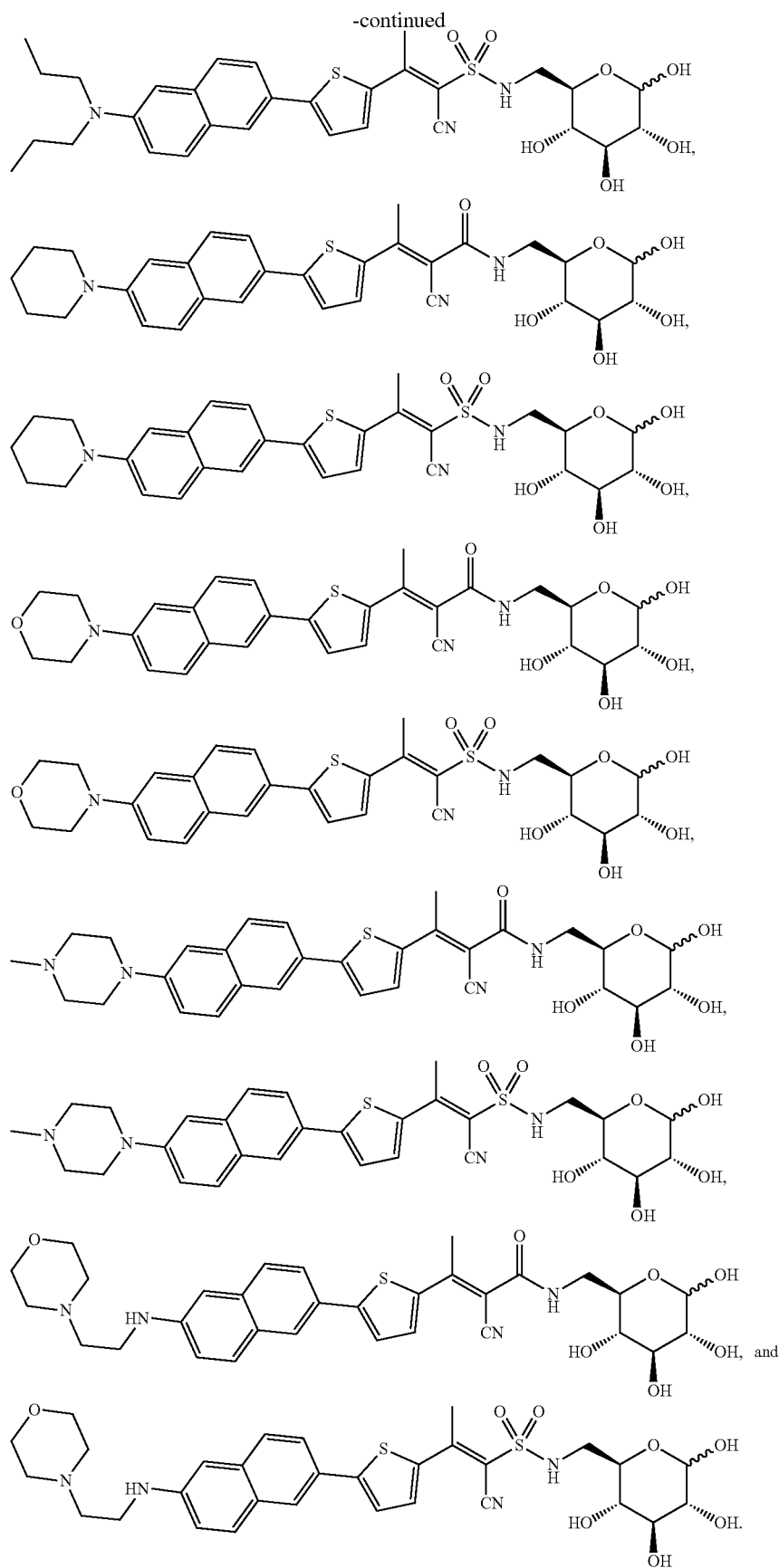

In some cases, the compound of Formula I is selected from a group consisting of
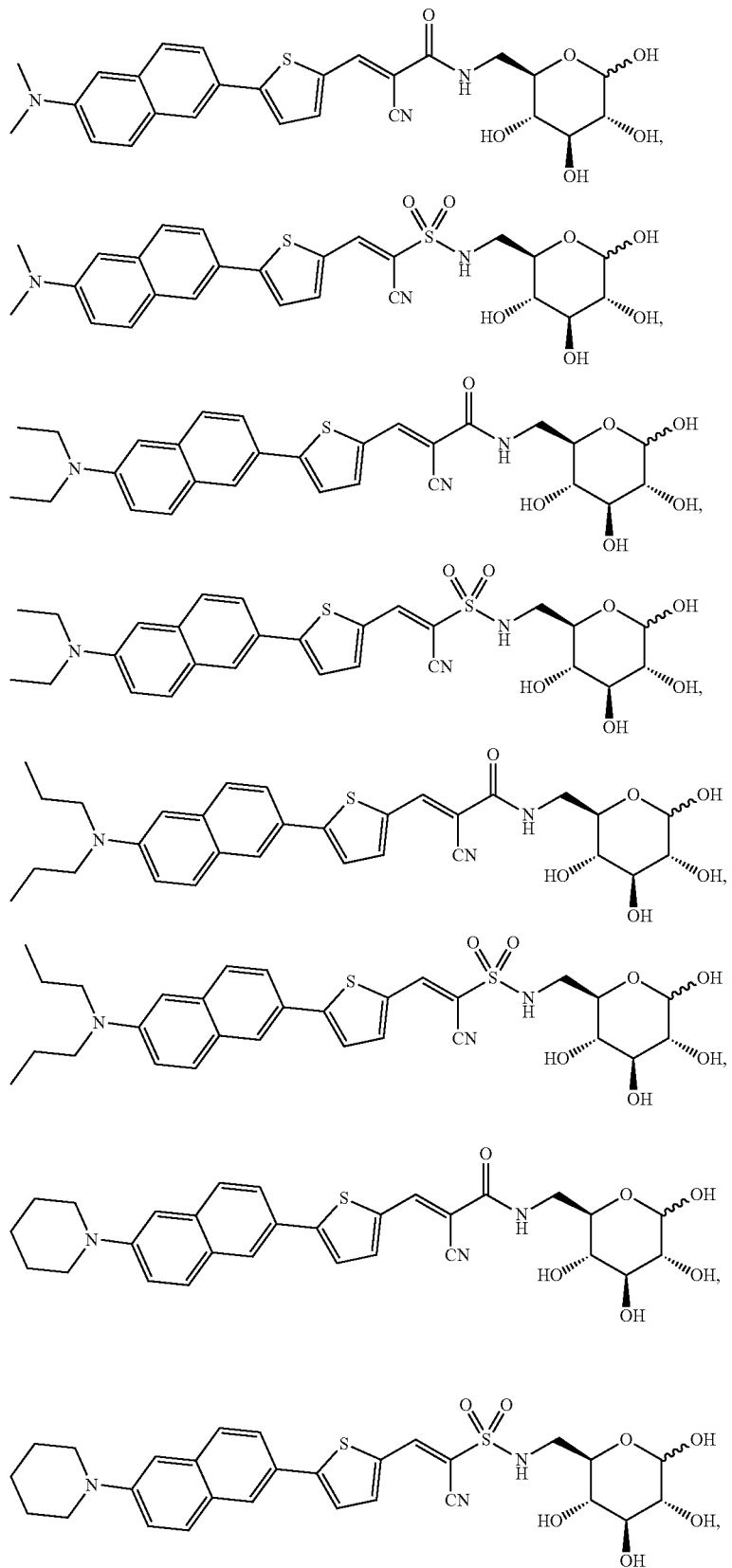

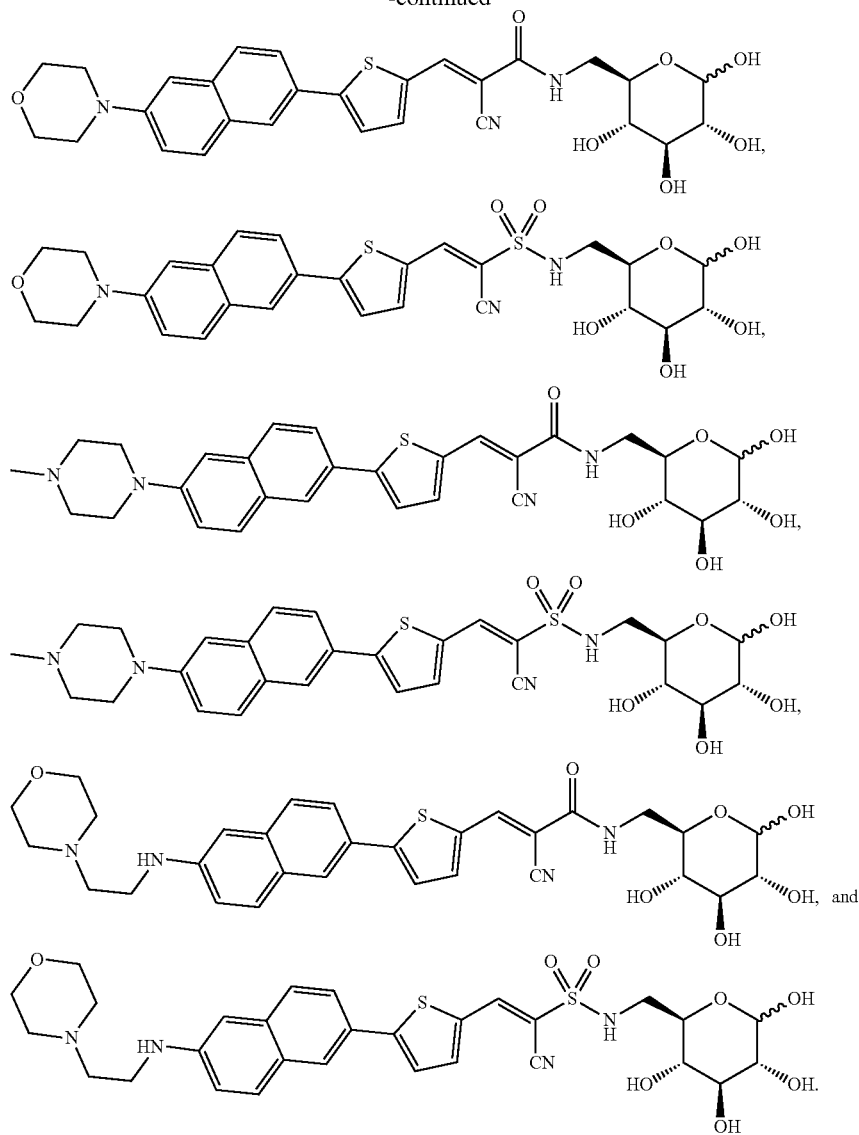
In some cases, the compound of Formula I is selected from a group consisting of
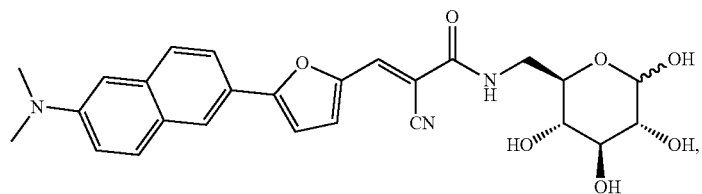
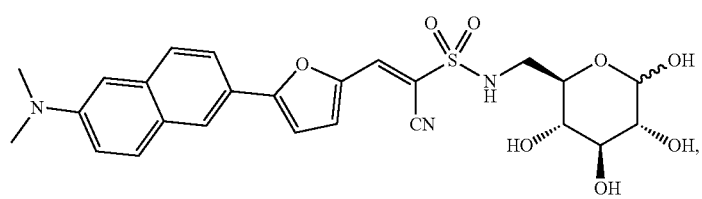

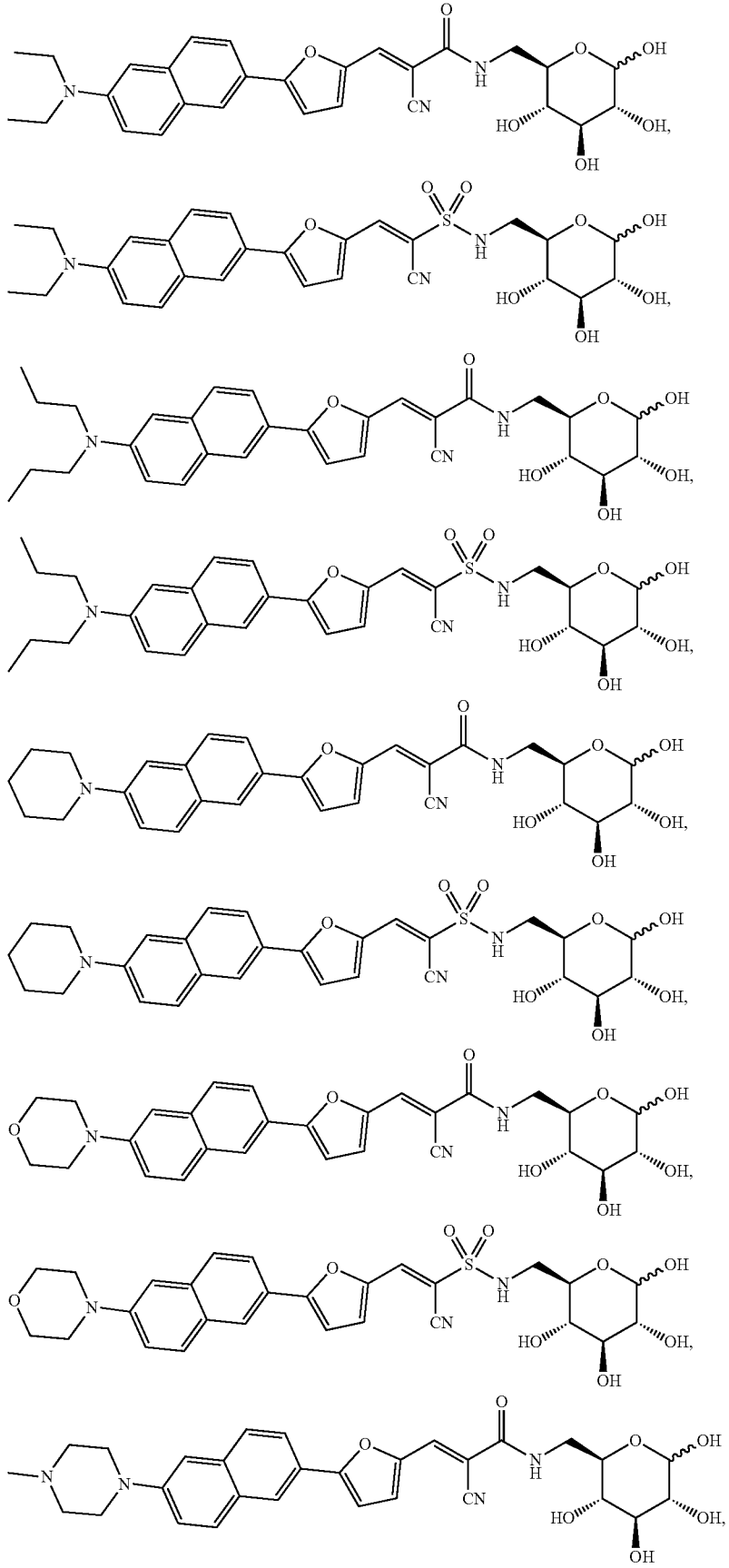

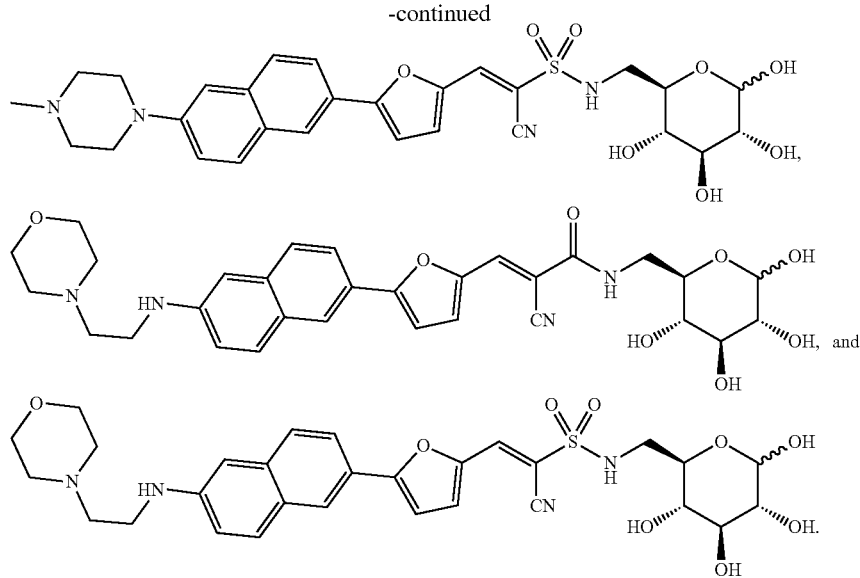
In some cases, the compound of Formula I is selected from a group consisting of
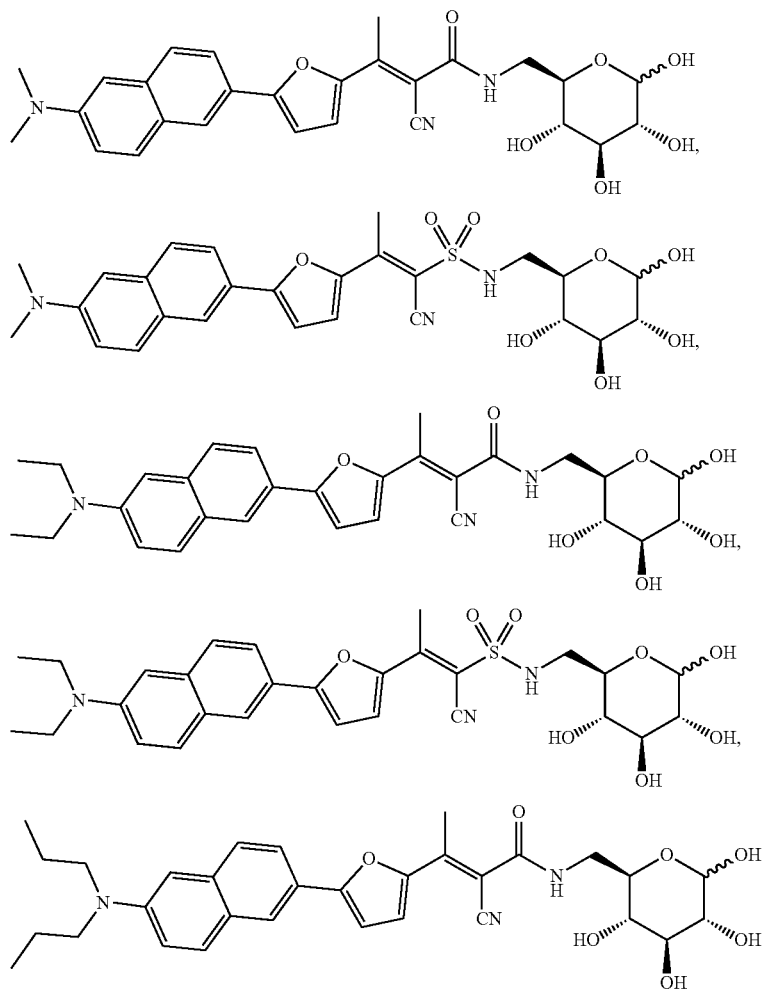

-continued
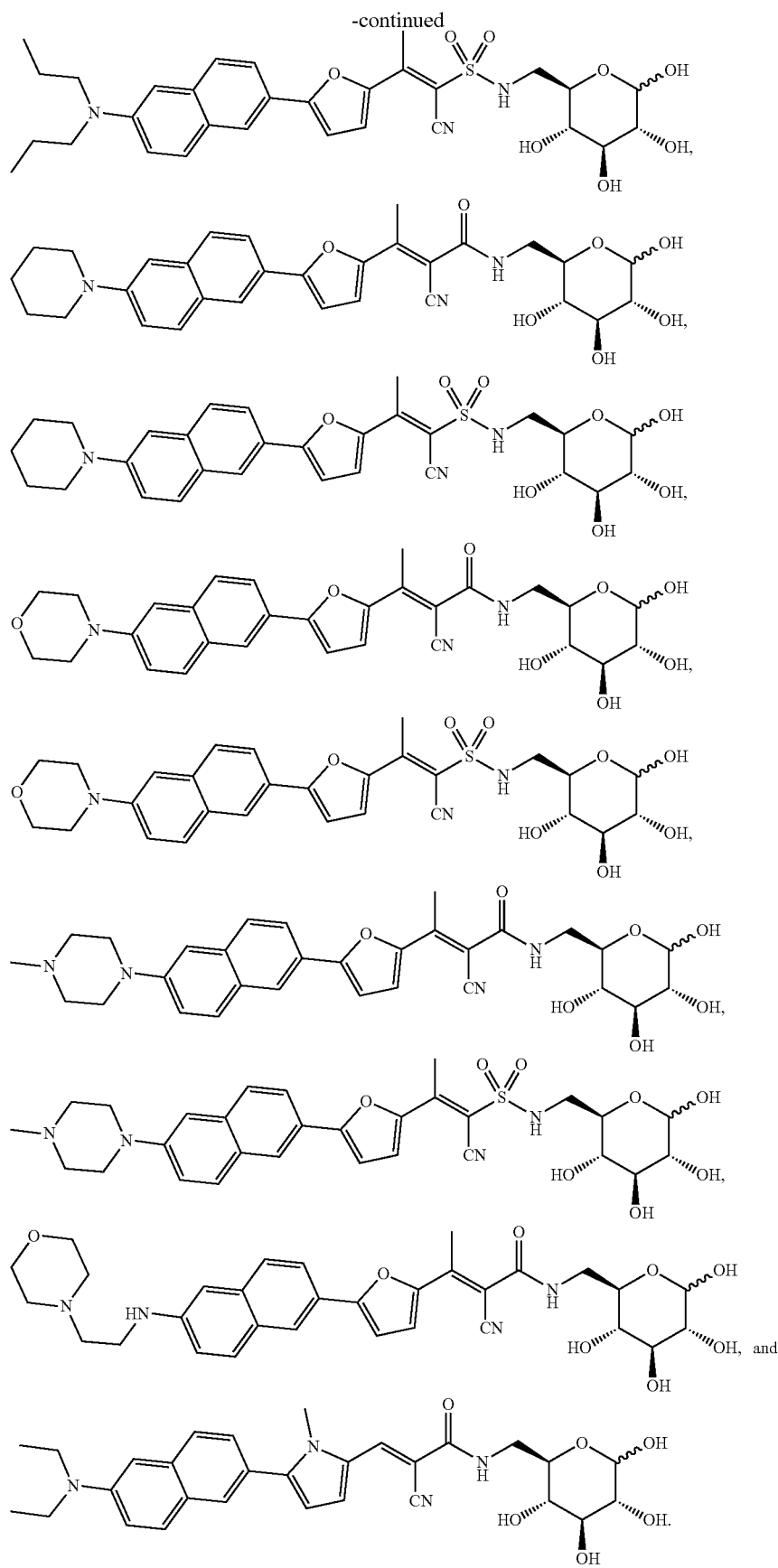

In some cases, the compound of Formula I is selected from a group consisting of
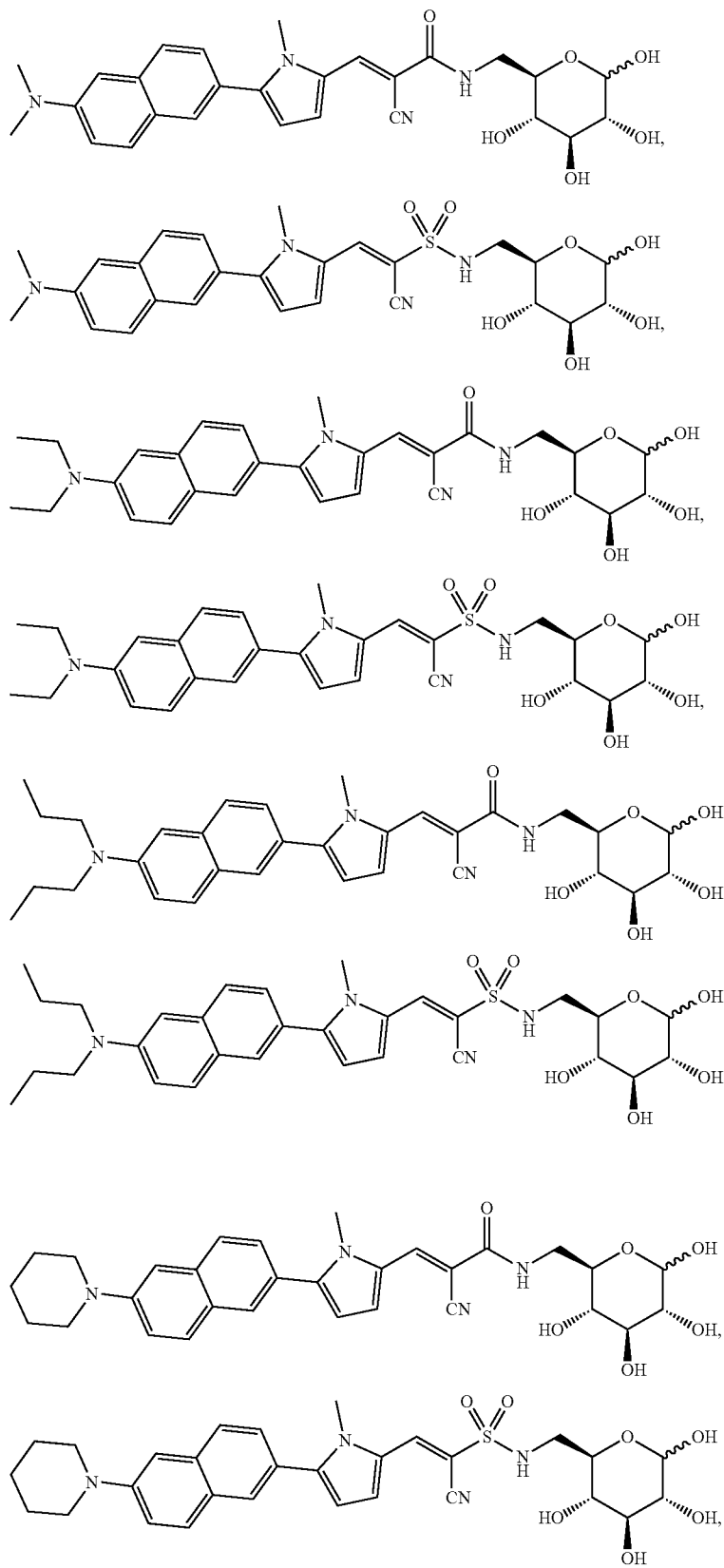

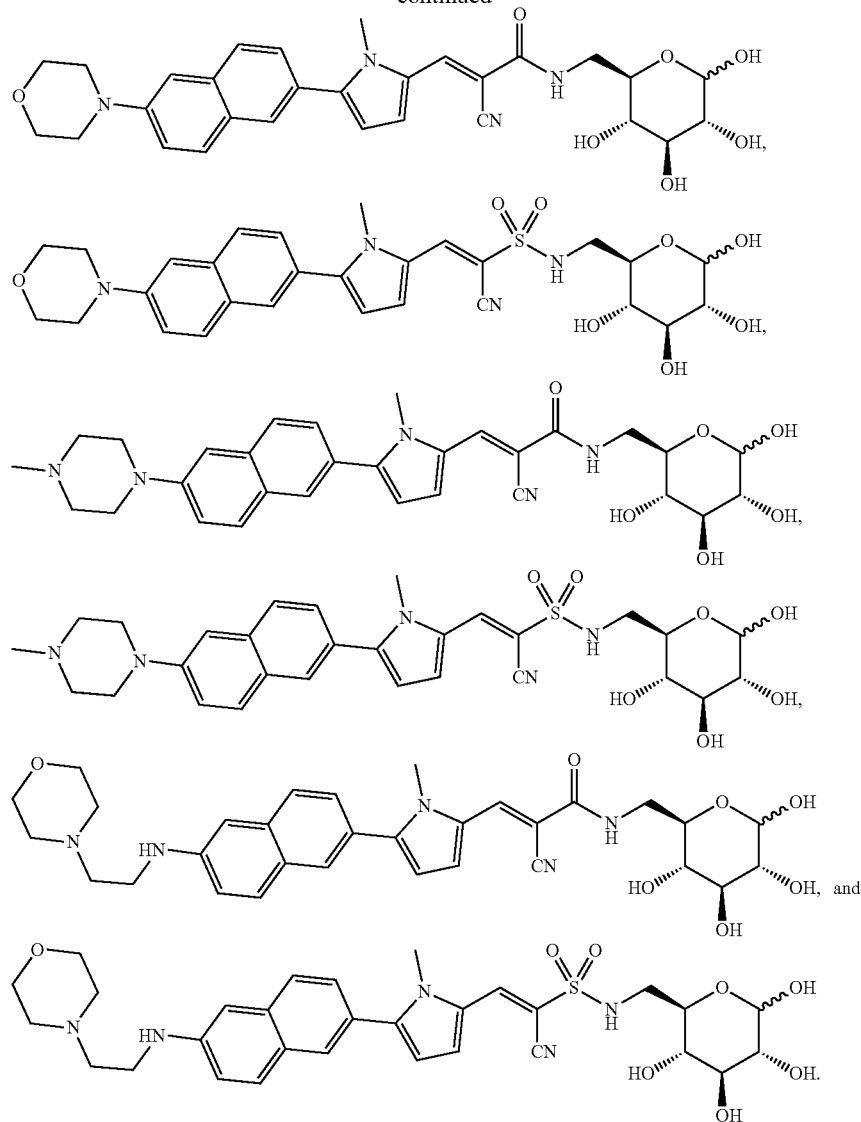
In some cases, the compound of Formula I is selected from a group consisting of
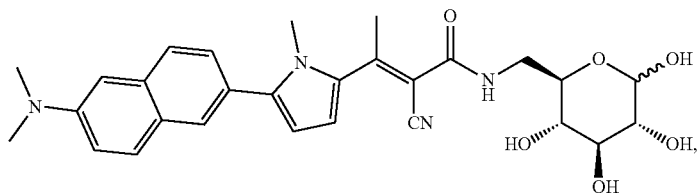
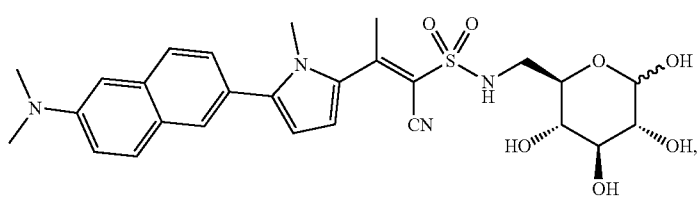

-continued
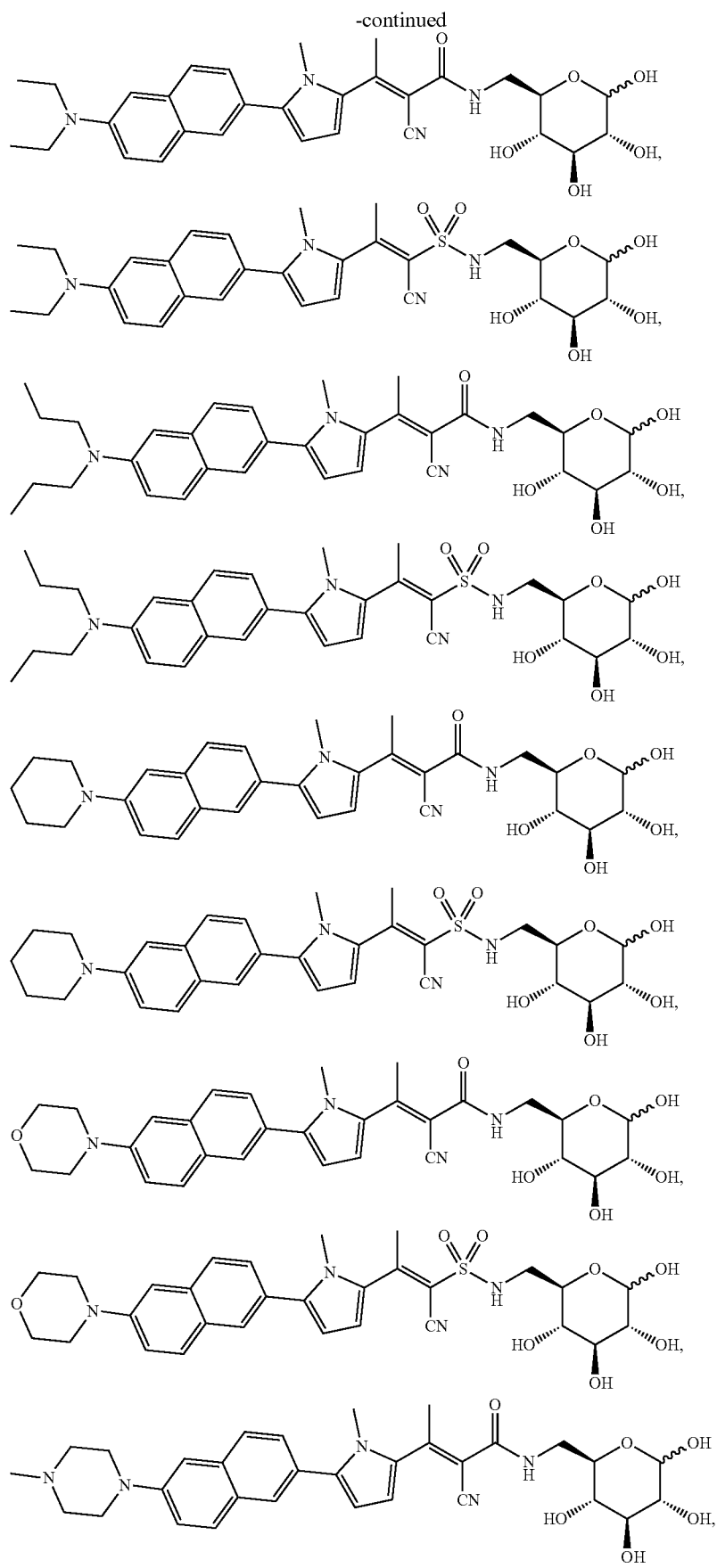

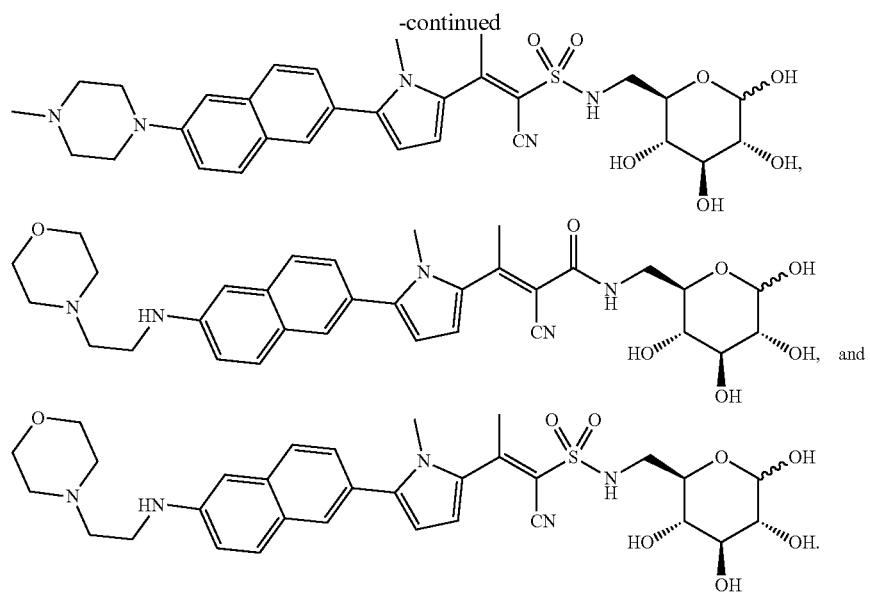
In some cases, the compound of Formula I is selected from a group consisting of
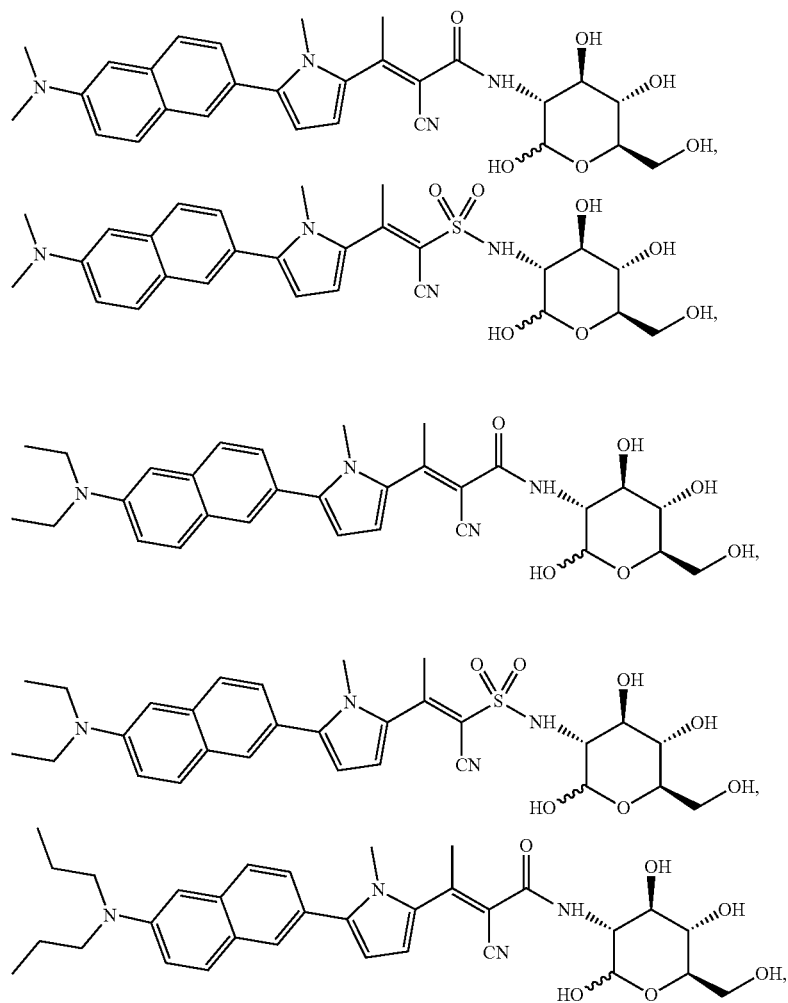

-continued
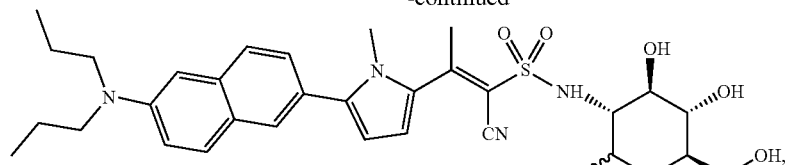
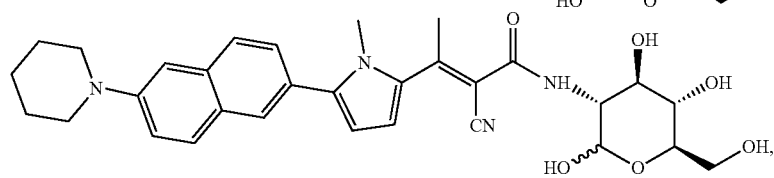
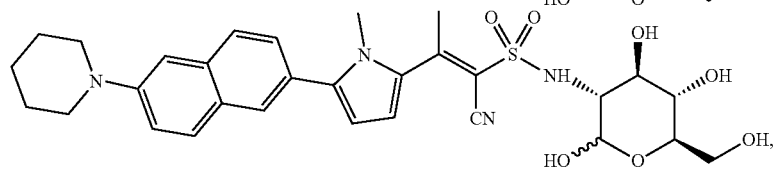
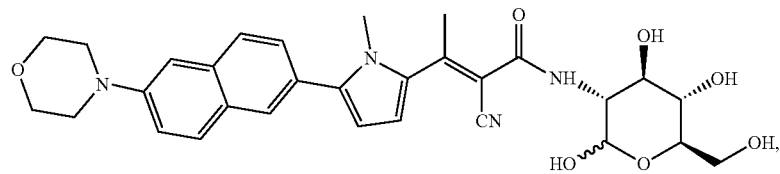
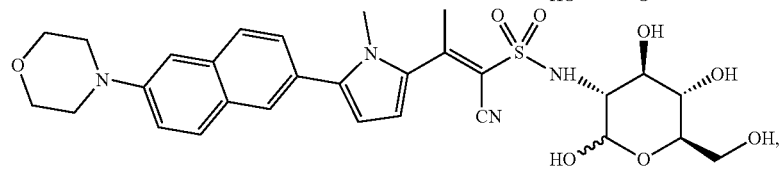
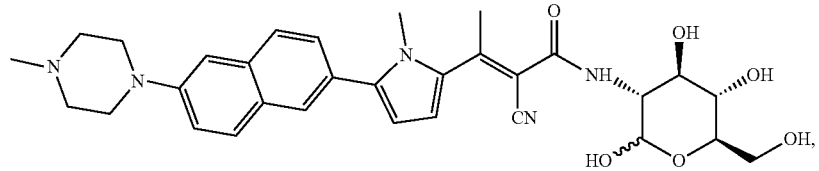
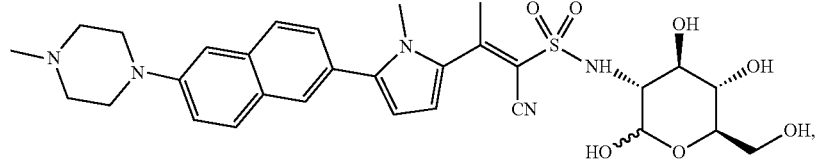
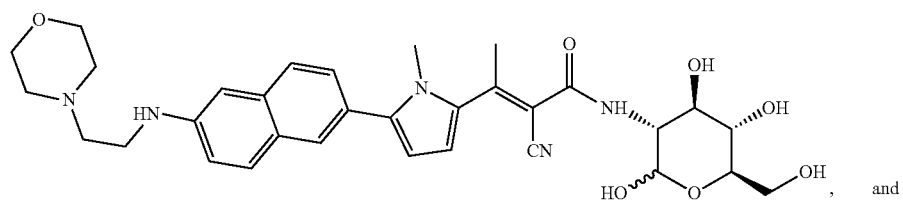
, and
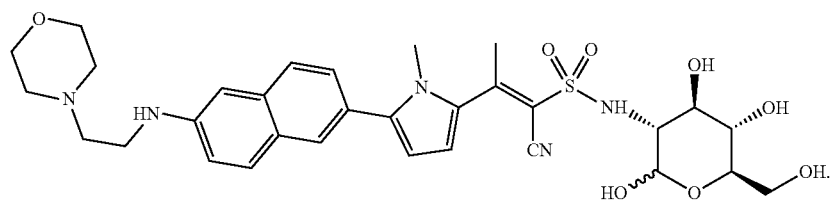

In some cases, the compound of Formula I is selected from a group consisting of
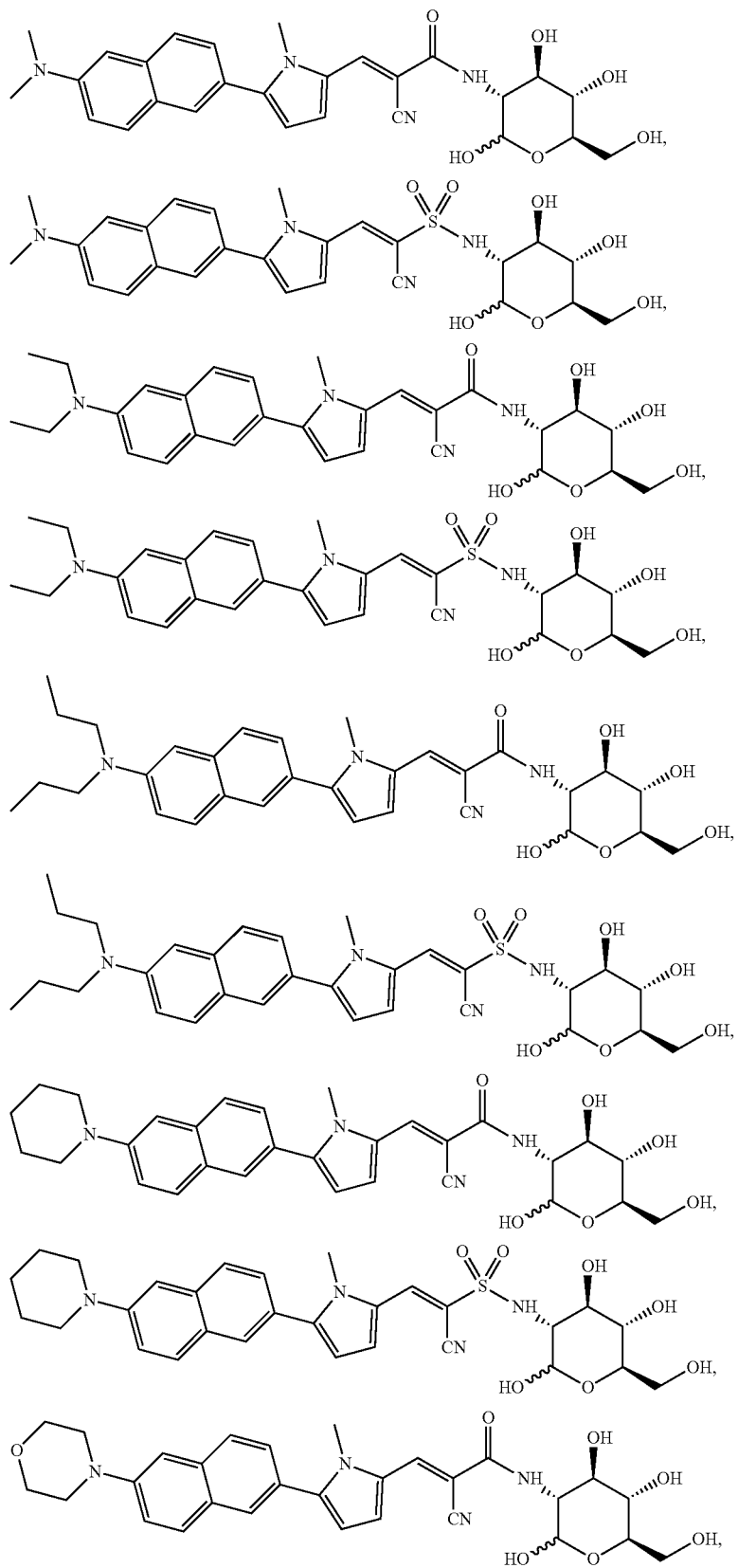

-continued
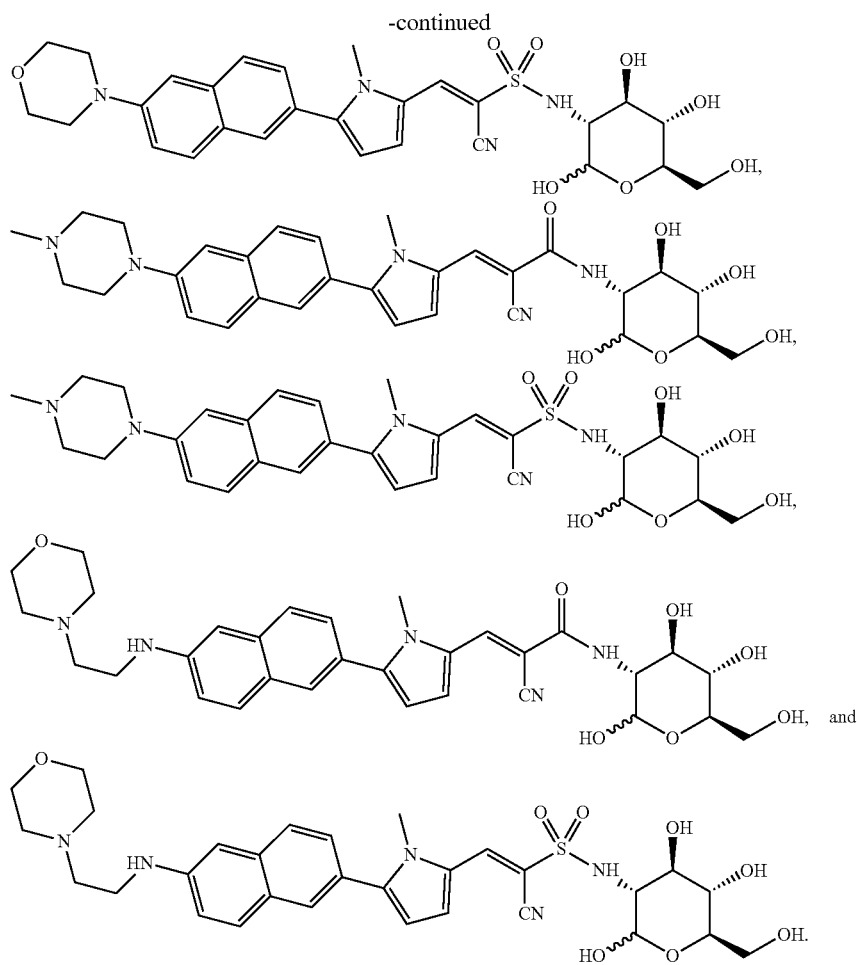
In some cases, the compound of Formula I is selected from a group consisting of
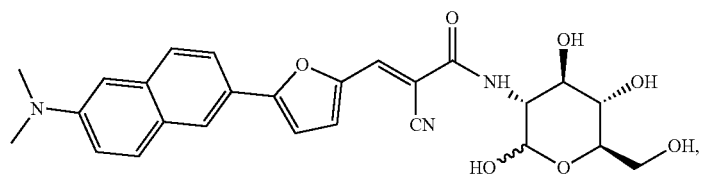
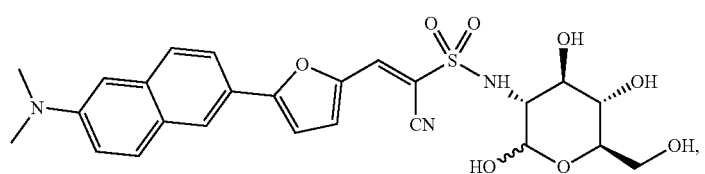
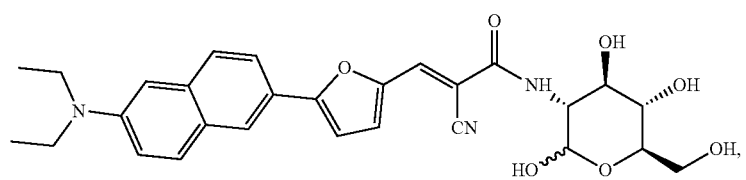

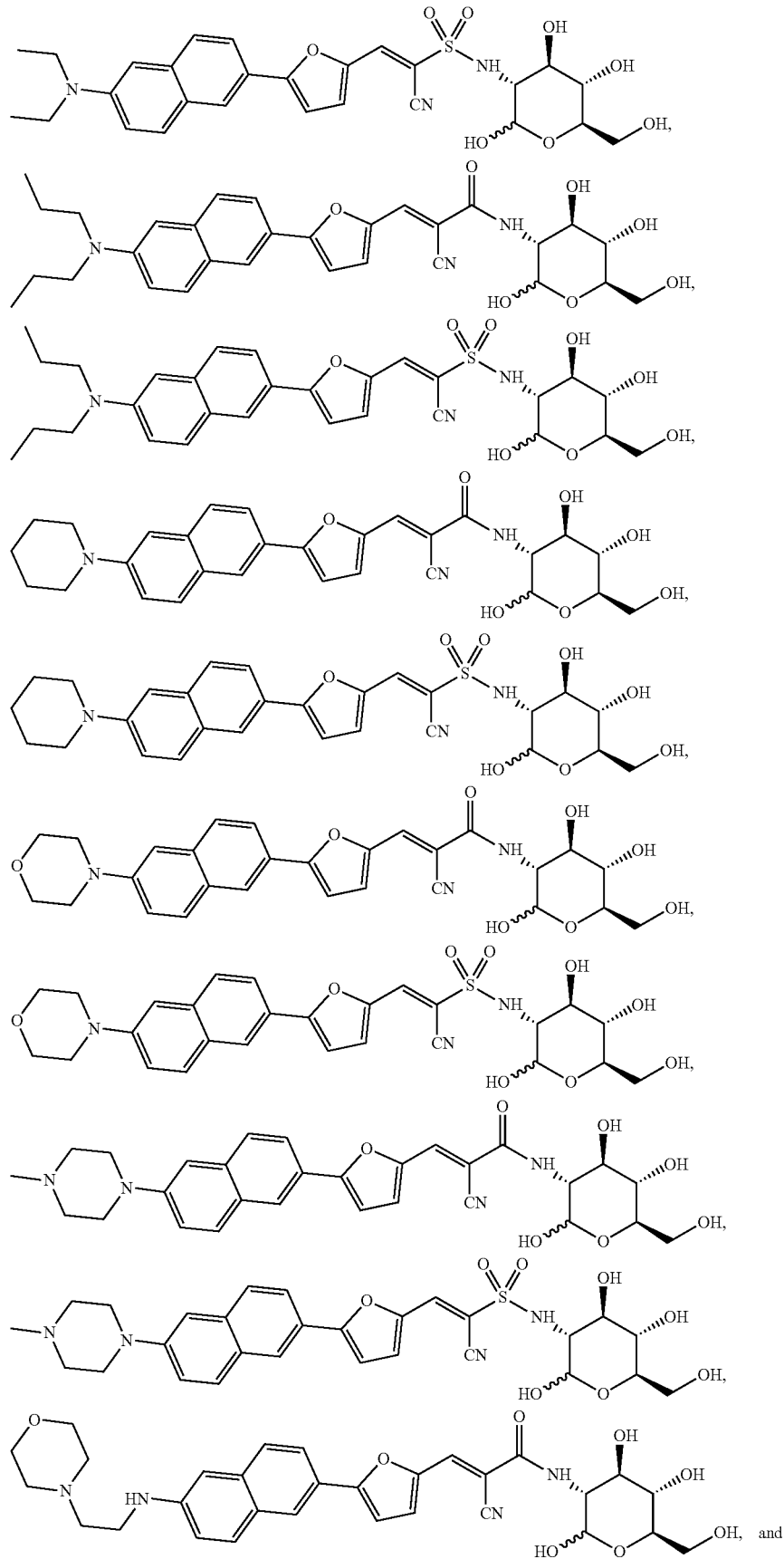

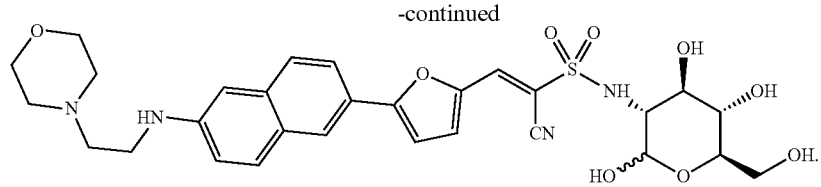
In some cases, the compound of Formula I is selected from a group consisting of
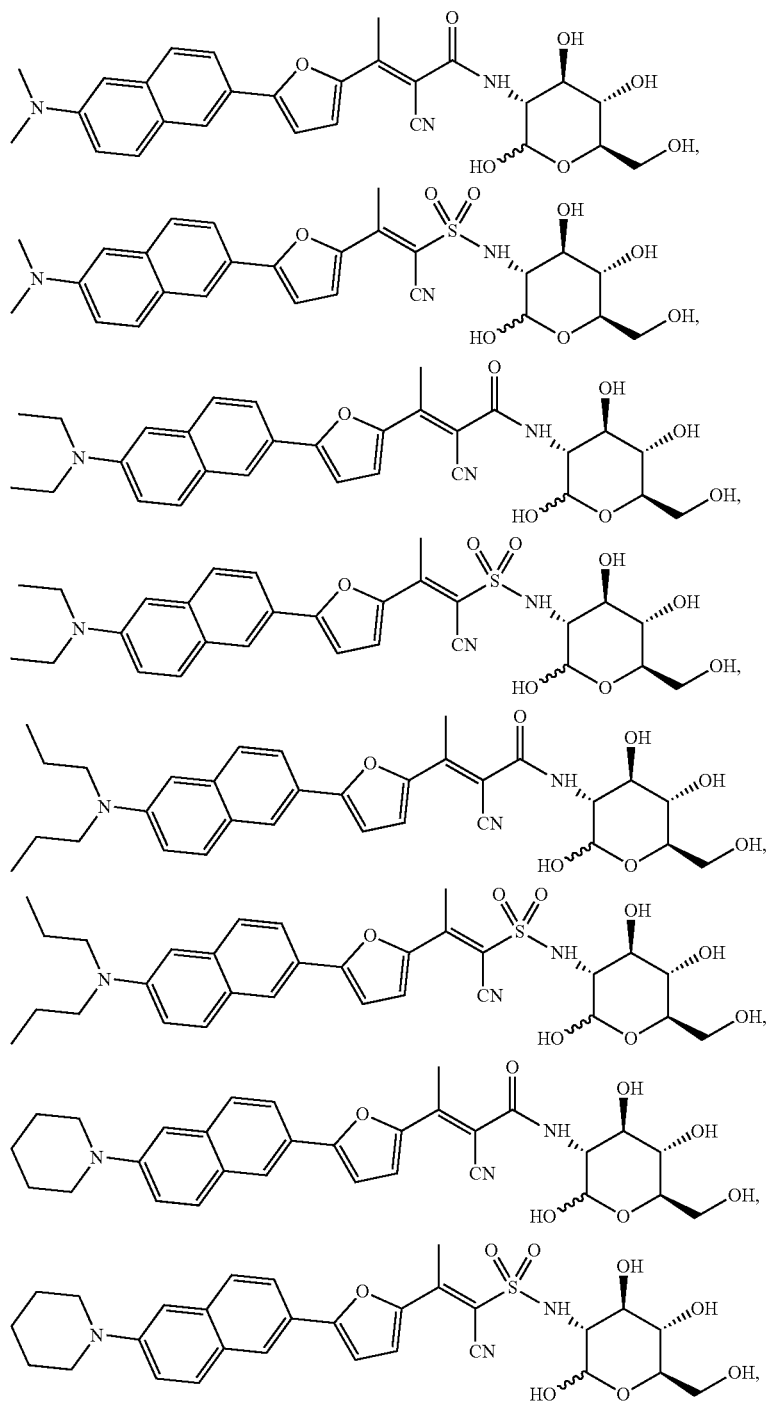

-continued
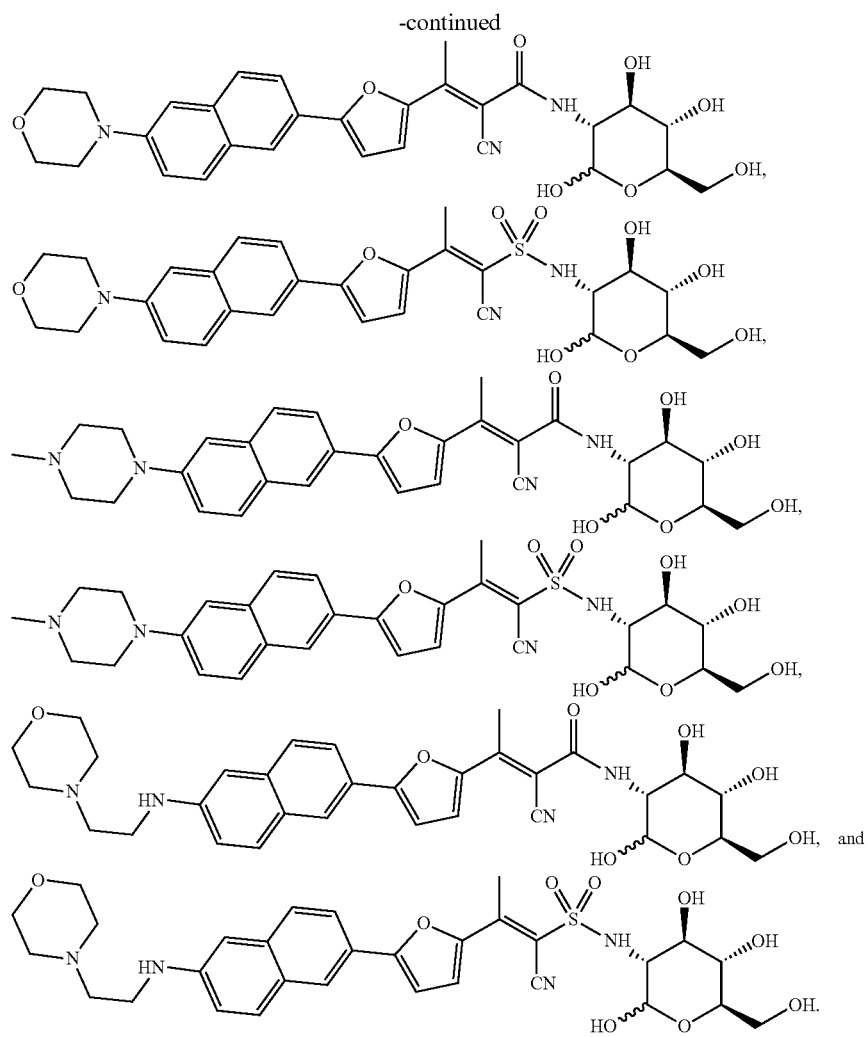
In some cases, the compound of Formula I is selected from a group consisting of
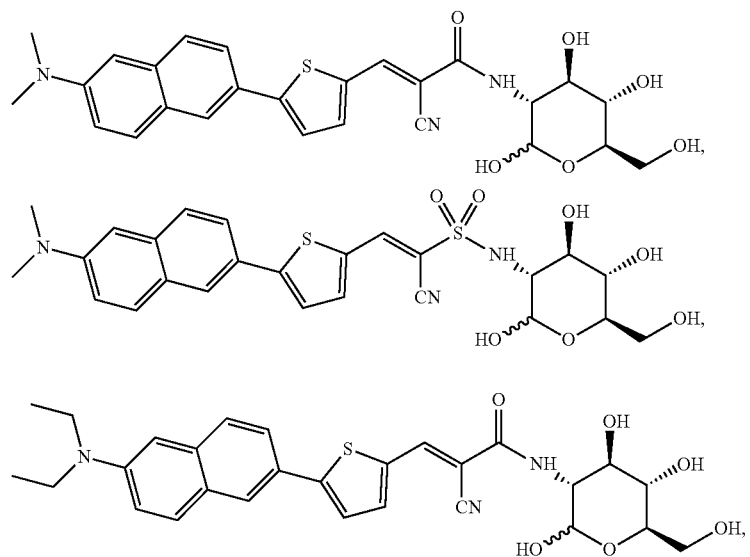

-continued
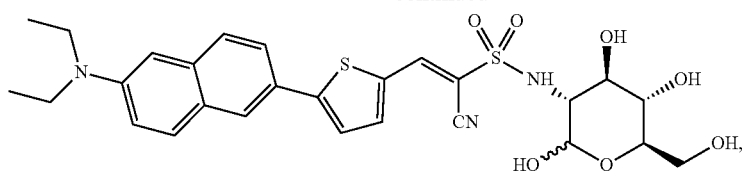
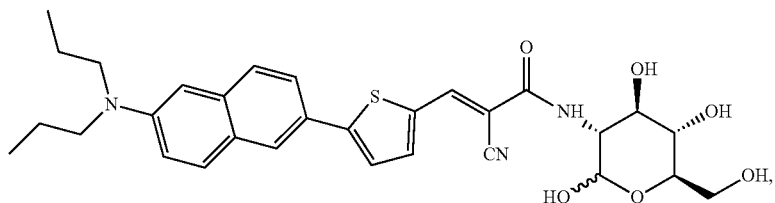
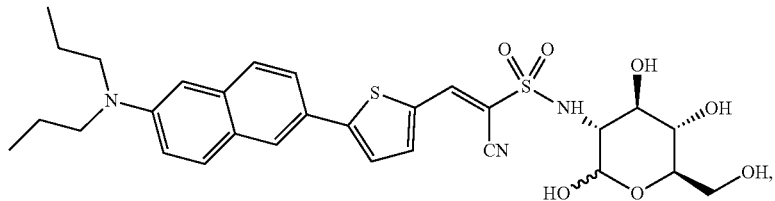
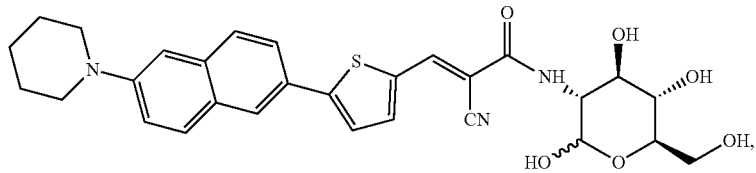
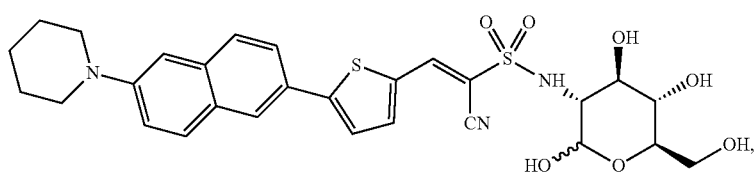
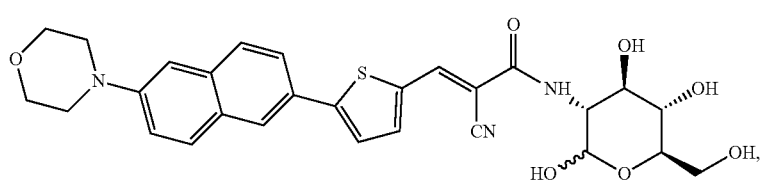
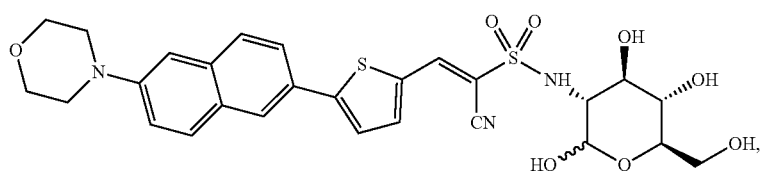
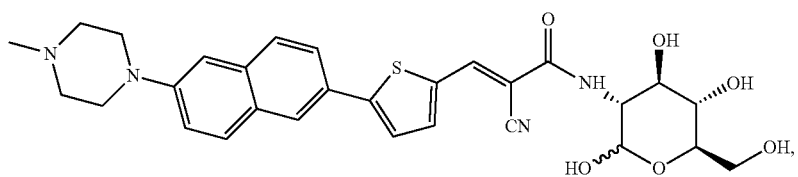
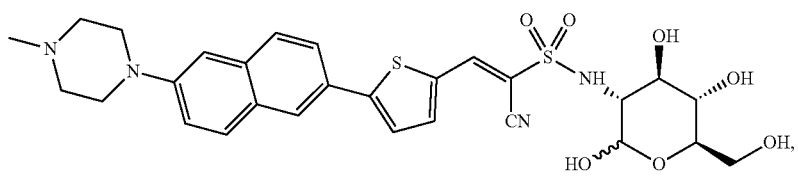

-continued
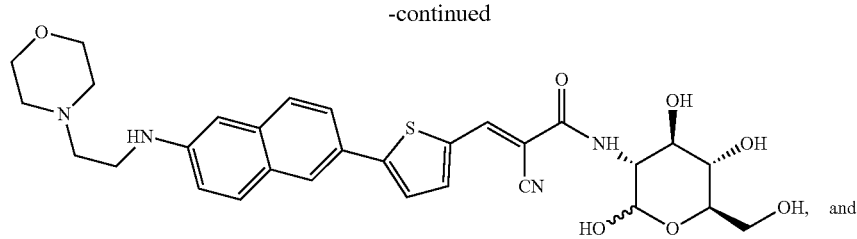
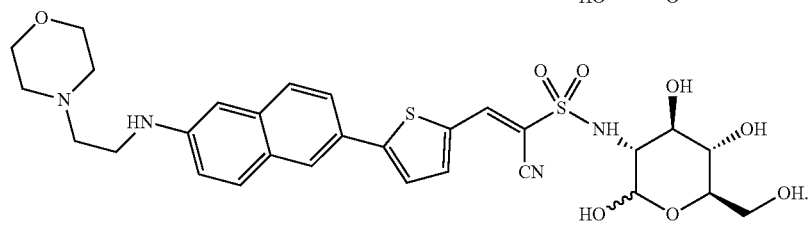
In some cases, the compound of Formula I is selected from a group consisting of
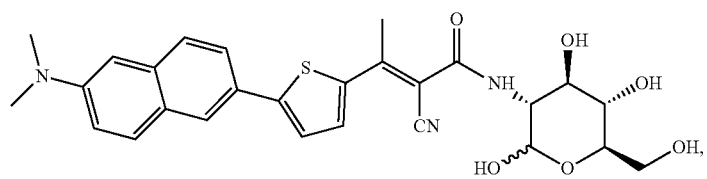
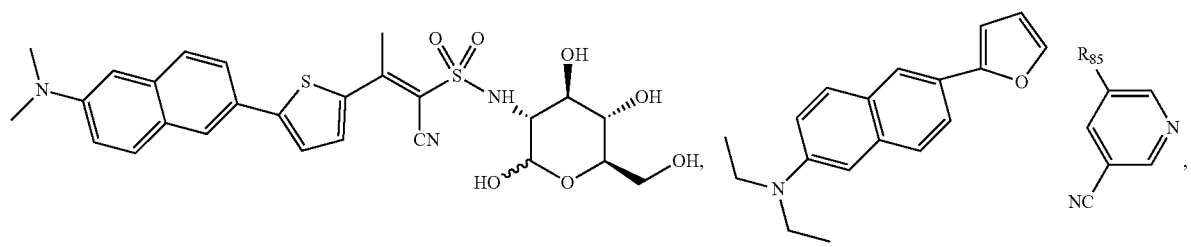
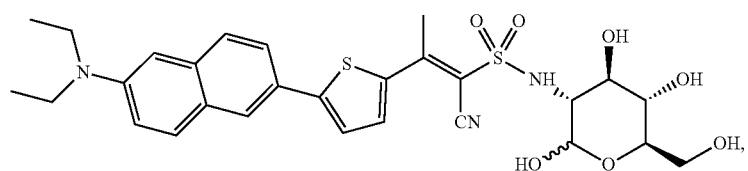
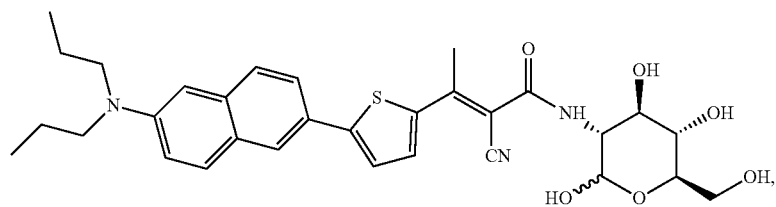
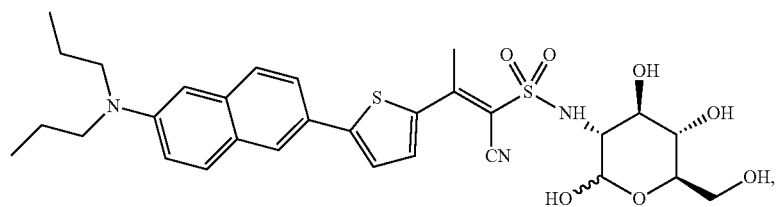

-continued
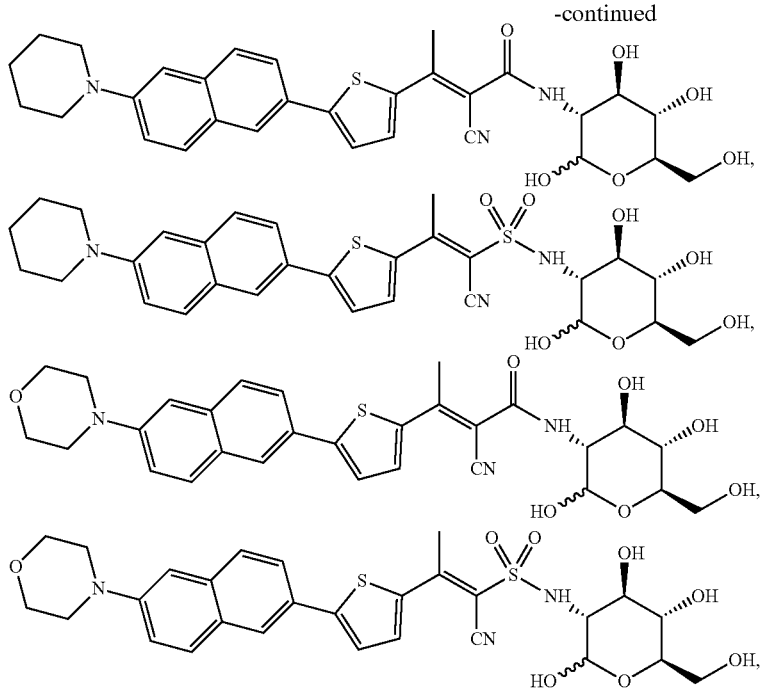
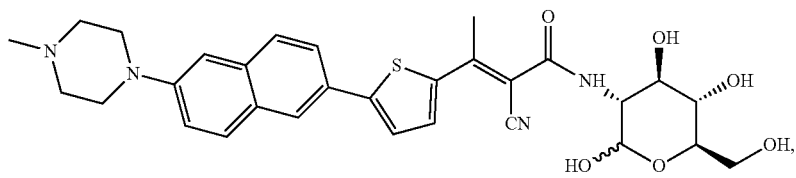
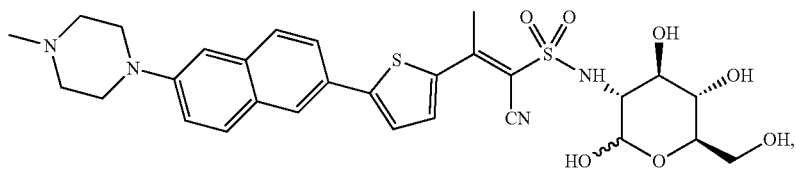
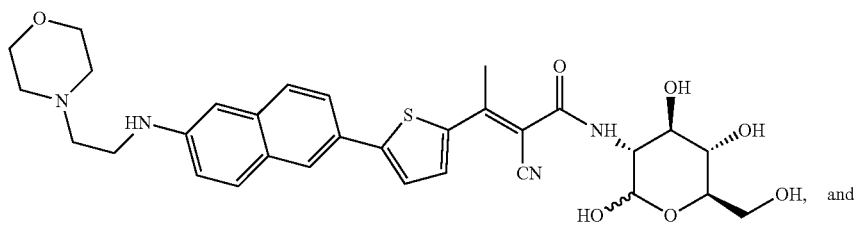
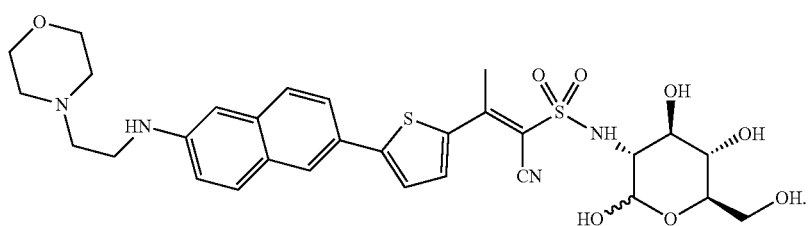

In some cases, the compound of Formula I

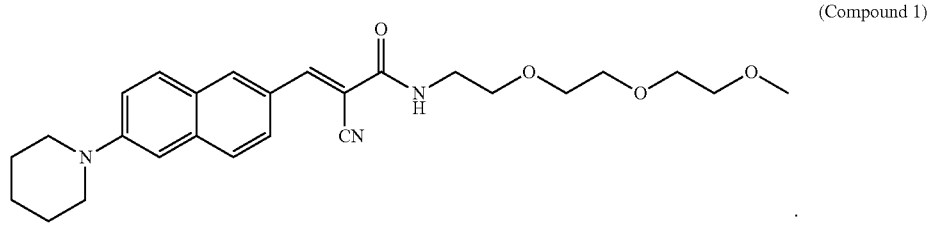 [SMILES: COCCOCCOCCNC(=O)/C(C#N)=C/c1ccc2cc(N3CCCCC3)ccc2c1]
(Compound 1)

In some cases, the compound of Formula I is (E)-2-cyano-N-(2-(2-(2-methoxyethoxy)ethoxy)ethyl)-3-(6-(piperidin-1-yl)naphthalen-2-yl)acrylamide. In some cases, the compound of Formula I is (Z)-2-cyano-N-(2-(2-(2-methoxyethoxy)ethoxy)ethyl)-3-(6-(piperidin-1-yl)naphthalen-2-yl)acrylamide.

In some cases, the compound of Formula I is:

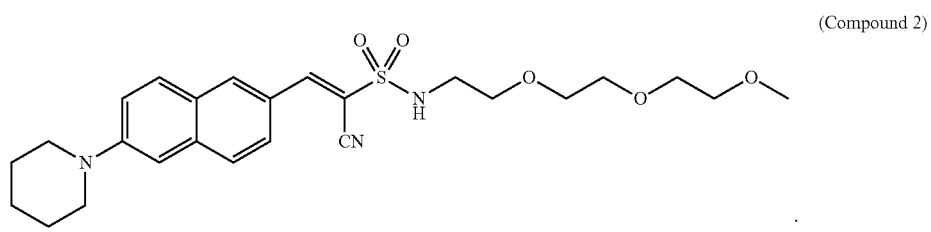 [SMILES: COCCOCCOCCNS(=O)(=O)/C(C#N)=C/c1ccc2cc(N3CCCCC3)ccc2c1]
(Compound 2)

In some cases, the compound of Formula I is (E)-1-cyano-N-(2-(2-(2-methoxyethoxy)ethoxy)ethyl)-2-(6-(piperidin-1-yl)naphthalen-2-yl)ethenesulfonamide. In some cases, the compound of Formula I is (Z)-1-cyano-N-(2-(2-(2-methoxyethoxy)ethoxy)ethyl)-2-(6-(piperidin-1-yl)naphthalen-2-yl)ethenesulfonamide.

In some cases, the compound of Formula I is:

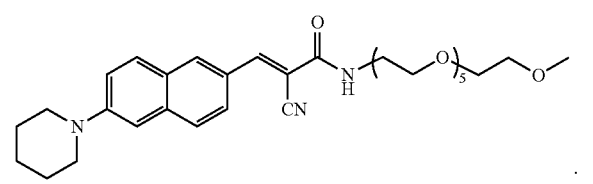
(Compound 3)

In some cases, the compound of Formula I is (E)-2-cyano-N-(2,5,8,11,14,17-hexaoxanonadecan-19-yl)-3-(6-(piperidin-1-yl)naphthalen-2-yl)acrylamide. In some cases, the compound of Formula I is (Z)-2-cyano-N-(2,5,8,11,14,17-hexaoxanonadecan-19-yl)-3-(6-(piperidin-1-yl)naphthalen-2-yl)acrylamide.

In some cases, the compound of Formula I is:

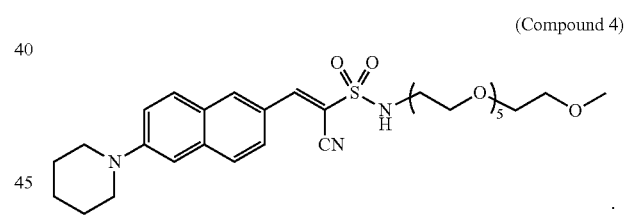
(Compound 4)

In some cases, the compound of Formula I is (E)-1-cyano-N-(2,5,8,11,14,17-hexaoxanonadecan-19-yl)-2-(6-(piperidin-1-yl)naphthalen-2-yl)ethenesulfonamide. In some cases, the compound of Formula I is (Z)-1-cyano-N-(2,5,8,11,14,17-hexaoxanonadecan-19-yl)-2-(6-(piperidin-1-yl)naphthalen-2-yl)ethenesulfonamide.

In some cases, the compound of Formula I is:

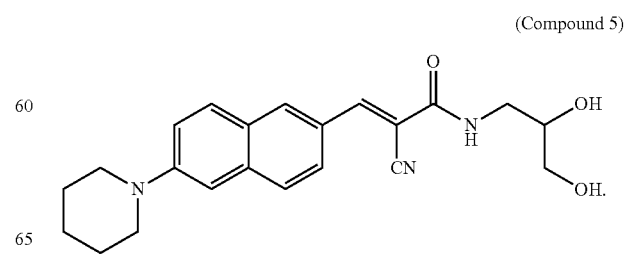
(Compound 5)

In some cases, the compound of Formula I is (E)-2-cyano-N-(2,3-dihydroxypropyl)-3-(6-(piperidin-1-yl)naphthalen-2-yl)acrylamide. In some cases, the compound of Formula I is (Z)-2-cyano-N-(2,3-dihydroxypropyl)-3-(6-(piperidin-1-yl)naphthalen-2-yl)acrylamide.

In some cases, the compound of Formula I is:

(Compound 6)

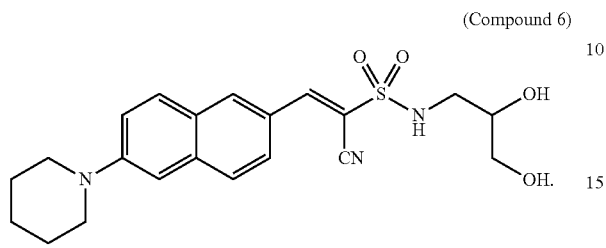

In some cases, the compound of Formula I is (E)-1-cyano-N-(2,3-dihydroxypropyl)-2-(6-(piperidin-1-yl)naphthalen-2-yl)ethenesulfonamide. In some cases, the compound of Formula I is (Z)-1-cyano-N-(2,3-dihydroxypropyl)-2-(6-(piperidin-1-yl)naphthalen-2-yl)ethenesulfonamide.

In some cases, the compound of Formula I is:

(Compound 7)

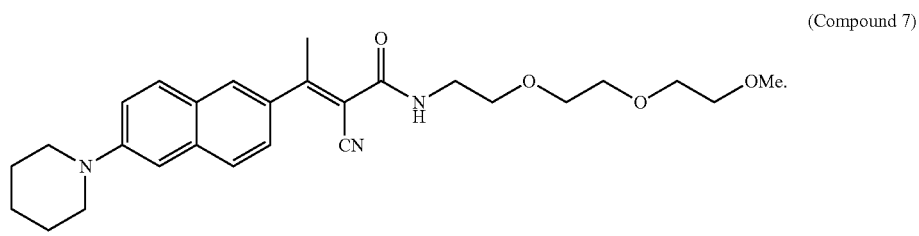 [SMILES: COCCOCCOCCNC(=O)/C(C#N)=C(\C)c1ccc2cc(N3CCCCC3)ccc2c1]

In some cases, the compound of Formula I is (E)-2-cyano-N-(2-(2-(2-methoxyethoxy)ethoxy)ethyl)-3-(6-(piperidin-1-yl)naphthalen-2-yl)but-2-enamide. In some cases, the compound of Formula I is (Z)-2-cyano-N-(2-(2-(2-methoxyethoxy)ethoxy)ethyl)-3-(6-(piperidin-1-yl)naphthalen-2-yl)but-2-enamide.

In some cases, the compound of Formula I is:

In some cases, the compound of Formula I is (E)-1-cyano-N-(2-(2-(2-methoxyethoxy)ethoxy)ethyl)-2-(6-(piperidin-1-yl)naphthalen-2-yl)prop-1-ene-1-sulfonamide. In some cases, the compound of Formula I is (Z)-1-cyano-N-(2-(2-(2-methoxyethoxy)ethoxy)ethyl)-2-(6-(piperidin-1-yl)naphthalen-2-yl)prop-1-ene-1-sulfonamide.

In some cases, the compound of Formula I is:

(Compound 9)

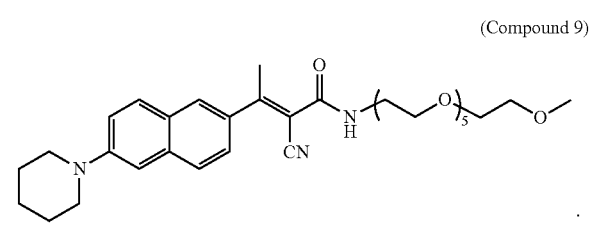

In some cases, the compound of Formula I is (E)-2-cyano-N-(2,5,8,11,14,17-hexaoxanonadecan-19-yl)-3-(6-(piperidin-1-yl)naphthalen-2-yl)but-2-enamide. In some cases, the compound of Formula I is (Z)-2-cyano-N-(2,5,8,11,14,17-hexaoxanonadecan-19-yl)-3-(6-(piperidin-1-yl)naphthalen-2-yl)but-2-enamide.

(Compound 8)

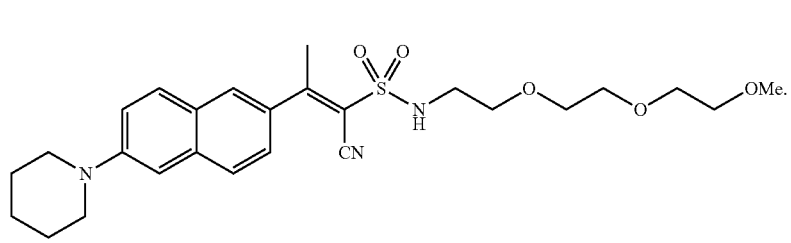

(Compound 10)

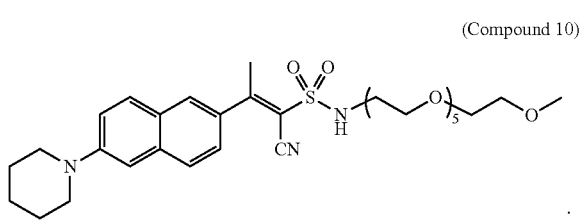

In some cases, the compound of Formula I is (E)-1-cyano-N-(2,5,8,11,14,17-hexaoxanonadecan-19-yl)-2-(6-(piperidin-1-yl)naphthalen-2-yl)prop-1-ene-1-sulfonamide. In some cases, the compound of Formula I is (Z)-1-cyano-N-(2,5,8,11,14,17-hexaoxanonadecan-19-yl)-2-(6-(piperidin-1-yl)naphthalen-2-yl)prop-1-ene-1-sulfonamide.

In some cases, the compound of Formula I is:

(Compound 11)

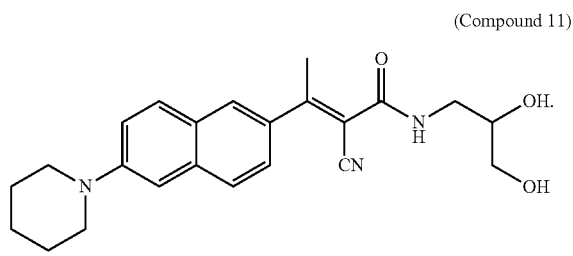 [SMILES: C/C(=C(/C#N)C(=O)NCC(O)CO)c1ccc2cc(N3CCCCC3)ccc2c1]

In some cases, the compound of Formula I is (E)-2-cyano-N-(2,3-dihydroxypropyl)-3-(6-(piperidin-1-yl)naphthalen-2-yl)but-2-enamide. In some cases, the compound of Formula I is (Z)-2-cyano-N-(2,3-dihydroxypropyl)-3-(6-(piperidin-1-yl)naphthalen-2-yl)but-2-enamide.

In some cases, the compound of Formula I is:

(Compound 12)

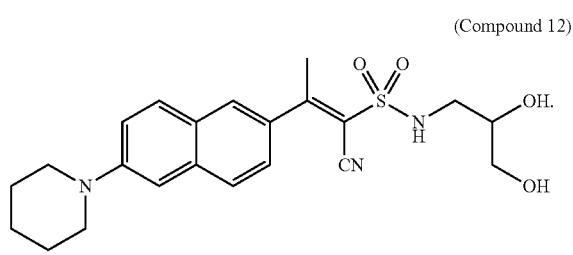 [SMILES: C/C(=C(/C#N)S(=O)(=O)NCC(O)CO)c1ccc2cc(N3CCCCC3)ccc2c1]

In some cases, the compound of Formula I is (E)-1-cyano-N-(2,3-dihydroxypropyl)-2-(6-(piperidin-1-yl)naphthalen-2-yl)prop-1-ene-1-sulfonamide. In some cases, the compound of Formula I is (Z)-1-cyano-N-(2,3-dihydroxypropyl)-2-(6-(piperidin-1-yl)naphthalen-2-yl)prop-1-ene-1-sulfonamide.

In some cases, the compound of Formula I is:

(Compound 13)

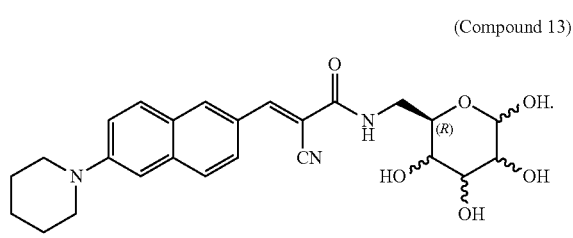

In some cases, the compound of Formula I is (R,E)-2-cyano-3-(6-(piperidin-1-yl)naphthalen-2-yl)-N-((3,4,5,6-tetrahydroxytetrahydro-2H-pyran-2-yl)methyl)acrylamide. In some cases, the compound of Formula I is (R,Z)-2-cyano-3-(6-(piperidin-1-yl)naphthalen-2-yl)-N-((3,4,5,6-tetrahydroxytetrahydro-2H-pyran-2-yl)methyl)acrylamide.

In some cases, the compound of Formula I is:

(Compound 14)

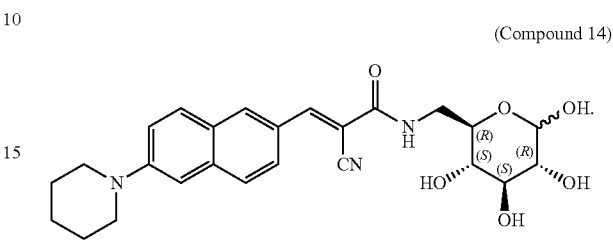

In some cases, the compound of Formula I is (E)-2-cyano-3-(6-(piperidin-1-yl)naphthalen-2-yl)-N-(((2R,3S,4S,5R)-3,4,5,6-tetrahydroxytetrahydro-2H-pyran-2-yl)methyl)acrylamide. In some cases, the compound of Formula I is (Z)-2-cyano-3-(6-(piperidin-1-yl)naphthalen-2-yl)-N-(((2R,3S,4S,5R)-3,4,5,6-tetrahydroxytetrahydro-2H-pyran-2-yl)methyl)acrylamide.

In some cases, the compound of Formula I is:

(Compound 15)

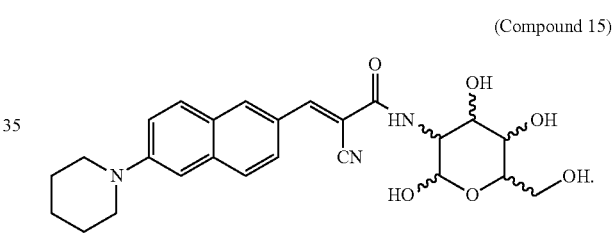

In some cases, the compound of Formula I is (E)-2-cyano-3-(6-(piperidin-1-yl)naphthalen-2-yl)-N-(2,4,5-trihydroxy-6-(hydroxymethyl)tetrahydro-2H-pyran-3-yl)acrylamide. In some cases, the compound of Formula I is (Z)-2-cyano-3-(6-(piperidin-1-yl)naphthalen-2-yl)-N-(2,4,5-trihydroxy-6-(hydroxymethyl)tetrahydro-2H-pyran-3-yl)acrylamide.

In some cases, the compound of Formula I is:

(Compound 16)

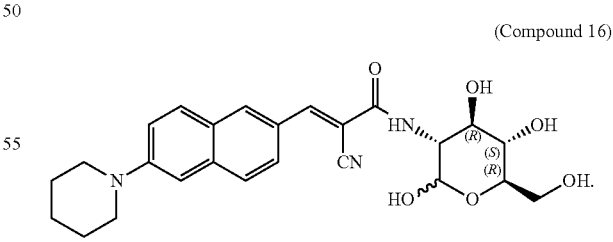

In some cases, the compound of Formula I is (E)-2-cyano-3-(6-(piperidin-1-yl)naphthalen-2-yl)-N-((3R,4R,5S,6R)-2,4,5-trihydroxy-6-(hydroxymethyl)tetrahydro-2H-pyran-3-yl)acrylamide. In some cases, the compound of Formula I is (Z)-2-cyano-3-(6-(piperidin-1-yl)naphthalen-2-yl)-N-((3R,4R,5S,6R)-2,4,5-trihydroxy-6-(hydroxyethyl)tetrahydro-2H-pyran-3-yl)acrylamide.

In some cases, the compound of Formula I is:

In some cases, the compound of Formula I is:

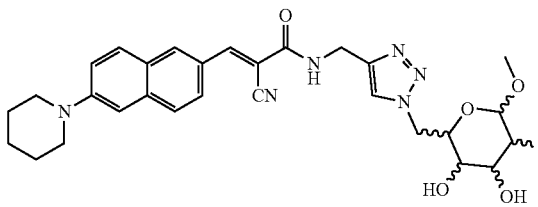

In some cases, the compound of Formula I is (E)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide. In some cases, the compound of Formula I is (Z)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide.

In some cases, the compound of Formula I is:

(Compound 20)

In some cases, the compound of Formula I is (E)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)acrylamide. In some cases, the compound of Formula I is (Z)-2-cyano-3-(6-(piperidin-1-yl)naphthalen-2-yl)-N-((1-(((2R,3S,4S,5R,6S)-3,4,5-trihydroxy-6-methoxytetrahydro-2H-pyran-2-yl)methyl)-1H-1,2,3-triazol-4-yl)methyl)acrylamide.

In some cases, the compound of Formula I is:

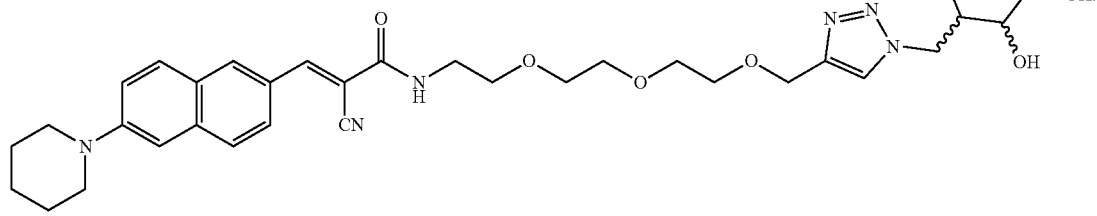

In some cases, the compound of Formula I is (E)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide. In some cases, the compound of Formula I is (Z)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide.

In some cases, the compound of Formula I is:

(Compound 19)

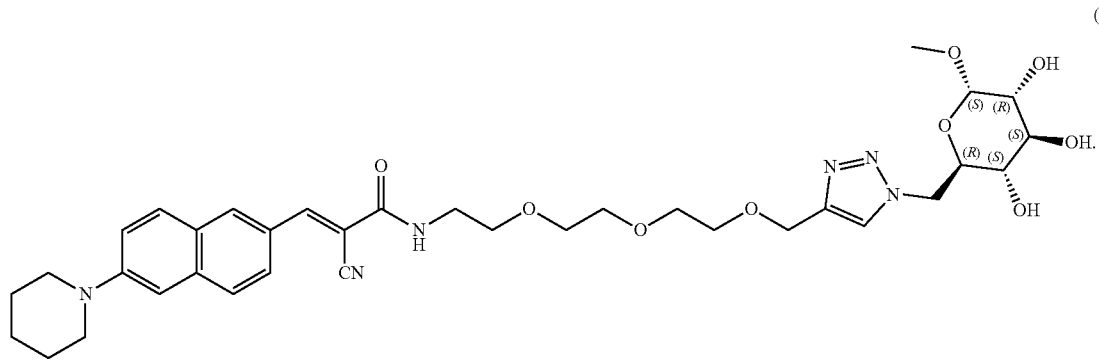

In some cases, the compound of Formula I is (E)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)acrylamide. In some cases, the compound of Formula I is (Z)-2-cyano-3-(6-(piperidin-1-yl)naphthalen-2-yl)-N-(2-(2-(2-((1-(((2R,3S,4S,5R,6S)-3,4,5-trihydroxy-6-methoxytetrahydro-2H-pyran-2-yl)methyl)-1H-1,2,3-triazol-4-yl)methoxy)ethoxy)ethoxy)ethyl)acrylamide.

The disclosure also provides compounds of Formula II:

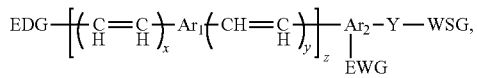

(Formula II)

wherein $Ar_2$ and each $Ar_1$ is independently $C_1$-$C_{14}$ arylene or $C_1$-$C_{14}$ heteroarylene, each optionally substituted with one or more $R_{41}$; wherein each $R_{41}$ is independently halogen, —CN, —$OR_{42}$, —$NR_{43}R_{44}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_{45}$; $R_{42}$, $R_{43}$ and $R_{44}$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{45}$; each $R_{45}$ is independently halogen, —$OR_{46}$, —$NR_{47}R_{48}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; and $R_{46}$, $R_{47}$ and $R_{48}$ are independently hydrogen or $C_1$-$C_{10}$ alkyl;

In some compounds of formula II each of $Ar_1$ is independently a substituted or unsubstituted naphthylene or a substituted or unsubstituted phenylene.

In some compounds of Formula I, $Ar_2$ is a substituted or unsubstituted naphthylene or a substituted or unsubstituted phenylene.

In some compounds of Formula II, $Ar_2$ is a substituted or unsubstituted pyridyl, substituted or unsubstituted pyrimidyl, substituted or unsubstituted pyrazinyl or substituted or unsubstituted pyradizinyl.

In some compounds of Formula II, $Ar_2$ is a substituted or unsubstituted pyridyl.

The substituent EDG in Formula II is an electron donating group. In some compounds of Formula II, EDG is any electron donating group known in the art. In some cases, it is any atom or functional group that is capable of donating some of its electron density into a conjugated pi system via resonance or inductive electron withdrawal, thus making the pi system more nucleophilic. In some compounds of Formula II, the EDG is —$OR_{49}$, —$NR_{50}R_{51}$, —$SR_{52}$, —$PR_{53}R_{54}$, —$NR_{55}C(O)R_{56}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{57}$; wherein each $R_{57}$ is independently halogen, —$OR_{58}$, —$NR_{59}R_{60}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_{49}$, $R_{50}$, $R_{51}$, $R_{52}$, $R_{53}$, $R_{54}$, $R_{55}$, $R_{56}$, $R_{58}$, $R_{59}$ and $R_{60}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{61}$ and wherein $R_{50}$ and $R_{51}$ are optionally joined together to form a heterocycloalkyl or heteroaryl optionally substituted with $R_{61}$; each of $R_{61}$ is independently halogen, —$OR_{62}$, —$NR_{63}R_{64}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{65}$; each of $R_{62}$, $R_{63}$ and $R_{64}$ is independently hydrogen or $C_1$-$C_{10}$ alkyl; and each $R_{65}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In some compounds of formula II, EDG is selected from a group consisting of

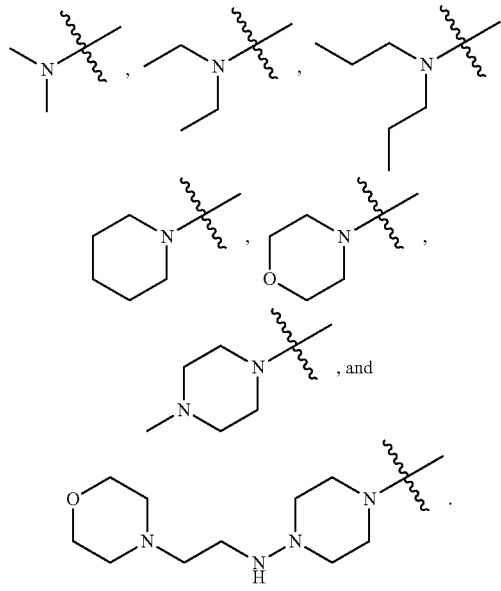

In some compounds of formula II, EDG is

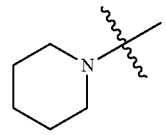

In some compounds of formula II, EDG is

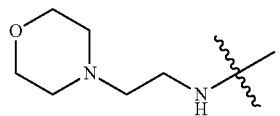

The substituent EWG in Formula II is an electron withdrawing group. In some compounds of Formula II, EWG may be any atom or group that may be capable of drawing electron density from neighboring atoms towards itself, either by resonance or inductive effects. In some compounds of Formula II, EWG is halogen, —CN, —$NO_2$, —$SO_3H$, —$CR_{66}R_{67}R_{68}$, —$COR_{69}$, or —$COOR_{70}$; wherein each $R_{66}$, $R_{67}$ and $R_{68}$ is independently hydrogen or halogen; $R_{69}$ is halogen, hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{71}$; $R_{70}$ is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{72}$; each $R_{71}$ and $R_{72}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

In some cases, EWG is selected from a group consisting of —F, —Cl, —Br, —CH═O, $NO_2$, —$CF_3$, —$CCl_3$, —$SO_3$ and —CN. In some cases, the EWG is —F, —Cl, or —Br. In some cases, the EWG is —CN.

The substituent WSG in Formula II is a water soluble group in some cases. In some compounds of Formula II, WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{73}$; wherein each $R_{73}$ is independently halogen, —$OR_{74}$, —$NR_{75}R_{76}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{77}$; each $R_{74}$, $R_{75}$ and $R_{76}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{77}$; each $R_{77}$ is independently halogen, —$OR_{78}$, —$NR_{79}R_{80}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, —($C_1$-$C_6$alkyl)($C_1$-$C_{10}$heterocycloalkyl), $C_1$-$C_{10}$ arylene, or $C_1$-$C_{10}$ heteroarylene; and each of $R_{78}$, $R_{79}$ and $R_{80}$ is independently hydrogen or $C_1$-$C_{10}$ alkyl.

The substituent WSG in the Formula II is a water soluble group. In some compounds, WSG groups serve to alter the solubility of the compounds of Formula II in aqueous systems. In some cases, WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{73}$; wherein each $R_{73}$ is independently halogen, —$OR_{74}$, —$NR_{75}R_{76}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{77}$; each $R_{74}$, $R_{75}$ and $R_{76}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{77}$; each $R_{77}$ is independently halogen, —$OR_{78}$, —$NR_{79}R_{80}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; and each of $R_{78}$, $R_{79}$ and $R_{80}$ is independently hydrogen or $C_1$-$C_{10}$ alkyl.

In some compounds of Formula II, the WSG is hydrogen.

In some compounds of Formula II, the WSG is

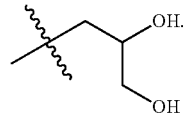 [SMILES: *CC(O)CO]

In other compounds of Formula II, the WSG is polyethylene glycol, polypropylene glycol, co-polymer of polyethylene glycol and polypropylene glycol, or alkoxy derivatives thereof. In some compounds of Formula II, WSG is

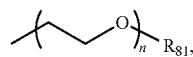

wherein n is an integer from 0-50 and $R_{81}$ is hydrogen, $C_1$-$C_{10}$ alkyl, a $C_1$-$C_{10}$ alkenyl, or a $C_1$-$C_{10}$ alkynyl wherein each wherein the alkyl, alkenyl, or alkynyl is optionally substituted with one or more $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene. In some compounds of Formula II, $R_{81}$ is hydrogen. In some compounds of Formula II, $R_{81}$ is methyl. In some compounds of Formula II, $R_{81}$ is ethyl. In some compounds of Formula II, $R_{81}$ is $CH_2$—C≡CH. In some compounds of Formula IIn is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some compounds of Formula IIn is an integer of value 1-10, 1-20, 1-30, 1-40, 1-50, 10-20, 10-30, 10-40, 10-50, 20-30, 20-40, 20-50, 30-40, 30-50, or 40-50. In some compounds of Formula II, n is 1, 2, 3, 4, 5, 6, 7, 8, 9, or 10. In some compounds of Formula II, n is 0, 3 or 6.

In some cases, the WSG is

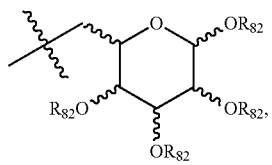

wherein each $R_{82}$ is hydrogen or $C_1$-$C_{10}$ alkyl. In some cases each $R_{82}$ is independently a hydrogen, methyl, ethyl, propyl, or butyl.

In some cases, the WSG is

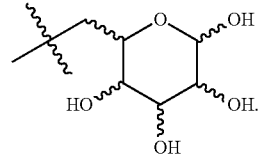 [SMILES: *CC1OC(O)C(O)C(O)C1O]

In some cases, the WSG is

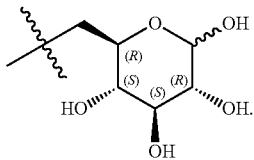

In some cases, the WSG is

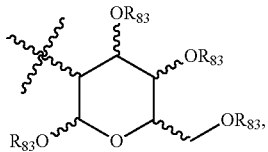

wherein each $R_{83}$ is hydrogen or $C_1$-$C_{10}$ alkyl. In some cases each $R_{83}$ is independently a hydrogen, methyl, ethyl, propyl, or butyl.

In some cases, the WSG is

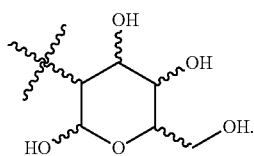

In some cases, the WSG is

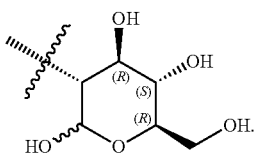

In some compounds of Formula II, WSG is —($C_1$-$C_{10}$ alkyl)-$R_{73}$—$R_{77}$. In some compounds of Formula II, WSG is —($C_1$-$C_{10}$ alkyl)-$R_{73}$—$R_{77}$ and $R_{73}$ is $C_1$-$C_{10}$ heteroarylene. In some compounds of Formula II, WSG is —($C_1$-$C_{10}$ alkyl)-$R_{73}$—$R_{77}$, $R_{73}$ is $C_1$-$C_{10}$ heteroarylene and $R_{77}$ is —($C_1$-$C_6$alkyl)($C_1$-$C_{10}$heterocycloalkyl).

In some compounds of Formula II, WSG is $CH_3$—$R_{73}$—$R_{77}$.

In some compounds of Formula II, WSG is —$CH_3$—$R_{73}$—$R_{77}$ and $R_{73}$ is triazole, imidazole, or pyrrazole.

In some compounds of Formula II, WSG is —$CH_3$—$R_{73}$—$R_{77}$ and $R_{73}$ is triazole.

In some compounds of Formula II, WSG is —$CH_3$—$R_{73}$—$R_{77}$ and $R_{73}$ is 1,2,4-triazole.

In some compounds of Formula II, WSG is —$CH_3$—$R_{73}$—$R_{77}$ and $R_{73}$ is 1,2,3-triazole.

In some compounds of Formula II, WSG is —$CH_3$—$R_{73}$—$R_{77}$, $R_{73}$ is 1,2,3-triazole and $R_{77}$ is —($C_1$-$C_6$alkyl)($C_1$-$C_{10}$heterocycloalkyl).

In some compounds of Formula II, WSG is —$CH_3$—$R_{73}$—$R_{77}$, $R_{73}$ is 1,2,3-triazole and $R_{77}$ is —($C_1$alkyl)($C_1$-$C_{10}$heterocycloalkyl).

In some compounds of Formula II, WSG is —$CH_3$—$R_{73}$—$R_{77}$, $R_{73}$ is 1,2,3-triazole, $R_{77}$ is —($C_1$alkyl)($C_1$-$C_{10}$heterocycloalkyl), and $C_1$-$C_{10}$heterocycloalkyl is a tetrahydropyran derivative.

In some compounds of Formula II, WSG is —$CH_3$—$R_{73}$—$R_{77}$, $R_{73}$ is 1,2,3-triazole, and $R_{77}$ is

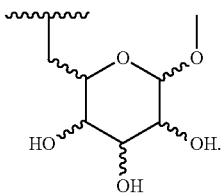 [SMILES: *CC1OC(OC)C(O)C(O)C1O]

In some compounds of Formula II, WSG is

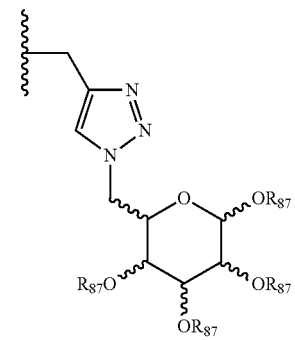

wherein each $R_{87}$ is hydrogen, $C_1$-$C_{10}$ alkyl, or —C(=O) $C_1$-$C_{10}$ alkyl. In some compounds of Formula II, each $R_{87}$ is independently a hydrogen, methyl, ethyl, propyl, butyl, acetate, propionate, or butyrate. In some compounds of Formula II, each $R_{87}$ is independently a hydrogen or methyl. In some compounds of Formula I, each $R_{87}$ is independently a methyl or acetate.

In some compounds of Formula II, WSG is

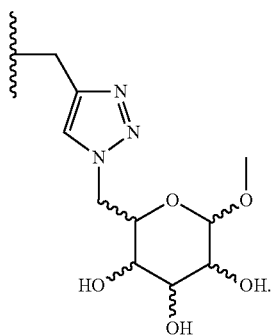 [SMILES: *Cc1cn(CC2OC(OC)C(O)C(O)C2O)nn1]

In some compounds of Formula II, WSG is

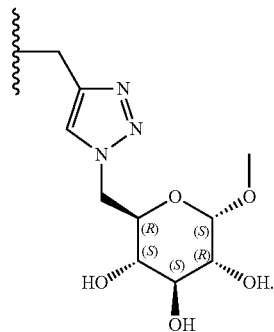

In some compounds of Formula II, WSG is —($C_1$-$C_{10}$ heteroalkyl)-$R_{73}$—$R_{77}$. In some compounds of Formula II, WSG is —($C_1$-$C_{10}$ heteroalkyl)-$R_{73}$—$R_{77}$ and $R_{73}$ is $C_1$-$C_{10}$ heteroarylene. In some compounds of Formula II, WSG is —($C_1$-$C_{10}$ heteroalkyl)-$R_{73}$—$R_{77}$ and $R_{73}$ is $C_1$-$C_{10}$ heteroarylene and $R_{77}$ is —($C_1$-$C_6$alkyl)($C_1$-$C_{10}$ heterocycloalkyl).

In some compounds of Formula II, WSG is

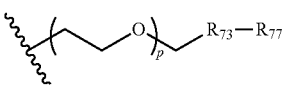

and p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some compounds of Formula II, p is an integer of value 1-10, 1-20, 1-30, 1-40, 1-50, 10-20, 10-30, 10-40, 10-50, 20-30, 20-40, 20-50, 30-40, 30-50, or 40-50.

In some compounds of Formula II, p is 1, 2, 3, 4, 5, 6, 7, 8, 9, or 10.

In some compounds of Formula II, p is 1, 2, 3, 4, 5, or 6.
In some compounds of Formula II, p is 3 or 6.

In some compounds of Formula II, WSG is

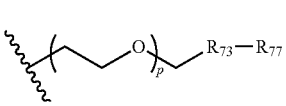

and p 3.

In some compounds of Formula II, WSG is

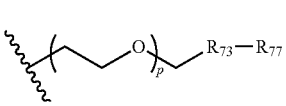

and $R_{73}$ is a $C_1$-$C_{10}$ heteroarylene.

In some compounds of Formula II, WSG is

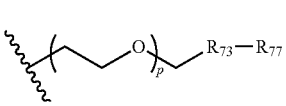

and $R_{73}$ is a $C_5$ heteroarylene.

In some compounds of Formula II, WSG is

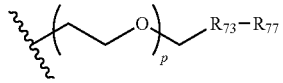

and $R_{73}$ is triazole, imidazole, or pyrrazole.

In some compounds of Formula I II WSG is

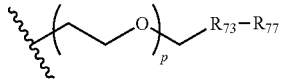

and $R_{73}$ is triazole.

In some compounds of Formula II, WSG is

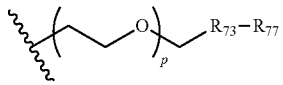

and $R_{73}$ is 1,2,4-triazole. In some compounds of Formula II, WSG is

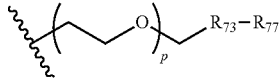

and $R_{73}$ is 1,2,3-triazole.

In some compounds of Formula II, WSG is

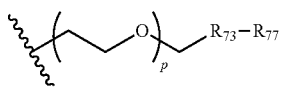

$R_{73}$ is 1,2,3-triazole, and p is 3.

In some compounds of Formula II, WSG is

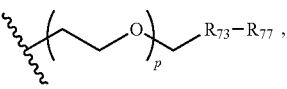

$R_{73}$ is 1,2,3-triazole and $R_{77}$ is —($C_1$-$C_6$alkyl)($C_1$-$C_{10}$ heterocycloalkyl).

In some compounds of Formula II, WSG is

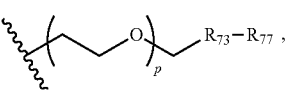

$R_{73}$ is 1,2,3-triazole and $R_{77}$ is —($C_1$alkyl)($C_1$-$C_{10}$heterocycloalkyl).

In some compounds of Formula II, WSG is

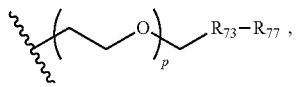

R$_{73}$ is 1,2,3-triazole, R$_{77}$ is a tetrahydropyran derivative.
In some compounds of Formula II, WSG is

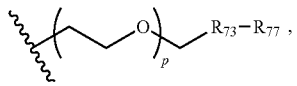

R$_{73}$ is 1,2,3-triazole, and R$_7$ is

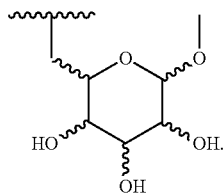 [SMILES: *CC1OC(OC)C(O)C(O)C1O]

In some compounds of Formula II, WSG is

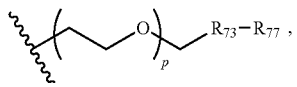

R$_{73}$ is 1,2,3-triazole, R$_{77}$ is

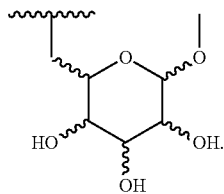

and p is 3.
In some compounds of Formula II, WSG is

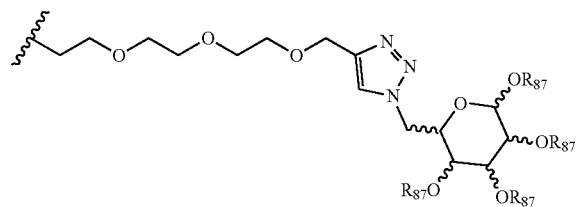

wherein each R$_{87}$ is hydrogen, C$_1$-C$_{10}$ alkyl, or —C(=O) C$_1$-C$_{10}$ alkyl. In some compounds of Formula II, each R$_{87}$ is independently a hydrogen, methyl, ethyl, propyl, butyl, acetate, propionate, or butyrate. In some compounds of Formula II, each R$_{87}$ is independently a hydrogen or methyl. In some compounds of Formula II, each R$_{87}$ is independently a methyl or acetate.

In some compounds of Formula II, WSG is

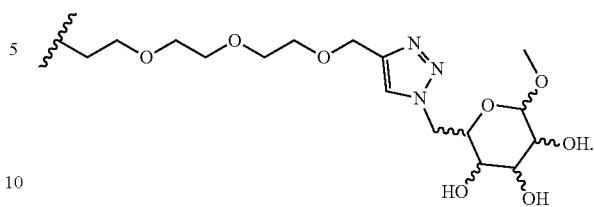

In some compounds of Formula II, WSG is

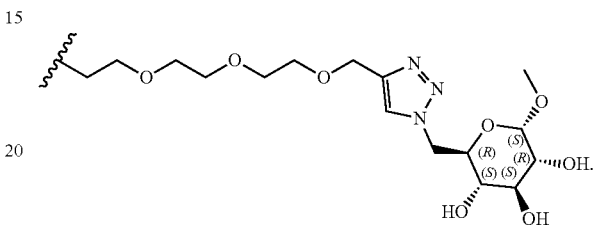

In some compounds of Formula II, Y is absent, O, NH, or S. In some compounds of Formula II, Y is absent (i.e. Y is a bond). In some compounds of Formula II, Y is O. In some compounds of Formula II, Y is NH. In some compounds of Formula II, Y is S.

The variable x in Formula II is an integer from 0-10. In some compounds of Formula II, x is 0. In some compounds of Formula II, x is 1. In some compounds of Formula II, x is 2. In some compounds of Formula II, x is 3. In some compounds of Formula II, x is 4. In some compounds of Formula II, x is 5. In some compounds of Formula II, x is 6. In some compounds of Formula II, x is 7. In some compounds of Formula II, x is 8. In some compounds of Formula II, x is 9. In some compounds of Formula II, x is 10.

The variable y in Formula II is an integer from 0-10. In some compounds of Formula II, y is 0. In some compounds of Formula II, y is 1. In some compounds of Formula II, y is 2. In some compounds of Formula II, y is 3. In some compounds of Formula II, y is 4. In some compounds of Formula II, y is 5. In some compounds of Formula II, y is 6. In some compounds of Formula II, y is 7. In some compounds of Formula II, y is 8. In some compounds of Formula II, y is 9. In some compounds of Formula II, y is 10.

The variable z in Formula II is an integer from 1-10. In some compounds of Formula II, z is 1. In some compounds of Formula II, z is 2. In some compounds of Formula II, z is 3. In some compounds of Formula II, z is 4. In some compounds of Formula II, z is 5. In some compounds of Formula II, z is 6. In some compounds of Formula II, z is 7. In some compounds of Formula II, z is 8. In some compounds of Formula II, z is 9. In some compounds of Formula II, z is 10.

In some compounds of formula II, x is 0, y is 0, z is 1, and Y is O.

In some compounds of formula II, x is 0, y is 0, z is 1, and Y is S.

In some compounds of formula II, x is 0, y is 0, z is 1, and Y is NH.

In some compounds of formula II, x is 0, y is 0, z is 1, and Y is absent.

In some compounds of formula II, x is 0, y is 0, z is 2, and Y is O.

In some compounds of formula II, x is 0, y is 0, z is 2, and Y is S.

In some compounds of formula II, x is 0, y is 0, z is 2, and Y is NH.

In some compounds of formula II, x is 0, y is 0, z is 2, and Y is absent.

In one aspect the disclosure provides a compound of Formula IIa:

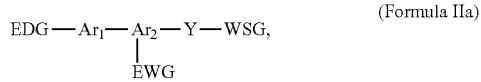

(Formula IIa)

wherein EDG, $Ar_1$, $Ar_2$, Y, EWG, and WSG are defined as above for Formula II.

In one aspect the disclosure provides a compound of Formula IIb:

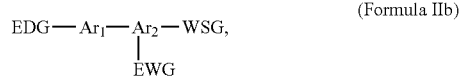

(Formula IIb)

wherein EDG, $Ar_1$, $Ar_2$, EWG, and WSG are defined as above for Formula II.

In some cases, the compound according to Formula II is selected from a group consisting of:

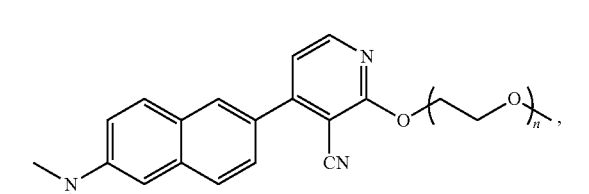

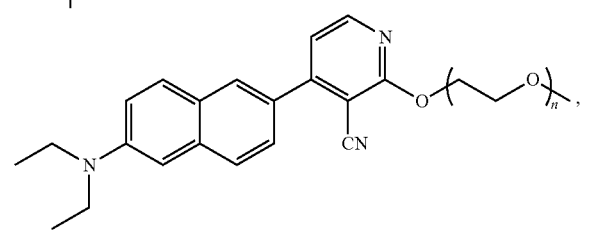

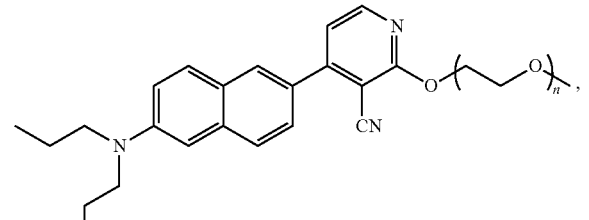

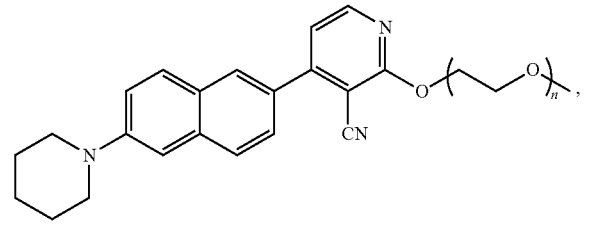

-continued

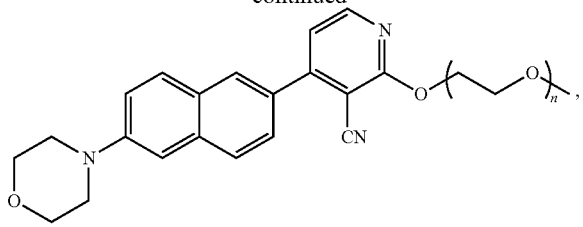

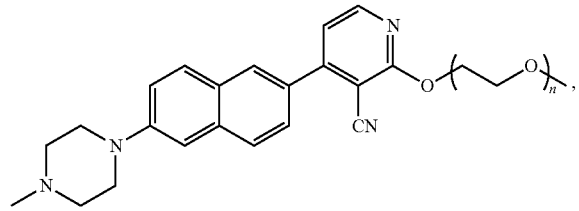

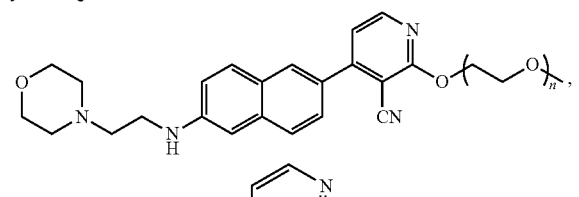

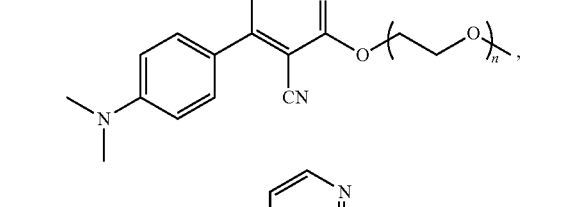

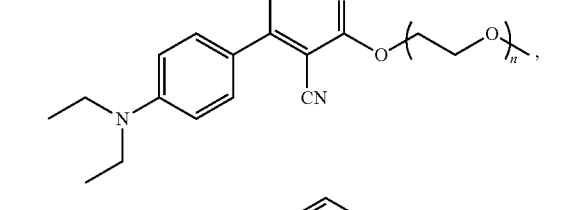

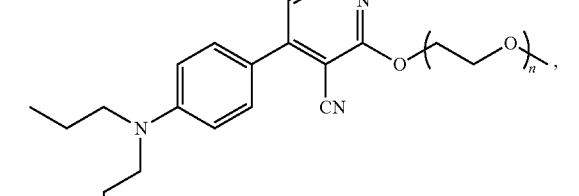

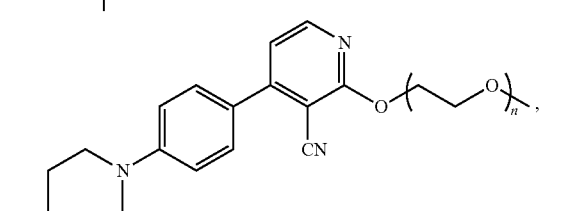

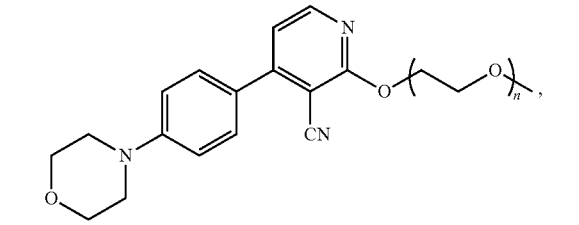

-continued
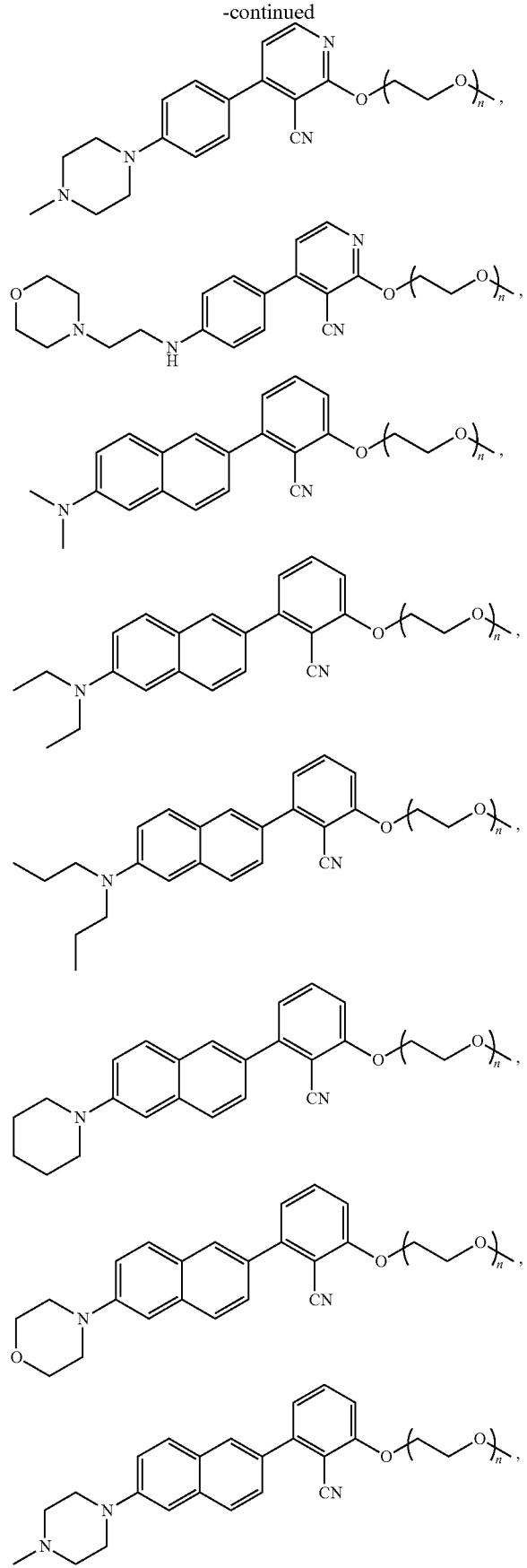
-continued
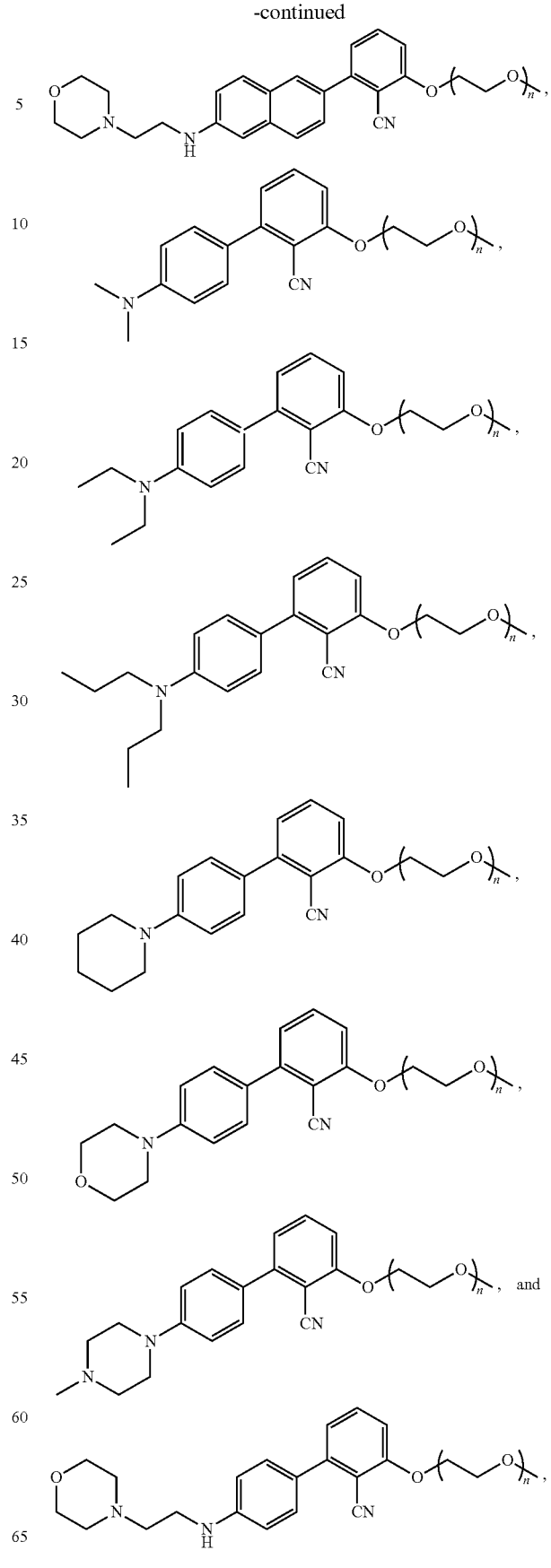

wherein n is an integer with value 0-50. In some compounds of Formula II, n is a integer of value 0-10, e.g. n is 0, 1, 2, 3, 4, 5, 6, 7, 8, 9, or 10.
In some cases the compound of Formula II is selected from a group consisting of:
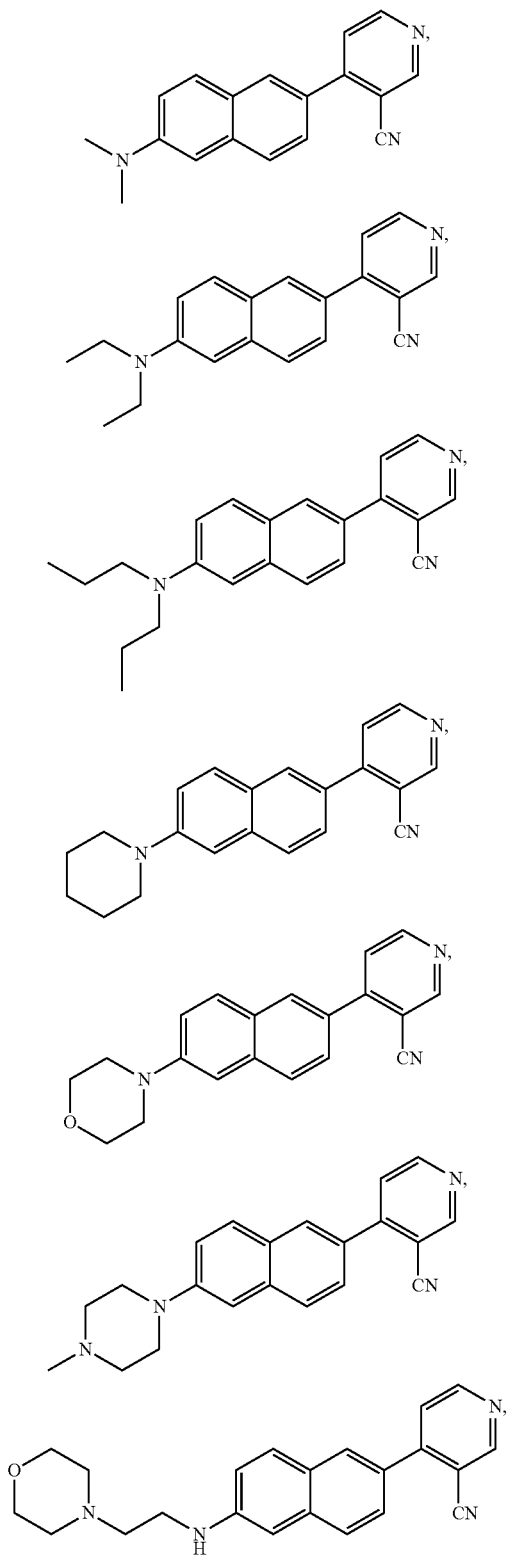
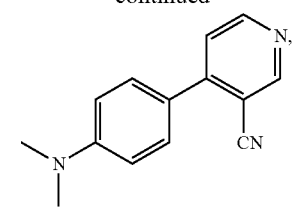
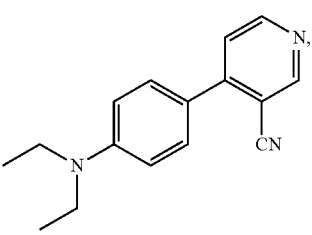
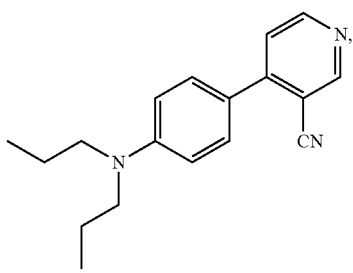
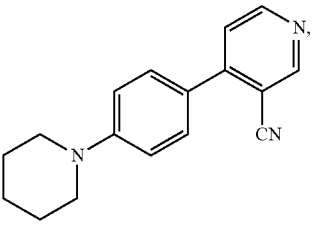
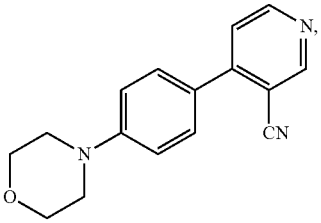
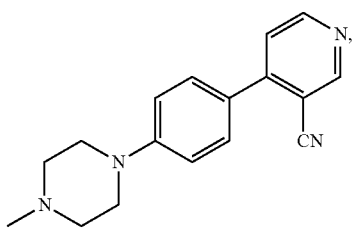
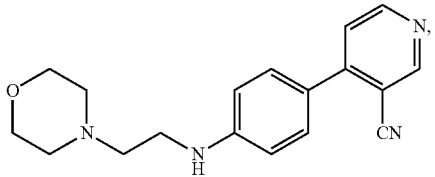

197
-continued
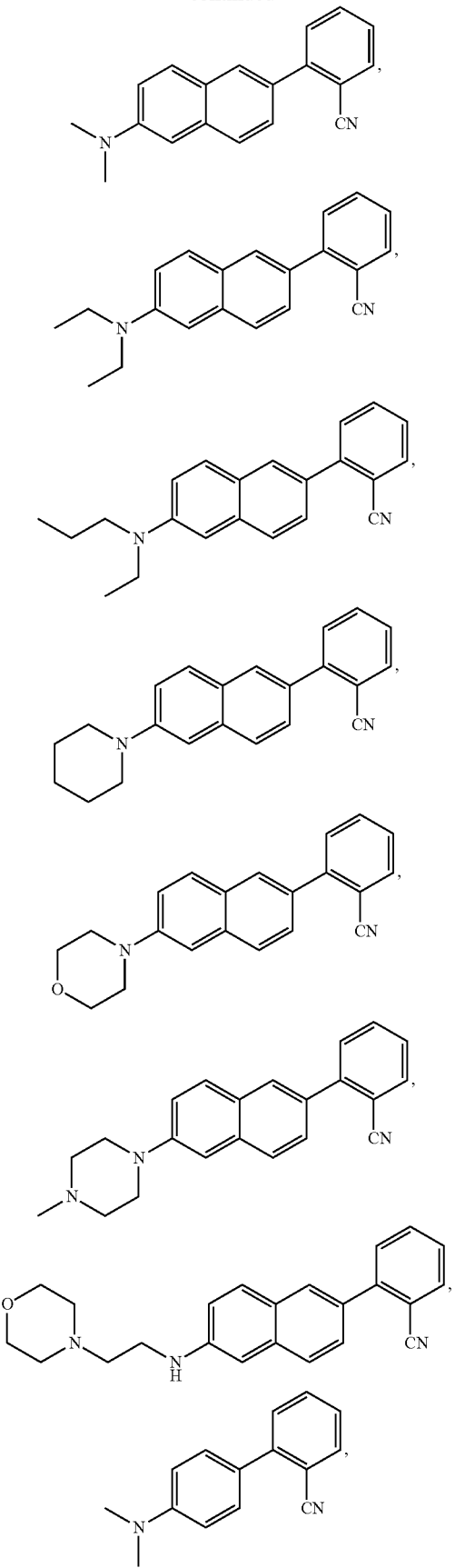
198
-continued
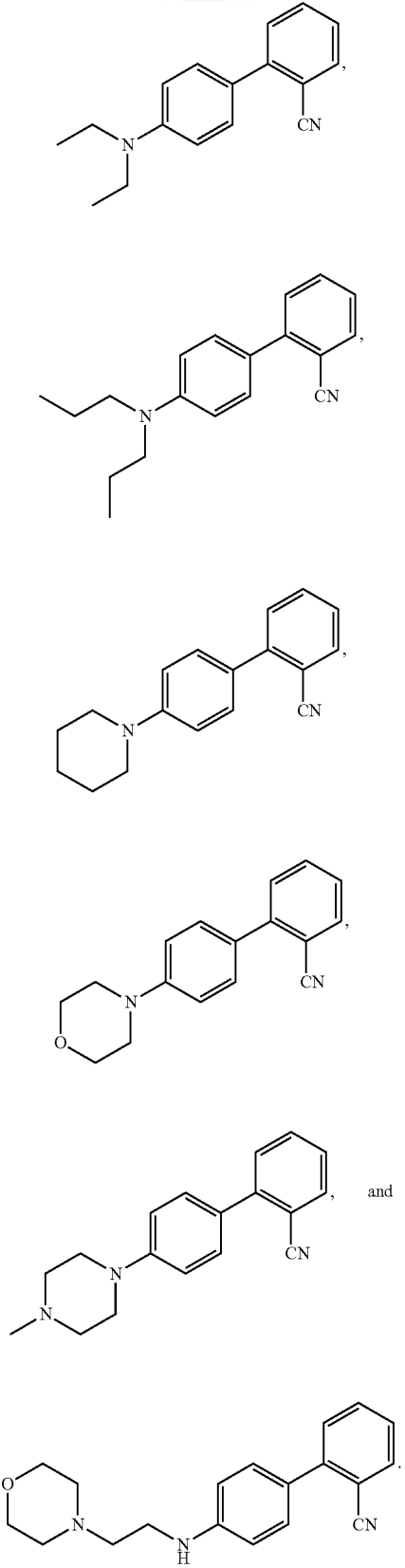
In some cases, the compound of Formula II is selected from a group consisting of 199
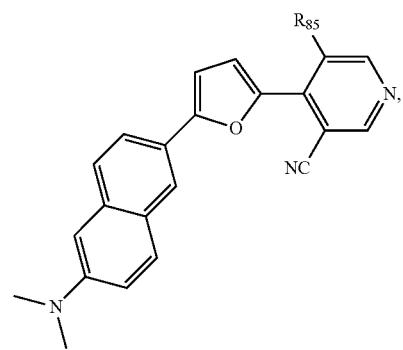
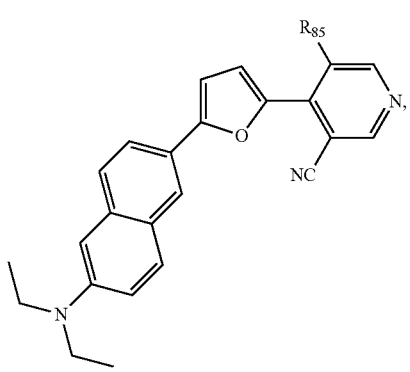
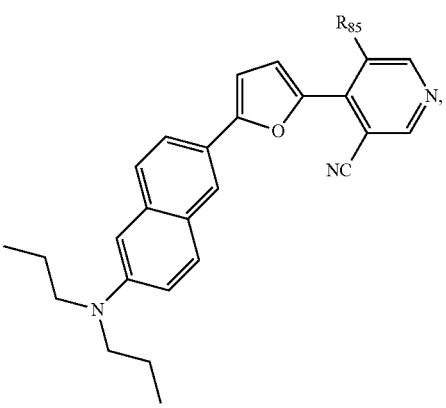
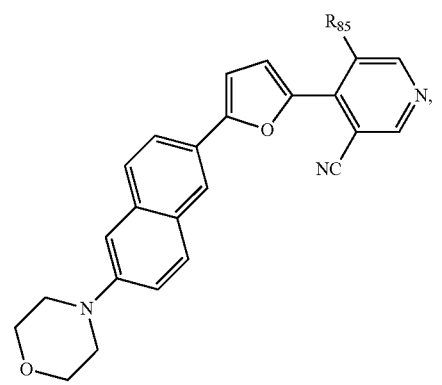
200
-continued
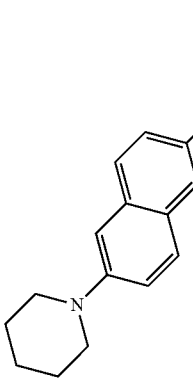
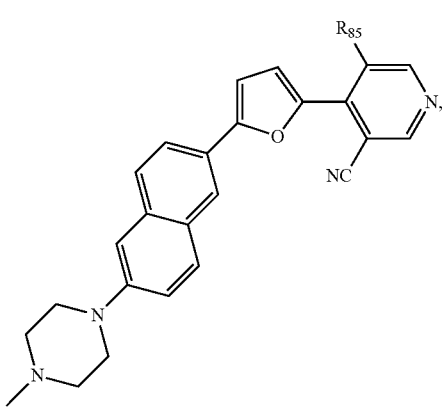
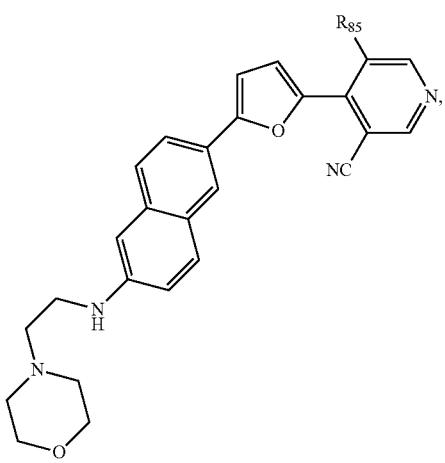
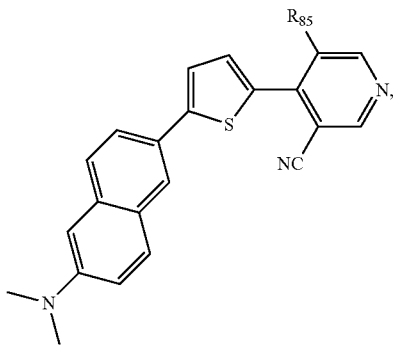

201
-continued
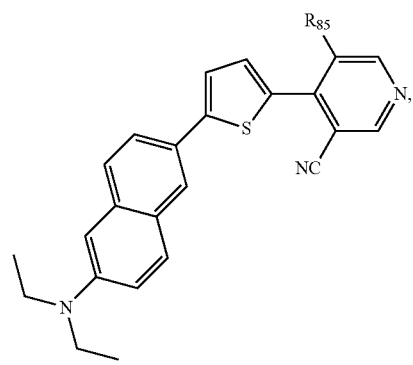
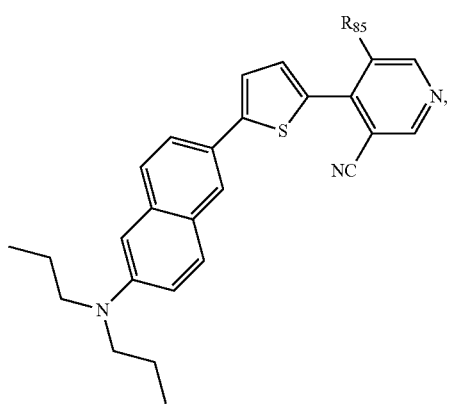
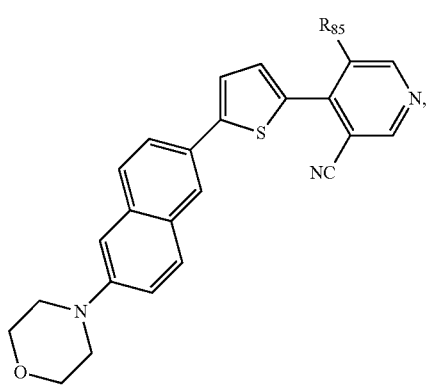
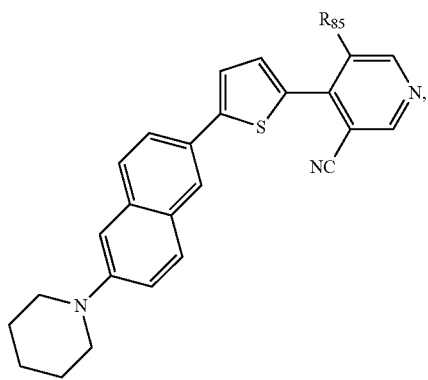
202
-continued
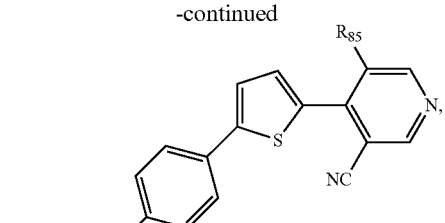
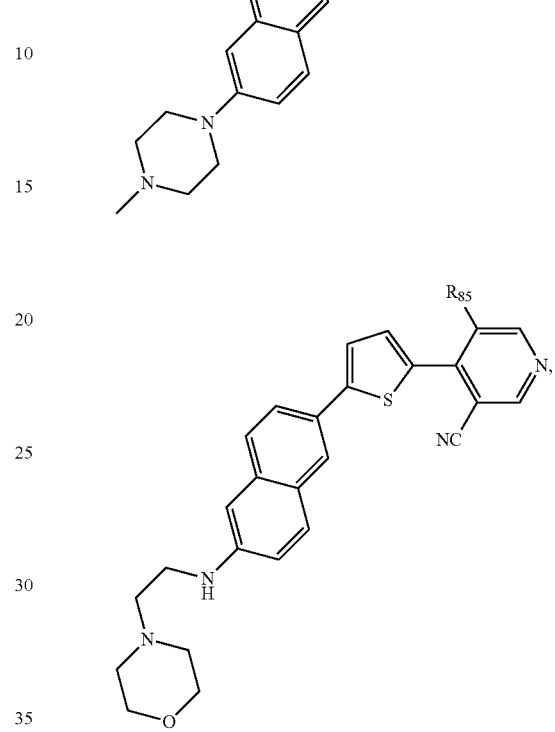
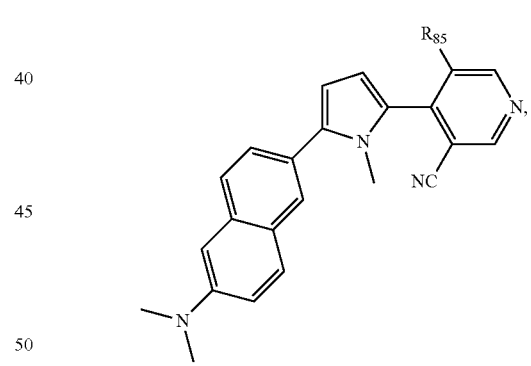
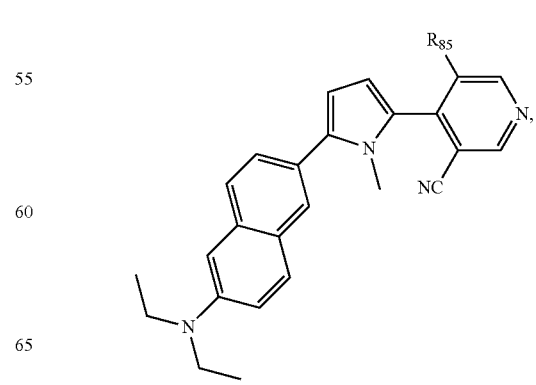

203
-continued
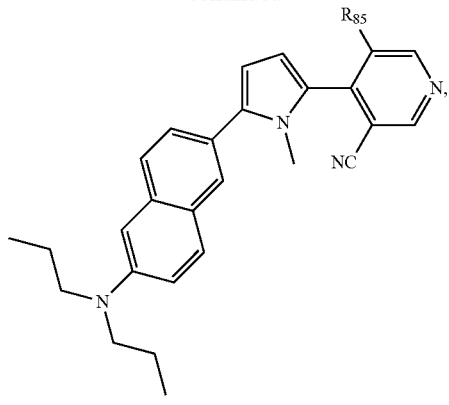
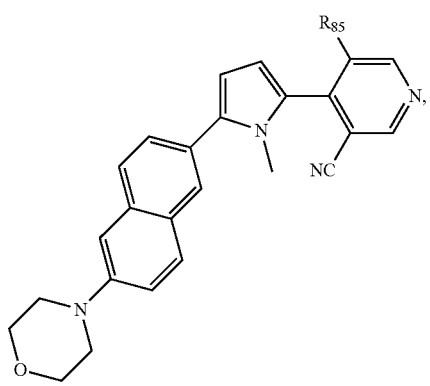
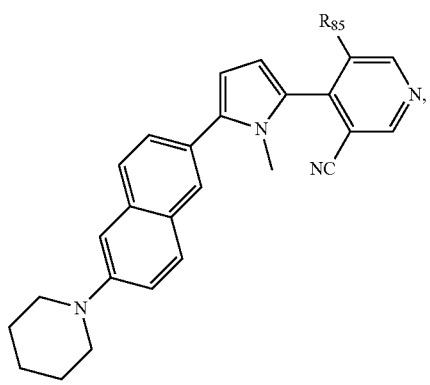
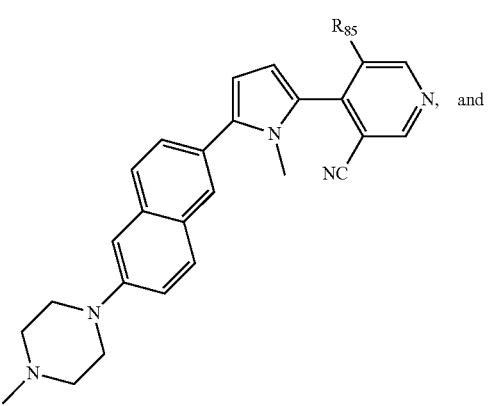
204
-continued
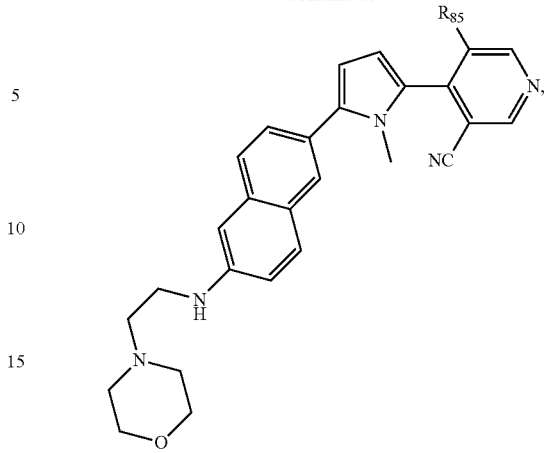
wherein $R_{85}$ is H or CN.
In some cases, the compound of Formula II is selected from a group consisting of
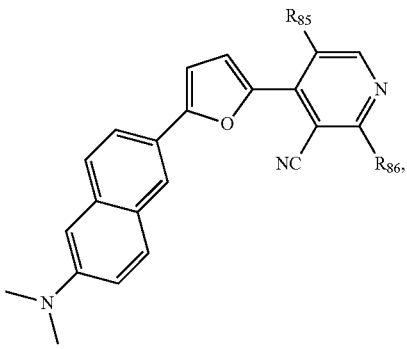
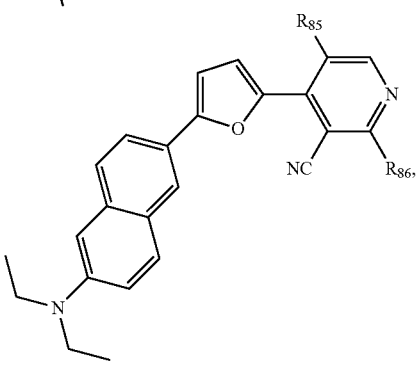
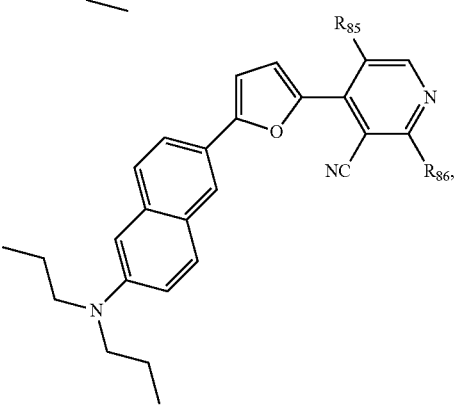

205
-continued
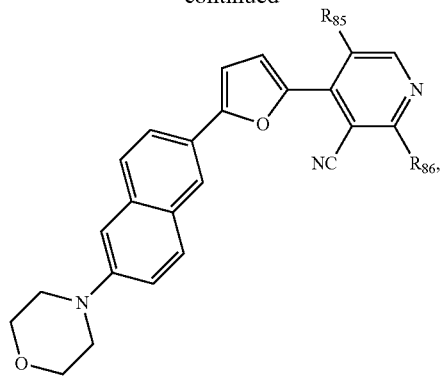
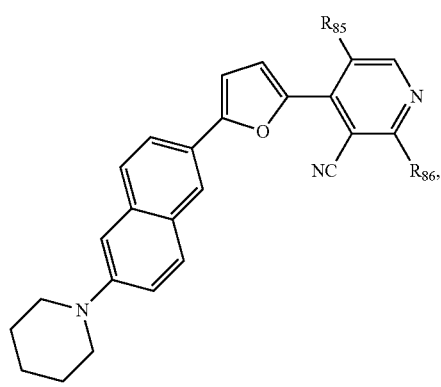
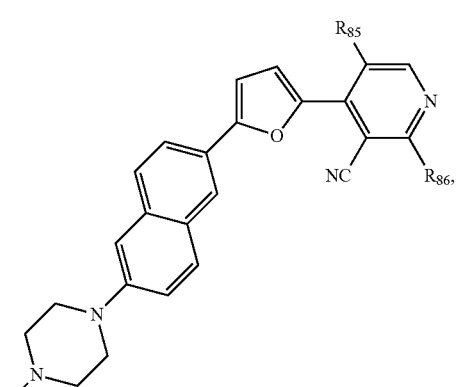
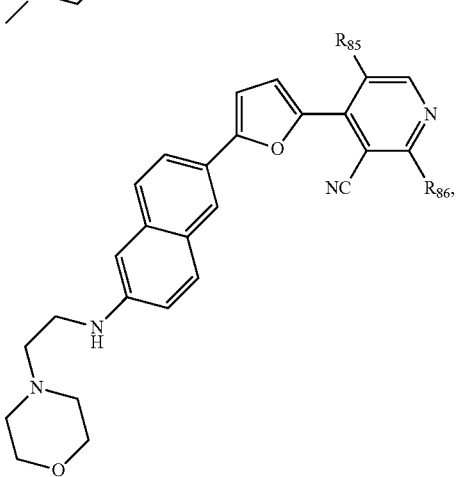
206
-continued
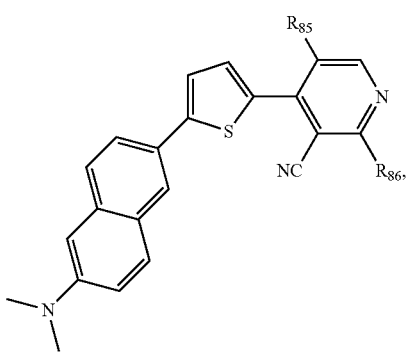
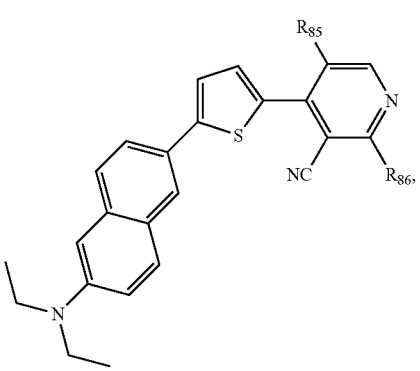
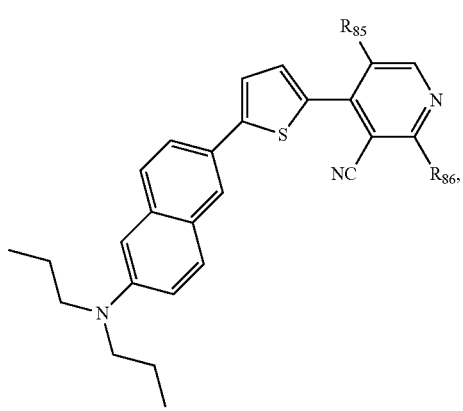
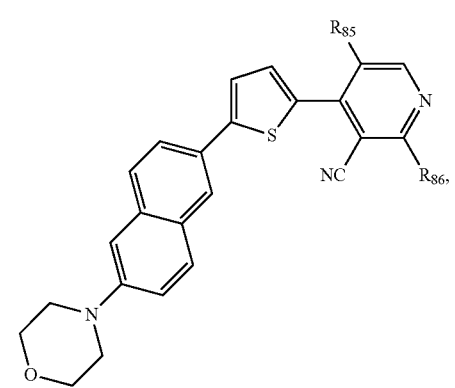

207
-continued
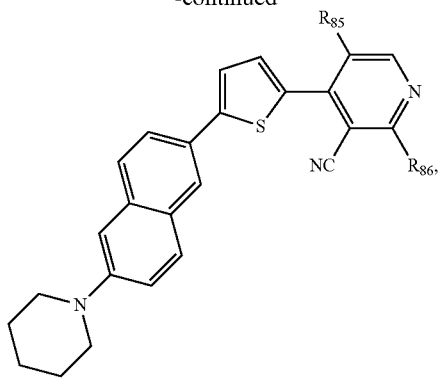
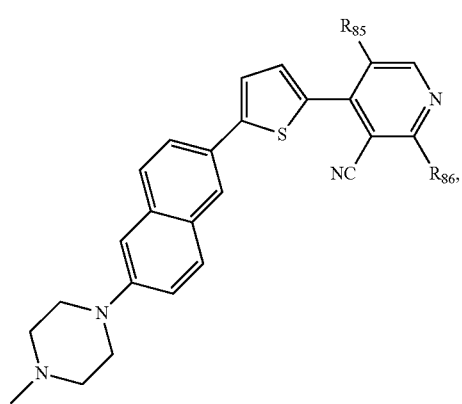
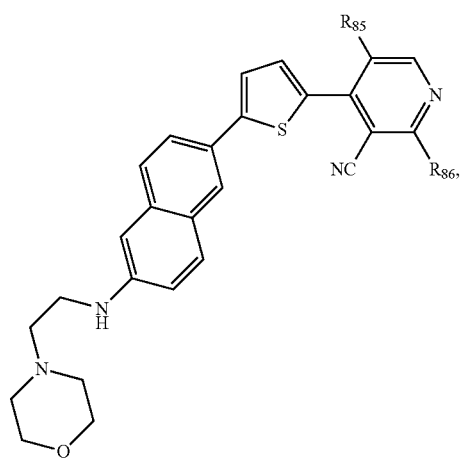
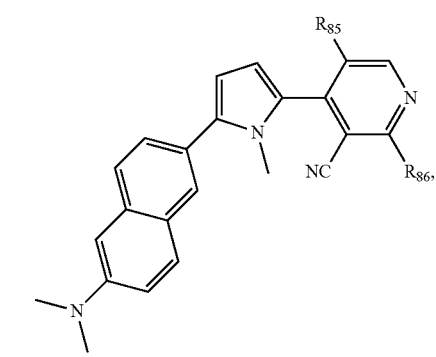
208
-continued
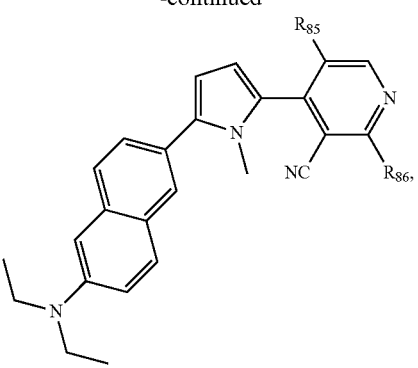
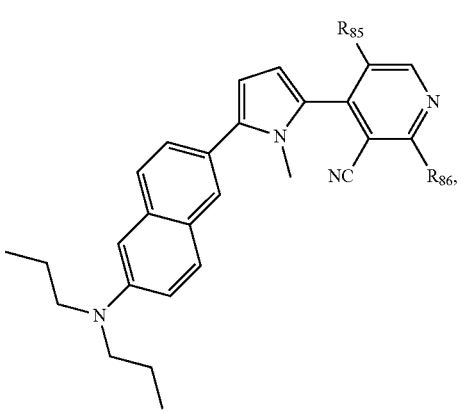
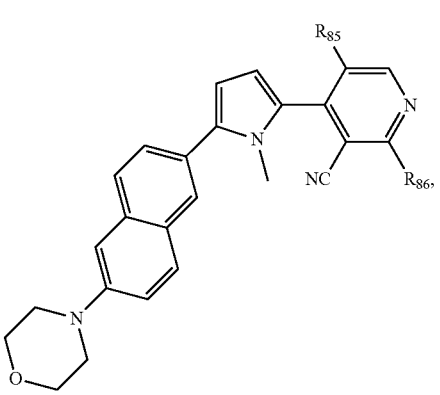
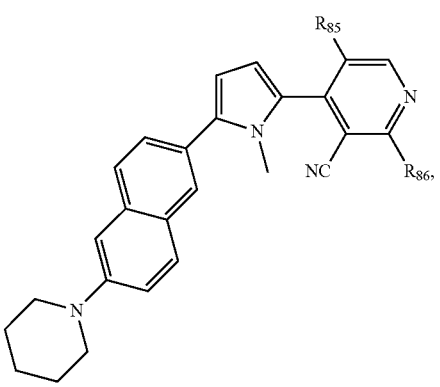

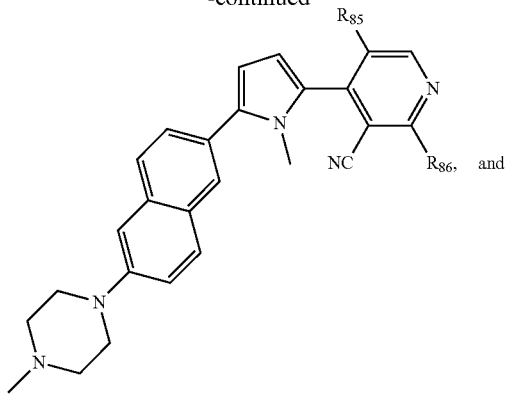
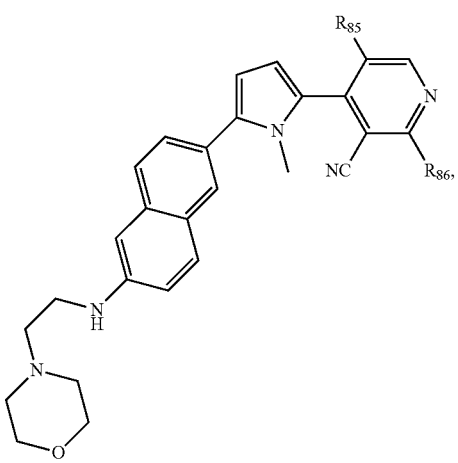
wherein R₈₅ is H or CN and R₈₆ is

wherein n is an integer with value 0-50. In some compounds of Formula II, n is a integer of value 0-10, e.g. n is 0, 1, 2, 3, 4, 5, 6, 7, 8, 9, or 10.
In some cases, the compound of Formula II is selected from a group consisting of
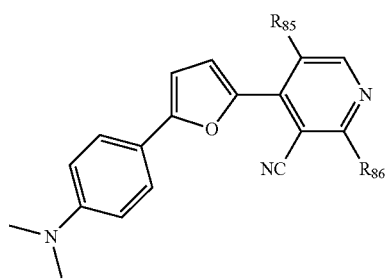
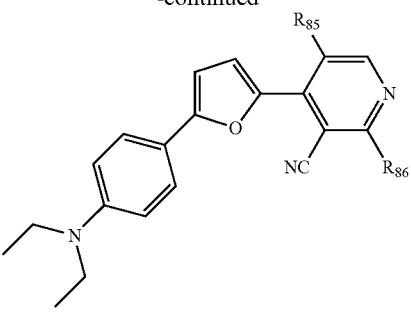
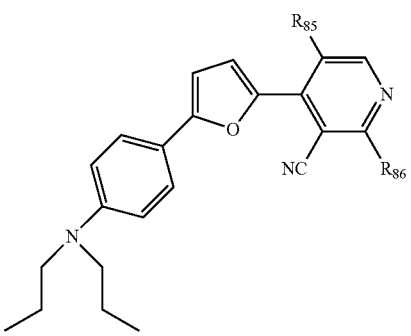
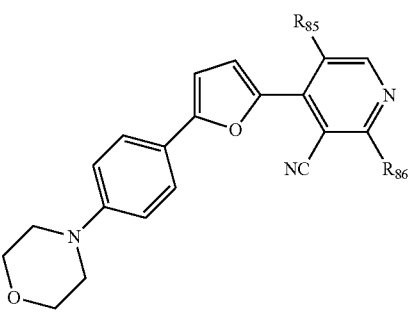
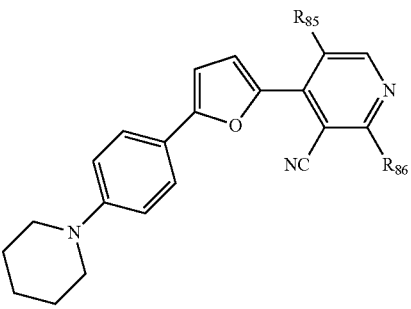

211
-continued
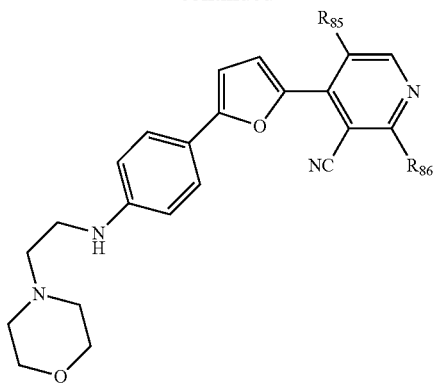
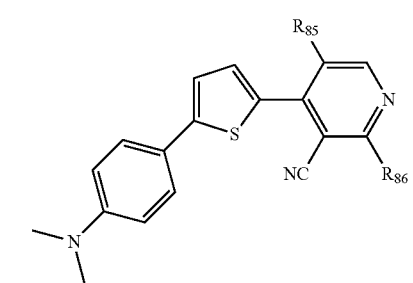
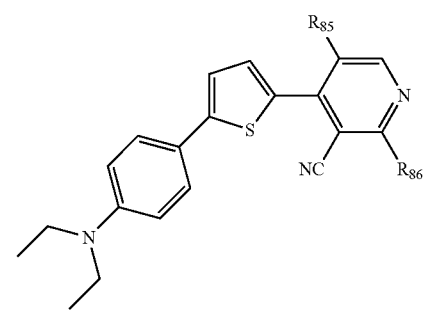
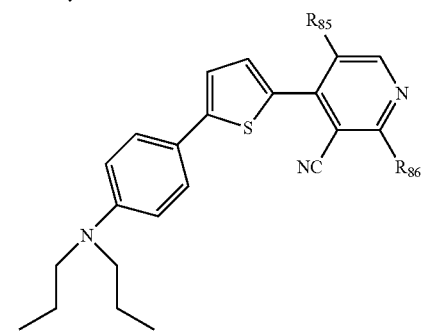
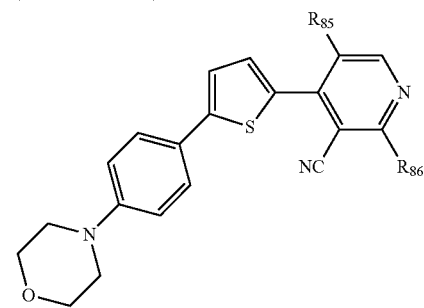
212
-continued
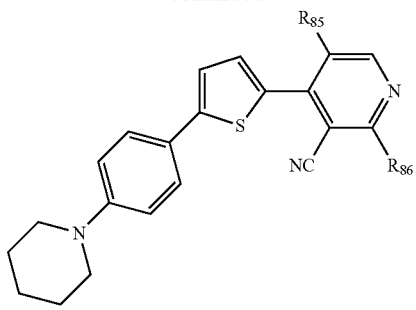
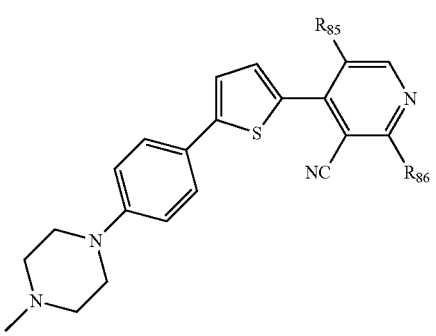
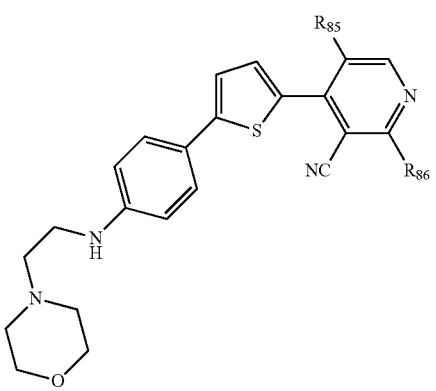
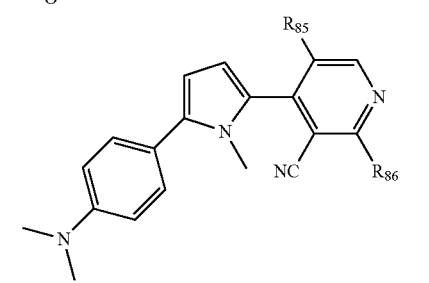
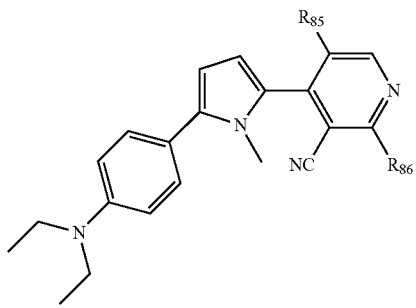

213
-continued
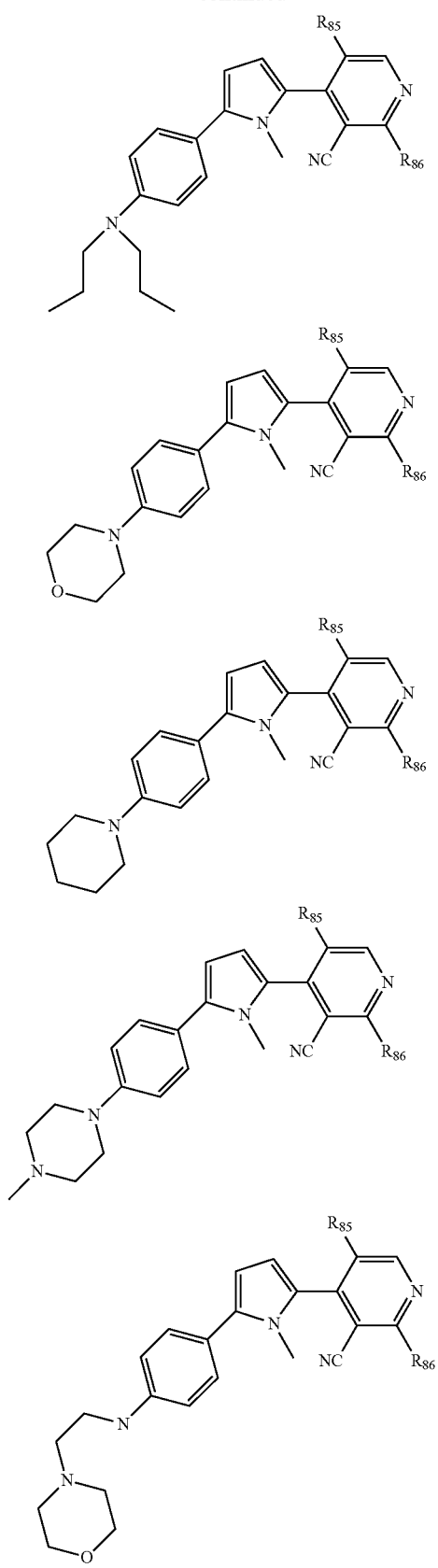
wherein R$_{85}$ is H or CN and R$_{86}$ is H.
214
In some cases, the compound of Formula II is selected from a group consisting of
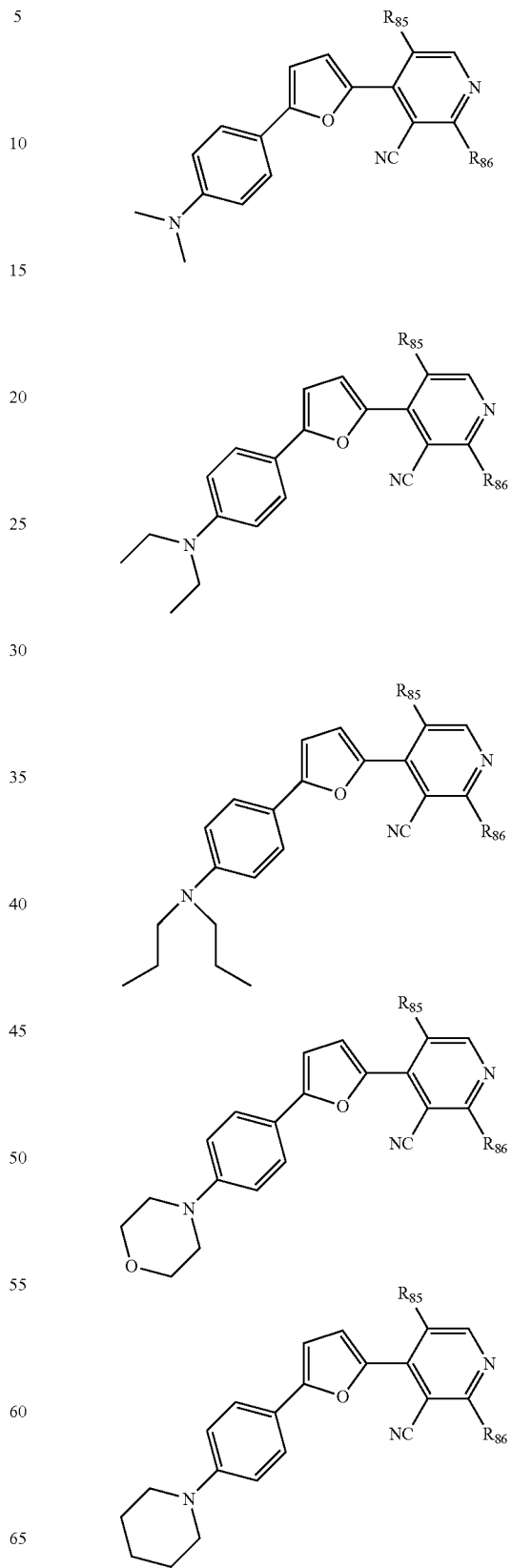
and 215
-continued
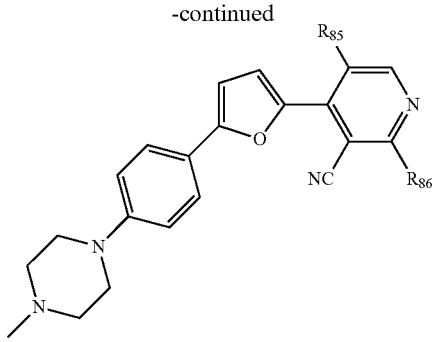
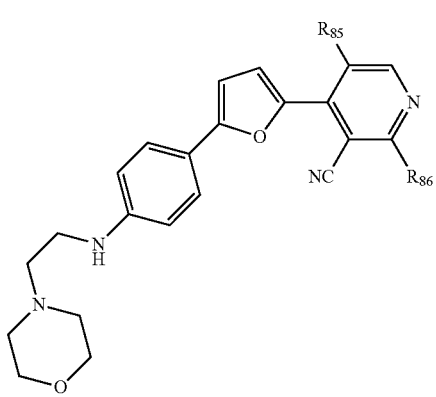
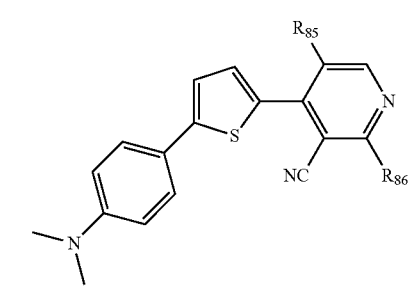
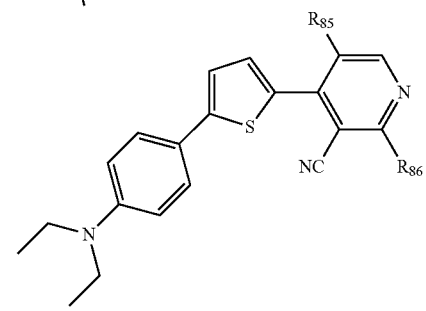
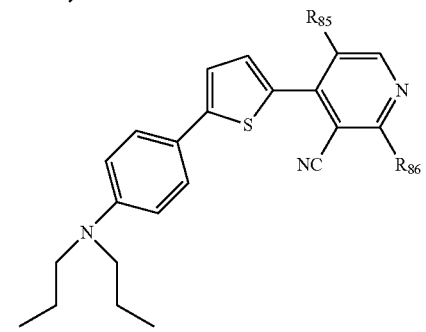
216
-continued
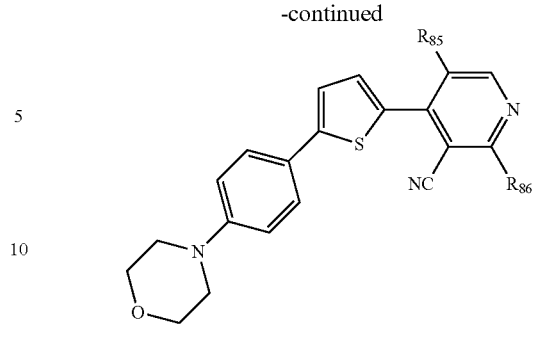
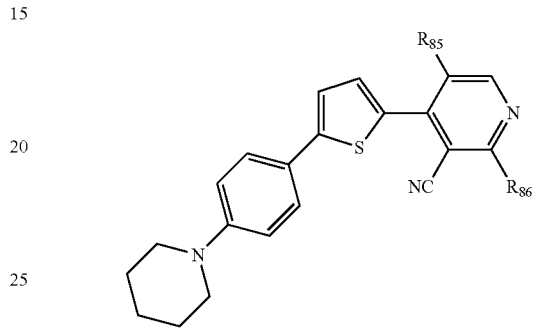
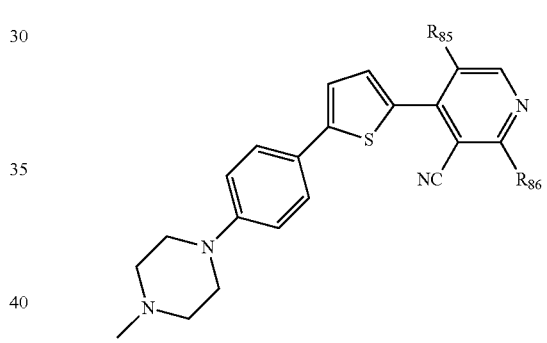
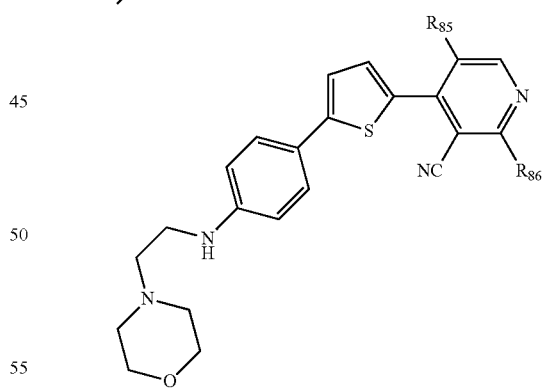
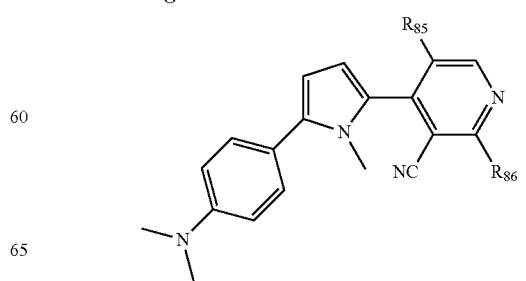

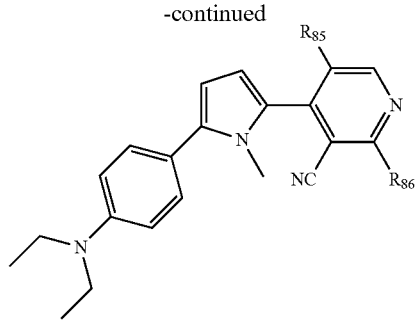
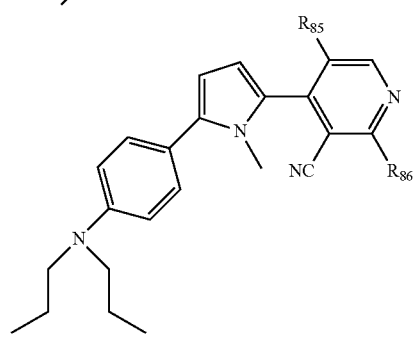
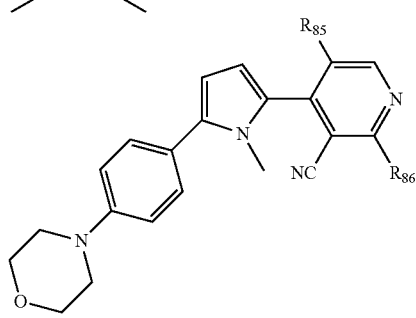
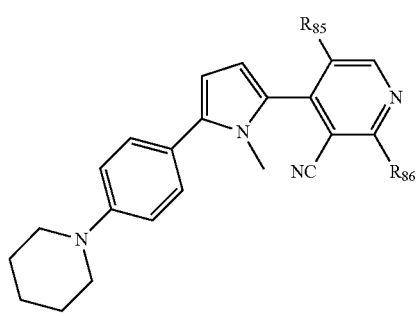
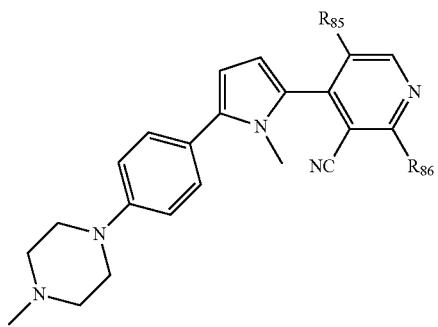
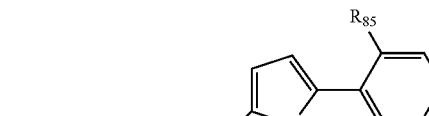
wherein R₈₅ is H or CN and R₈₆ is
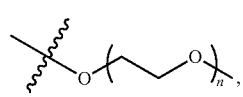
wherein n is an integer with value 0-50. In some compounds of Formula II, n is a integer of value 0-10, e.g. n is 0, 1, 2, 3, 4, 5, 6, 7, 8, 9, or 10.
In some cases the compound of Formula II is:
(Compound 17)
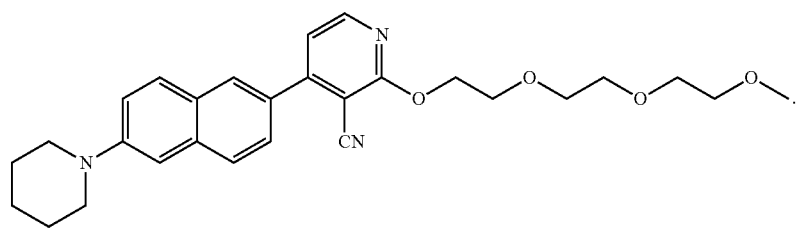

In some cases the compound of Formula II is 2-(2-(2-(2-methoxyethoxy)ethoxy)ethoxy)-4-(6-(piperidin-1-yl)naphthalen-2-yl)nicotinonitrile.

In some cases the compound of Formula II is:

(Compound 18)

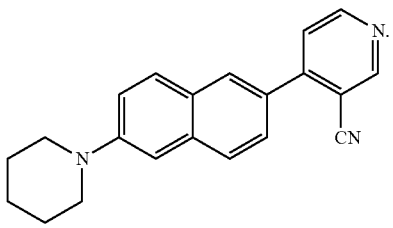

In some cases the compound of Formula II is 4-(6-(piperidin-1-yl)naphthalen-2-yl)nicotinonitrile.

Routes of Administration

In some cases, the formulations of the present disclosure draw upon many suitable modes of administration. In some cases, delivery is achieved either via local or systemic administration. Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. In some cases, the compounds of the disclosure are administered in a systemic manner. In some cases administration is parenteral. In some cases the administration is intravenous. In some cases the administration is subcutaneous. In some cases the administration is intramuscular. In some cases the administration is intrathecal. Administration can take place via enteral administration (absorption of the drug through the gastrointestinal tract) or parenteral administration, for example by injection, infusion, or implantation. In some cases administration is transmucosal, such as oral, buccal, sublingual, nasal, pulmonary, or rectal. In some cases administration is oral. In some cases administration is buccal. In some cases administration is sublingual. In some cases administration is nasal. In some cases administration is pulmonary. In some cases administration is rectal. In some cases administration is transdermal. In some cases administration is intradermal. In some cases administration is topical. In some cases administration is topical ocular.

In certain cases, a compound as described herein is administered in a local rather than systemic manner, for example, via injection of the compound directly into an organ, often in a depot preparation or sustained release formulation. In specific cases, long acting formulations are administered by implantation (for example subcutaneously or intramuscularly) or by intramuscular injection. Furthermore, in other cases, the drug is delivered in a targeted drug delivery system, for example, in a liposome coated with organ-specific antibody. In such cases, the liposomes are targeted to and taken up selectively by the organ. In yet other cases, the compound as described herein is provided in the form of a rapid release formulation, in the form of an extended release formulation, or in the form of an intermediate release formulation. In yet other cases, the compound described herein is administered topically.

In some cases, the compounds are administered to the eye. In some cases, the pharmaceutical composition of the disclosure administered to eye is delivered to the retina, intraocular space, ocular surface, interconnecting innervation, conjunctiva, lacrimal glands, or meibomian glands. In some cases, the compounds are administered topically to the eye. In some cases, the compounds are administered as an eye drop.

The compounds according to the disclosure are effective over a wide dosage range. In some cases, in the treatment of adult humans, dosages are from 0.01 to 1000 mg, from 0.5 to 100 mg, from 1 to 50 mg per day, and from 5 to 40 mg per day are examples of dosages that are used. An exemplary dosage is 10 to 30 mg per day. In some cases the effective amount the compound corresponds to about 50-500 mg of compound per adult subject. The exact dosage will depend upon the route of administration, the form in which the compound is administered, the subject to be treated, the body weight of the subject to be treated, and the preference and experience of the attending physician.

In some cases the effective amount the compound corresponds to about 0.01-1000 mg of compound per adult human subject per dosage. In some cases, the effective dose of compound is be 50-500 mg per adult human per dosage. In some cases the effective amount corresponds to about 0.01-100 mg, 0.01-200 mg, 0.01-300 mg, 0.01-400 mg, 0.01-500 mg, 0.01-600 mg, 0.01-700 mg, 0.01-800 mg, 0.01-900 mg, 0.01-1000 mg, 0.1-100 mg, 0.1-200 mg, 0.1-300 mg, 0.1-400, 0.1-500 mg, 0.1-600 mg, 0.1-700 mg, 0.1-800 mg, 0.1-900 mg, 0.1-1000 mg, 1-100 mg, 1-200 mg, 1-300 mg, 1-400 mg, 1-500 mg, 1-600 mg, 1-700 mg, 1-800 mg, 1-900 mg, 100-200 mg, 100-300 mg, 100-400 mg, 100-500 mg, 100-600 mg, 100-700 mg, 100-800 mg, 100-900 mg, 100-1000 mg, 200-300 mg, 200-400 mg, 200-500 mg, 200-600 mg, 200-700 mg, 200-800 mg, 200-900 mg, 200-1000 mg, 300-400 mg, 300-500 mg, 300-600 mg, 300-700 mg, 300-800 mg, 300-900 mg, 300-1000 mg, 400-500 mg, 400-600 mg, 400-700 mg, 400-800 mg, 400-900 mg, 400-1000 mg, 500-600 mg, 500-700 mg, 500-800 mg, 500-900 mg, 500-1000 mg, 600-700 mg, 600-800 mg, 600-900 mg, 600-1000 mg, 700-800 mg, 700-900 mg, 700-1000 mg, 800-900 mg, 800-1000 mg or about 900-1000 mg per adult human per dosage. In some cases, the effective amount corresponds to about 50-100 mg, 50-400 mg, 50-500 mg, 100-200 mg, 100-300 mg, 100-400 mg, 100-500 mg, 200-300 mg, 200-400 mg, 200-500, 300-400 mg, 300-500 mg, or 400-500 mg per adult human per dosage. The exact dosage will depend upon the route of administration, the form in which the compound is administered, the subject to be treated, the body weight of the subject to be treated, and the preference and experience of the attending physician.

In some cases, a compound of the disclosure is administered in a single dose. In some cases, a compound of the disclosure is administered in multiple doses. In some cases, dosing is about once, twice, three times, four times, five times, six times, or more than six times per day. In some cases, dosing is about once a month, once every two weeks, once a week, or once every other day. In another case a compound of the disclosure and another agent are administered together about once per day to about 6 times per day. In some cases the administration of a compound of the disclosure and an agent continues for less than about 7 days. In yet another case the administration continues for more than about 6, 10, 14, 28 days, two months, six months, or one year. In some cases, continuous dosing is achieved and maintained as long as necessary.

In some cases, administration of the compounds of the disclosure continues as long as necessary. In some cases, a compound of the disclosure is administered for more than 1, 2, 3, 4, 5, 6, 7, 14, or 28 days. In some cases, a compound of the disclosure is administered for less than 28, 14, 7, 6, 5, 4, 3, 2, or 1 day. In some cases, a compound of the disclosure is administered chronically on an ongoing basis, e.g., for the treatment of chronic effects.

In some cases, for administration to the eyes, compounds are administered several times a day per eye. In some cases, the compounds are administered one to ten times, one to four times, or once a day. In some cases, the compounds are administered 1, 2, 3, 4, 5, 6, 7, 8, 9, or 10 times a day. In some cases, the size of the drop administered is in the range of about 10-100 µL, about 10-90 µL, about 10-80 µL, about 10-70 µL, about 10-60 µL, about 10-50 µL, about 10-40 µL, about 10-30 µL, about 20-100 µL, about 20-90 µL, about 20-80 µL, about 20-70 µL, about 20-60 µL, about 20-50 µL, about 20-40 µL, or about 20-30 µL. One example of the disclosure administers a drop in the range of about 10 to about 30 µL. One example of the disclosure administers a drop in the range of about 10 to about 100 µL. One example of the disclosure administers a drop in the range of about 20 to about 50 µL. One example of the disclosure administers a drop in the range of about 20 to about 40 µL. One example of the disclosure administers a drop in the range of about 10 to about 60 µL. In some cases, the eye formulations of the disclosure is administered several drops per time, for example 1-3 drops per time, 1-3 drops per time, 1-4 drops per time, 1-5 drops per time, 1-6 drops per time, 1-7 drops per time, 1-8 drops per time, 1-9 drops per time, 1-10 drops per time, 3-4 drops per time, 3-5 drops per time, 3-6 drops per time, 3-7 drops per time, 3-8 drops per time, 3-9 drops per time, 3-10 drops per time, 5-6 drops per time, 5-7 drops per time, 5-8 drops per time, 5-9 drops per time, 5-10 drops per time, 7-8 drops per time, 7-9 drops per time or 9-10 drops per time. In one example, the formulations of the disclosure are administered about one drop per time and 1-6 times per day.

In some cases, the compounds of the disclosure are administered in dosages. It is known in the art that due to intersubject variability in compound pharmacokinetics, individualization of dosing regimen is necessary for optimal therapy. In some cases, dosing for a compound of the disclosure is found by routine experimentation in light of the instant disclosure.

Pharmaceutical Compositions/Formulations

In some cases, the compounds described herein are formulated into pharmaceutical compositions. In some cases, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound of Formula I or Formula II and a pharmaceutically acceptable diluent(s), excipient(s), or carrier(s). In certain cases, the compounds described are administered as pharmaceutical compositions in which compounds of any of Formula I or Formula II, are mixed with other active ingredients, as in combination therapy. In specific cases, the pharmaceutical compositions include one or more compounds of any of Formula I or Formula II.

A pharmaceutical composition, as used herein, refers to a mixture of a compound of any of Formula I or Formula II, with other chemical components, such as carriers, stabilizers, diluents, dispersing agents, suspending agents, thickening agents, and/or excipients. In certain cases, the pharmaceutical composition facilitates administration of the compound to an organism. In some cases, practicing the methods of treatment or use provided herein, therapeutically effective amounts of compounds of any of Formula I or Formula I, provided herein are administered in a pharmaceutical composition to a mammal having a disease or condition to be detected, diagnosed or treated. In specific cases, the mammal is a human. In certain cases, therapeutically effective amounts vary depending on the severity of the disease, the age and relative health of the subject, the potency of the compound used and other factors. The compounds described herein are used singly or in combination with one or more therapeutic agents as components of mixtures.

In some cases, one or more compounds of any of Formula I or Formula II is formulated in an aqueous solution. In specific cases, the aqueous solution is selected from, by way of example only, a physiologically compatible buffer, such as Hank's solution, Ringer's solution, aqueous acetate buffer, aqueous citrate buffer, aqueous carbonate buffer, aqueous phosphate buffer or physiological saline buffer.

In other cases, one or more compound of any of Formula I or Formula II is formulated for transmucosal administration. In specific cases, transmucosal formulations include penetrants that are appropriate to the barrier to be permeated. In still other cases wherein the compounds described herein are formulated for other parenteral injections, appropriate formulations include aqueous or nonaqueous solutions. In specific cases, such solutions include physiologically compatible buffers and/or excipients.

In some cases, the compounds described herein are formulated for ocular administration. In some cases, the ocular formulations is liquid (in form of solutions, suspensions, powder for reconstitution, sol to gel systems), semi solids (ointments and gels), solids (ocular inserts), and intraocular dosage forms (injections, irrigating solutions and implants).

In another case, compounds described herein are formulated for oral administration. Compounds described herein, including compounds of any of Formula I or Formula II, are formulated by combining the active compounds with, e.g., pharmaceutically acceptable carriers or excipients. In various cases, the compounds described herein are formulated in oral dosage forms that include, by way of example only, tablets, powders, pills, dragees, capsules, liquids, gels, syrups, elixirs, slurries, suspensions and the like.

In certain cases, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific cases, disintegrating agents are optionally added. Disintegrating agents include, by way of example only, cross-linked croscarmellose sodium, polyvinylpyrrolidone, agar, or alginic acid or a salt thereof such as sodium alginate.

In some cases, dosage forms, such as dragee cores and tablets, are provided with one or more suitable coating. In specific cases, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain cases, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific cases, push-fit capsules contain the active ingredients in admixture with one or more filler. Fillers include, by way of example only, lactose, binders such as starches, and/or lubricants such as talc or magnesium stearate and, optionally, stabilizers. In other cases, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other cases, therapeutically effective amounts of at least one of the compounds described herein are formulated for buccal or sublingual administration. Formulations suitable for buccal or sublingual administration include, by way of example only, tablets, lozenges, or gels. In still other cases, the compounds described herein are formulated for parental injection, including formulations suitable for bolus injection or continuous infusion. In specific cases, formulations for injection are presented in unit dosage form (e.g., in ampoules) or in multi-dose containers. Preservatives are, optionally, added to the injection formulations. In still other cases, the pharmaceutical composition of any of Formula I or Formula II, are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific cases, pharmaceutical formulations for parenteral administration include aqueous solutions of the active compounds in water-soluble form. In additional cases, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific cases, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other cases, the active ingredient is in powder form for constitution with a suitable vehicle, e.g., sterile pyrogen-free water, before use.

In still other cases, the compounds of any of Formula I or Formula II are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other cases, the compounds of any of Formula I or Formula II are formulated for transdermal administration. In specific cases, transdermal formulations employ transdermal delivery devices and transdermal delivery patches and can be lipophilic emulsions or buffered, aqueous solutions, dissolved and/or dispersed in a polymer or an adhesive. In various cases, such patches are constructed for continuous, pulsatile, or on demand delivery of pharmaceutical agents. In additional cases, the transdermal delivery of the compounds of any of Formula I or Formula II is accomplished by means of iontophoretic patches and the like. In certain cases, transdermal patches provide controlled delivery of the compounds of any of Formula I or Formula II. In specific cases, the rate of absorption is slowed by using rate-controlling membranes or by trapping the compound within a polymer matrix or gel. In alternative cases, absorption enhancers are used to increase absorption. Absorption enhancers or carriers include absorbable pharmaceutically acceptable solvents that assist passage through the skin. In some cases, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other cases, the compounds of any of Formula I or Formula II are formulated for administration by inhalation. Various forms suitable for administration by inhalation include, but are not limited to, aerosols, mists or powders. Pharmaceutical compositions of any of Formula I or Formula II are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific cases, the dosage unit of a pressurized aerosol is determined by providing a valve to deliver a metered amount. In certain cases, capsules and cartridges of, such as, by way of example only, gelatin for use in an inhaler or insufflator are formulated containing a powder mix of the compound and a suitable powder base such as lactose or starch.

In still other cases, the compounds of any of Formula I or Formula II are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain cases, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of any of Formula I or Formula II are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of any of Formula I or Formula II described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some cases, pharmaceutical composition comprising at least one compound of any of Formula I or Formula II illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some cases, a liquid composition includes a gel formulation. In other cases, the liquid composition is aqueous.

In certain cases, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of any of Formula I or Formula II. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In some cases, the formulations of the disclosure is packaged in multidose form or in single dose units. In some cases, the formulations are packaged in multidose forms. In some cases the formulations are packaged as single dose from. In some cases of the disclosure single dose packaging of the formulations can offer several advantages over multi dose packaging including dosage control, increased patient compliance, improved product labeling, and reduced counterfeiting. In various cases single dosage packaging of the formulations of the disclosure can be in form of vials, ampoules, tubes, bottles, pouches, packets, syringes or blister packs.

In alternative cases, other delivery systems for hydrophobic pharmaceutical compounds are employed. Liposomes and emulsions are examples of delivery vehicles or carriers useful herein. In certain cases, organic solvents such as N-methylpyrrolidone are also employed. In additional cases, the compounds described herein are delivered using a sustained-release system, such as semipermeable matrices of solid hydrophobic polymers containing the therapeutic agent. Various sustained-release materials are useful herein. In some cases, sustained-release capsules release the compounds for a few weeks up to over 100 days. Depending on the chemical nature and the biological stability of the therapeutic reagent, additional strategies for protein stabilization are employed.

In certain cases, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some cases, the concentration of one or more compounds provided in the pharmaceutical compositions of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some cases, the concentration of one or more compounds of the disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25% 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some cases, the concentration of one or more compounds of the disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some cases, the concentration of one or more compounds of the disclosure is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some cases, the amount of one or more compounds of the disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some cases, the amount of one or more compounds of the disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some cases, the amount of one or more compounds of the disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

The disclosure also provides a kit comprising a compound according to the disclosure. In some cases, the compounds of the disclosure are contained in a container as formulations. In some cases, the kit comprises the compounds of the disclosure contained in a container as a sterile liquid formulation. In some cases, the compounds are also placed in the containers as a sterile freeze-dried formulation. In some cases, the container is a vial. In some cases, the container is an amber vial. In some cases, the container is capable of protecting light sensitive compounds or formulation.

In some cases, such kits comprise a carrier, package, or container that is compartmentalized to receive one or more containers such as vials, tubes, and the like, wherein one or more of the container(s) comprise the compound of Formula I or Formula II. Suitable containers include, for example, bottles, vials, syringes, and test tubes. The containers are formed from a variety of materials such as glass or plastic. In some cases, the containers are chosen so as to protect, limit or minimize the exposure of the compounds of Formula I or Formula II to light. In some cases, the container is an amber vial.

The articles of manufacture provided herein contain packaging materials. Packaging materials for use in packaging pharmaceutical products Include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

In some cases, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain cases, the pharmaceutical composition is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some cases, Compositions containing a compound provided herein formulated in a compatible pharmaceutical carrier are prepared, placed in an appropriate container, and labeled for treatment of an indicated condition.

Methods of Use

In one aspect, the disclosure provides a method for detecting one or more amyloid or amyloid like proteins comprising contacting a compound according to according to any one of Formula I or II or a pharmaceutical composition thereof with a sample potentially comprising the amyloid or amyloid like protein, wherein in presence of an amyloid or amyloid like protein the compound forms a detectable complex, detecting the formation of the detectable complex such that the presence or absence of the detectable complex correlates with the presence or absence of the amyloid or amyloid like protein.

In some cases, the compounds of the instant disclosure is used for detecting one or more amyloid or amyloid like protein with high sensitivity. In some cases, the compounds predict the presence and or absence of a disease with greater than 10%, 15%, 20%, 25%, 30%, 35%, 40%, 45%, 50%, 55%, 60%, 65%, 70%, 75%, 80%, 85%, 90%, 95% or 99% sensitivity. In some cases the compounds are capable of detecting one or more amyloid or amyloid like protein with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sensitivity. In some cases the compounds are capable of detecting one or more amyloid or amyloid like protein with greater than 99.5%, 99.6%, 99.7%, 99.8% or 99.9% sensitivity.

In some cases, the compounds of the instant disclosure are used for detecting one or more amyloid or amyloid like protein with high specificity. In some cases, the compounds detect one or more amyloid or amyloid like protein with greater than 10%, 15%, 20%, 25%, 30%, 35%, 40%, 45%, 50%, 55%, 60%, 65%, 70%, 75%, 80%, 85%, 90%, 95% or 99% specificity. In some cases the compounds are capable of detecting one or more amyloid or amyloid like protein with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% specificity. In some cases the compounds are capable of detecting one or more amyloid or amyloid like protein with greater than 99.5%, 99.6%, 99.7%, 99.8% or 99.9% specificity.

In some cases, the compounds of the disclosure are also used for detecting one or more amyloid or amyloid like protein with both high specificity and high specificity. In some cases, the compounds are capable of detecting one or more amyloid or amyloid like protein with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sensitivity and greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% specificity.

The disclosure also provides a method for treating or preventing one or more disease or condition comprising administering to a subject in need of treatment an effective amount of a compound to any one of Formula I or II or a pharmaceutical composition thereof. In some cases, the compounds of the disclosure are used to treat or prevent diseases or conditions characterized by protein aggregation or protein misfolding. In some cases, the disease or condition is an amyloid-based disease or condition.

In some cases, the compounds of the instant disclosure are used for treating or preventing a disease or condition with high sensitivity. In some cases, the compounds treat or prevent a disease or condition with greater than 10%, 15%, 20%, 25%, 30%, 35%, 40%, 45%, 50%, 55%, 60%, 65%, 70%, 75%, 80%, 85%, 90%, 95% or 99% sensitivity. In some cases the compounds are capable of treating or preventing a disease or condition with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sensitivity. In some cases the compounds are capable of treating or preventing a disease or condition with greater than 99.5%, 99.6%, 99.7%, 99.8% or 99.9% sensitivity.

In some cases, the compounds of the instant disclosure are used for treating or preventing a disease or condition with high specificity. In some cases, the compound predict the presence and or absence of a disease with greater than 10%, 15%, 20%, 25%, 30%, 35%, 40%, 45%, 50%, 55%, 60%, 65%, 70%, 75%, 80%, 85%, 90%, 95% or 99% specificity. In some cases the compounds are capable of diagnosis with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% specificity. In some cases the compounds are capable of diagnosis with greater than 99.5%, 99.6%, 99.7%, 99.8% or 99.9% specificity.

In some cases, the compounds of the disclosure are also used for treating or preventing a disease or condition with both high specificity and high specificity. In some cases, the compounds are capable of diagnosis with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sensitivity and greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% specificity.

Also provided herein is a method of determining the presence or absence of one or more disease or condition in a subject comprising administering to the subject an effective amount of a compound according to any one of Formula I or II or a pharmaceutical composition thereof, wherein in presence of the disease or condition the administered compound forms a detectable complex, and detecting the formation of the detectable complex such that presence or absence of detectable complex correlates with the presence or absence of the disease or condition. In some cases, the compounds of the disclosure are used for determining the presence or absence of one or more amyloid-based disease or condition, wherein in presence of the amyloid-based disease or condition the administered compound forms a detectable complex, and detecting the formation of the detectable complex such that presence or absence of detectable complex correlates with the presence or absence of the amyloid-based disease or condition. In some cases, the compounds of the disclosure are used for determining the presence or absence of one or more disease or condition characterized by protein aggregation or protein misfolding.

In some cases, the method includes comparing the amount of the detectable complex to a normal control value, wherein an increase in the amount of the complex compared to a normal control value indicates that said patient is suffering from or is at risk of developing the disease or condition.

In some cases a single dose of the compounds of the disclosure is used to determining the presence or absence of multiple diseases disease or conditions in a subject. In some cases, a single dose is used to detect the presence or absence of 2, 3, 4, 5, 6, 7, 8, 9, 10, 11, 12, 13, 14, 15, 16, 17, 18, 19 or 20 diseases in a subject. In some cases, a single dose is used to determine the presence of 1, 2, 3, 4, or 5 disease or conditions.

In some cases, the compounds of the instant disclosure are used for diagnosis with high sensitivity. In some cases, the compounds predict the presence and or absence of a disease with greater than 10%, 15%, 20%, 25%, 30%, 35%, 40%, 45%, 50%, 55%, 60%, 65%, 70%, 75%, 80%, 85%, 90%, 95% or 99% sensitivity. In some cases the compounds are capable of diagnosis with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sensitivity. In some cases the compounds are capable of diagnosis with greater than 99.5%, 99.6%, 99.7%, 99.8% or 99.9% sensitivity.

In some cases, the compounds of the instant disclosure are used for diagnosis with high specificity. In some cases, the compounds predict the presence and or absence of a disease with greater than 10%, 15%, 20%, 25%, 30%, 35%, 40%, 45%, 50%, 55%, 60%, 65%, 70%, 75%, 80%, 85%, 90%, 95% or 99% specificity. In some cases the compounds are capable of diagnosis with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% specificity. In some cases the compounds are capable of diagnosis with greater than 99.5%, 99.6%, 99.7%, 99.8% or 99.9% specificity.

In some cases, the compounds of the disclosure are also used for diagnosis with both high specificity and high specificity. In some cases, the compounds are capable of diagnosis with greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sensitivity and greater than 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% specificity.

Also provided herein is a method of monitoring minimal residual disease in a patient following treatment with a compound or a mixture according to the disclosure. The method includes bringing the sample or a specific body part or body area suspected to contain the amyloid or amyloid like protein into contact with a compound of the disclosure, allowing the compound to bind to the amyloid or amyloid like protein to form a detectable complex, detecting the formation of the detectable complex and correlating the presence or absence of the detectable complex with the presence or absence of amyloid or amyloid like protein in the sample or specific body part or area. In some cases, the method includes comparing the amount of said detectable complex to a normal control value, wherein an increase in the amount of said detectable complex compared to a normal control value indicates that said patient is still be suffering from a minimal residual disease.

Also provided herein is a method of predicting responsiveness of a patient to a treatment, wherein the method includes bringing the sample or a specific body part or body area suspected to contain the amyloid or amyloid like protein into contact with a compound of the disclosure, allowing the compound to bind to the amyloid or amyloid like protein to form a detectable complex, detecting the formation of the detectable complex and correlating the presence or absence of the detectable complex with the presence or absence of amyloid or amyloid like protein in the sample or specific body part or area. In some cases, the method optionally includes comparing the amount of the detectable complex before and after onset of the treatment, wherein a decrease in the amount of the detectable complex indicates that the patient is being responsive to the treatment.

Also provided herein is screening method, wherein the method comprises administering to a subject an effective amount of a compound of Formula I or II, or a pharmaceutical composition thereof. In some cases, upon administration, the compound of Formula I or 11 forms a detectable complex. In some cases, the method further comprises measuring a signal generated by the compound of Formula I or Formula II upon administration to the subject, or by the detectable complex formed by the compound of Formula I or II. In some cases, the method also comprises making a clinical decision based on the measured signal.

In some cases, the detection of the detectable complex disclosure comprises illuminating the sample with light of an appropriate wavelength for a peak region of a fluorescent excitation spectrum for the detectable complex and detecting light received from the sample of an appropriate wavelength for a peak region of a fluorescent emission spectrum for the detectable complex. In some cases, the detectable complex is a complex of a compound of Formula I or II with a amyloid or amyloid-like protein. In some cases, the excitation spectrum has a peak at about 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 n, 490 nm, 500 nm, 510 nm, 520 nm, 530 nm, 540 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, or 900 nm. In some cases, the fluorescent excitation spectrum of the detectable complex has a peak at about 350-400, 350-450 nm, 350-500 nm, 350-550 nm, 350-600 nm, 400-450 nm, 400-500, 400-550 nm, 400-600 nm, 450-500 nm, 450-550 nm, 450-600 nm, 500-550, or 550-600 nm. In some cases, the fluorescent excitation spectrum of the detectable complex has a peak at about 350-400 nm, 400-500 nm or 450-500 nm. In some cases, the illuminating of the sample is at a wavelength within plus or minus about 100 nm, 90 nm, 80 nm, 70 nm, 60 nm, 50 nm, 40 nm, 30 nm, 20 nm, 10 nm, or 0 nm of the peak of the excitation spectrum. In some cases, the illuminating light has a wavelength of 300-500 nm, 350-450 nm, 400-500 nm. In some cases, the illuminating light has a wavelength of 400 nm.

In some cases, the emission spectrum has a peak of about 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 n, 490 nm, 500 nm, 510 nm, 520 nm, 530 nm, 540 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, or 900 nm. In some cases, the emission spectrum of the detectable complex has a peak at about 500-550 nm, in some cases at about 510-540 nm. In some cases, the emission spectrum of the detectable complex has a peak at about 520 nm, 521 nm, 522 nm, 523 nm, 524 nm, 525 nm, 526 nm, 527 nm, 528 nm, 529 nm, 530 nm, 531 nm, 532 nm, 533 nm, 534 nm, 535 nm, 536 nm, 537 nm, 538 nm, 539 nm or 540 nm. In some cases, the detecting of light received from the sample is at a wavelength within plus or minus about 100 nm, 90 nm, 80 nm, 70 nm, 60 nm, 50 nm, 40 nm, 30 nm, 20 nm, 10 nm, or 0 nm of the peak of the emission spectrum.

In some cases, the term amyloid-based disease or condition refers to any disease or condition. The term also includes any disease or condition characterized by protein aggregation or protein misfolding. In some cases, amyloid-based disease or condition is any disease or condition that is associated with the increased or decreased presence of amyloid or amyloid like proteins or proteins, such as the presence of amyloid plaques. In some cases the amyloid based disease or condition is a neuronal disease or condition, for example, neurodegenerative diseases, in which amyloid-beta peptides, oligomers, fibrils, or plaques are implicated. Non limiting examples of amyloid-based neurodegenerative diseases include Alzheimer's disease, Parkinson's disease, Huntington's disease, Down's Syndrome, and spongiform encephalopathies such as, for example, bovine spongiform encephalopathy (mad cow disease), kuru, Creutzfeldt-Jakob disease, and fatal familial insomnia. In some cases, other amyloid based diseases that are detected, treated or prevented by the methods of the disclosure include reactive systemic amyloidosis, senile systemic amyloidosis (SAA), familial amyloid polyneuropathy (FAP), familial amyloid cardiomyopathy (FAC), prion disease, coronary heart disease, atherosclerosis, cerebral hemorrhage, AL amyloidosis, type 2 diabetes, diseases or conditions characterized by a loss of cognitive memory capacity such as, for example, mild cognitive impairment (MCI), Lewy body dementia (LBD), hereditary cerebral hemorrhage with amyloidosis (Dutch type) and the Guam Parkinson-Dementia complex. Other diseases which are based on or associated with amyloid-like proteins are progressive supranuclear palsy, multiple sclerosis, HIV-related dementia, ALS (amyotropic lateral sclerosis), inclusion-body myositis (IBM), Adult Onset Diabetes; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidosis; the retina, including primary retinal degenerations and macular degeneration, in particular age-related macular degeneration; the optic nerve, including optic nerve drusen, optic neuropathy and optic neuritis; and the cornea, including lattice dystrophy.

In some cases the compounds of the present disclosure can be employed for the treatment of Alzheimer's disease, Alzheimer's disease (AD), Parkinson's disease, Huntington's disease, amyotrophic, lateral sclerosis (ALS), Lewy body dementia (LBD), or Down's syndrome. In some cases, the compounds of the present disclosure can be employed for the detection, diagnosis, treatment and monitoring of Alzheimer's disease. Or the compounds of the present disclosure can be employed for the detection, diagnosis, treatment and monitoring of Creutzfeldt-Jakob disease (CJD).

In some cases, amyloid diseases or conditions also include ocular diseases associated with pathological abnormalities/changes in the tissues of the visual system, particularly associated with amyloid-beta-related pathological abnormalities/changes in the tissues of the visual system, such as, for example, neuronal degradation. In some cases, said pathological abnormalities occur in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidosis; the retina leading to primary retinal degeneration and macular degeneration, for example age-related macular degeneration; the optic nerve leading to optic nerve drusen, optic neuropathy and optic neuritis; and the cornea leading to lattice dystrophy.

In some cases, the amyloid or amyloid like proteins and/or proteins that are detected using the methods of the disclosure include amyloid beta peptides (Aβ), prion peptide (PrP), alpha-synuclein, IAPP (amylin), huntingtin, calcitonin (ACal), atrial natriuretic factor (AANF), apolipoprotein A1 (ApoA1), serum amyloid A (SAA), medin (AMed), prolactin (APro), transthyretin (ATTR), lysozyme (ALys), beta 2 microglobulin (Aβ2M), gelsolin (AGel), keratoepithelin (Aker), cystatin (ACys), immunoglobulin light chain AL (AL), S-IBM or superoxide dismutase. In some cases, the amyloid peptide detected by the method of the disclosure is Aβ peptide, prion peptide, alpha-synuclein, or superoxide dismutase.

In some cases, the subjects for the methods of the instant disclosure are any mammal. In some cases, the subject is a primate (such as a human), canine, feline, ovine, bovine and the like. In some cases, biological samples that are used in the diagnosis of an amyloid-associated disease or condition for diagnosing a predisposition to an amyloid-associated disease or condition or for monitoring minimal residual disease in a patient or for predicting responsiveness of a patient to a treatment with a compound or a composition or a mixture according to the disclosure and as described herein before are, for example, fluids such as serum, plasma, saliva, gastric secretions, mucus, cerebrospinal fluid, lymphatic fluid, and the like, or tissue or cell samples obtained from an organism such as neural, brain, cardiac or vascular tissue. For determining the presence or absence of the amyloid or amyloid like protein in a sample any immunoassay known to those of ordinary skill in the art may be used such as, for example, assays which utilize indirect detection methods using secondary reagents for detection, ELISA's and immunoprecipitation and agglutination assays.

EMBODIMENTS

Specific embodiments of the subject matter disclosed herein is set forth in the following embodiments.

Embodiment P1

A compound of Formula I

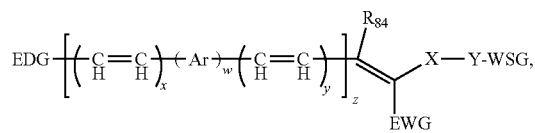

(Formula I), wherein EDG is an electron donating group; each Ar is independently $C_1$-$C_{14}$ arylene or $C_1$-$C_{14}$ heteroarylene, each optionally substituted with one more $R_1$; each $R_1$ is independently halogen, —$OR_2$, —$NR_3R_4$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_5$; $R_2$, $R_3$ and $R_4$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_5$; each $R_5$ is independently halogen, —$OR_6$, —$NR_7R_8$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_6$, $R_7$, $R_8$ and $R_{84}$ are independently hydrogen or $C_1$-$C_{10}$ alkyl; EWG is an electron withdrawing group; WSG is a water soluble group; X is C=O or $SO_2$; Y is NH, or S; each w is independently an integer from 1-5; each x is independently an integer from 0-10; each y is independently an integer from 0-10; and z is an integer from 1-10.

Embodiment P2

The compound of embodiment P1, wherein EDG is —$OR_9$, —$NR_{10}R_{11}$, —$SR_{12}$, —$PR_{13}R_{14}$, —$NR_{15}C(O)R_{16}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{17}$; each $R_{17}$ is independently halogen, —$OR_{18}$, —$NR_{19}R_{20}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_9$, $R_{10}$, $R_{11}$, $R_{12}$, $R_{13}$, $R_{14}$, $R_{15}$, $R_{16}$, $R_{18}$, $R_{19}$ and $R_{20}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{21}$ and wherein $R_{10}$ and $R_{11}$ are optionally joined together to form a heterocycloalkyl or heteroaryl optionally substituted with $R_{21}$; each of $R_{21}$ is independently halogen, —$OR_{22}$, —$NR_{23}R_{24}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{25}$; each of $R_{22}$, $R_{23}$ and $R_{24}$ is independently hydrogen or $C_1$-$C_{10}$ alkyl; and each $R_{25}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment P3

The compound of embodiment P1, wherein EDG is selected from a group consisting of

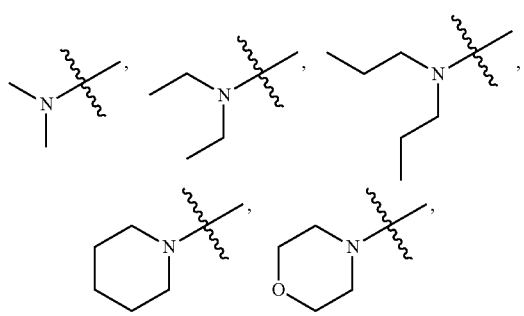

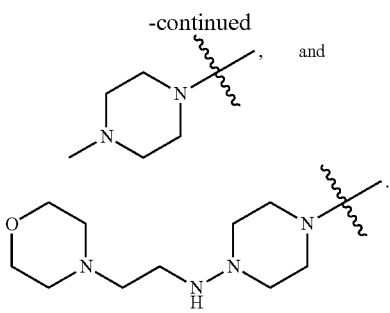, and

Embodiment P4

The compound of embodiment P1, wherein EDG is

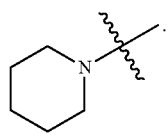 [SMILES: *N1CCCCC1]

Embodiment P5

The compound of embodiment P1, wherein EWG is halogen, —CN, —NO$_2$, —SO$_3$H, —CR$_{26}$R$_{27}$R$_{28}$, —COR$_{29}$, or —COOR$_{30}$; each R$_{26}$, R$_{27}$ and R$_{28}$ is independently hydrogen or halogen; R$_{29}$ is halogen, hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{31}$; R$_{30}$ is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{32}$; and each R$_{31}$ and R$_{32}$ is independently C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene.

Embodiment P6

The compound of embodiment P1, wherein EWG is selected from a group consisting of —F, —Cl, —Br, —C═O, NO$_2$, —CF$_3$, —CCl$_3$, —SO$_3$ and —CN.

Embodiment P7

The compound of embodiment P6, wherein EWG is —CN.

Embodiment P8

The compound of embodiment P1, wherein WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{33}$; each R$_{33}$ is independently halogen, —OR$_{34}$, —NR$_{35}$R$_{36}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{34}$, R$_{35}$ and R$_{36}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{37}$ is independently halogen, —OR$_{38}$, —NR$_{39}$R$_{40}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene; and each of R$_{38}$, R$_{39}$ and R$_{40}$ is independently hydrogen or C$_1$-C$_{10}$ alkyl.

Embodiment P9

The compound of embodiment P8, wherein WSG is

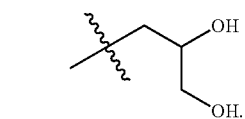 [SMILES: *CC(O)CO]

Embodiment P10

The compound of embodiment P1, wherein WSG comprises polyethylene glycol, polypropylene glycol, co-polymer of polyethylene glycol and polypropylene glycol, or alkoxy derivatives thereof.

Embodiment P11

The compound of embodiment P10, wherein WSG is

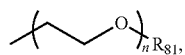

wherein n is an integer from 1-50 and R$_{81}$ is hydrogen, a C$_1$-C$_{10}$ alkyl, a C$_1$-C$_{10}$ alkenyl, or a C$_1$-C$_{10}$ alkynyl wherein each wherein the alkyl, alkenyl, or alkynyl is optionally substituted with one or more C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene.

Embodiment P12

The compound of embodiment P11, wherein R$_{81}$ is methyl.

Embodiment P13

The compound of embodiment P11, wherein R$_{81}$ is CH$_2$—C≡CH.

Embodiment P14

The compound of embodiment P11, wherein n is 1, 2, 3, 4, 5, 6, 7, 8, 9, or 10.

Embodiment P15

The compound of embodiment P11, wherein n is 3 or 6.

Embodiment P16

The compound of embodiment P8, wherein the WSG is

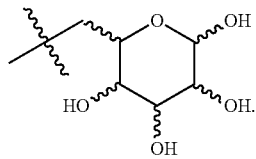 [SMILES: *CC1OC(O)C(O)C(O)C1O]

Embodiment P17

The compound of embodiment P16, wherein the WSG is

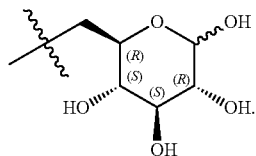

Embodiment P18

The compound of embodiment P8, wherein the WSG is

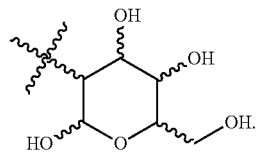

Embodiment P19

The compound of embodiment P18, wherein the WSG is

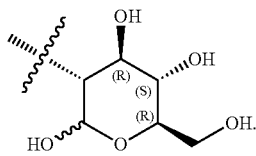

Embodiment P20

The compound of embodiment P1, wherein $R_{84}$ is hydrogen.

Embodiment P21

The compound of embodiment P1, wherein $R_{84}$ is methyl.

Embodiment P22

The compound of embodiment P1, wherein the compound is selected from a group consisting of j

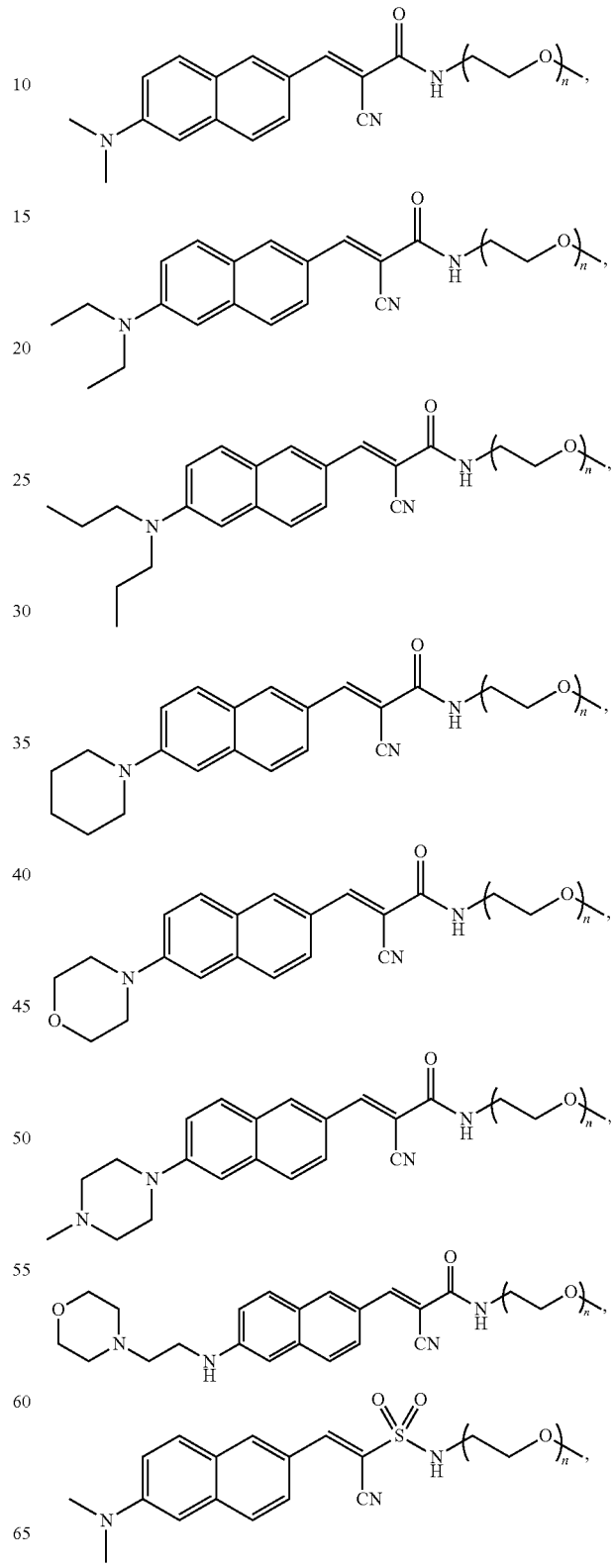

-continued
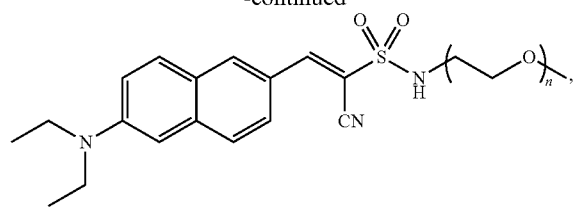
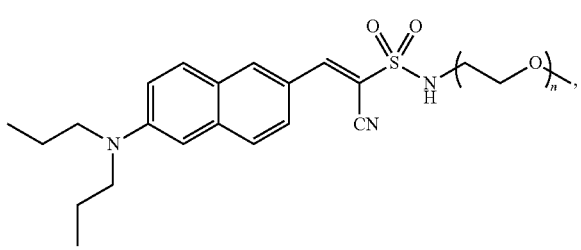
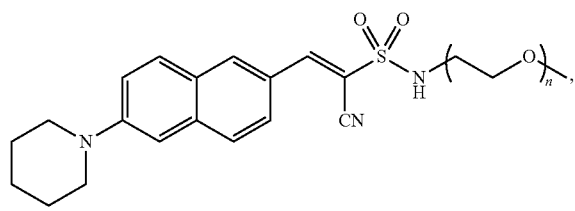
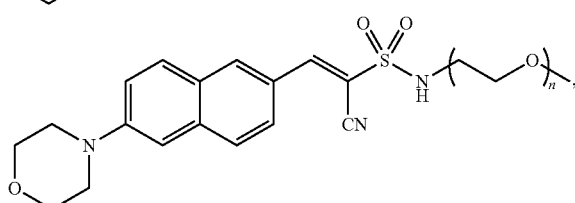
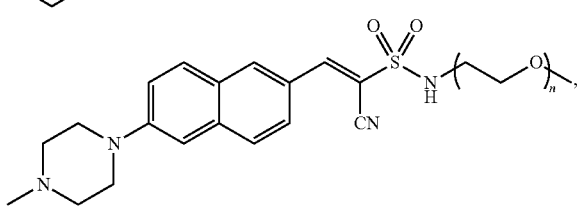
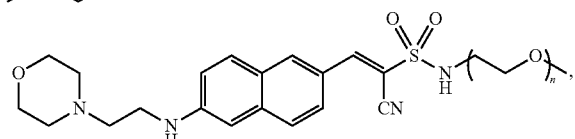
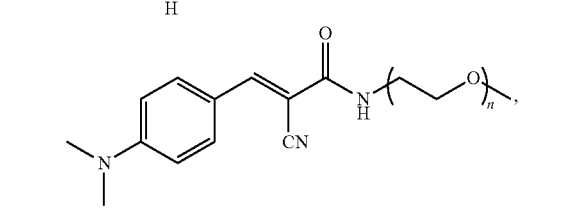
-continued
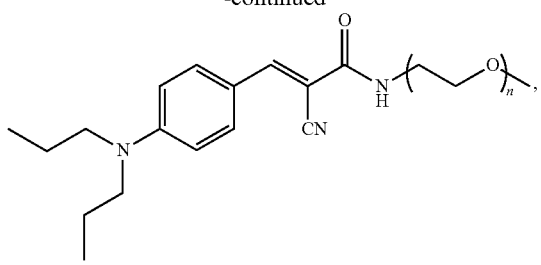
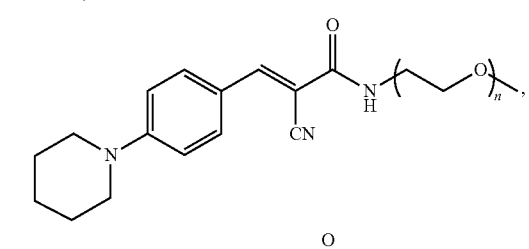
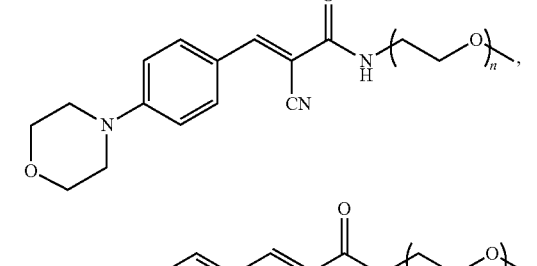
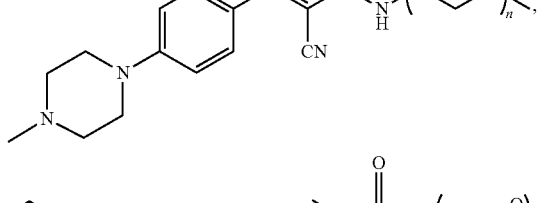
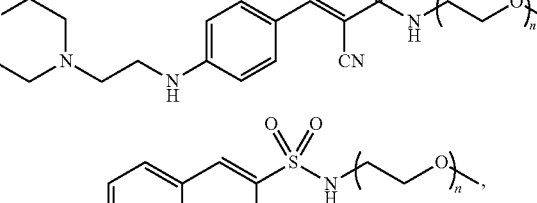
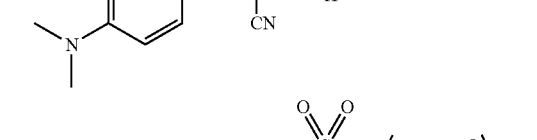
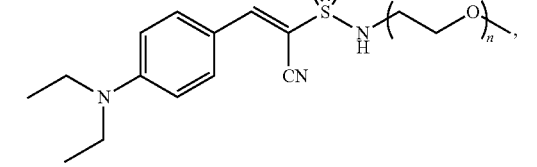

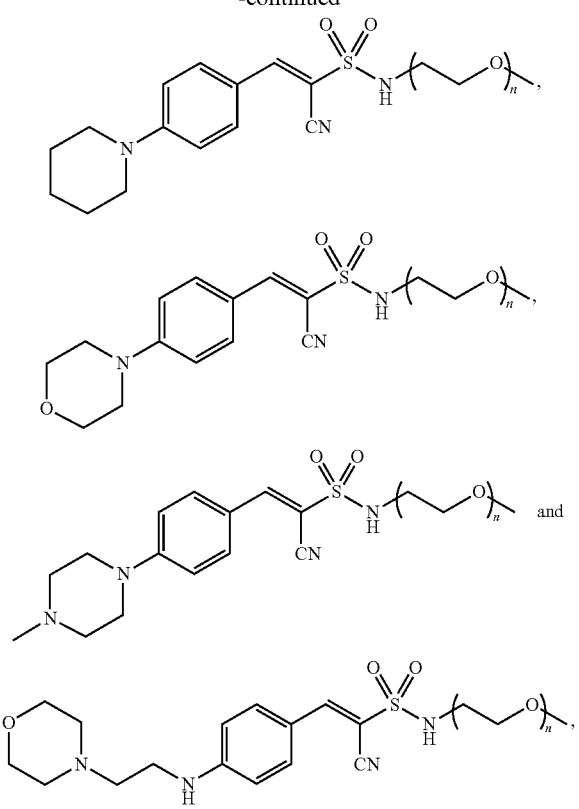
wherein n is an integer with value 1-10.
Embodiment P23
The compound of embodiment P1, wherein the compound is selected from a group consisting of
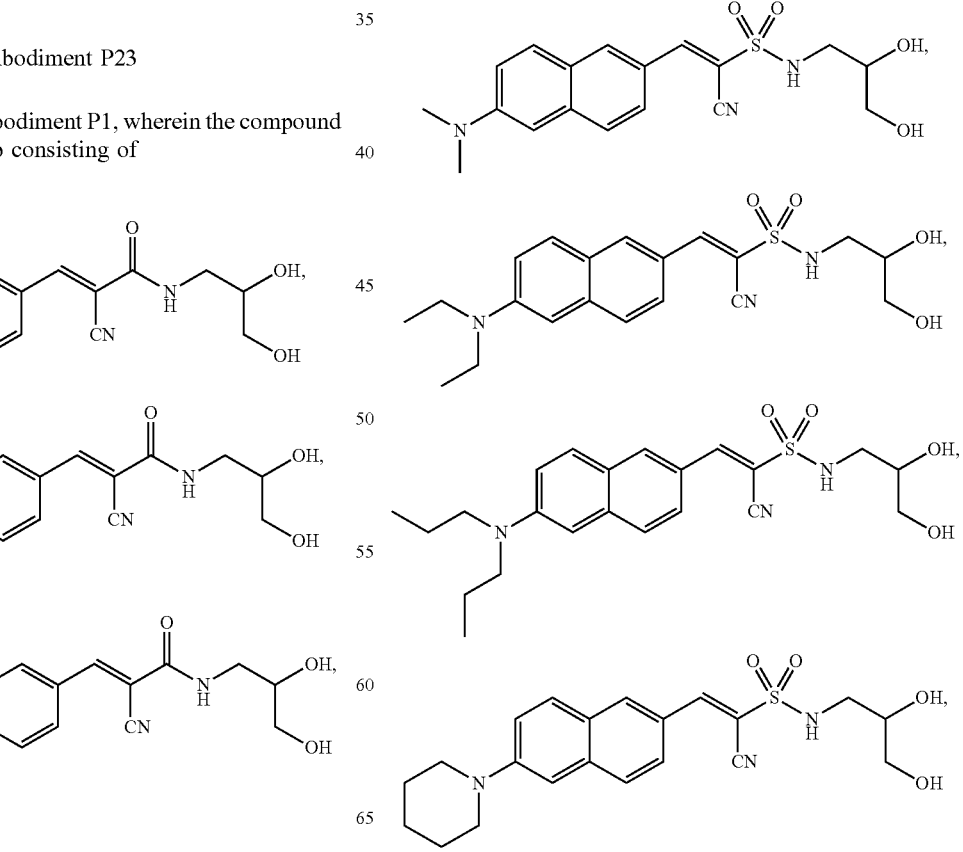

245
-continued
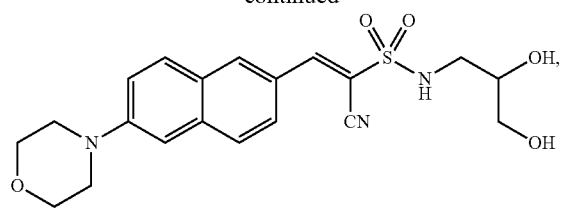
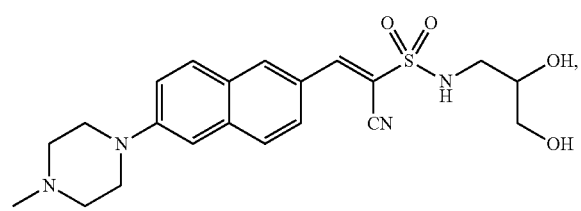
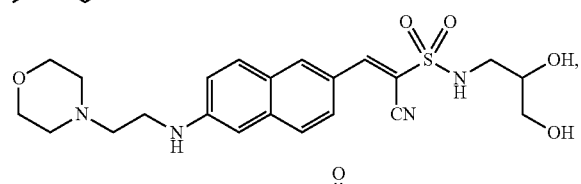
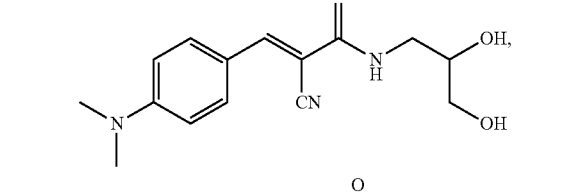
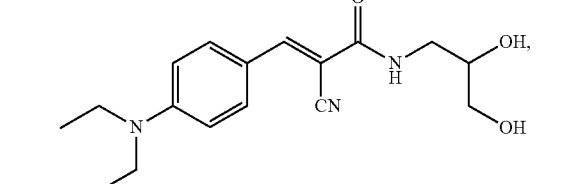
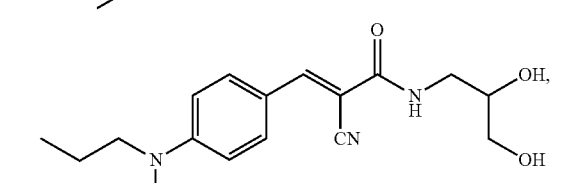
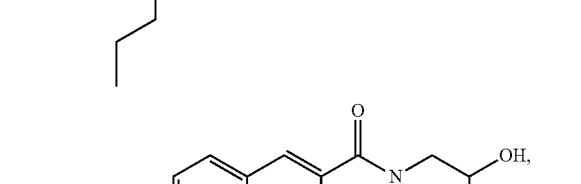
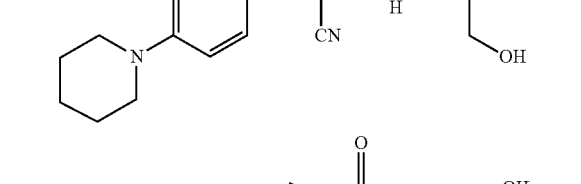
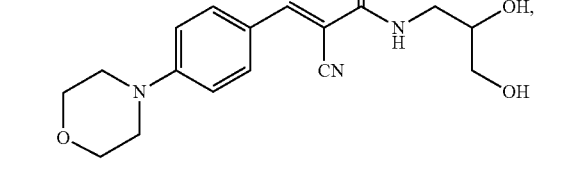
246
-continued
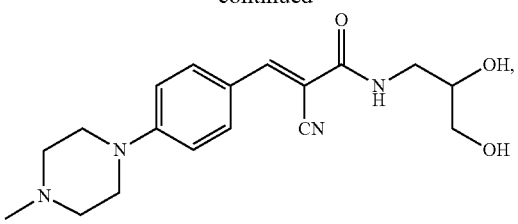
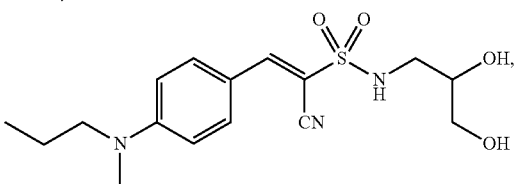
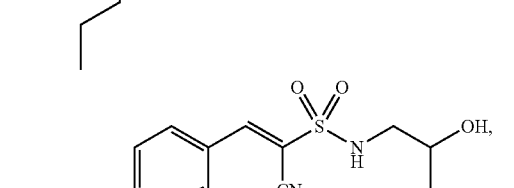
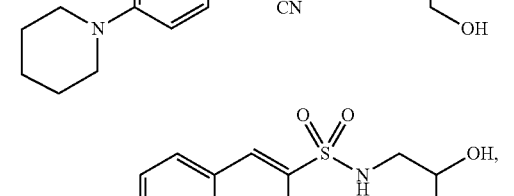
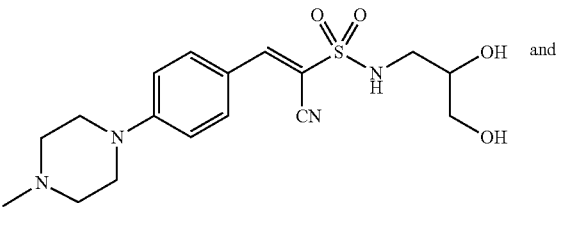 and -continued

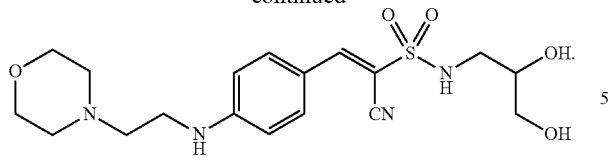

Embodiment P24

The compound of embodiment P1, wherein the compound is

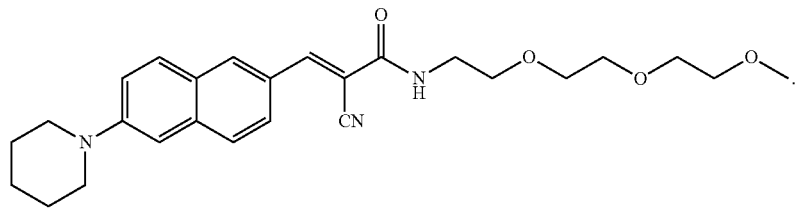 [SMILES: COCCOCCOCCNC(=O)/C(C#N)=C/c1ccc2cc(N3CCCCC3)ccc2c1]

Embodiment P25

The compound of embodiment P1, wherein the compound is

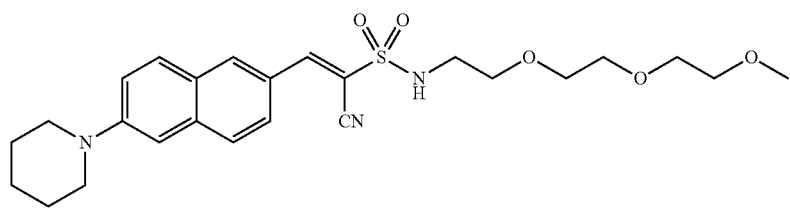 [SMILES: COCCOCCOCCNS(=O)(=O)/C(C#N)=C/c1ccc2cc(N3CCCCC3)ccc2c1]

Embodiment P26

The compound of embodiment P1, wherein the compound is

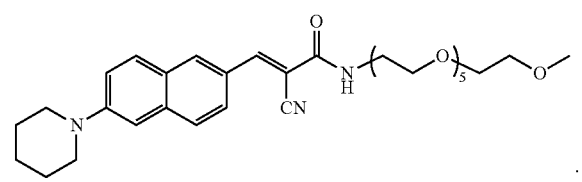

Embodiment P27

The compound of embodiment P1, wherein the compound is

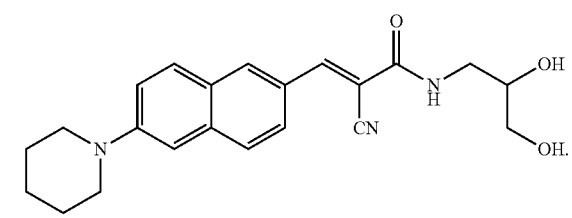 [SMILES: N#C/C(=C\c1ccc2cc(N3CCCCC3)ccc2c1)C(=O)NCC(O)CO]

Embodiment P28

The compound of embodiment P1, wherein the compound is

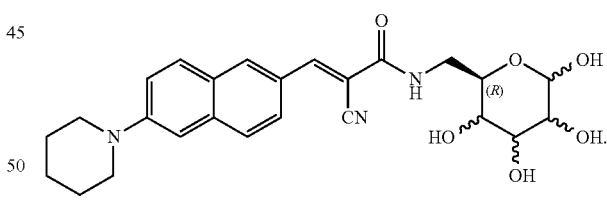

Embodiment P29

The compound of embodiment P28, wherein the compound is

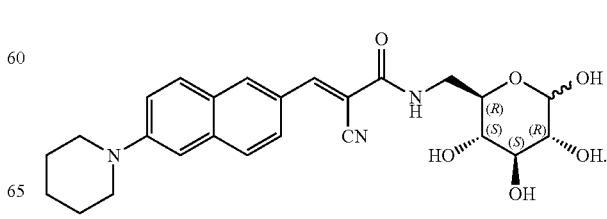

249
Embodiment P30
The compound of embodiment P1, wherein the compound is
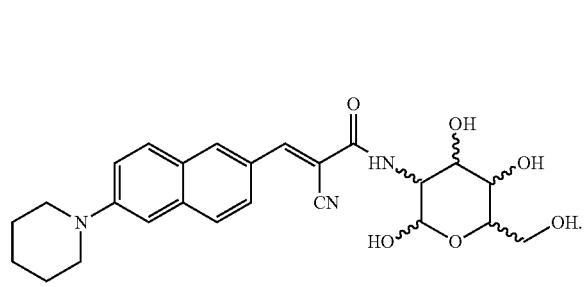 [SMILES: N#C/C(=C\c1ccc2cc(N3CCCCC3)ccc2c1)C(=O)NC1C(O)OC(CO)C(O)C1O]
Embodiment P31
The compound of embodiment P30, wherein the compound is
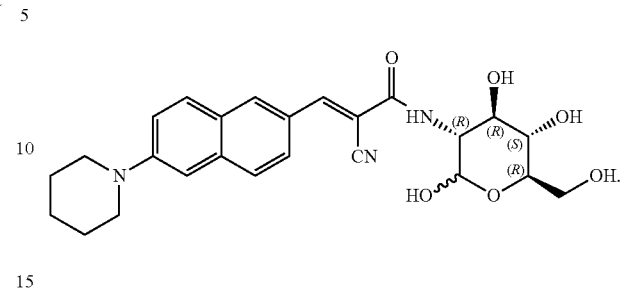
Embodiment P32
The compound of embodiment P1, wherein the compound is
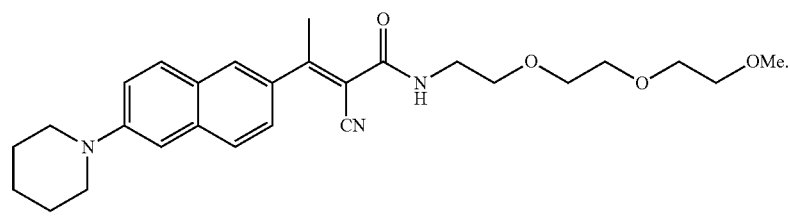 [SMILES: COCCOCCOCCNC(=O)/C(C#N)=C(\C)c1ccc2cc(N3CCCCC3)ccc2c1]
Embodiment P33
The compound of embodiment P1, wherein the compound is
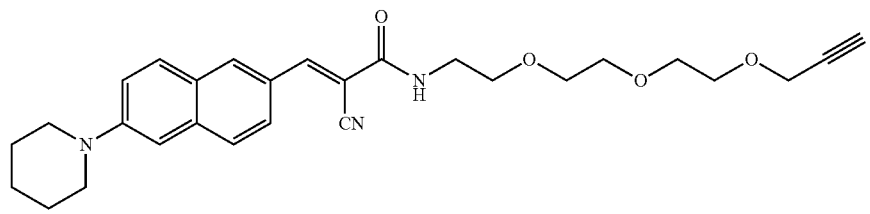
Embodiment P34
The compound of embodiment P1, wherein the compound is
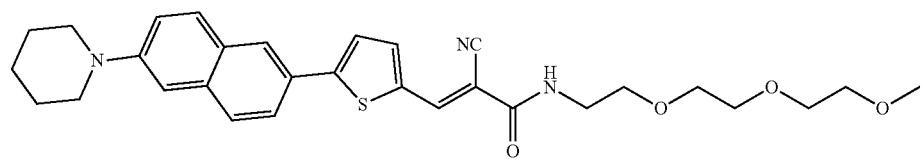

Embodiment P35
The compound of embodiment P1, wherein the compound is
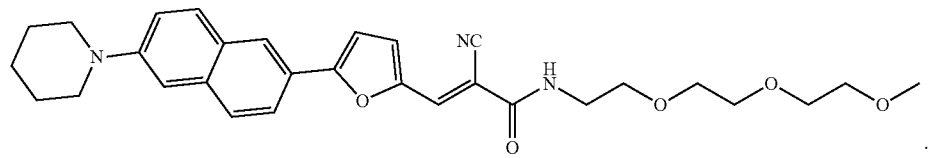 [SMILES: COCCOCCOCCNC(=O)/C(C#N)=C/c1ccc(-c2ccc3cc(N4CCCCC4)ccc3c2)o1]
Embodiment P36
The compound of embodiment P1, wherein the compound is
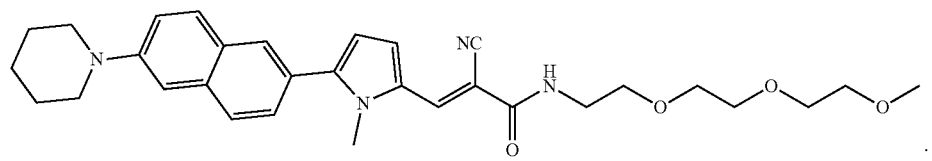 [SMILES: COCCOCCOCCNC(=O)/C(C#N)=C/c1ccc(-c2ccc3cc(N4CCCCC4)ccc3c2)n1C]
Embodiment P37
The compound of embodiment P1, wherein the compound is
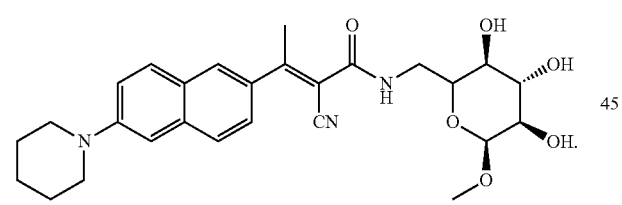
Embodiment P38
The compound of embodiment P1, wherein the compound is
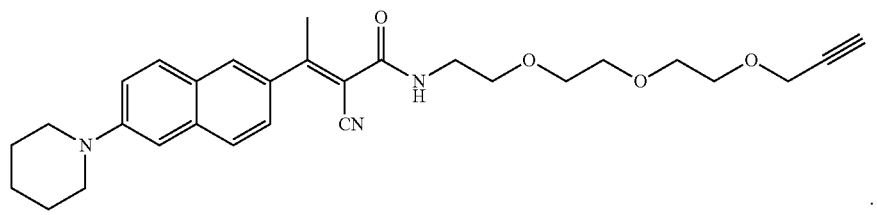 [SMILES: C#CCOCCOCCOCCNC(=O)/C(C#N)=C(\C)c1ccc2cc(N3CCCCC3)ccc2c1]

Embodiment P39

The compound of embodiment P1, wherein the compound is

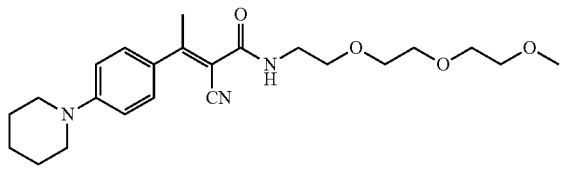

Embodiment P40

A compound of Formula II

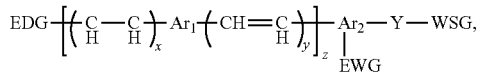

(Formula II)

wherein EDG is an electron donating group; $Ar_2$ and each $Ar_1$ is independently $C_1$-$C_{14}$ arylene or $C_1$-$C_{14}$ heteroarylene, each optionally substituted with one more $R_{41}$; each $R_{41}$ is independently halogen, —$OR_{42}$, —CN, —$NR_{43}R_{44}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_{45}$; $R_{42}$, $R_{43}$ and $R_{44}$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{45}$; each $R_{45}$ is independently halogen, —$OR_{46}$, —$NR_{47}R_{48}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_{46}$, $R_{47}$ and $R_{48}$ are independently hydrogen or $C_1$-$C_{10}$ alkyl; EWG is an electron withdrawing group; Y is absent, O, NH, or S; WSG is hydrogen or a water soluble group; x is an integer from 0-10; y is an integer from 0-10; and z is an integer from 1-10.

Embodiment P41

The compound of embodiment P40, wherein EDG is $OR_{49}$, $NR_{50}R_{51}$, —$SR_{52}$, —$PR_{53}R_{54}$, —$NR_{55}C(O)R_{56}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{57}$; each $R_{57}$ is independently halogen, —$OR_{58}$, —$NR_{59}R_{60}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_{49}$, $R_{50}$, $R_{51}$, $R_{52}$, $R_{53}$, $R_{54}$, $R_{55}$, $R_{56}$, $R_{58}$, $R_{59}$ and $R_{60}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{61}$ and wherein $R_{50}$ and $R_{51}$ are optionally joined together to form a heterocycloalkyl or heteroaryl optionally substituted with $R_{61}$; each of $R_{61}$ is independently halogen, —$OR_{62}$, —$NR_{63}R_{64}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{65}$; each of $R_{62}$, $R_{63}$ and $R_{64}$ is independently hydrogen or $C_1$-$C_{10}$ alkyl; and each $R_{65}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment P42

The compound of embodiment P40, wherein EDG is

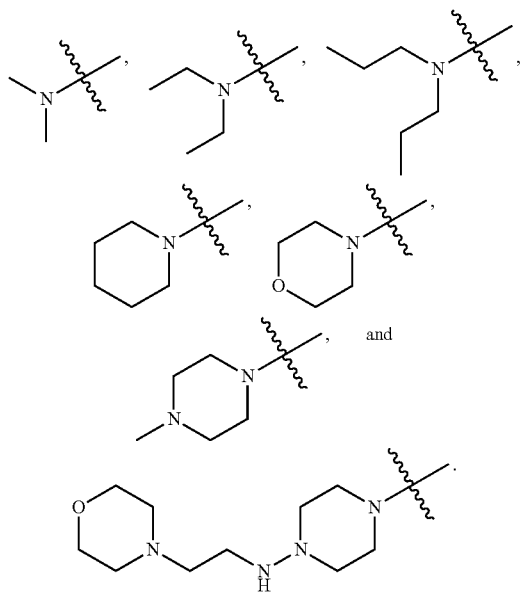

and

Embodiment P43

The compound of embodiment P40, wherein EDG is

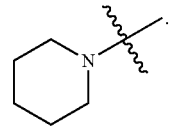 [SMILES: *N1CCCCC1]

Embodiment P44

The compound of embodiment P40, wherein EWG is halogen, —CN, —$NO_2$, —$SO_3H$, —$CR_{66}R_{67}R_{68}$, $COR_{69}$, or $COOR_{70}$; each $R_{66}$, $R_{67}$ and $R_{68}$ is independently hydrogen or halogen; $R_{69}$ is halogen, hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{71}$; $R_{70}$ is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{72}$; and each $R_{71}$ and $R_{72}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment P45

The compound of embodiment P40, wherein EWG is selected from a group consisting of F, Cl, Br, —C=O, $NO_2$, —$CF_3$, —$CCl_3$, —$SO_3$ and —CN.

Embodiment P46

The compound of embodiment P45, wherein EWG is —CN.

Embodiment P47

The compound of embodiment P40, wherein Y is absent.

Embodiment P48

The compound of embodiment P40, wherein WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{73}$; each $R_{73}$ is independently halogen, —$OR_{74}$, —$NR_{75}R_{76}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{77}$; each $R_{74}$, $R_{75}$ and $R_{76}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{77}$; each $R_{77}$ is independently halogen, —$OR_{78}$, —$NR_{79}R_{80}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; and each of $R_{78}$, $R_{79}$ and $R_{80}$ is independently hydrogen or $C_1$-$C_{10}$ alkyl.

Embodiment P49

The compound of embodiment P48, wherein WSG is hydrogen.

Embodiment P50

The compound of embodiment P48, wherein WSG is

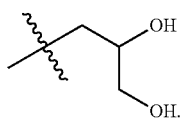 [SMILES: *CC(O)CO]

Embodiment P51

The compound of embodiment P40 wherein WSG is polyethylene glycol, polypropylene glycol, co-polymer of polyethylene glycol and polypropylene glycol, or alkoxy derivatives thereof.

Embodiment P52

The compound of embodiment P51, wherein WSG is

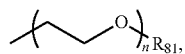

wherein n is an integer from 0-50 and $R_{81}$ is H, a $C_1$-$C_{10}$ alkyl, a $C_1$-$C_{10}$ alkenyl, or a $C_1$-$C_{10}$ alkynyl wherein each wherein the alkyl, alkenyl, or alkynyl is optionally substituted with one or more $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment P53

The compound of embodiment P52, wherein $R_{81}$ is methyl.

Embodiment P54

The compound of embodiment P52, wherein $R_{81}$ is $CH_2$—C≡CH.

Embodiment P55

The compound of embodiment P52, wherein n is 0, 1, 2, 3, 4, 5, 6, 7, 8, 9, or 10.

Embodiment P56

The compound of embodiment P52, wherein n is 3 or 6.

Embodiment P57

The compound of embodiment P48, wherein the WSG is

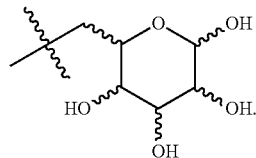 [SMILES: *CC1OC(O)C(O)C(O)C1O]

Embodiment P58

The compound of embodiment P57, wherein the WSG is

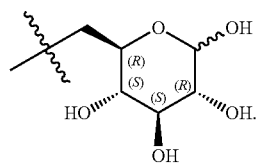

Embodiment P59

The compound of embodiment P48, wherein the WSG is

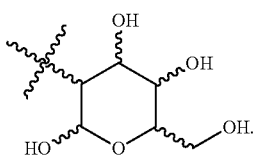

Embodiment P60

The compound of embodiment P59, wherein the WSG is

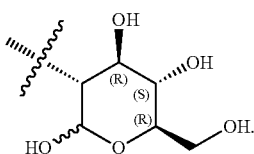

Embodiment P61

The compound of embodiment P40, wherein each of $Ar_1$ is independently a naphthalene or a phenylene.

Embodiment P62

The compound of embodiment P40, wherein $Ar_2$ is naphthalene or a phenylene.

Embodiment P63

The compound of embodiment P40, wherein the compound is selected from a group consisting of

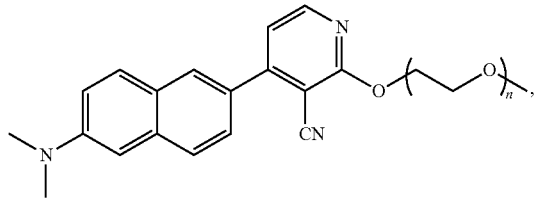

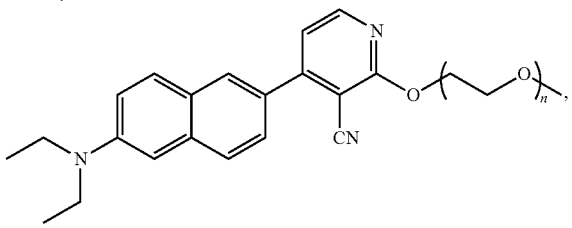

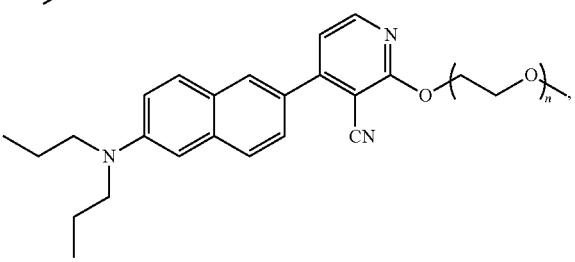

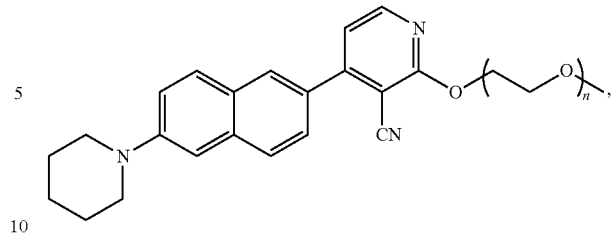

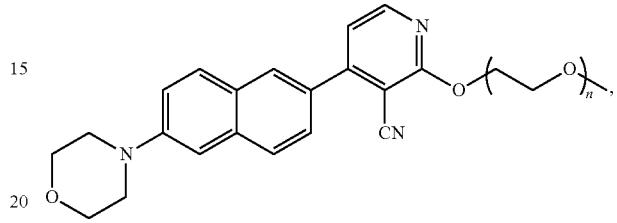

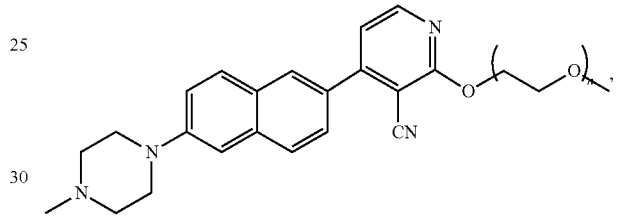

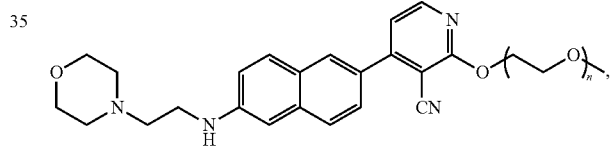

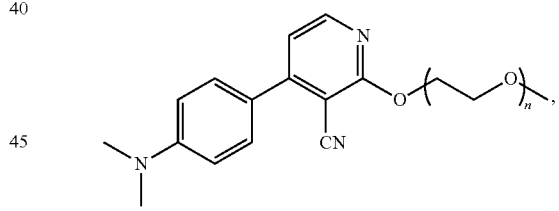

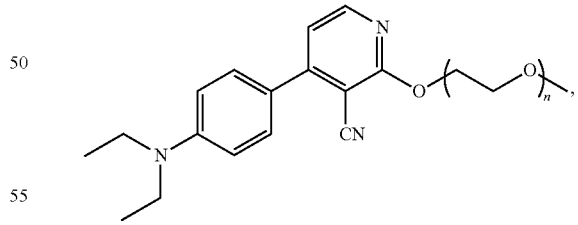

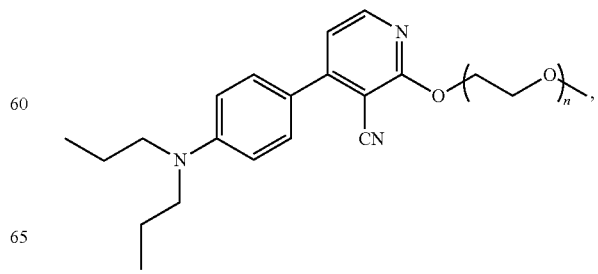

259
-continued
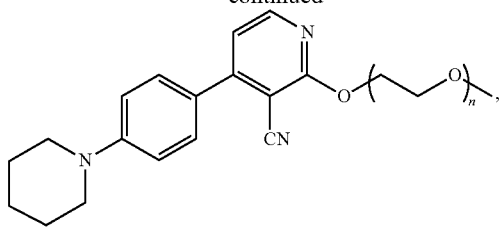
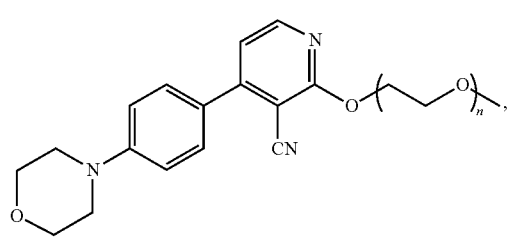
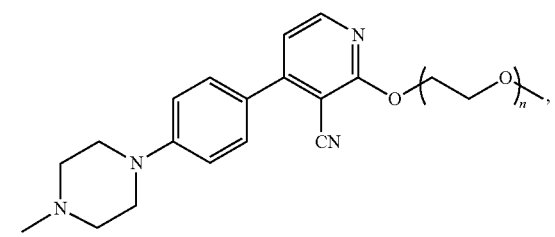
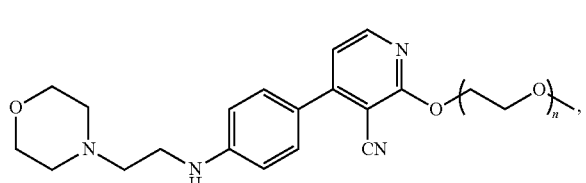
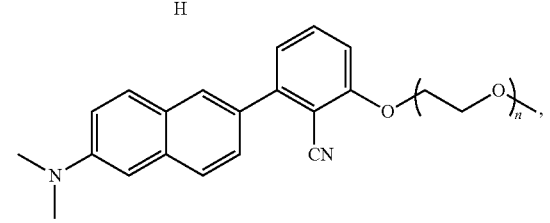
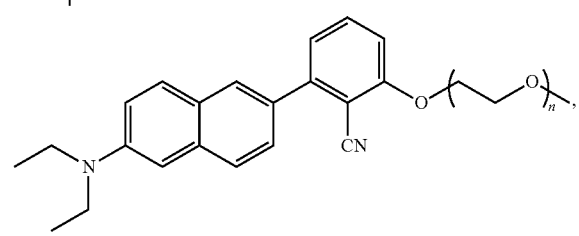
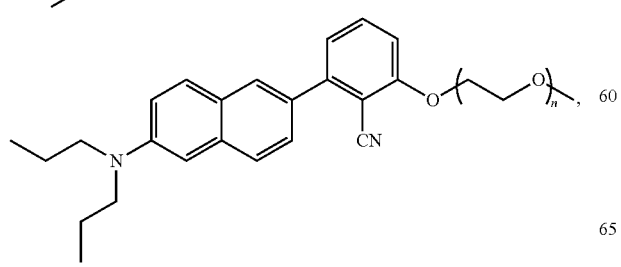
260
-continued
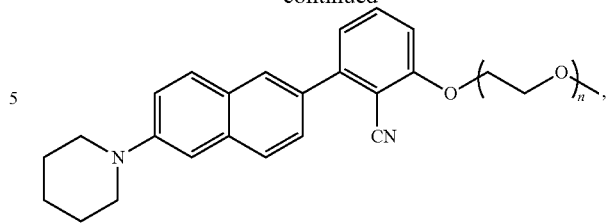
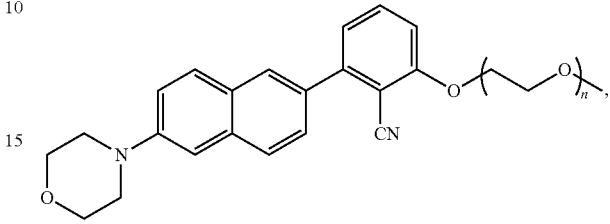
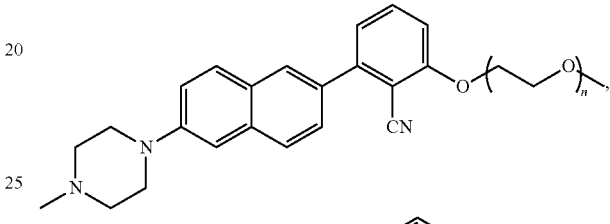
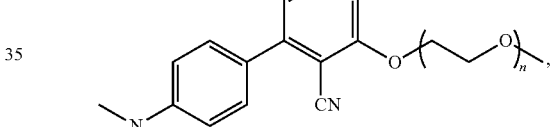
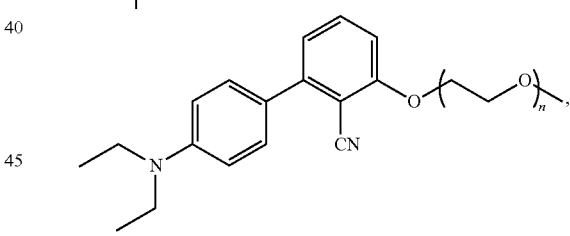
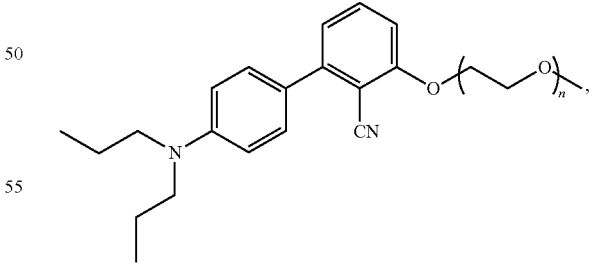
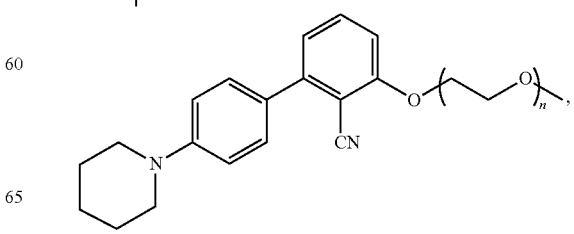

-continued
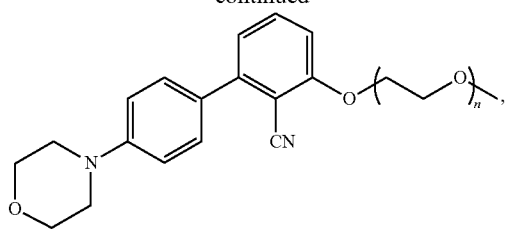
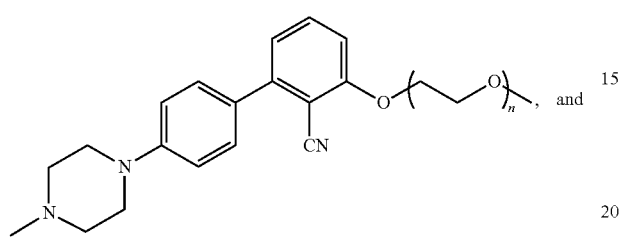, and
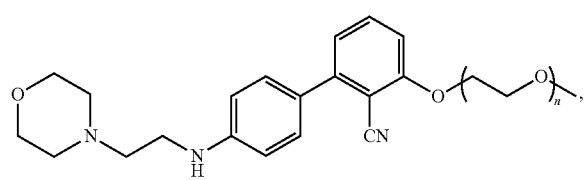
wherein n is an integer with value 0-10.
Embodiment P64
The compound of embodiment P40, wherein the compound is selected from a group consisting of,
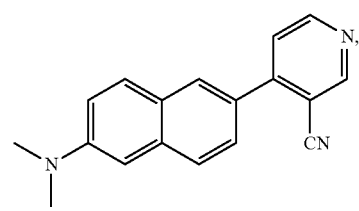
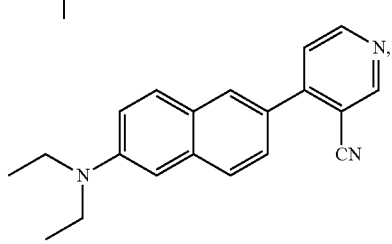
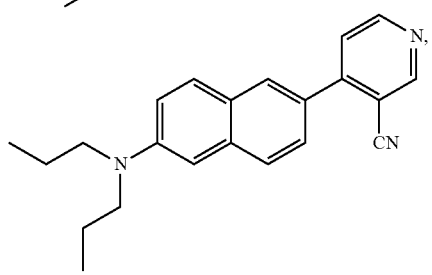
-continued
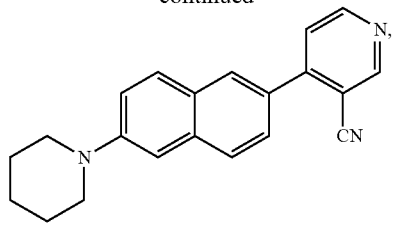
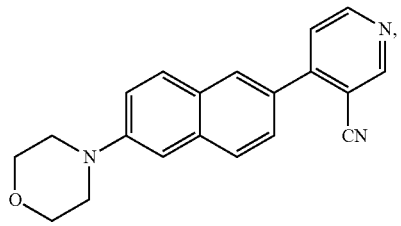
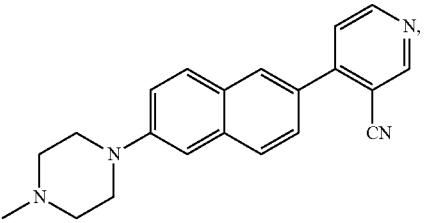
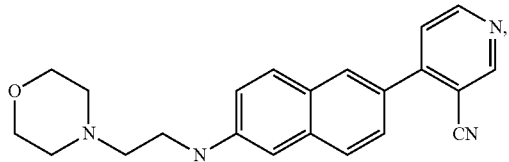
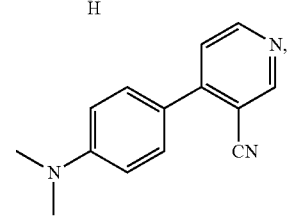
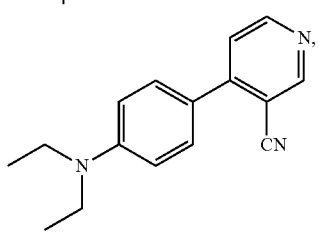
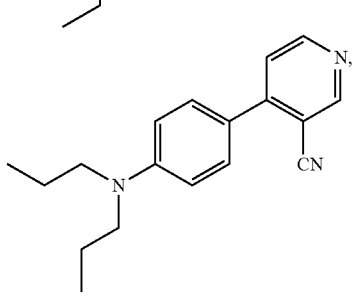

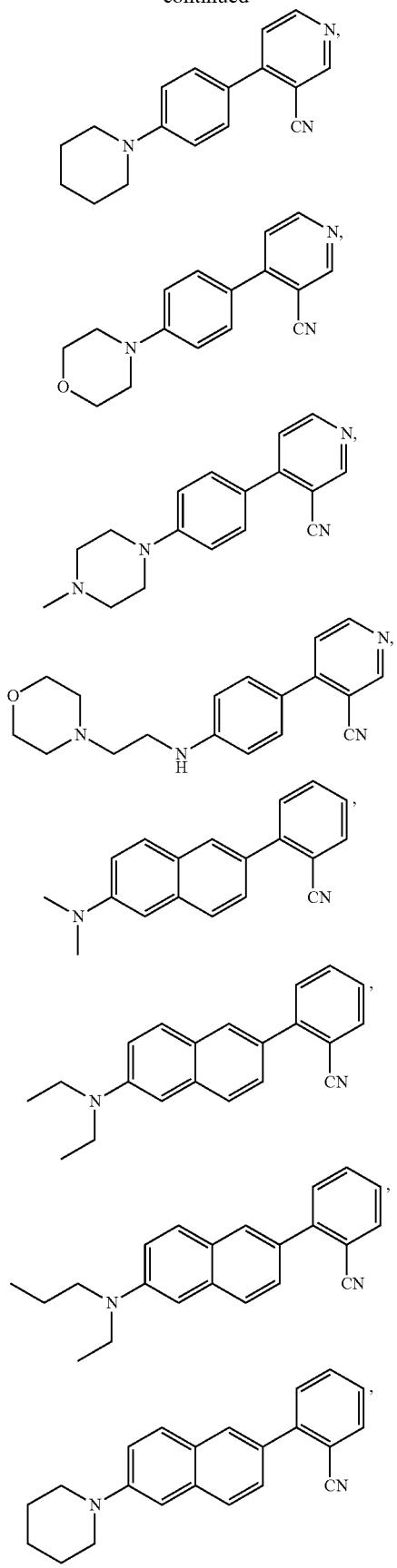
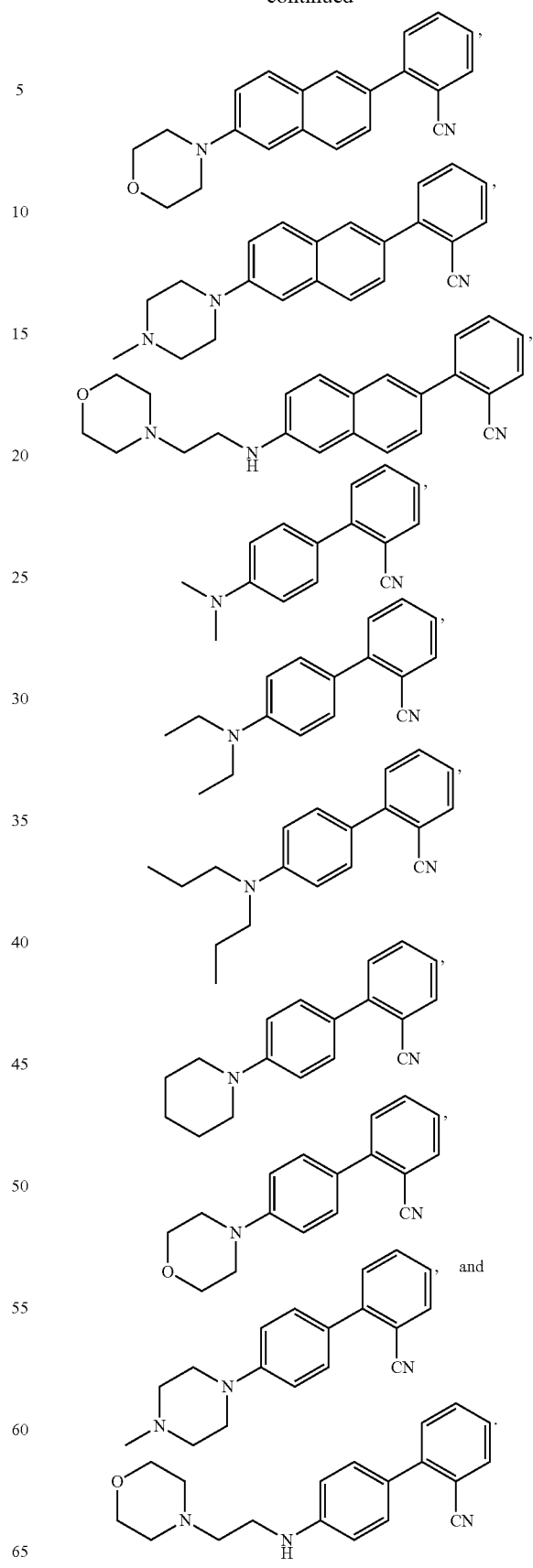

Embodiment P65

The compound of embodiment P40, wherein the compound is

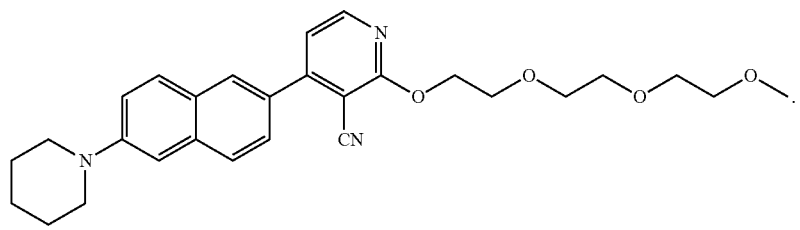 [SMILES: COCCOCCOCCOc1nccc(-c2ccc3cc(N4CCCCC4)ccc3c2)c1C#N]

Embodiment P66

The compound of embodiment P40, wherein the compound is

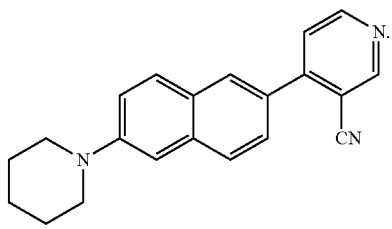 [SMILES: N#Cc1cnccc1-c1ccc2cc(N3CCCCC3)ccc2c1]

Embodiment P67

The compound of embodiment P40, wherein the compound is

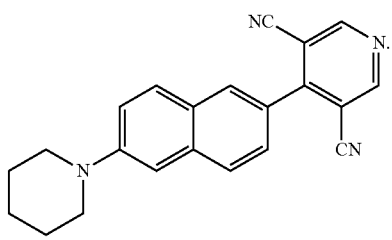 [SMILES: N#Cc1cncc(C#N)c1-c1ccc2cc(N3CCCCC3)ccc2c1]

Embodiment P68

The compound of embodiment P40, wherein the compound is

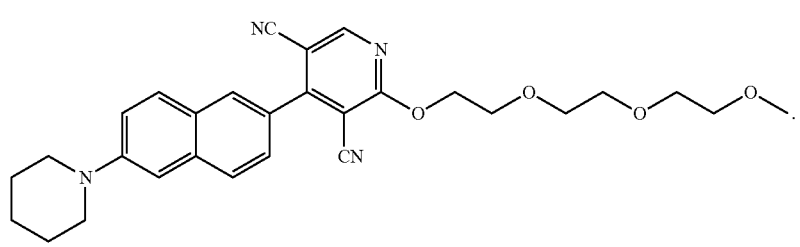 [SMILES: COCCOCCOCCOc1ncc(C#N)c(-c2ccc3cc(N4CCCCC4)ccc3c2)c1C#N]

Embodiment P69

A pharmaceutical composition comprising a compound according to any one of embodiments P1-P66.

Embodiment P70

A pharmaceutical composition of embodiment P69, further comprising one or more pharmaceutically acceptable additive, carrier or excipient selected from a group consisting of ethanol, DMSO, polyethylene glycol, polypropylene glycol, aqueous acetate buffers, aqueous citrate buffers, aqueous phosphate buffers, aqueous carbonate buffers, cyclodextrins, corn oil, vitamin E, polysorbates, polyethyleneglycol-15 hydroxystearate (SOLUTOL®) and bile acids.

Embodiment P71

A composition comprising a compound according to any one of embodiments P1-P66 and an amyloid or amyloid like protein.

Embodiment P72

The composition of embodiment P71, wherein the amyloid or amyloid like protein is Aβ peptide, prion peptide, alpha-synuclein, or superoxide dismutase.

Embodiment P73

A method of detecting an amyloid or amyloid like protein comprising: a) contacting a compound according to any one of embodiments P1-P66 with a sample potentially comprising the amyloid or amyloid like protein, wherein in presence of an amyloid or amyloid like protein the compound forms a detectable complex; and b) detecting the formation of the detectable complex such that the presence or absence of the detectable complex correlates with the presence or absence of the amyloid or amyloid like protein.

Embodiment P74

The method of embodiment P73, wherein the detection of the formation of the detectable complex is performed by measuring a signal generated by the detectable complex.

Embodiment P75

The method of embodiment P74, wherein the signal generated by the detectable complex is an electromagnetic signal.

Embodiment P76

The method of embodiment P74, wherein the electromagnetic signal is a fluorescence signal.

Embodiment P77

The method of embodiment P76, wherein the fluorescence signal is measures at a wavelength of 450-650 nm.

Embodiment P78

The method of embodiment P76, wherein the fluorescence signal is measures at a wavelength of 520-540 nm.

Embodiment P79

The method of embodiment P73, wherein the amyloid or amyloid like protein is Aβ peptide, prion peptide, alpha-synuclein, or superoxide dismutase.

Embodiment P80

The method of embodiment P73, wherein the amyloid or amyloid like protein is beta amyloid (1-42) (Aβ (1-42)).

Embodiment P81

The method of embodiment P73, wherein the detection of the formation of the detectable complex is performed within about 1 sec, about 5 sec, about 1 min, about 10 min, about 30 min or about 60 min of the contacting of the compound according to any one of embodiments P1-P66 with the sample.

Embodiment P82

The method of embodiment P73, wherein the detection of the formation of the detectable complex is performed within about 1-5 minutes of the contacting of the compound according to any one of embodiments P1-P66 with the sample.

Embodiment P83

A method of determining the presence or absence of one or more disease or condition in a subject comprising: a) administering to the subject an effective amount of a compound according to any one of embodiments P1-P66 or a pharmaceutical composition thereof, wherein in presence of the disease or condition the administered compound forms a detectable complex; and b) detecting the formation of the detectable complex such that presence or absence of detectable complex correlates with the presence or absence of the disease or condition.

Embodiment P84

The method of embodiment P83, wherein the disease or condition is characterized by protein aggregation or protein misfolding.

Embodiment P85

The method of embodiment P83, wherein the disease or condition is an amyloid based disease or condition.

Embodiment P86

The method of embodiment P83, wherein the disease or condition is Alzheimer's disease (AD), Parkinson's disease, Huntington's disease, amyotrophic lateral sclerosis (ALS), Lewy body dementia (LBD), or Down's syndrome.

Embodiment P87

The method of embodiment P83, wherein the disease of condition is Alzheimer's disease.

Embodiment P88

The method of embodiment P83, wherein the disease or condition is a prion disease or condition.

Embodiment P89

The method of embodiment P88, wherein the prion disease or condition is Creutzfeldt-Jakob disease (CJD).

Embodiment P90

The method of embodiment P83, wherein the administering is to the eye of the subject.

Embodiment P91

The method of embodiment P83, wherein the administering is systemic or topical administration.

Embodiment P92

The method of embodiment P83, wherein the detection of the formation of the detectable is performed within about 1 sec, about 5 sec, about 1 min, about 10 min, about 30 min or about 60 min of the administration of the compound according to any one of embodiments P1-P66 to the subject.

Embodiment P93

The method of embodiment P83, wherein the detection of the formation of the detectable complex is performed within about 1-5 min of the administration of the compound according to any one of embodiments P1-P66 to the subject.

Embodiment P94

The method of embodiment P83, wherein the effective amount the compound corresponds to about 50-500 mg of compound per adult human subject.

Embodiment P95

The method of embodiment P83, wherein the detection of the formation of the detectable complex is performed by measuring a signal generated by the detectable complex.

Embodiment P96

The method of embodiment P95, the signal generated by the detectable complex is an electromagnetic signal.

Embodiment P97

The method of embodiment P96, wherein the electromagnetic signal is a fluorescence signal.

Embodiment P98

The method of embodiment P97, wherein the fluorescence signal is measures at a wavelength of 450-650 nm.

Embodiment P99

The method of embodiment P97, wherein the fluorescence signal is measures at a wavelength of 520-540 nm.

Embodiment P100

A method of treating or preventing a one or more disease or condition comprising administering to a subject in need of treatment an effective amount of a compound according to any one of embodiments P1-P66 or a pharmaceutical composition thereof.

Embodiment P101

The method of embodiment P100, wherein the disease or condition is characterized by protein aggregation or protein misfolding,

Embodiment P102

The method of embodiment P100, wherein the disease or condition is an amyloid based disease or condition.

Embodiment P103

The method of embodiment P100, wherein the disease or condition is Alzheimer's disease (AD), Parkinson's disease, Huntington's disease, amyotrophic lateral sclerosis (ALS), Lewy body dementia (LBD), or Down's syndrome.

Embodiment P104

The method of embodiment P103, wherein the neurological disorder is Alzheimer's disease.

Embodiment P105

The method of embodiment P100, wherein the disease or condition is a prion disease or condition.

Embodiment P106

The method of embodiment P105, wherein the prion disease or condition is Creutzfeldt-Jakob disease.

Embodiment P107

The method of embodiment P100, wherein effective amount the compound corresponds to about 50-500 mg.

Embodiment P108

A screening method comprising administering to a subject an effective amount of a compound according to any one of embodiments P1-P66 or a pharmaceutical composition thereof, wherein upon administration the a compound according to any one of embodiments P1-P66 may form a detectable complex.

Embodiment P109

The screening method of embodiment P108, further comprising measuring a signal generated by the by the detectable complex or by the compound, according to any one of embodiments P1-P66, administered to the subject.

Embodiment P110

The screening method of embodiment P109, further comprising making a clinical decision based on the measured signal.

Embodiment P111

The screening method of embodiment P109, wherein the signal is an electromagnetic signal.

Embodiment P112

The screening method of embodiment P111, wherein the electromagnetic signal is a fluorescence signal.

Embodiment P113

The method of embodiment P112, wherein the fluorescence signal is measures at a wavelength of 450-650 nm.

Embodiment P114

The method of embodiment P112, wherein the fluorescence signal is measures at a wavelength of 520-540 nm.

Embodiment P115

The screening method of embodiment P108, wherein the said administering is to the eye of the subject.

Embodiment P116

The screening method of embodiment P108, wherein the said administering is systemic or topical administration.

Embodiment P117

A kit for comprising a compound according to any one of embodiments P1-P66.

Embodiment 118

The kit of embodiment P117, further comprising instructions for a) using the compound for the binding to an amyloid or amyloid like protein to form a detectable complex; and b) detecting the formation of the detectable complex such that presence or absence of detectable complex correlates with the presence or absence of the amyloid or amyloid like protein.

Embodiment P119

The kit of embodiment P117, further comprising instructions for a) using the compound for binding to an amyloid or amyloid like protein to form a detectable complex; and b) detecting changes in abundance of the detectable complex over time such that the changes in the abundance of the detectable complex over time are correlated to changes in abundance of amyloid or amyloid like protein over time.

Embodiment P120

The kit of embodiment P119, further comprising instructions for correlating the changes in the abundance of the detectable complex to monitor progression of a disease.

Embodiment P121

The kit of embodiment P117, the compound according to any one of embodiments P1-P66 is contained in a container as a sterile liquid formulation.

Embodiment P122

The kit of embodiment P117, the compound according to any one of embodiments P1-P66 is contained in a container as a sterile freeze-dried formulation.

Embodiment P123

The kit of embodiment P120 or P122, wherein the container a vial, for example an amber vial.

Embodiment P124

The kit of embodiment P120 or P122, wherein the container is capable of protecting light sensitive compounds or formulation.

Further embodiments are provided as follows.

Embodiment 1

A compound of Formula I

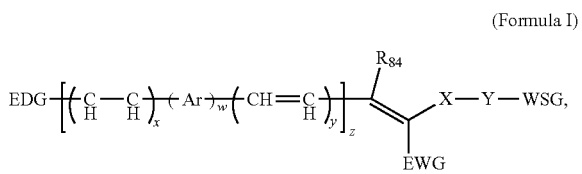

(Formula I)

wherein EDG is an electron donating group; each Ar is independently $C_1$-$C_{14}$ arylene or $C_1$-$C_{14}$ heteroarylene, each optionally substituted with one or more $R_1$; each $R_1$ is independently halogen, —$OR_2$, —$NR_3R_4$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_5$; $R_2$, $R_3$ and $R_4$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_5$; each $R_5$ is independently halogen, —$OR_6$, —$NR_7R_8$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_6$, $R_7$, $R_8$ and $R_{84}$ are independently hydrogen or $C_1$-$C_{10}$ alkyl; EWG is an electron withdrawing group; WSG is a water soluble group; X is C=O or $SO_2$; Y is NH, or S; each w is independently an integer from 1-5; each x is independently an integer from 0-10; each y is independently an integer from 0-10; and z is an integer from 1-10.

Embodiment 2

The compound of embodiment 1, wherein EDG is —$OR_9$, —$NR_{10}R_{11}$, —$SR_{12}$, —$PR_{13}R_{14}$, —$NR_{15}C(O)R_{16}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{17}$; each $R_{17}$ is independently halogen, —$OR_{18}$, —$NR_{19}R_{20}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_9$, $R_{10}$, $R_{11}$, $R_{12}$, $R_{13}$, $R_{14}$, $R_{15}$, $R_{16}$, $R_{18}$, $R_{19}$ and $R_{20}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{21}$ and wherein $R_{10}$ and $R_{11}$ are optionally joined together to form a heterocycloalkyl or heteroaryl optionally substituted with $R_{21}$; each of $R_{21}$ is independently halogen, —$OR_{22}$, —$NR_{23}R_{24}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{25}$; each of $R_{22}$, $R_{23}$ and $R_{24}$ is independently hydrogen or $C_1$-$C_{10}$ alkyl; and each $R_{25}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment 3

The compound of any one of embodiments 1 or 2, wherein EDG is selected from a group consisting of

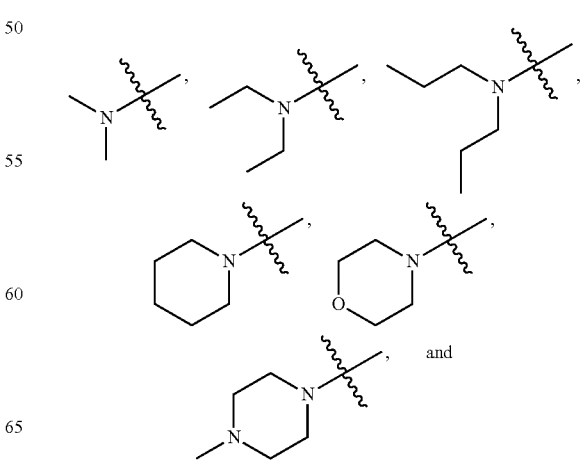

-continued

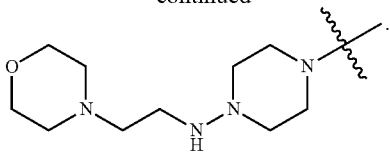

Embodiment 4

The compound of any one of embodiments 1-3, wherein EDG is

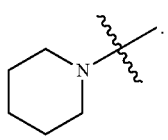 [SMILES: *N1CCCCC1]

Embodiment 5

The compound of any one of embodiments 1-4, wherein EWG is halogen, —CN, —NO$_2$, —SO$_3$H, —CR$_{26}$R$_{27}$R$_{28}$, —COR$_{29}$, or —COOR$_{30}$; each R$_{26}$, R$_{27}$ and R$_{28}$ is independently hydrogen or halogen; R$_{29}$ is halogen, hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{31}$; R$_{30}$ is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{32}$; and each R$_{31}$ and R$_{32}$ is independently C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene.

Embodiment 6

The compound of any one of embodiments 1-5, wherein EWG is selected from a group consisting of —F, —Cl, —Br, —CH═O, NO$_2$, —CF$_3$, —CCl$_3$, —SO$_3$ and —CN.

Embodiment 7

The compound of embodiment 6, wherein EWG is —CN.

Embodiment 8

The compound of any one of embodiments 1-7, wherein WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{33}$; each R$_{33}$ is independently halogen, —OR$_{34}$, —NR$_{35}$R$_{36}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{34}$, R$_{35}$ and R$_{36}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{37}$ is independently halogen, —OR$_{38}$, —NR$_{39}$R$_{40}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, —(C$_1$-C$_6$alkyl)(C$_1$-C$_{10}$heterocycloalkyl), C$_1$-C$_{10}$ arylene, or C$_1$-C$_{10}$ heteroarylene; and each of R$_{38}$, R$_{39}$ and R$_{40}$ is independently hydrogen or C$_1$-C$_{10}$ alkyl.

Embodiment 9

The compound of any one of embodiments 1-8, wherein WSG is hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{33}$; each R$_{33}$ is independently halogen, —OR$_{34}$, —NR$_{35}$R$_{36}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{34}$, R$_{35}$ and R$_{36}$ is independently hydrogen, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene, wherein the alkyl, heteroalkyl, cycloalkyl, heterocycloalkyl, arylene, or heteroarylene is optionally substituted with one or more R$_{37}$; each R$_{37}$ is independently halogen, —OR$_{38}$, —NR$_{39}$R$_{40}$, C$_1$-C$_{10}$ alkyl, C$_1$-C$_{10}$ heteroalkyl, C$_1$-C$_{10}$ cycloalkyl, C$_1$-C$_{10}$ heterocycloalkyl, C$_1$-C$_{10}$ arylene, or C$_1$-C$_{10}$ heteroarylene; and each of R$_{38}$, R$_{39}$ and R$_{40}$ is independently hydrogen or C$_1$-C$_{10}$ alkyl.

Embodiment 10

The compound of any one of embodiments 1-9, wherein WSG is

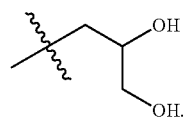 [SMILES: *CC(O)CO]

Embodiment 11

The compound of any one of embodiments 1-9, wherein WSG is polyethylene glycol, polypropylene glycol, co-polymer of polyethylene glycol and polypropylene glycol, or alkoxy derivatives thereof.

Embodiment 12

The compound of embodiment 11, wherein WSG is a

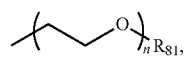

wherein n is an integer from 1-50 and R$_{81}$ is hydrogen, a C$_1$-C$_{10}$ alkyl, a C$_1$-C$_{10}$ alkenyl, or a C$_1$-C$_{10}$ alkynyl wherein each wherein the alkyl, alkenyl, or alkynyl is optionally substituted with one or more C$_1$-C$_{10}$ alkyl, C$_1$-C$_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment 13

The compound of any one of embodiments 11 to 12, wherein $R_{81}$ is methyl.

Embodiment 14

The compound of any one of embodiments 11 to 12, wherein $R_{81}$ is $CH_2$—C≡CH.

Embodiment 15

The compound of any one of embodiments 11-14, wherein n is 1, 2, 3, 4, 5, 6, 7, 8, 9, or 10.

Embodiment 16

The compound of any one of embodiments 11-15, wherein n is 3 or 6.

Embodiment 17

The compound of any one of embodiments 1-9, wherein the WSG is

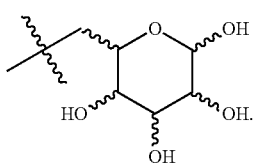 [SMILES: *CC1OC(O)C(O)C(O)C1O]

Embodiment 18

The compound of embodiment 17, wherein the WSG is

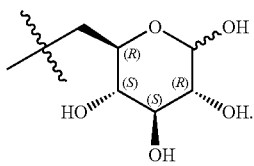

Embodiment 19

The compound of any one of embodiments 1-9, wherein the WSG is

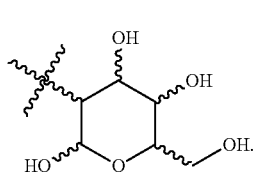

Embodiment 20

The compound of embodiment 19, wherein the WSG is

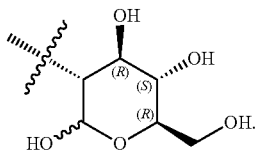

Embodiment 21

The compound of any one of embodiments 1-8, wherein WSG is —($C_1$-$C_{10}$ alkyl)-$R_{33}$—$R_{37}$, wherein: $R^{33}$ is $C_1$-$C_{10}$ heteroarylene; and $R_{37}$ is —($C_1$-$C_6$alkyl)($C_1$-$C_{10}$heterocycloalkyl).

Embodiment 22

The compound of embodiment 21, wherein WSG is —$CH_3$—$R_{33}$—$R_{37}$.

Embodiment 23

The compound of any one of embodiments 21 or 22, wherein $R_{33}$ is a triazole.

Embodiment 24

The compound of any of embodiments 21-23, wherein $R_{37}$ is

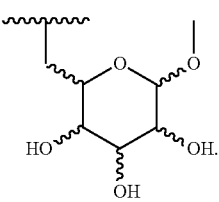 [SMILES: *CC1OC(OC)C(O)C(O)C1O]

Embodiment 25

The compound of embodiment 8, wherein the WSG is

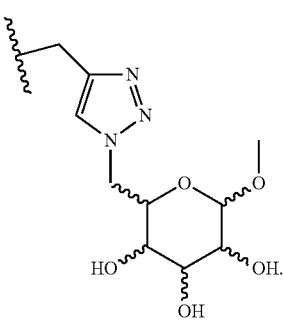 [SMILES: *Cc1cn(CC2OC(OC)C(O)C(O)C2O)nn1]

Embodiment 26

The compound of embodiment 25, wherein the WSG is

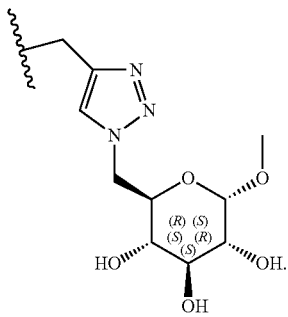

Embodiment 27

The compound of any one of embodiments 1-8, wherein WSG is —($C_1$-$C_{10}$ heteroalkyl)-$R_{33}$—$R_{37}$, wherein: $R_{33}$ is $C_1$-$C_{10}$ heteroarylene; and $R_{37}$ is —($C_1$-$C_6$alkyl)($C_1$-$C_{10}$heterocycloalkyl).

Embodiment 28

The compound of embodiment 27, wherein WSG is

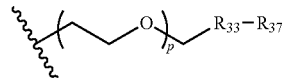

and p is 1, 2, 3, 4, 5, or 6.

Embodiment 29

The compound of embodiment 28, wherein p is 3.

Embodiment 30

The compound of any one of embodiments 27-29, wherein $R_{33}$ is a triazole.

Embodiment 31

The compound of any one of embodiments 27-30, wherein $R_{37}$ is

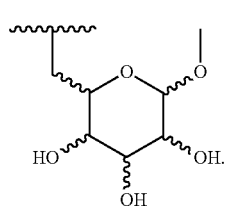

Embodiment 32

The compound of any one of embodiments 27-31, wherein WSG is

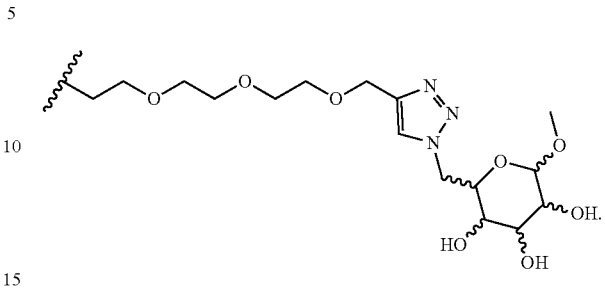

Embodiment 33

The compound of embodiment 32, wherein WSG is

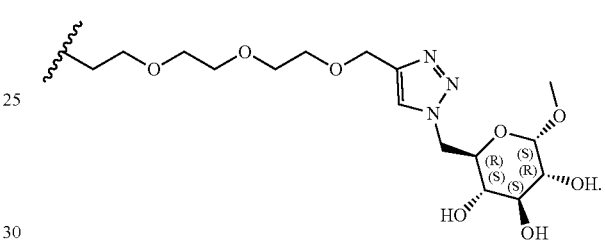

Embodiment 34

The compound of any one of embodiments 1-33, wherein $R_{84}$ is hydrogen.

Embodiment 35

The compound of any one of embodiments 1-34, wherein $R_{84}$ is methyl.

Embodiment 36

The compound of any one of embodiments 1-35, wherein the compound of Formula (I) is of formula (Ic):

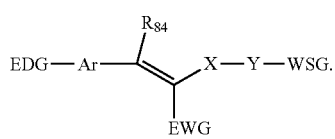

Embodiment 37

The compound of any one of embodiments 1-36, wherein the compound of formula (I) is of formula (Id):

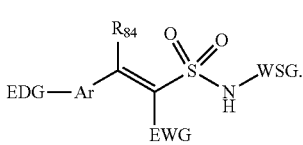

Embodiment 38
The compound of any one of embodiments 1-36, wherein the compound of formula (I) is of formula (Ie):
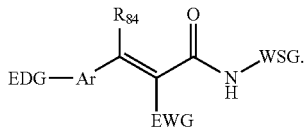
Embodiment 39
The compound of embodiment 1, wherein the compound is selected from a group consisting of
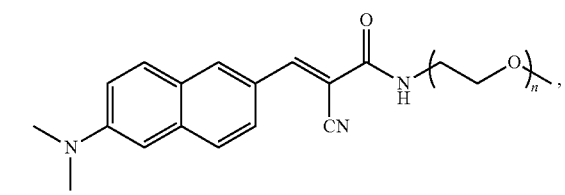
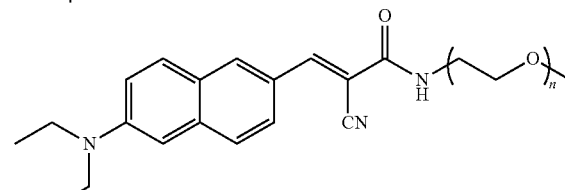
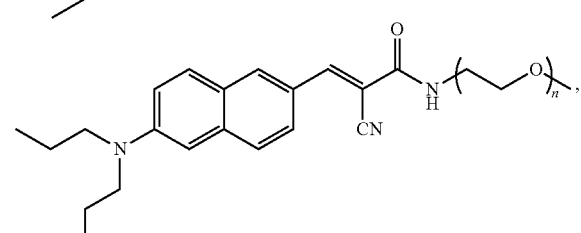
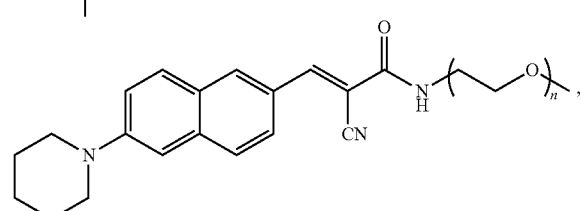
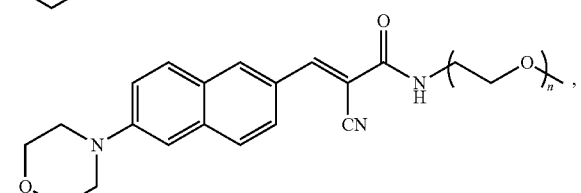
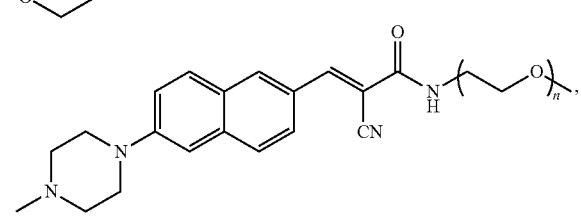
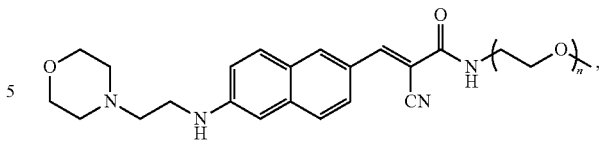
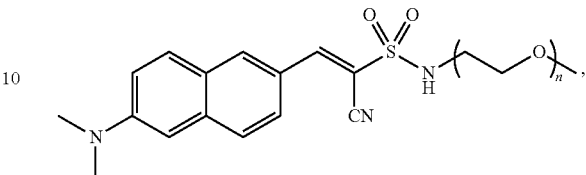
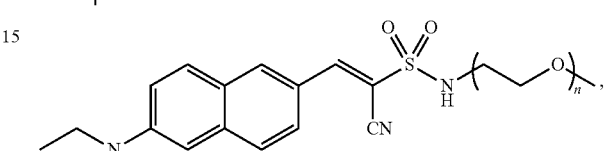
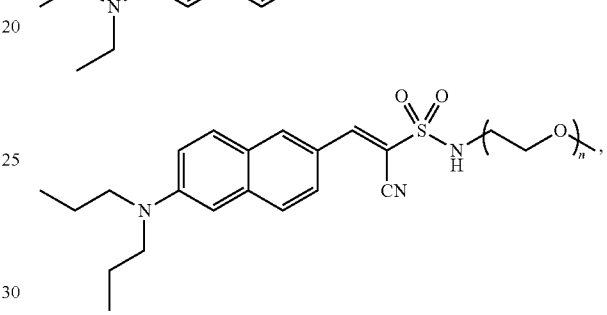
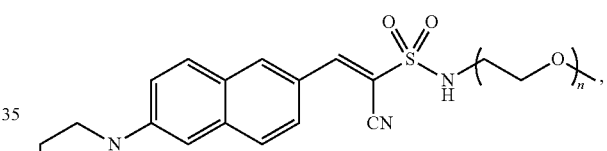
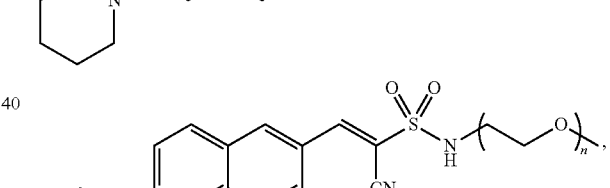
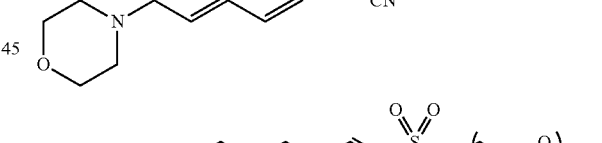
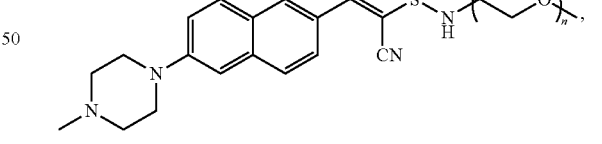
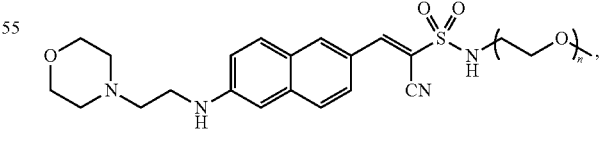
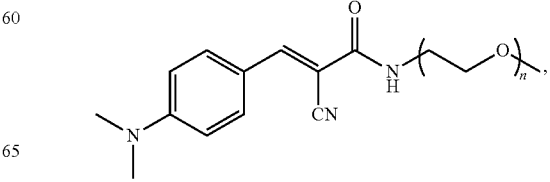

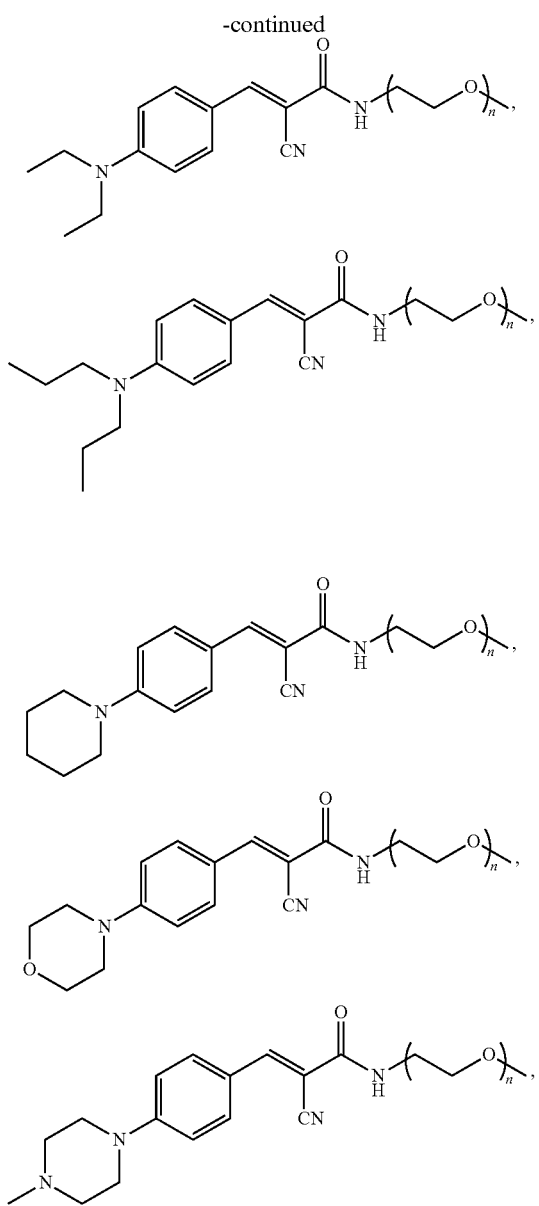
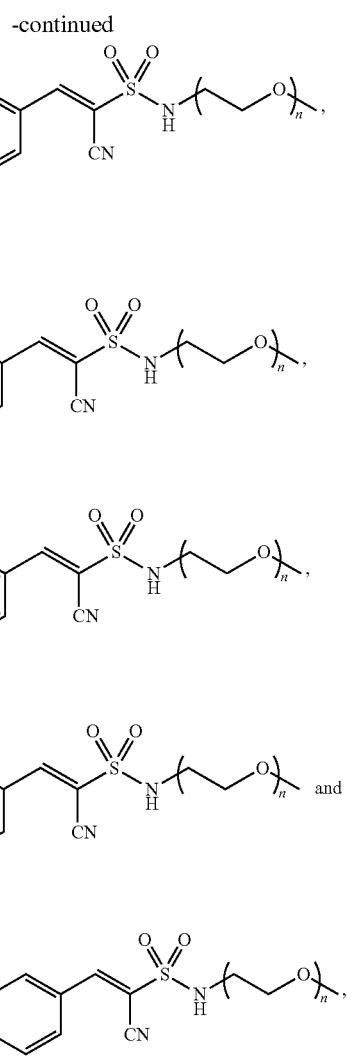
wherein n is an integer having a value from 1-10.
Embodiment 40
The compound of embodiment 1, wherein the compound is selected from a group consisting of
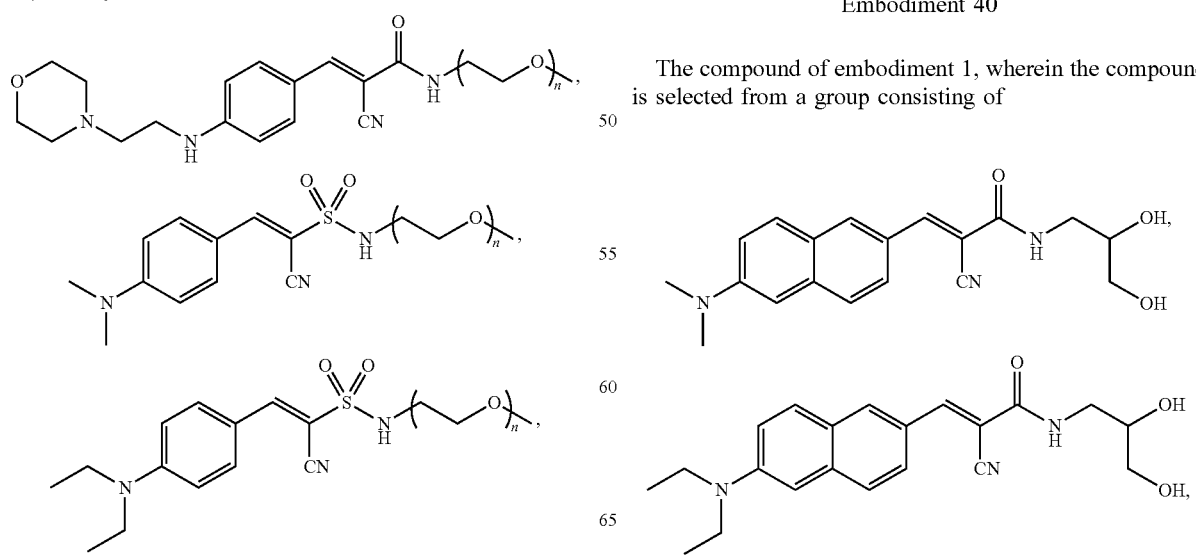

283
-continued
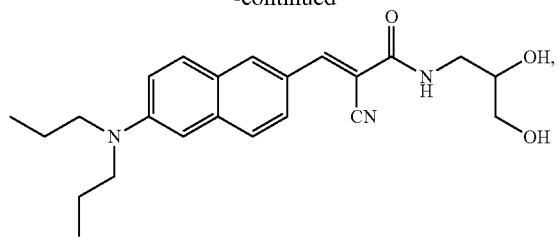
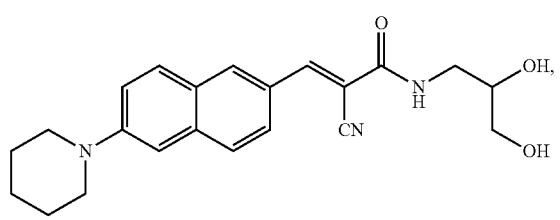
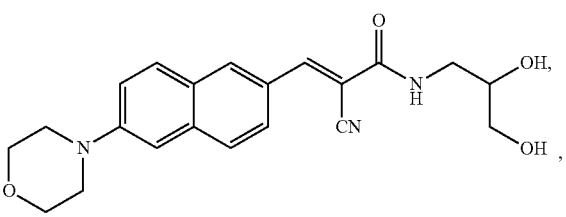
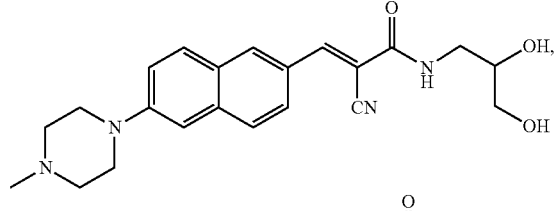
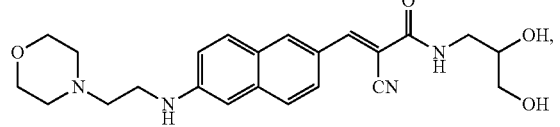
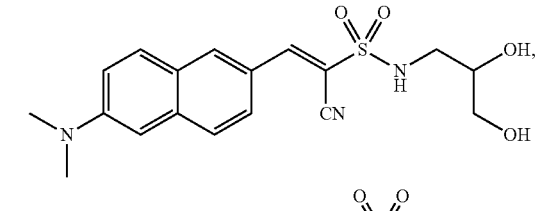
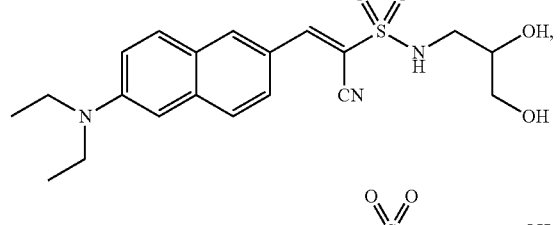
284
-continued
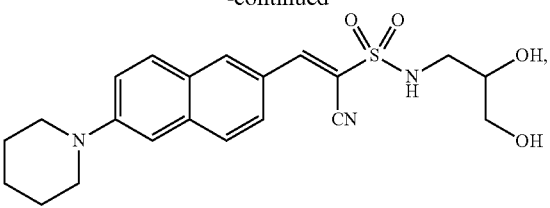
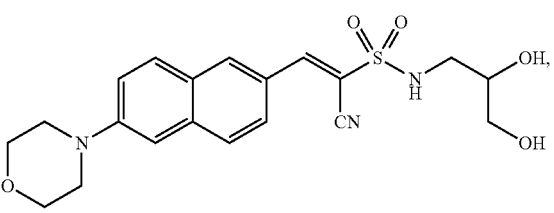
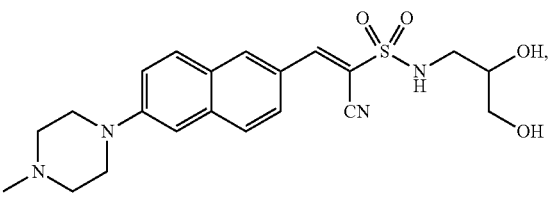
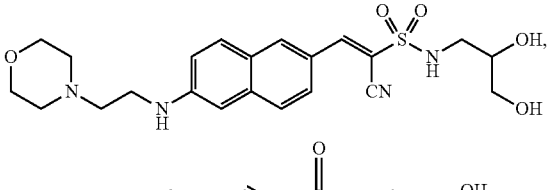
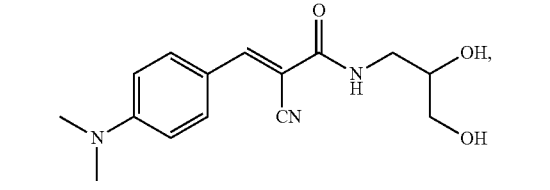
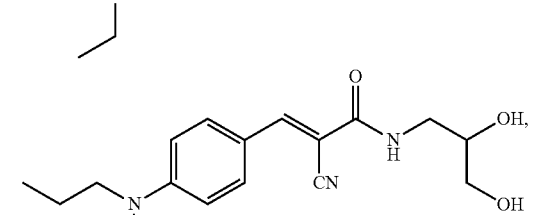
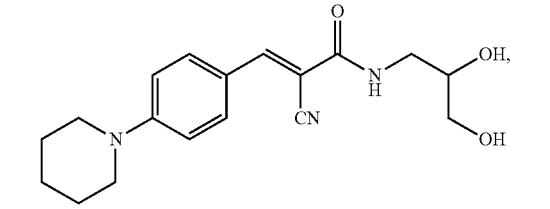

285
-continued
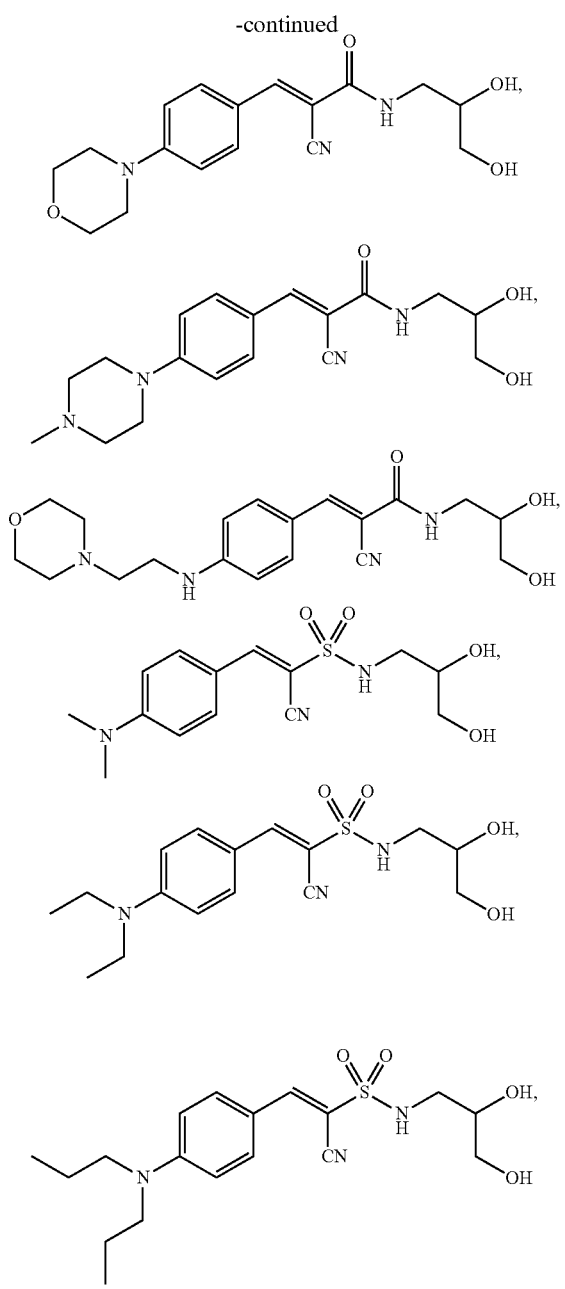
286
-continued
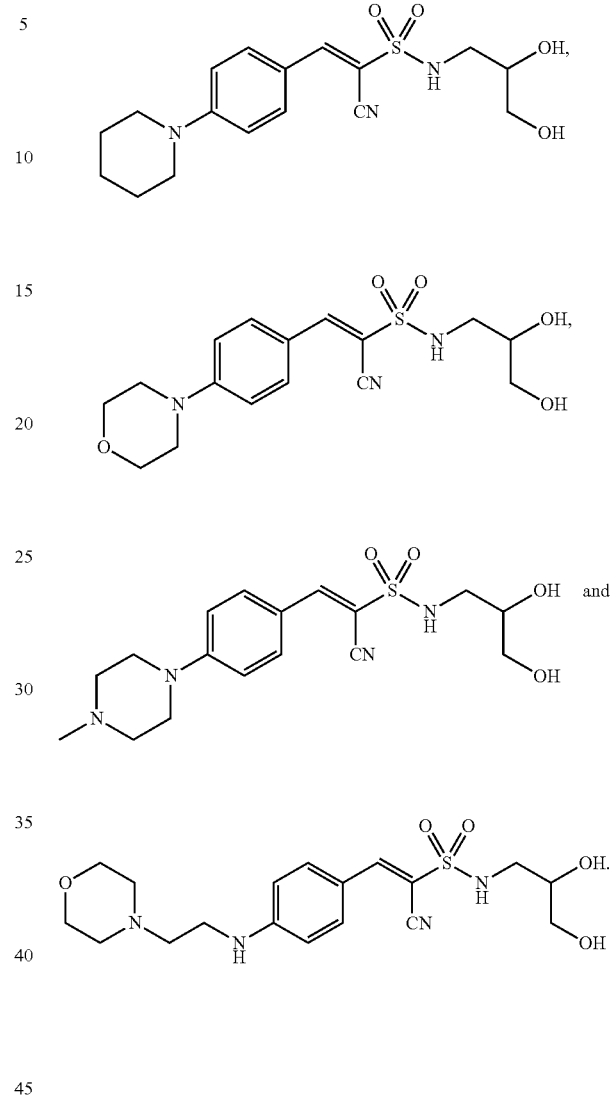
Embodiment 41
The compound of embodiment 1, wherein the compound is
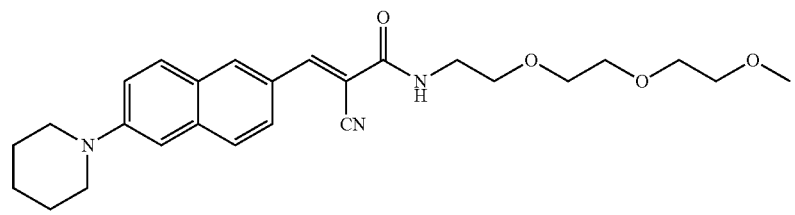

Embodiment 42

The compound of embodiment 1, wherein the compound is

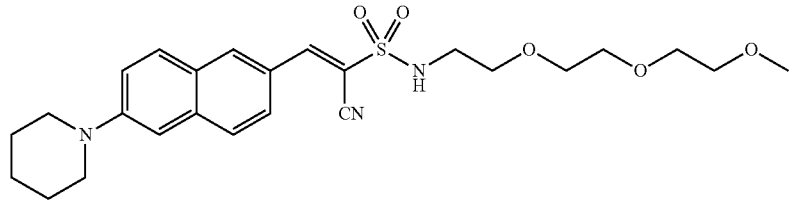

Embodiment 43

The compound of embodiment 1, wherein the compound is

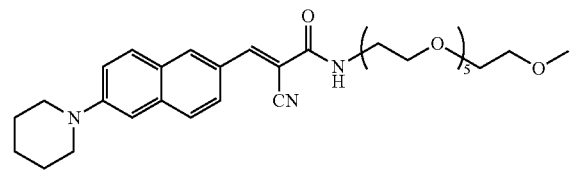

Embodiment 44

The compound of embodiment 1, wherein the compound is

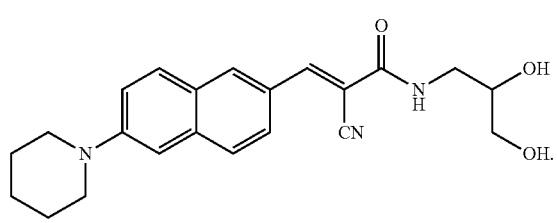 [SMILES: N#C/C(=C\c1ccc2cc(N3CCCCC3)ccc2c1)C(=O)NCC(O)CO]

Embodiment 45

The compound of embodiment 1, wherein the compound is

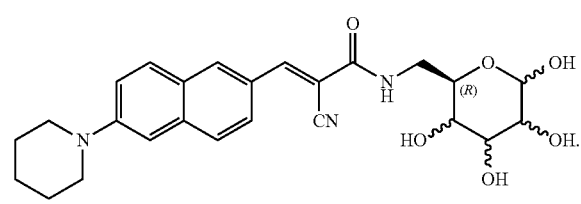

Embodiment 46

The compound of embodiment 45, wherein the compound is

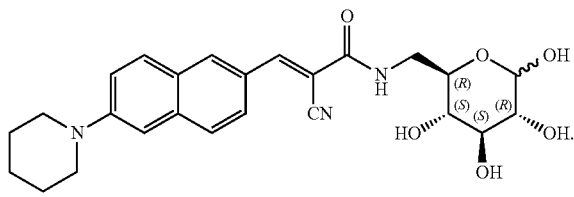

Embodiment 47

The compound of embodiment 1 wherein the compound is

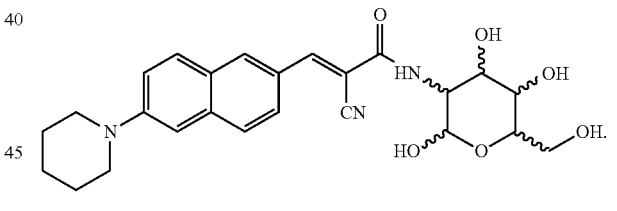

Embodiment 48

The compound of embodiment 47, wherein the compound is

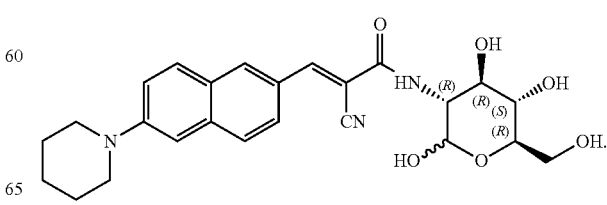

Embodiment 49
The compound of embodiment 11 wherein the compound is
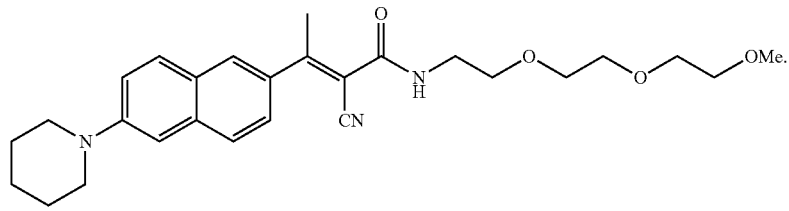 [SMILES: COCCOCCOCCNC(=O)/C(C#N)=C(\C)c1ccc2cc(N3CCCCC3)ccc2c1]
Embodiment 50
The compound of embodiment 1, wherein the compound is
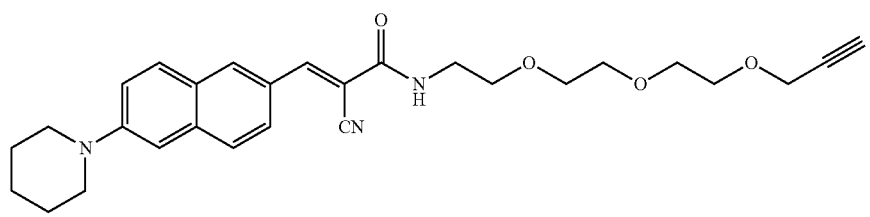
Embodiment 51
The compound of embodiment 1, wherein the compound is
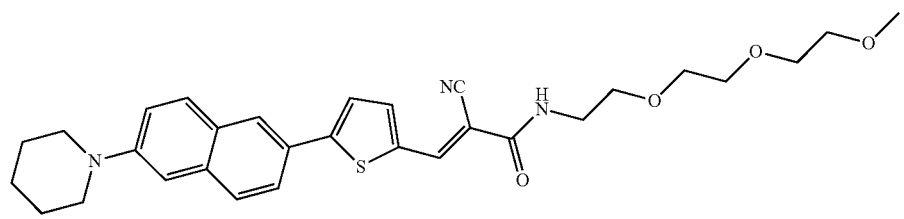
Embodiment 52
The compound of embodiment 1, wherein the compound is
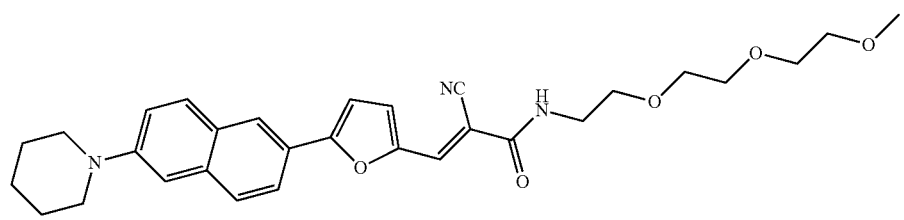

Embodiment 53

The compound of embodiment 1, wherein the compound is

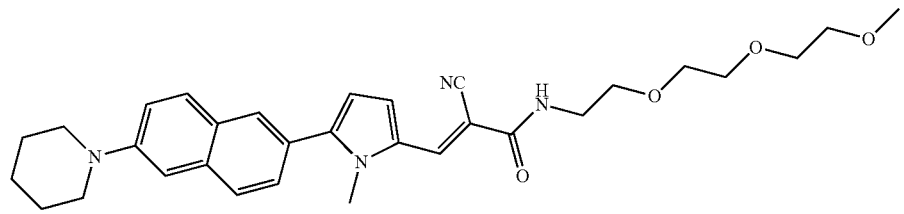

Embodiment 54

The compound of embodiment 1, wherein the compound is

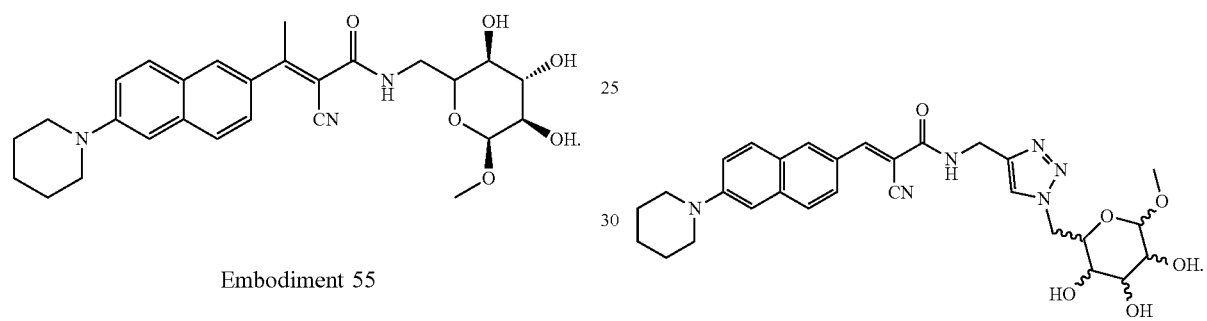

Embodiment 55

The compound of embodiment 1, wherein the compound is

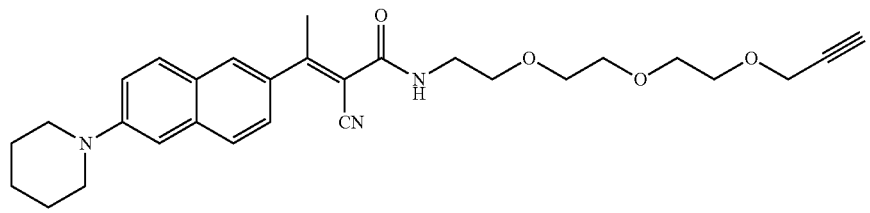

Embodiment 56

The compound of embodiment 1, wherein the compound is

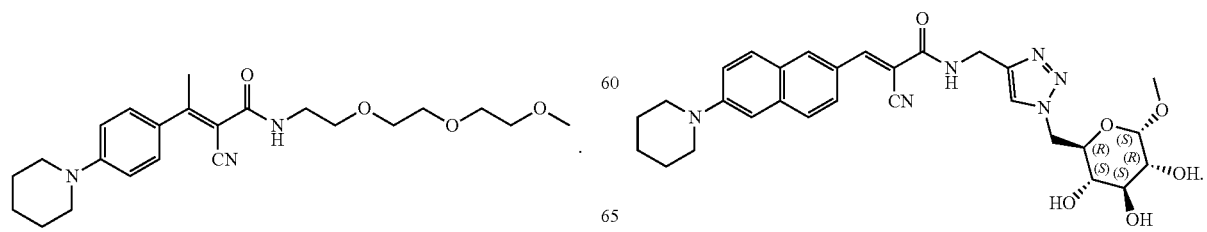

Embodiment 57

The compound of embodiment 1, wherein the compound is

Embodiment 58

The compound of embodiment 57, wherein the compound is

Embodiment 59

The compound of embodiment 1, wherein the compound is

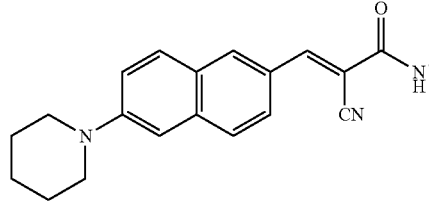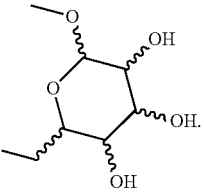

Embodiment 60

The compound of embodiment 59, wherein the compound is

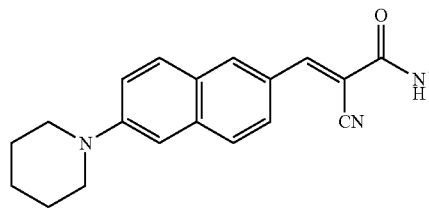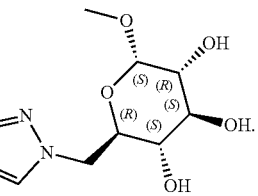

Embodiment 61

A compound of Formula II

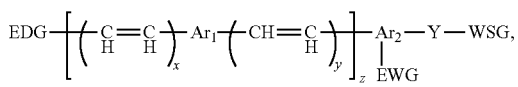

(Formula II)

wherein EDG is an electron donating group; $Ar_2$ and each $Ar_1$ is independently $C_1$-$C_{14}$ arylene or $C_1$-$C_{14}$ heteroarylene, each optionally substituted with one more $R_{41}$; each $R_{41}$ is independently halogen, —$OR_{42}$, —CN, —$NR_{43}R_{44}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene wherein the alkyl, heteroalkyl, cycloalkyl, heterocycloalkyl, arylene, or heteroarylene is optionally substituted with one or more $R_{45}$; $R_{42}$, $R_{43}$ and $R_{44}$ are independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{45}$; each $R_{45}$ is independently halogen, —$OR_{46}$, —$NR_{47}R_{48}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; $R_{46}$, $R_{47}$ and $R_{48}$ are independently hydrogen or $C_1$-$C_{10}$ alkyl; EWG is an electron withdrawing group; Y is absent, O, NH, or S; WSG is hydrogen or a water soluble group; x is an integer from 0-10; y is an integer from 0-10; and z is an integer from 1-10.

Embodiment 62

The compound of embodiment 61, wherein EDG is $OR_{49}$, $NR_{50}R_{51}$, —$SR_{52}$, —$PR_{53}R_{54}$, —$NR_{55}C(O)R_{56}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{57}$; each $R_{57}$ is independently halogen, —$OR_{58}$, —$NR_{59}R_{60}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; each of $R_{49}$, $R_{50}$, $R_{51}$, $R_{52}$, $R_{53}$, $R_{54}$, $R_{55}$, $R_{56}$, $R_{58}$, $R_{59}$ and $R_{60}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, each of which except for hydrogen is optionally substituted with one or more $R_{61}$ and wherein $R_{50}$ and $R_{51}$ are optionally joined together to form a heterocycloalkyl or heteroaryl optionally substituted with $R_{61}$; each of $R_{61}$ is independently halogen, —$OR_{62}$, —$NR_{63}R_{64}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more $R_{65}$; each of $R_{62}$, $R_{63}$ and $R_{64}$ is independently hydrogen or $C_1$-$C_{10}$ alkyl; and each $R_{65}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment 63

The compound of any one of embodiments 61 or 62, wherein EDG

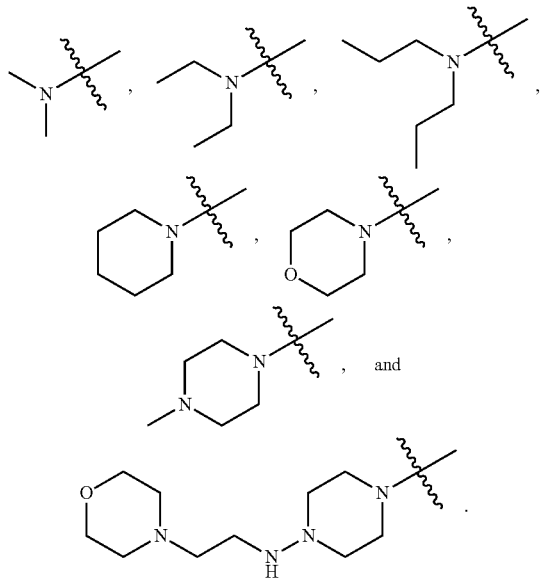

Embodiment 64

The compound of any one of embodiments 61-63, wherein EDG is

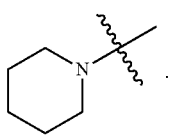 [SMILES: *N1CCCCC1]

Embodiment 65

The compound of any one of embodiments 61-64, wherein EWG is halogen, —CN, —NO$_2$, —SO$_3$H, —CR$_{66}$R$_{67}$R$_{68}$, COR$_{69}$, or COOR$_{70}$; each R$_{66}$, R$_{67}$ and R$_{68}$ is independently hydrogen or halogen; R$_{69}$ is halogen, hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more R$_{71}$; R$_{70}$ is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more R$_{72}$; each R$_{71}$ and R$_{72}$ is independently $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment 66

The compound of one of embodiments 61-65, wherein EWG is selected from a group consisting of F, Cl, Br, —CH=O, NO$_2$, —CF$_3$, —CCl$_3$, —SO$_3$ and —CN.

Embodiment 67

The compound of embodiment 66, wherein EWG is —CN.

Embodiment 68

The compound of any one of embodiments 61-67, wherein Y is absent.

Embodiment 69

The compound of any one of embodiments 61-68, wherein WSG is hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more R$_{73}$; each R$_{73}$ is independently halogen, —OR$_{74}$, —NR$_{75}$R$_{76}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more R$_{77}$; each R$_{74}$, R$_{75}$ and R$_{76}$ is independently hydrogen, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene, wherein the alkyl, heteroalkyl, cycloalkyl, heterocycloalkyl, arylene, or heteroarylene is optionally substituted with one or more R$_{77}$; each R$_{77}$ is independently halogen, —OR$_{78}$, —NR$_{79}$R$_{80}$, $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene; and each of R$_{78}$, R$_{79}$ and R$_{80}$ is independently hydrogen or $C_1$-$C_{10}$ alkyl.

Embodiment 70

The compound of any one of embodiments 61-69, wherein WSG is hydrogen.

Embodiment 71

The compound of any one of embodiments 61-69, wherein WSG is

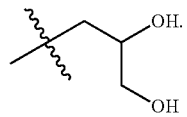 [SMILES: *CC(O)CO]

Embodiment 72

The compound of embodiment 61-69, wherein WSG is polyethylene glycol, polypropylene glycol, co-polymer of polyethylene glycol and polypropylene glycol, or alkoxy derivatives thereof.

Embodiment 73

The compound of embodiment 72, wherein WSG is

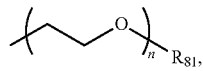

wherein n is an integer from 0-50 and $R_{81}$ is H, a $C_1$-$C_{10}$ alkyl, a $C_1$-$C_{10}$ alkenyl, or a $C_1$-$C_{10}$ alkynyl wherein each wherein the alkyl, alkenyl, or alkynyl is optionally substituted with one or more $C_1$-$C_{10}$ alkyl, $C_1$-$C_{10}$ heteroalkyl, $C_1$-$C_{10}$ cycloalkyl, $C_1$-$C_{10}$ heterocycloalkyl, $C_1$-$C_{10}$ arylene, or $C_1$-$C_{10}$ heteroarylene.

Embodiment 74

The compound of any one of embodiments 72 or 73, wherein $R_{81}$ is methyl.

Embodiment 75

The compound of any one of embodiments 72 or 73, wherein $R_{81}$ is $CH_2$—C≡CH.

Embodiment 76

The compound of any one of embodiments 72-75, wherein n is 0, 1, 2, 3, 4, 5, 6, 7, 8, 9, or 10.

Embodiment 77

The compound of any one of embodiments 72-76, wherein n is 3 or 6.

Embodiment 78

The compound of any one of embodiments 61-69, wherein the WSG is

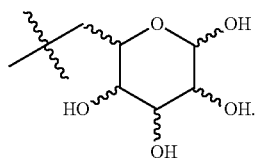 [SMILES: *CC1OC(O)C(O)C(O)C1O]

Embodiment 79

The compound of embodiment 78, wherein the WSG is

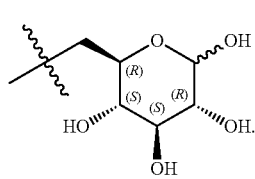

Embodiment 80

The compound of any one of embodiments 61-69, wherein the WSG is

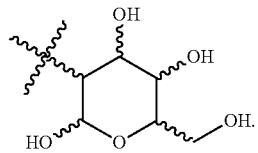

Embodiment 81

The compound of embodiment 80, wherein the WSG is

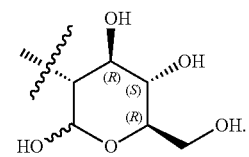

Embodiment 82

The compound of any one of embodiments 61-81, wherein each of $Ar_1$ is independently a naphthylene or a phenylene.

Embodiment 83

The compound of embodiment 61-82, wherein $Ar_2$ is naphthylene, phenylene, or pyridyl.

Embodiment 84

The compound of embodiment 83, wherein $Ar_2$ is naphthylene or a phenylene.

Embodiment 85

The compound of embodiment 83, wherein $Ar_2$ is pyridyl.

Embodiment 86

The compound of embodiment 61, wherein the compound is selected from a group consisting of

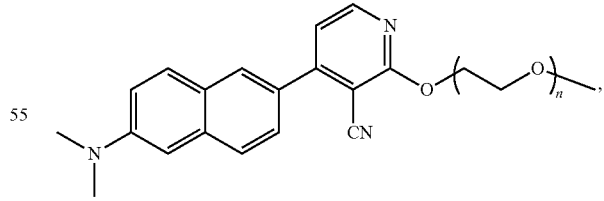

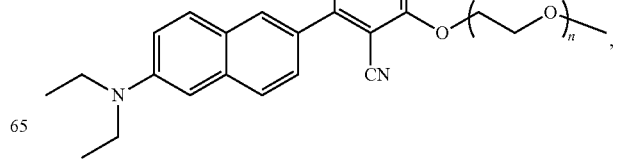

299
-continued
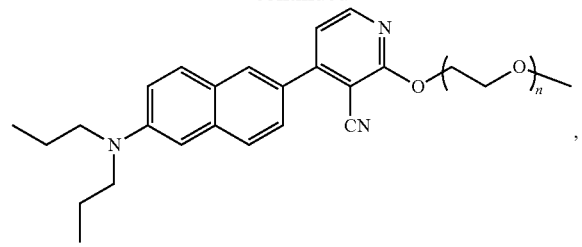,
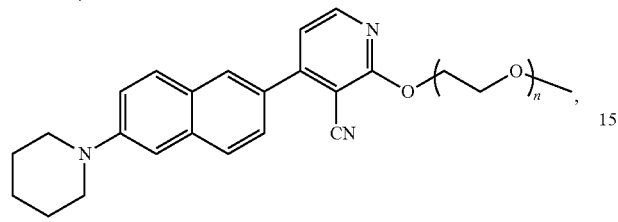,
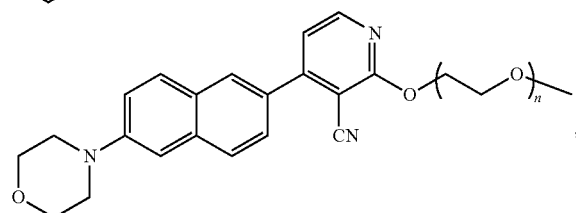,
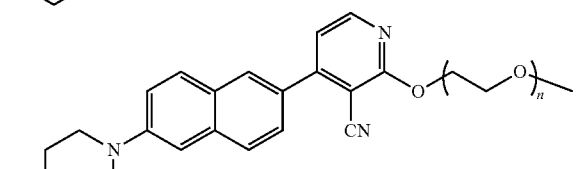,
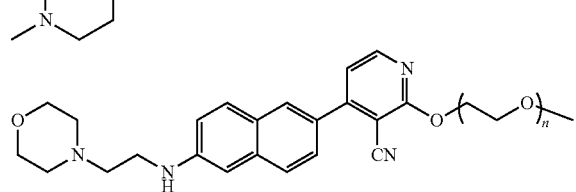,
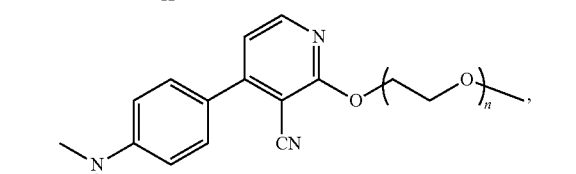,
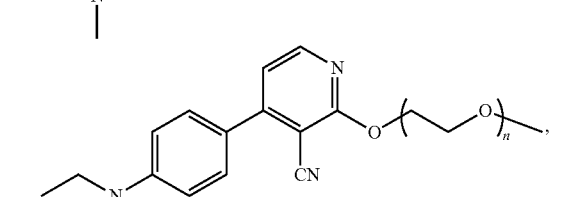,
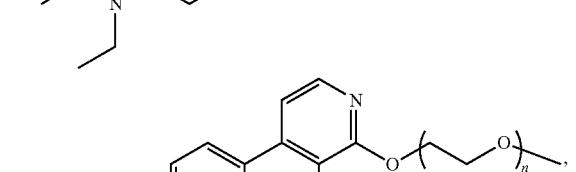,
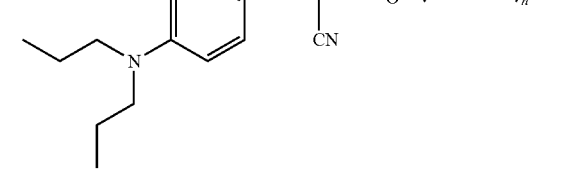,
300
-continued
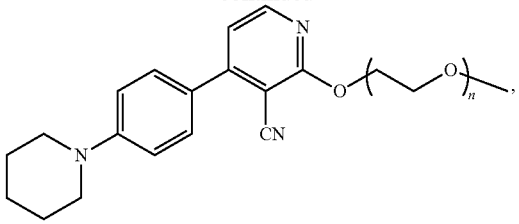,
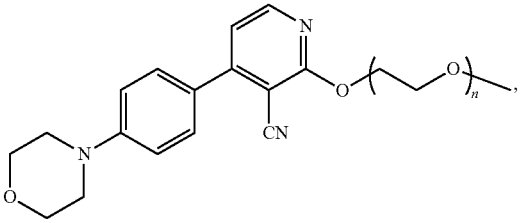,
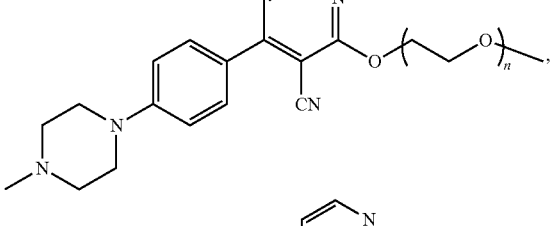,
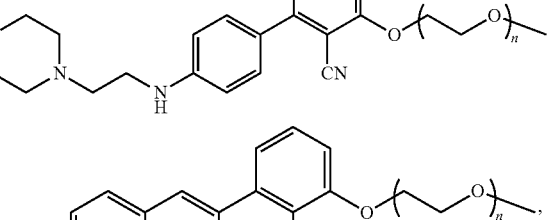,
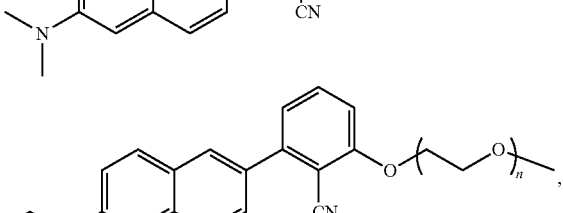,
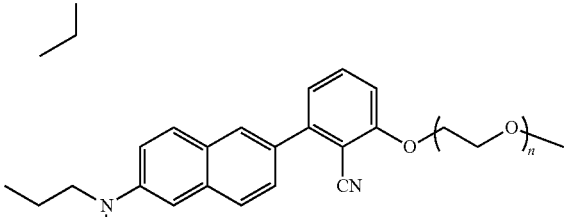,
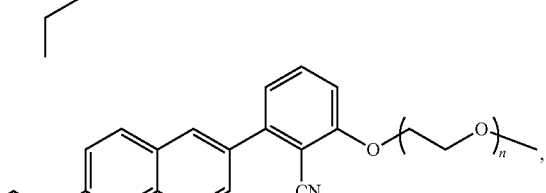,
,

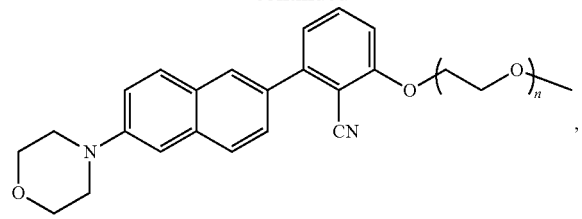
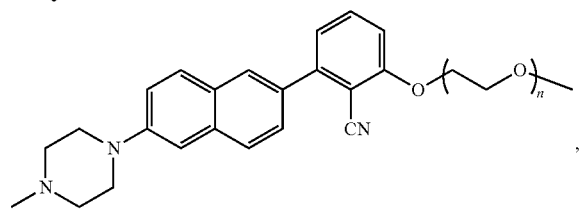
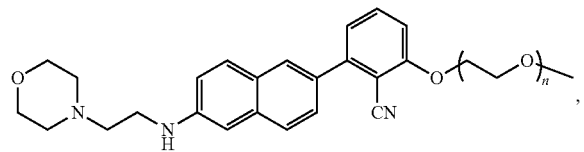
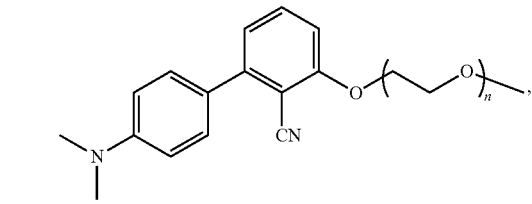
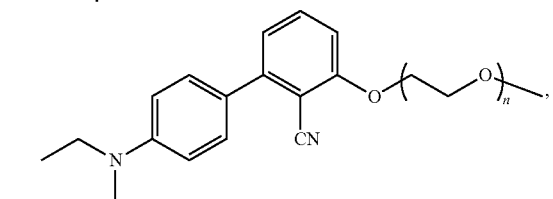
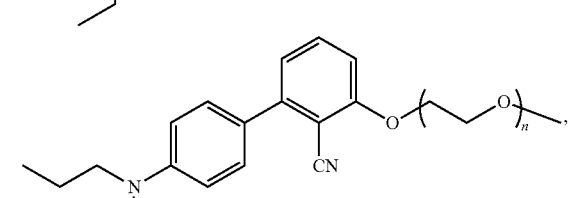
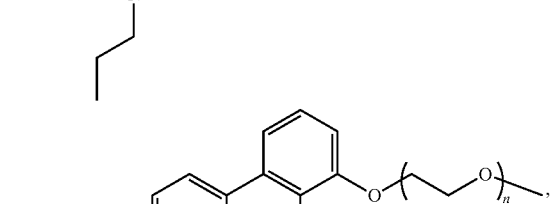
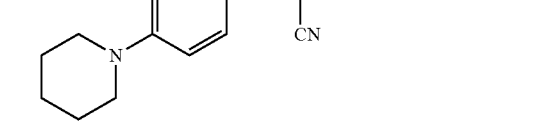
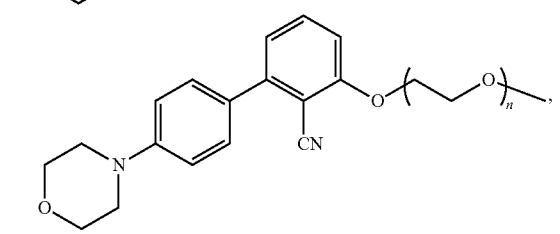
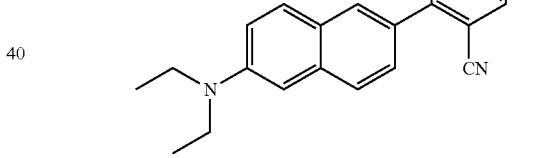
wherein n is an integer with value 0-10.
Embodiment 87
The compound of embodiment 61, wherein the compound is selected from a group consisting of
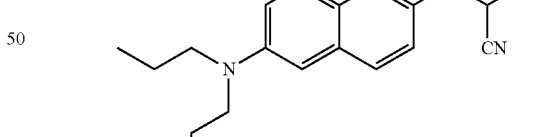
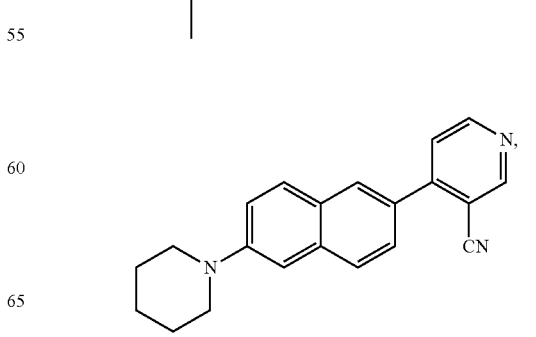

303
-continued
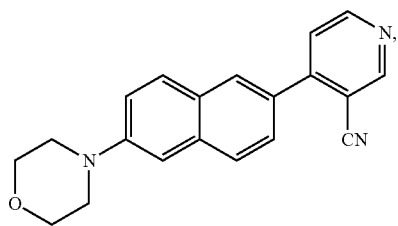
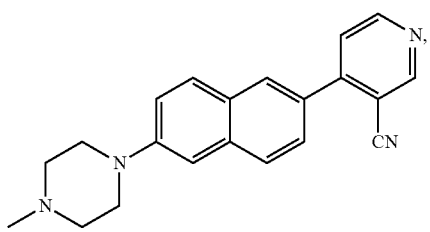
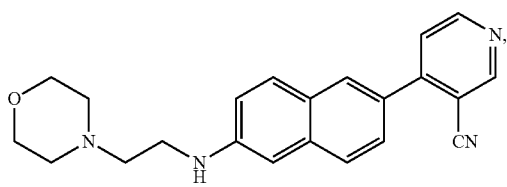
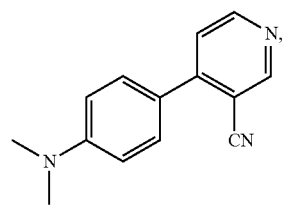
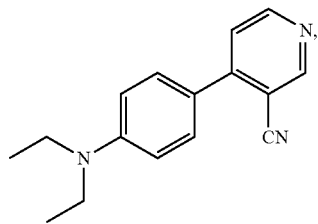
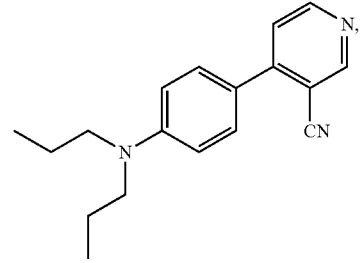
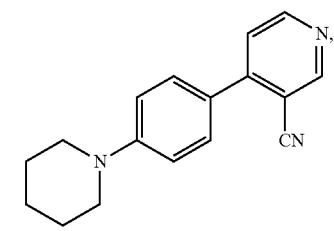
304
-continued
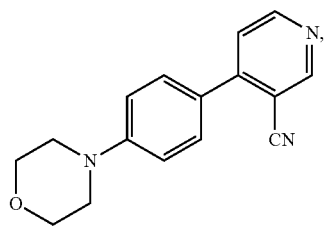
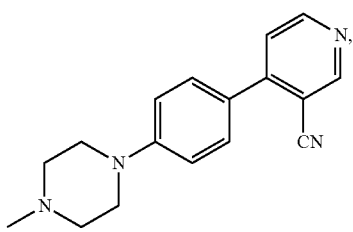
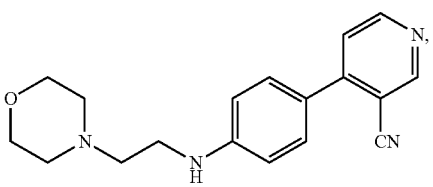
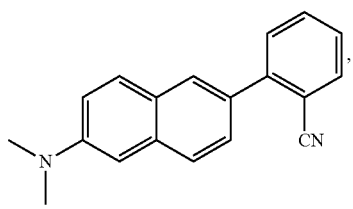
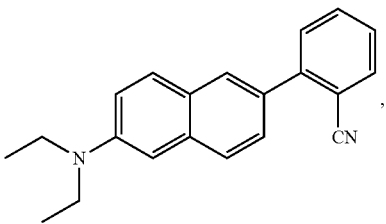
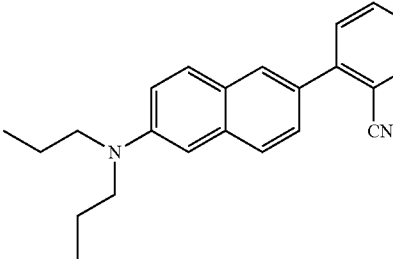
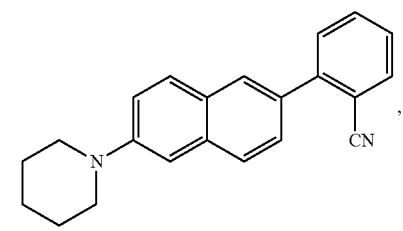

305
-continued
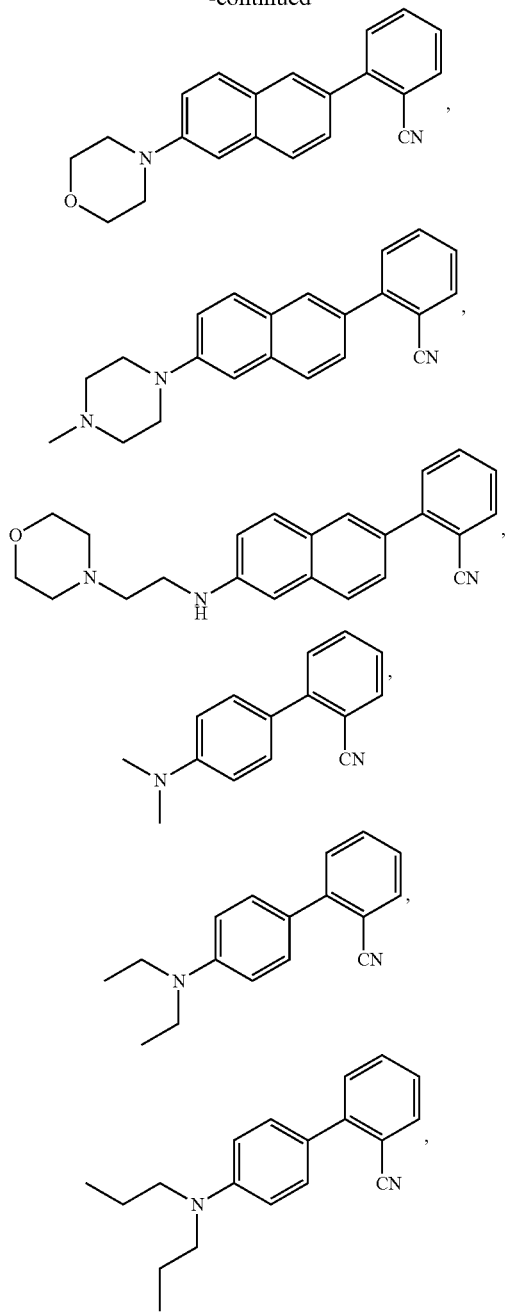
306
-continued
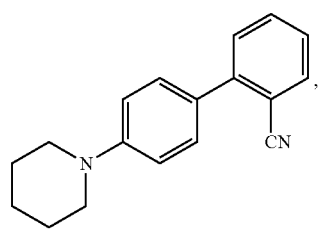
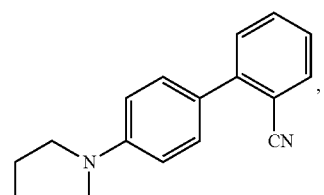
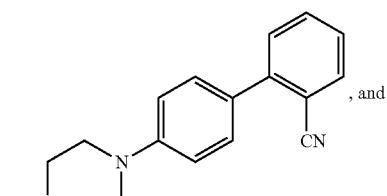, and
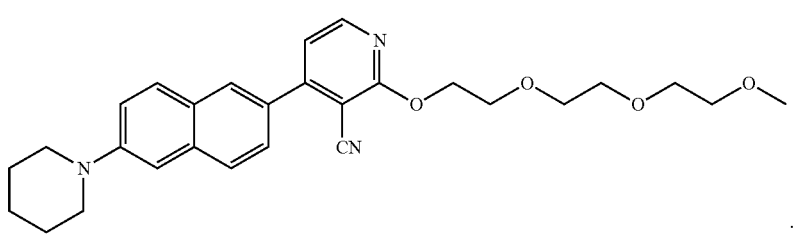 [SMILES: COCCOCCOCCOc1nccc(-c2ccc3cc(N4CCCCC4)ccc3c2)c1C#N]
Embodiment 88
The compound of embodiment 61, wherein the compound is

Embodiment 89

The compound of embodiment 61, wherein the compound is

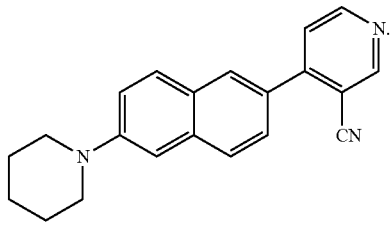 [SMILES: N#Cc1cnccc1-c1ccc2cc(N3CCCCC3)ccc2c1]

Embodiment 90

The compound of embodiment 61, wherein the compound is

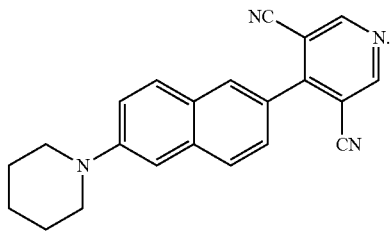 [SMILES: N#Cc1cncc(C#N)c1-c1ccc2cc(N3CCCCC3)ccc2c1]

Embodiment 91

The compound of embodiment 61, wherein the compound is

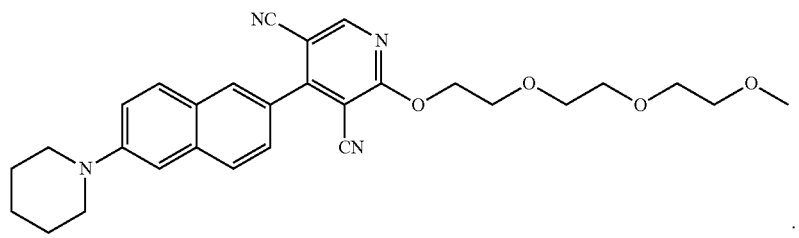 [SMILES: COCCOCCOCCOc1ncc(C#N)c(-c2ccc3cc(N4CCCCC4)ccc3c2)c1C#N]

Embodiment 92

A pharmaceutical composition comprising a compound according to any one of embodiments 1-91.

Embodiment 93

The pharmaceutical composition of embodiment 92, further comprising one or more pharmaceutically acceptable additive, carrier or excipient selected from a group consisting of ethanol, DMSO, polyethylene glycol, polypropylene glycol, aqueous acetate buffers, aqueous citrate buffers, aqueous phosphate buffers, aqueous carbonate buffers, cyclodextrins, corn oil, vitamin E, polysorbates, polyethyleneglycol-15 hydroxystearate (SOLUTOL®) and bile acids.

Embodiment 94

A composition comprising a compound according to any one of embodiments 1-91 for use as a medicament.

Embodiment 95

The composition for use as a medicament of embodiment 92, further comprising one or more pharmaceutically acceptable additive, carrier or excipient selected from a group consisting of ethanol, DMSO, polyethylene glycol, polypropylene glycol, aqueous acetate buffers, aqueous citrate buffers, aqueous phosphate buffers, aqueous carbonate buffers, cyclodextrins, corn oil, vitamin E, polysorbates, polyethyleneglycol-15 hydroxystearate (SOLUTOL®) and bile acids

Embodiment 96

A composition comprising a compound according to any one of embodiments 1-91 and an amyloid or amyloid like protein.

Embodiment 97

The composition of embodiment 96, wherein the amyloid or amyloid like protein is Aβ peptide, prion peptide, alpha-synuclein, or superoxide dismutase.

Embodiment 98

A method of detecting an amyloid or amyloid like protein comprising: a) contacting a compound according to any one of embodiments 1-91 with a sample potentially comprising the amyloid or amyloid like protein, wherein in presence of an amyloid or amyloid like protein the compound forms a detectable complex; and b) detecting the formation of the detectable complex such that the presence or absence of the detectable complex correlates with the presence or absence of the amyloid or amyloid like protein.

Embodiment 99

The method of embodiment 98, wherein the detection of the formation of the detectable complex is performed by measuring a signal generated by the detectable complex.

Embodiment 100

The method of embodiment 99, wherein the signal generated by the detectable complex is an electromagnetic signal.

Embodiment 101

The method of embodiment 99, wherein the electromagnetic signal is a fluorescence signal.

Embodiment 102

The method of embodiment 101, wherein the fluorescence signal is measures at a wavelength of 450-650 nm.

Embodiment 103

The method of embodiment 101, wherein the fluorescence signal is measures at a wavelength of 520-540 nm.

Embodiment 104

The method of embodiment 98, wherein the amyloid or amyloid like protein is Aβ peptide, prion peptide, alpha-synuclein, or superoxide dismutase.

Embodiment 105

The method of embodiment 98, wherein the amyloid or amyloid like protein is beta amyloid (1-42) (Aβ (1-42)).

Embodiment 106

The method of embodiment 98, wherein the detection of the formation of the detectable complex is performed within about 1 sec, about 5 sec, about 1 min, about 10 min, about 30 min or about 60 min of the contacting of the compound according to any one of embodiments 1-91 with the sample.

Embodiment 107

The method of embodiment 98, wherein the detection of the formation of the detectable complex is performed within about 1-5 minutes of the contacting of the compound according to any one of embodiments 1-91 with the sample.

Embodiment 108

A method of determining the presence or absence of one or more disease or condition in a subject comprising: a) administering to the subject an effective amount of a compound according to any one of embodiments 1-91 or a pharmaceutical composition thereof, wherein in presence of the disease or condition the administered compound forms a detectable complex; and b) detecting the formation of the detectable complex such that presence or absence of detectable complex correlates with the presence or absence of the disease or condition.

Embodiment 109

The method of embodiment 108, wherein the disease or condition is characterized by protein aggregation or protein misfolding.

Embodiment 110

The method of embodiment 108, wherein the disease or condition is an amyloid based disease or condition.

Embodiment 111

The method of embodiment 108, wherein the disease or condition is Alzheimer's disease (AD), Parkinson's disease, Huntington's disease, amyotrophic lateral sclerosis (ALS), Lewy body dementia (LBD), or Down's syndrome.

Embodiment 112

The method of embodiment 108, wherein the disease of condition is Alzheimer's disease.

Embodiment 113

The method of embodiment 112, wherein the compound

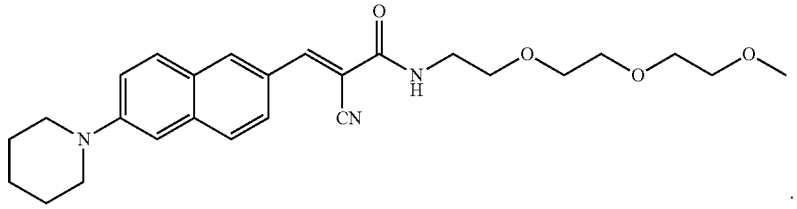 [SMILES: COCCOCCOCCNC(=O)/C(C#N)=C/c1ccc2cc(N3CCCCC3)ccc2c1]

Embodiment 114

The method of embodiment 108, wherein the disease or condition is a prion disease or condition.

Embodiment 115

The method of embodiment 114, wherein the prion disease or condition is Creutzfeldt-Jakob disease (CJD).

Embodiment 116

The method of embodiment 108, wherein the administering is to the eye of the subject.

Embodiment 117

The method of embodiment 108, wherein the administering is parenteral.

Embodiment 118

The method of embodiment 108, wherein the administering is intravenous.

Embodiment 119

The method of embodiment 108, wherein the administering is subcutaneous.

Embodiment 120

The method of embodiment 108, wherein the administering is intramuscular.

Embodiment 121

The method of embodiment 108, wherein the administering is intrathecal.

Embodiment 122

The method of embodiment 108, wherein the administering is transmucosal.

Embodiment 123

The method of embodiment 108, wherein the administering is oral.

Embodiment 124

The method of embodiment 108, wherein the administering is buccal.

Embodiment 125

The method of embodiment 108, wherein the administering is sublingual.

Embodiment 126

The method of embodiment 108, wherein the administering is nasal.

Embodiment 127

The method of embodiment 108, wherein the administering is pulmonary.

Embodiment 128

The method of embodiment 108, wherein the administering is rectal.

Embodiment 129

The method of embodiment 108, wherein the administering is topical.

Embodiment 130

The method of embodiment 108, wherein the administering is ocular.

Embodiment 131

The method of embodiment 108, wherein the administering is transdermal.

Embodiment 132

The method of embodiment 108, wherein the administering is intradermal.

Embodiment 133

The method of embodiment 108, wherein the administering is systemic.

Embodiment 134

The method of embodiment 108, wherein the detection of the formation of the detectable is performed within about 1 sec, about 5 sec, about 1 min, about 10 min, about 30 min or about 60 min of the administration of the compound according to any one of embodiments 1-91 to the subject.

Embodiment 135

The method of embodiment 108, wherein the detection of the formation of the detectable complex is performed within about 1-5 min of the administration of the compound according to any one of embodiments 1-91 to the subject.

Embodiment 136

The method of embodiment 108, wherein the effective amount the compound corresponds to about 50-500 mg of compound per adult human subject.

Embodiment 137

The method of embodiment 108, wherein the detection of the formation of the detectable complex is performed by measuring a signal generated by the detectable complex.

Embodiment 138

The method of embodiment 137, the signal generated by the detectable complex is an electromagnetic signal.

Embodiment 139

The method of embodiment 138, wherein the electromagnetic signal is a fluorescence signal.

Embodiment 140

The method of embodiment 139, wherein the fluorescence signal is measures at a wavelength of 450-650 nm.

Embodiment 141

The method of embodiment 139, wherein the fluorescence signal is measures at a wavelength of 520-540 nm.

Embodiment 142

Use of a composition containing a therapeutically effective amount of a compound according to any one of embodiments 1-91 for treating, ameliorating the symptoms of or preventing at least one disease or condition.

Embodiment 143

The use of embodiment 142, wherein the disease or condition is characterized by protein aggregation or protein misfolding,

Embodiment 144

The use of any one of embodiments 142 or 143, wherein the disease or condition is an amyloid based disease or condition.

Embodiment 145

The use of any one of embodiments 142-144, wherein the disease or condition is Alzheimer's disease (AD), Parkinson's disease, Huntington's disease, amyotrophic lateral sclerosis (ALS), Lewy body dementia (LBD), or Down's syndrome.

Embodiment 146

The use of embodiment 145, wherein the disease is Alzheimer's disease.

Embodiment 147

The use of any one of embodiments 142-146, wherein the compound is:

Embodiment 148

The use of embodiment 142, wherein the disease or condition is a prion disease or condition.

Embodiment 149

The use of embodiment 148, wherein the prion disease or condition is Creutzfeldt-Jakob disease.

Embodiment 150

The use of any one of embodiments 142-149, wherein the therapeutically effective amount corresponds to about 50-500 mg.

Embodiment 151

A screening method comprising administering to a subject an effective amount of a compound according to any one of embodiments 1-91 or a pharmaceutical composition thereof, wherein upon administration of a compound according to any one of embodiments 1-91 form a detectable complex.

Embodiment 152

The screening method of embodiment 151, further comprising measuring a signal generated by the by the detectable complex or by the compound, according to any one of embodiments 1-91, administered to the subject.

Embodiment 153

The screening method of embodiment 152, further comprising making a clinical decision based on the measured signal.

Embodiment 154

The screening method of embodiment 152, wherein the signal is an electromagnetic signal.

Embodiment 155

The screening method of embodiment 154, wherein the electromagnetic signal is a fluorescence signal.

Embodiment 156

The method of embodiment 155, wherein the fluorescence signal is measures at a wavelength of 450-650 nm.

Embodiment 157

The method of embodiment 155, wherein the fluorescence signal is measures at a wavelength of 520-540 nm.

Embodiment 158

The screening method of embodiment 151, wherein the administering is to the eye of the subject.

Embodiment 159

The screening method of embodiment 151, wherein the administering is parenteral.

Embodiment 160

The screening method of embodiment 151, wherein the administering is intravenous.

Embodiment 161

The screening method of embodiment 151, wherein the administering is subcutaneous.

Embodiment 162

The screening method of embodiment 151, wherein the administering is intramuscular.

Embodiment 163

The screening method of embodiment 151, wherein the administering is intrathecal.

Embodiment 164

The screening method of embodiment 151, wherein the administering is transmucosal.

Embodiment 165

The screening method of embodiment 151, wherein the administering is oral.

Embodiment 166

The screening method of embodiment 151, wherein the administering is buccal.

Embodiment 167

The screening method of embodiment 151, wherein the administering is sublingual.

Embodiment 168

The screening method of embodiment 151, wherein the administering is nasal.

Embodiment 169

The screening method of embodiment 151, wherein the administering is pulmonary.

Embodiment 170

The screening method of embodiment 151, wherein the administering is rectal.

Embodiment 171

The screening method of embodiment 151, wherein the administering is topical.

Embodiment 172

The screening method of embodiment 151, wherein the administering is ocular.

Embodiment 173

The screening method of embodiment 151, wherein the administering is transdermal.

Embodiment 174

The screening method of embodiment 151, wherein the administering is intradermal.

Embodiment 175

The screening method of embodiment 151, wherein the said administering is systemic.

Embodiment 176

A kit for comprising a compound according to any one of embodiments 1-91.

Embodiment 177

The kit of embodiment 176 further comprising instructions for a) using the compound for the binding to an amyloid or amyloid like protein to form a detectable complex; and b) detecting the formation of the detectable complex such that presence or absence of detectable complex correlates with the presence or absence of the amyloid or amyloid like protein.

Embodiment 178

The kit of embodiment 176 further comprising instructions for a) using the compound for binding to an amyloid or amyloid like protein to form a detectable complex; and b) detecting changes in abundance of the detectable complex over time such that the changes in the abundance of the detectable complex over time are correlated to changes in abundance of amyloid or amyloid like protein over time.

Embodiment 179

The kit of embodiment 178, further comprising instructions for correlating the changes in the abundance of the detectable complex to monitor progression of a disease.

Embodiment 180

The kit of embodiment 176, wherein the compound according to any one of embodiments 1-91 is contained in a container as a sterile liquid formulation.

Embodiment 181

The kit of embodiment 176, wherein the compound according to any one of embodiments 1-91 is contained in a container as a sterile freeze-dried formulation.

Embodiment 182

The kit of embodiment 176, wherein the container is an amber vial.

Embodiment 183

The kit of embodiment 176, wherein the container is capable of protecting light sensitive compounds or formulation.

EXAMPLES

The following examples are intended to illustrate but not limit the disclosed embodiments.

Example 1: (E)-2-Cyano-N-(2-(2-(2-methoxyethoxy)ethoxy)ethyl)-3-(6-(piperidin-1-yl)naphthalen-2-yl)acrylamide (Compound 1)

See FIG. 1A for synthetic scheme

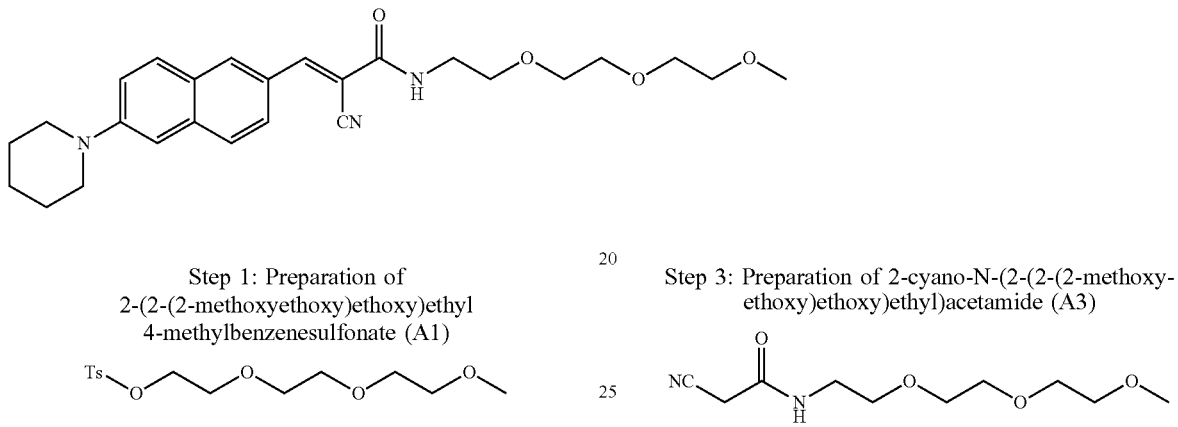

Step 1: Preparation of 2-(2-(2-methoxyethoxy)ethoxy)ethyl 4-methylbenzenesulfonate (A1)

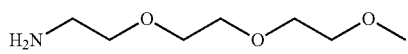

To a solution of dry pyridine (49 mL) in dichloromethane (DCM) (152 mL) was added commercially available triethylene glycol monomethyl ether (TEGMe) (20 g, 0.122 mol). The solution was cooled to 0° C., upon which para-toluenesulfonyl chloride (27.9 g, 0.146 mol) was added in one portion with stirring. The reaction was let stir to room temperature (r.t.) over 24 hours, upon which the reaction as concentrated under reduced pressure. The resulting yellow oil was resuspended with ethyl acetate (EtOAc), filtered, and concentrated to dry. The oil was purified by silica gel chromatography (2:8 EtOAc:hexanes) to obtain 2-(2-(2-methoxyethoxy)ethoxy)ethyl 4-methylbenzenesulfonate A1 as a clear oil in 53% yield.

Step 2: Preparation of 2-(2-(2-methoxyethoxy)ethoxy)ethanamine (A2)

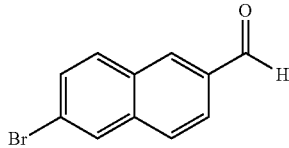 [SMILES: O=Cc1ccc2cc(Br)ccc2c1]

To a solution of 2-(2-(2-methoxyethoxy)ethoxy)ethyl 4-methylbenzenesulfonate (A1, 1.0 g, 3.14 mmol) in dry dimethylformamide (DMF) (125 mL) was added sodium azide (510 mg, 7.85 mmol) in one portion with stir. The solution was flushed with argon and refluxed at 67° C. for 12 hours, upon which the reaction was cooled to r.t., diluted with ice-cold water (125 mL) and extracted with diethyl ether (Et₂O). The organic washes were combined, washed with water and brine, dried over magnesium sulfate, and concentrated to partial dryness in vacuo to obtain the azido-TEGMe as a clear oil.

The azide (3.0 g, 15.7 mmol) was dissolved in Et₂O (630 mL) and cooled to 0° C. with stir. To the reaction was added triphenyl phosphine (5.0 g, 18.8 mmol) in one portion and the resulting solution let stir to r.t. over 24 hours, upon which water (200 mL) was then added and stirred for an additional 12 hours. Finally, toluene (150 mL) was added and the aqueous layer extracted, washed with toluene, and concentrated under reduced pressure to obtain 2-(2-(2-methoxyethoxy)ethoxy)ethanamine A2 as a yellow oil in 70% yield.

Step 3: Preparation of 2-cyano-N-(2-(2-(2-methoxyethoxy)ethoxy)ethyl)acetamide (A3)

A solution of cyanoacetic acid (621 mg, 7.3 mmol) in anhydrous DCM (15 mL) was cooled to 0° C. Separately, a solution of hydroxybenzothiazole (HOBt) (1.48 g, 10.97 mmol) and 2-(2-(2-methoxyethoxy)ethoxy)ethanamine (A2, 1.79 g, 10.97 mmol) was prepared in DCM (10 mL); this solution was then added dropwise to the cooled solution of cyanoacetic acid. The resulting solution was allowed to stir for 10 minutes at 0° C., upon which 1-ethyl-3-(3-dimethylaminopropyl)carbodiimide (EDC) (2.1 g, 10.97 mmol) was added in one portion and the reaction stirred under argon at 0° C. for 12 hours. The reaction was then concentrated and purified by silica gel chromatography (0-2% MeOH/DCM) to obtain 2-cyano-N-(2-(2-(2-methoxyethoxy)ethoxy)ethyl) acetamide A3 as a yellow oil in 83% yield.

Step 4: Preparation of 6-bromo-2-naphthaldehyde (A5)

A solution of commercially available methyl 6-bromo-2-naphthoate (A4, 3.5 g, 13.2 mmol) in anhydrous tetrahydrofuran (THF) (70 mL) was cooled to 0° C. under nitrogen, upon which a solution of diisobutylaluminum hydride (DIBAL-H) in THF (15.8 mmol) was added dropwise over 5 minutes with stir. The reaction was let stir to r.t. overnight, upon which it was quenched with MeOH (50 mL) and a saturated sodium potassium tartrate solution (50 mL). The solution was then extracted with EtOAc and the organic layers washed with water and brine, dried over sodium sulfate, and concentrated to obtain the corresponding alcohol as a white solid.

The alcohol (1.3 g, 5.48 mmol) was then dissolved in anhydrous DCM (28 mL) under nitrogen with stir. To this solution was added pyridinium chlorochromate (PCC) (1.4 g, 6.58 mmol) in one portion and the resulting brown solution refluxed at 60° C. under nitrogen. After 6 hours, the resulting black solution was cooled to r.t. and poured into ice-cold Et₂O, filtered through celite over a pad of silica, concentrated to a yellow solid, and finally purified with silica gel chromatography (8:2 hexanes:EtOAc) to obtain the 6-bromo-2-naphthaldehyde A5 as a white solid in 95% yield.

Step 5: Preparation of 6-(piperidin-1-yl)-2-naphthaldehyde (A6)

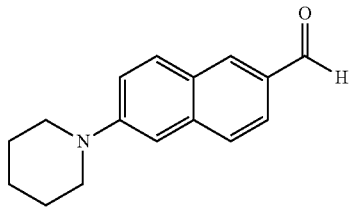 [SMILES: O=Cc1ccc2cc(N3CCCCC3)ccc2c1]

6-Bromo-2-naphthaldehyde (A5, 1.5 g, 6.38 mmol), palladium (II) acetate (0.17 g, 0.64 mmol), and cesium carbonate (3.2 g, 9.57 mmol) were added to dry, degassed toluene (16 mL) under argon and let stir for 30 minutes at r.t., upon which tri-t-butyl phosphine (2.55 mmol) was added dropwise and the orange solution let stir an additional 10 minutes. Piperidine (0.75 mL, 7.66 mmol) was then added dropwise and the reaction refluxed at 110° C. for three days. The reaction was then cooled, diluted with DCM, filtered, and concentrated under reduced pressure to obtain a red oil which was purified by silica gel chromatography (0-1% MeOH/DCM) to obtain the 6-(piperidin-1-yl)-2-naphthaldehyde A6 as a yellow solid in 70% yield.

Step 6: Preparation of (E)-2-Cyano-N-(2-(2-(2-methoxyethoxy)ethoxy)ethyl)-3-(6-(piperidin-1-yl)naphthalen-2-yl)acrylamide (Compound 1)

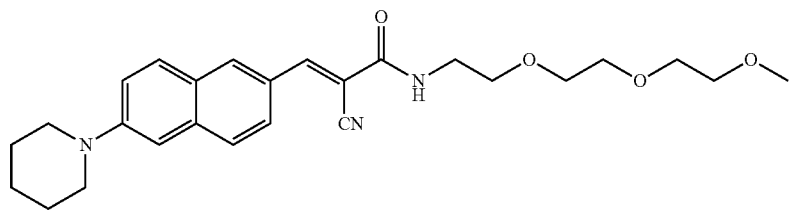 [SMILES: COCCOCCOCCNC(=O)/C(C#N)=C/c1ccc2cc(N3CCCCC3)ccc2c1]

6-(Piperidin-1-yl)-2-naphthaldehyde (A6, 150 mg, 0.627 mmol) and 2-cyano-N-(2-(2-(2-methoxyethoxy)ethoxy)ethyl)acetamide (115 mg, 0.501 mmol) were dissolved in anhydrous THF (2.5 mL). To this reaction was added piperidine (0.013 mmol) and the reaction heated to 50° C.; a change in reaction color of yellow to orange was observed. After 12 hours of heating, the reaction was cooled, concentrated to an oil, and purified by silica gel chromatography (0-20% acetone/toluene) to obtain (E)-2-Cyano-N-(2-(2-(2-methoxyethoxy)ethoxy)ethyl)-3-(6-(piperidin-1-yl)naphthalen-2-yl)acrylamide as a yellow solid in 61% yield. $R_f$=0.25 (5% acetone/toluene); $^1$H NMR (500 MHz, CDCl₃) δ 8.33 (s, 1H), 8.11 (s, 1H), 8.00-8.02 (dd, J=8.5 Hz, 1.5 Hz, 1H), 7.69-7.71 (d, J=9.5 Hz, 1H), 7.60-7.62 (d, J=8.5 Hz, 1H), 7.24-7.26 (m, 1H), 7.01 (bs, 1H), 6.84 (m, 1H), 3.64-3.66 (m, 6H), 3.62-3.63 (m, 4H), 3.54-3.55 (m, 2H), 3.35 (s, 3H), 3.12-3.34 (m, 4H), 1.69 (m, 4H), 1.61-1.62 (m, 2H); $^{13}$C (125 MHz, CDCl₃) δ 161.2, 152.9, 151.6, 137.2, 133.8, 130.3, 127.2, 126.6, 126.1, 125.7, 119.4, 117.8, 108.6, 100.5, 71.9, 70.6, 70.6, 70.5, 69.4, 59.0, 49.5, 40.2, 25.5, 24.3; HRMS calcd for $C_{26}H_{32}N_2O_5Na$ [M+Na]⁺ 474.2363, found 474.2363 by ESI.

Example 2: (E)-1-cyano-N-(2-(2-(2-methoxyethoxy)ethoxy)ethyl)-2-(6-(piperidin-1-yl)naphthalen-2-yl)ethenesulfonamide (Compound 2)

Figure 3:
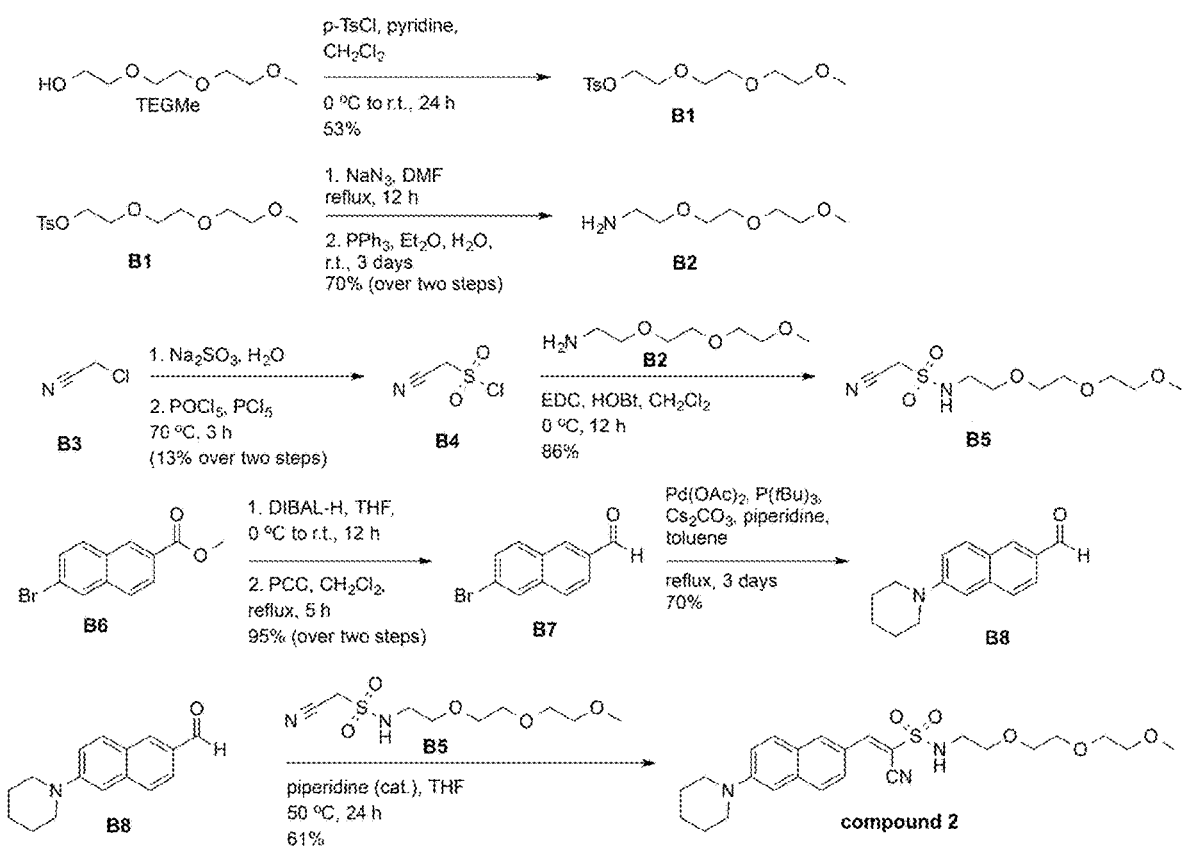
FIG. 3 Shows a synthetic strategy towards the synthesis of compound 2.
Figure 4:
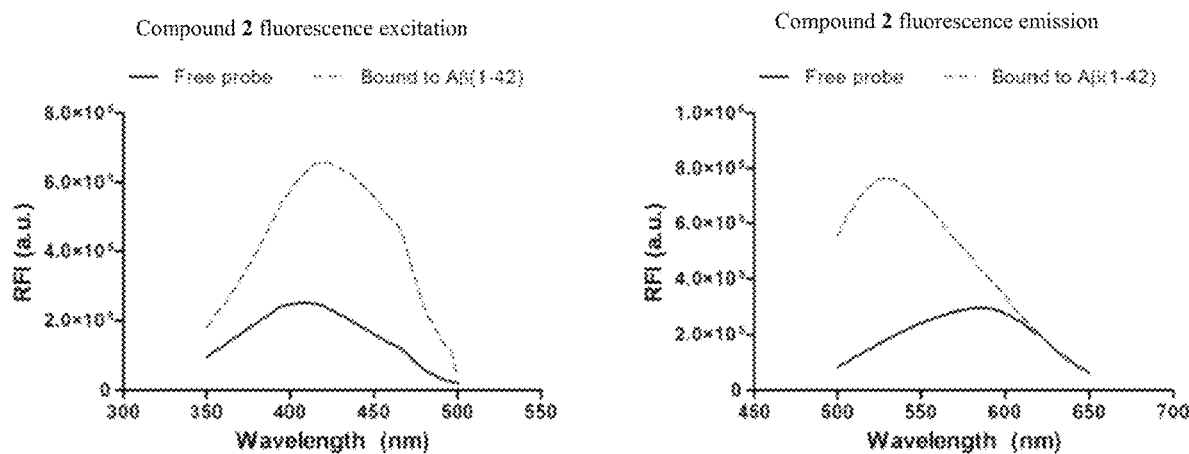
FIG. 4 Shows the fluorescence excitation and emission profiles of compound 2, measured using 4 µM compound 2 and 5 µM Aβ (1-42) in 5% DMSO in water.

See FIG. 3 for synthetic scheme.

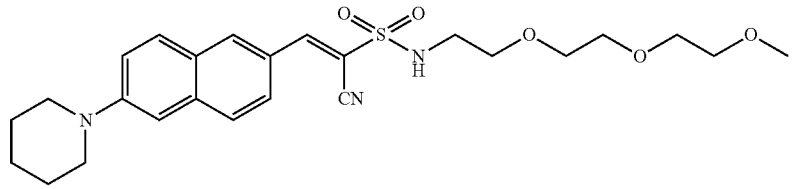 [SMILES: COCCOCCOCCNS(=O)(=O)/C(C#N)=C/c1ccc2cc(N3CCCCC3)ccc2c1]

Step 1: Preparation of cyanomethanesulfonyl chloride (B4)

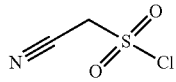

Chloroacetonitrile (B3, 5.0 g, 41.68 mmol) was added to a suspension of sodium sulfite (5.3 g, 41.68 mmol) in water (25 mL). The mixture was stirred at r.t. for 1 hour, upon which the water was removed under reduced pressure, and the resulting solid recrystallized from 98% ethanol (EtOH). The crude recrystallized product (3.0 g, 20.97 mmol) was suspended in phosphoryl chloride (7.35 mL) and powdered phosphorous pentachloride (4.4 g, 20.97 mmol) and the solution stirred for 3 hours at 70° C. under argon with exclusion of moisture. The reaction was then filtered and excess phosphoryl chloride removed by reduced pressure; the crude oil was then distilled and cyanomethanesulfonyl chloride B4 isolated as a clear-yellow oil in 13% yield.

Step 2: Preparation of 1-cyano-N-(2-(2-(2-methoxyethoxy)ethoxy)ethyl)methanesulfonamide (B5)

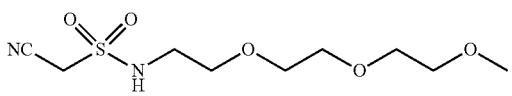 [SMILES: COCCOCCOCCNS(=O)(=O)CC#N]

Cyanomethanesulfonyl chloride was found to be relatively unstable in air and was reacted immediately (3.44 mmol) with previously synthesized 2-(2-(2-methoxyethoxy)ethoxy)ethanamine (A2, 5.41 mmol) in DCM (10 mL). HOBt (5.43 mmol) was added dropwise to the reaction mixture once cooled to 0° C., followed by EDC (5.43 mmol). The reaction was then let stir for 6 hours at 0° C., concentrated under reduced pressure, and purified by silica gel chromatography to obtain the 1-cyano-N-(2-(2-(2-methoxyethoxy)ethoxy)ethyl)methanesulfonamide B5 in 86% yield as a clear oil.

Step 3: Preparation of (E)-1-cyano-N-(2-(2-(2-methoxyethoxy)ethoxy)ethyl)-2-(6-(piperidin-1-yl)naphthalen-2-yl)ethenesulfonamide (Compound 2)

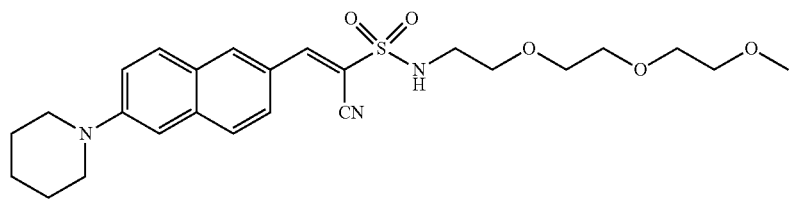 [SMILES: COCCOCCOCCNS(=O)(=O)/C(C#N)=C/c1ccc2cc(N3CCCCC3)ccc2c1]

6-(Piperidin-1-yl)-2-naphthaldehyde (A6, 22.4 mg, 0.094 mmol) and 1-cyano-N-(2-(2-(2-methoxyethoxy)ethoxy)ethyl)methanesulfonamide (B5, 20.0 mg, 0.075 mmol) were dissolved in anhydrous THF (0.38 mL). To this reaction was added piperidine (0.009 mmol) and the reaction heated to 50° C. After 5 hours of heating, the reaction was cooled, concentrated to an oil, and purified by silica gel chromatography (0-20% Et$_2$O/hexanes) to obtain (E)-1-cyano-N-(2-(2-(2-methoxyethoxy)ethoxy)ethyl)-2-(6-(piperidin-1-yl)naphthalen-2-yl)ethenesulfonamide as an orange oil in 73% yield. R$_f$=0.5 (100% diethyl ether); $^1$H NMR (500 MHz, CDCl$_3$) δ 8.12 (s, 1H), 8.05 (s, 1H), 7.98-8.00 (dd, J=9.0 Hz, 2.0 Hz, 1H), 7.74-7.76 (d, J=9.5 Hz, 1H), 7.64-7.66 (d, J=9.0 Hz, 1H), 7.29-7.31 (dd, J=9.0 Hz, 2.5 Hz, 1H), 7.05 (d, J=2.0 Hz, 1H), 5.48 (bs, 1H), 3.64-3.68 (m, 8H), 3.53-3.57 (m, 3H), 3.39-3.42 (m, 3H), 3.38 (s, 3H), 3.33-3.35 109 (m, 2H), 1.73 (m, 4H), 1.67 (m, 2H); $^{13}$C NMR (125 MHz, CDCl$_3$) δ 161.2, 152.9, 151.6, 137.2, 133.8, 130.3, 127.2, 126.6, 126.1, 125.7, 119.4, 117.8, 108.6, 100.5, 71.9, 70.6, 70.6, 70.5, 69.4, 59.0, 49.5, 40.2, 25.5, 24.3; HRMS calcd. for C$_{25}$H$_{33}$N$_3$O$_5$SNa [M+Na]$^+$ 510.2033, found 510.2035 by ESI.

Example 3: (E)-2-cyano-N-(2,5,8,11,14,17-hexaoxanonadecan-19-yl)-3-(6-(piperidin-1-yl)naphthalen-2-yl)acrylamide (Compound 3)

Figure 5:
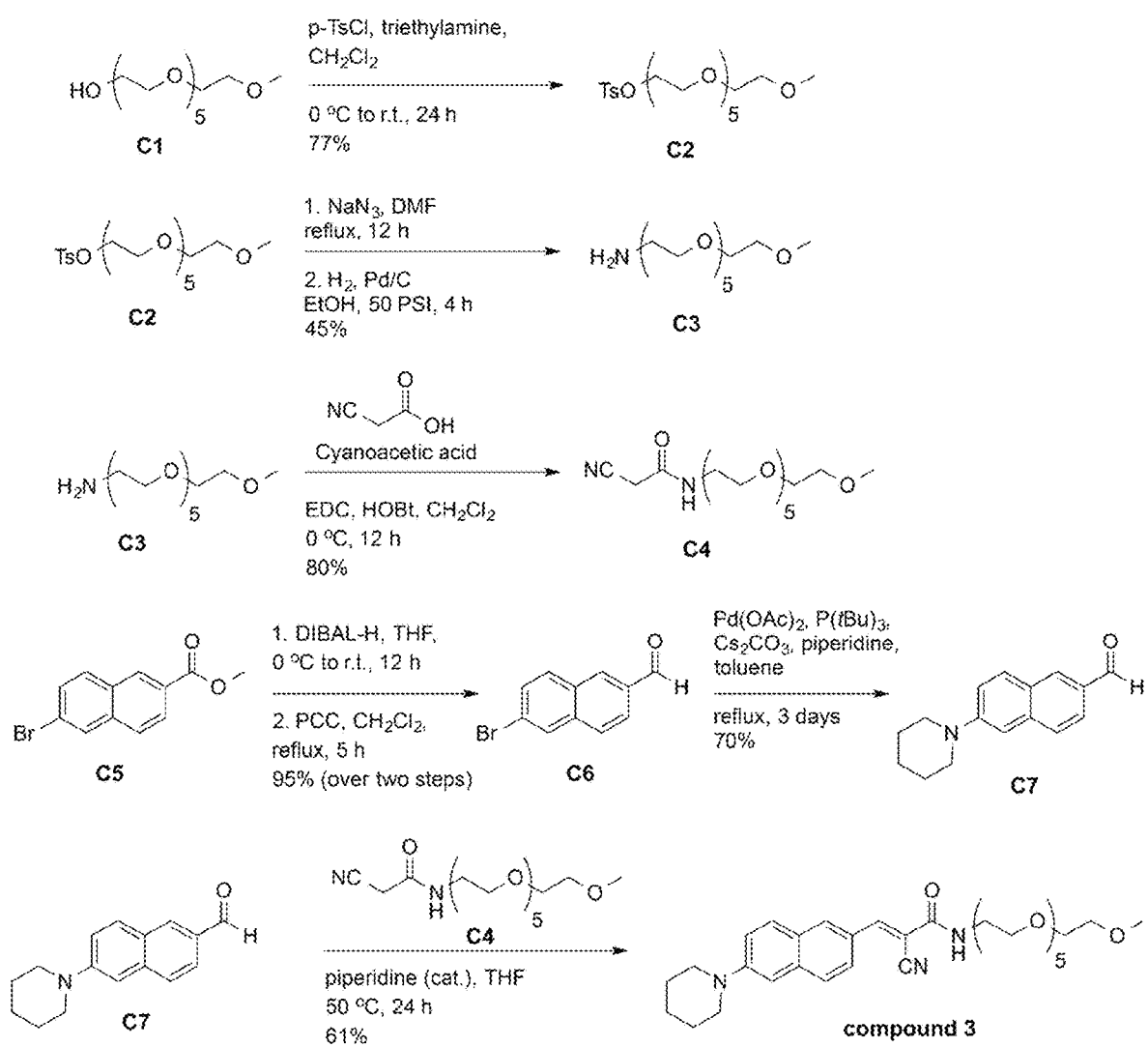
FIG. 5 Shows a synthetic strategy towards the synthesis of compound 3.
Figure 6A:
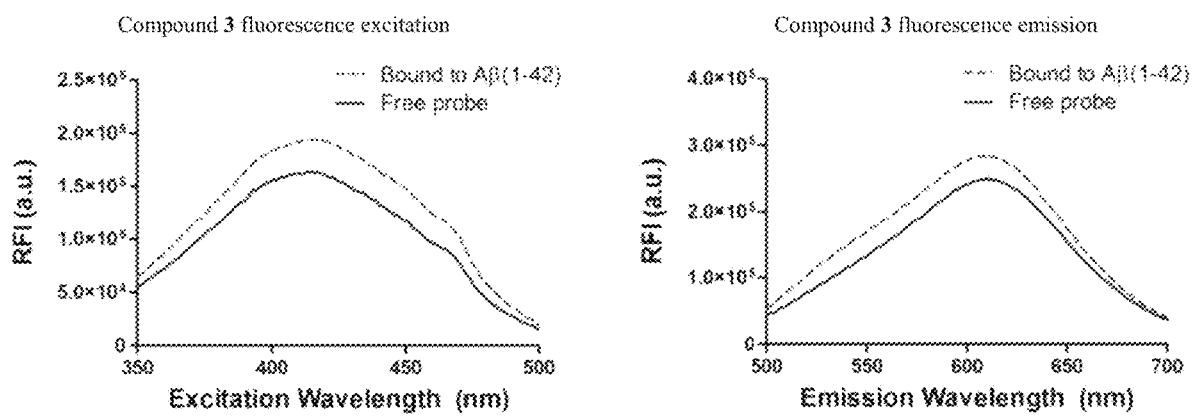
FIG. 6A Shows the fluorescence excitation and emission profiles of compound 3, measured using 4 µM compound 3 and 5 µM Aβ (1-42) in 5% DMSO in water.
Figure 6B:
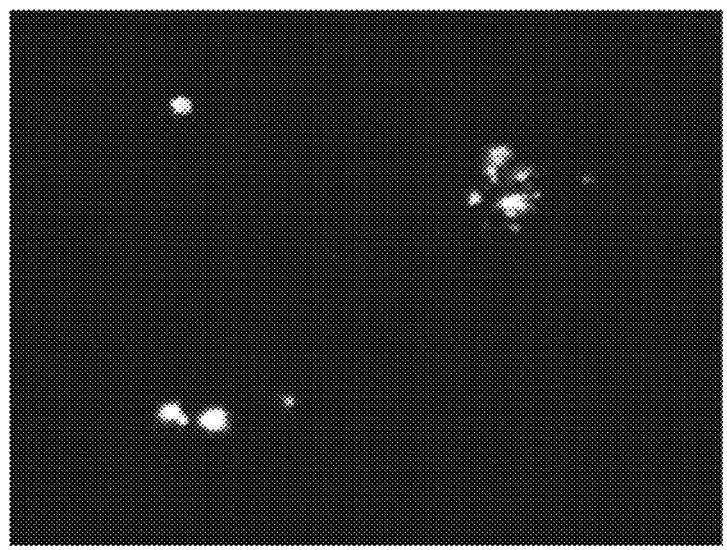
FIG. 6B Shows staining of amyloid deposits in murine AD neuronal tissue by compound 3.

See FIG. 5 for synthetic scheme.

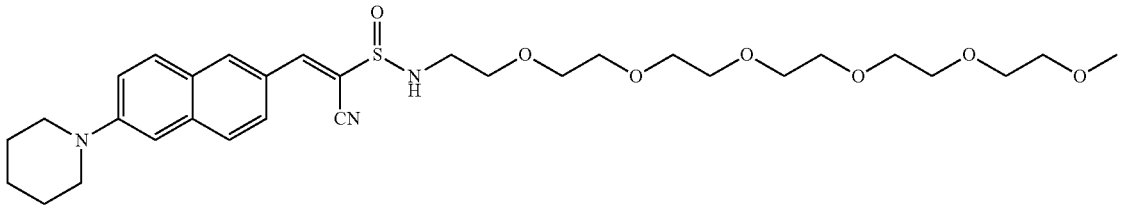 [SMILES: COCCOCCOCCOCCOCCOCCNS(=O)/C(C#N)=C/c1ccc2cc(N3CCCCC3)ccc2c1]

Step 1: Preparation of 2,5,8,11,14,17-hexaoxanonadecan-19-ol 2-(2-(2-Methoxyethoxy)ethoxy)ethyl 4-methylbenzenesulfonate (A1, 1.0 g, 3.14 mmol) was added with stir to triethylene glycol (2.10 mL, 15.7 mmol). Potassium hydroxide (510 mg, 9.42 mmol) was ground into a powder and added to the reaction and the mixture refluxed at 100° C. for 12 hours, upon which the reaction was diluted with water (50 mL) and extracted with DCM. The organic layers were combined, dried over sodium sulfate, and concentrated under reduced pressure to obtain 2,5,8,11,14,17-hexaoxanonadecan-19-ol as a yellow oil in 69% yield.

Step 2: Preparation of 2,5,8,11,14,17-hexaoxanonadecan-19-yl 4-methylbenzenesulfonate

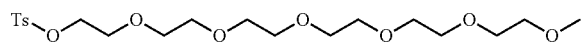 [SMILES: COCCOCCOCCOCCOCCOCCOS(=O)(=O)c1ccc(C)cc1]

2,5,8,11,14,17-Hexaoxanonadecan-19-ol (4.0 g, 13.5 mmol) was dissolved in DCM (55 mL) with stir. Triethylamine (2.82 mL, 20.2 mmol) was then added and the resulting mixture cooled to 0° C., upon which para-toluenesulfonyl chloride (3.86 g, 20.2 mmol) was added in one portion. The reaction mixture was then stirred to r.t. for 24 hours, and then concentrated under reduced pressure to obtain an oil. The oil was resuspended in EtOAc, filtered, concentrated, and purified by silica gel chromatography (80% EtOAc/hexanes to 5% MeOH/EtOAc) to yield 2,5,8,11,14,17-hexaoxanonadecan-19-yl 4-methylbenzenesulfonate C2 as a yellow oil in 77% yield.

Step 3: Preparation of 2,5,8,11,14,17-hexaoxanonadecan-19-amine (C3)

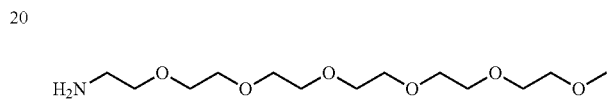

To a solution of 2,5,8,11,14,17-hexaoxanonadecan-19-yl 4-methylbenzenesulfonate (C2, 1.0 g, 3.37 mmol) in dry DMF (55 mL) was added sodium azide (360 mg, 5.54 mmol) in one portion with stir. The solution was flushed with argon and refluxed at 70° C. for 12 hours, upon which the reaction was cooled to r.t., diluted with ice-cold water (50 mL) and extracted with Et$_2$O. The organic washes were combined, washed with water and brine, dried over magnesium sulfate, and concentrated in vacuo to obtain the azido-hexaethylene glycol monomethyl ether as a clear oil in 91% yield.

Azido-hexaethylene glycol monomethyl ether (130 mg, 0.44 mmol) was dissolved in anhydrous ethanol and 15% activated palladium on carbon (Pd/C) was added. The reaction mixture was subjected to a high-pressure hydrogenation for 4 hours at 50-60 PSI. Upon completion, the reaction mixture was filtered with MeOH and the solution was concentrated under reduced pressure to obtain 2,5,8,11,14,17-hexaoxanonadecan-19-amine C3 as a clear oil in 45% yield over the two steps.

Step 4: Preparation of 2-cyano-N-(2,5,8,1,14,17-hexaoxanonadecan-19-yl)acetamide (C4)

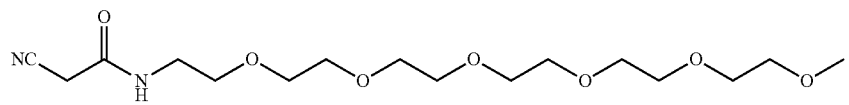 [SMILES: COCCOCCOCCOCCOCCOCCNC(=O)CC#N]

To a solution of 2,5,8,11,14,17-hexaoxanonadecan-19-amine (C3, 50 mg, 0.169 mmol) and cyanoacetic acid (9.6 mg, 0.588 mmol) in DCM (0.45 mL) cooled to 0° C. was added HOBt (38.8 mg, 0.254 mmol) dropwise as a solution in DCM (0.40 mL). EDC (40 mg, 0.254 mmol) was then added in one portion and the reaction let stir at 0° C. for 12 hours, upon which it was concentrated under reduced pressure and purified via silica gel chromatography (1:1 EtOAc: hexanes to 10% MeOH/EtOAc) to obtain 2-cyano-N-(2,5,8,11,14,17-hexaoxanonadecan-19-yl)acetamide C4 as a clear oil in 80% yield.

Step 5: Preparation of (E)-2-cyano-N-(2,5,8,11,14,17-hexaoxanonadecan-19-yl)-3-(6-(piperidin-1-yl)naphthalen-2-yl)acrylamide (Compound 3)

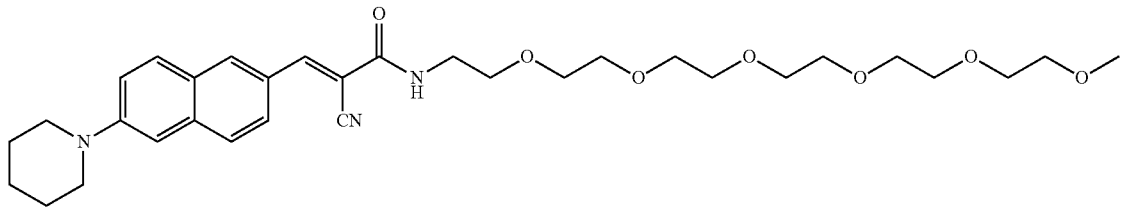 [SMILES: COCCOCCOCCOCCOCCOCCNC(=O)/C(C#N)=C/c1ccc2cc(N3CCCCC3)ccc2c1]

6-(Piperidin-1-yl)-2-naphthaldehyde (A6, 12 mg, 0.050 mmol) and 2-cyano-N-(2,5,8,11,14,17-hexaoxanonadecan-19-yl)acetamide (C4, 15 mg, 0.041 mmol) were dissolved in anhydrous THF (0.25 mL). To this reaction was added piperidine (0.005 mmol) and the reaction heated to 50° C. After 12 hours of heating, the reaction was cooled, concentrated to an oil, and purified by silica gel chromatography (3% MeOH/EtOAc) to obtain (E)-2-cyano-N-(2,5,8,11,14,17-hexaoxanonadecan-19-yl)-3-(6-(piperidin-1-yl)naphthalen-2-yl)acrylamide as an orange oil in 62% yield. $R_f$=0.35 (3% MeOH/EtOAc); $_1$H NMR (500 MHz, δ, ppm, CDCl$_3$): 1.68 (m, 6H); 3.30 (s, 3H); 3.33 (m, 3H); 3.46 (t, 2H); 3.53-3.62 (m, 20H); 6.83 (bs, 1H); 6.99 (d, 2H); 7.22-7.24 (dd, 1H); 7.59 (d, 1H); 7.69 (d, 1H); 7.98 (dd, 1H); 8.10 (s, 1H). 13C NMR (125 MHz, δ, ppm, CDCl$_3$): 136.4, 132.9, 129.5, 126.4, 125.8, 125.2, 124.9, 118.6, 116.9, 107.8, 99.7, 71.0, 69.7, 69.6, 69.5, 68.6, 58.1, 51.9, 48.7, 39.3, 28.8, 24.7, 23.5, 7.2; HRMS: calcd. for $C_{32}H_{45}N_3O_7$: $[M+Na]^+$ 606.3150, found 606.3151 by ESI.

Figure 7:
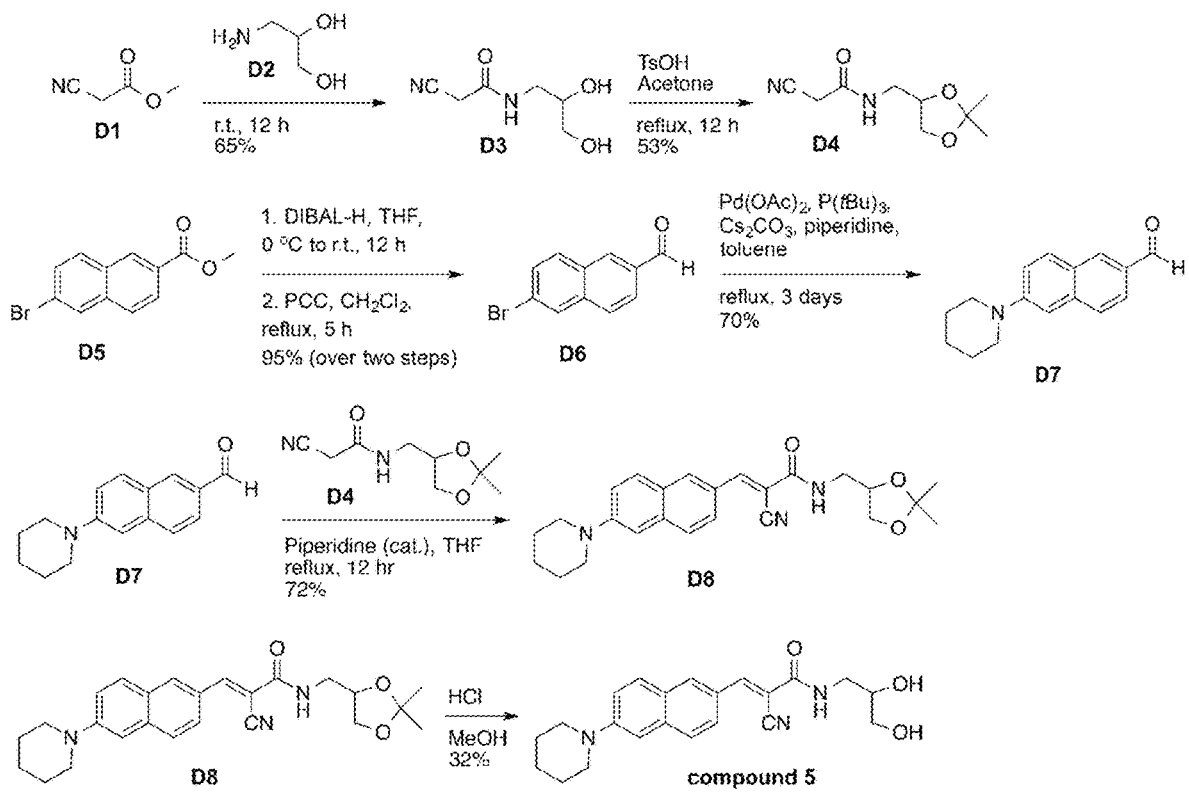
FIG. 7 Shows a synthetic strategy towards the synthesis of compound 5.
Figure 8A:
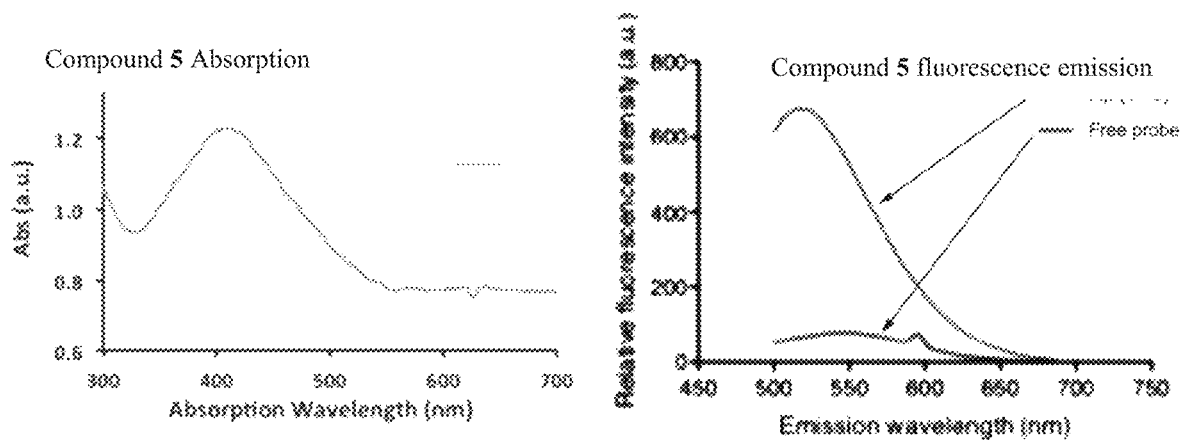
FIG. 8A Shows the fluorescence excitation and emission profiles of compound 5, measured using 4 µM compound 5 and 5 µM Aβ (1-42) in 5% DMSO in water.
Figure 8B:
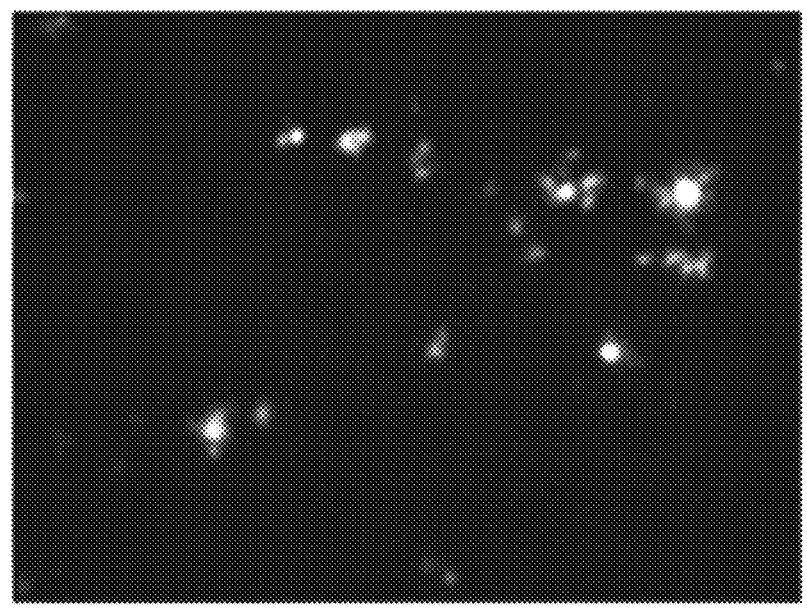
FIG. 8B Shows staining of amyloid deposits in murine AD neuronal tissue by compound 5.

Example 4: (E)-2-cyano-N-(2,3-dihydroxypropyl)-3-(6-(piperidin-1-yl)naphthalen-2-yl)acrylamide See FIG. 7 for a synthetic scheme.

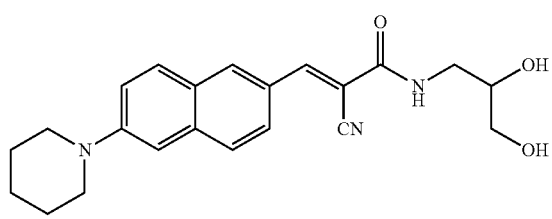 [SMILES: N#C/C(=C\c1ccc2cc(N3CCCCC3)ccc2c1)C(=O)NCC(O)CO]

Step 1: Preparation of 2-cyano-N-(2,3-dihydroxypropyl)acetamide (D3)

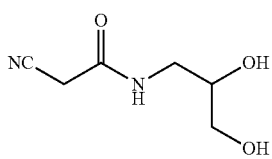 [SMILES: N#CCC(=O)NCC(O)CO]

To a solution of 3-amino-1,2-propanediol (D2, 455 mg, 5.0 mmol) was added methyl cyanoacetate (D1, 457 mg, 4.6 mmol) with stir. The mixture was let stir overnight at r.t., upon which the reaction was purified by silica gel chromatography (10% MeOH/EtOAc) to yield 2-cyano-N-(2,3-dihydroxypropyl)acetamide D3 as a white solid in 65% yield.

Step 2: Preparation of 2-cyano-N-((2,2-dimethyl-1,3-dioxolan-4-yl)methyl)acetamide (D4)

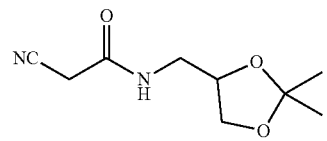

2-Cyano-N-(2,3-dihydroxypropyl)acetamide (D3, 120 mg, 0.76 mmol) was dissolved in acetone (3 mL) and para-toluenesulfonic acid (80 mg, 0.42 mmol) was added. The resulting mixture was refluxed for 12 hours, upon which the crude reaction was purified by silica gel chromatography (2.5% MeOH/DCM) to yield 2-cyano-N-((2,2-dimethyl-1,3-dioxolan-4-yl)methyl)acetamide D4 as a white solid in 53% yield.

Step 3: Preparation of (E)-2-cyano-N-((2,2-dimethyl-1,3-dioxolan-4-yl)methyl)-3-(6-(piperidin-1-yl)naphthalen-2-yl)acrylamide (D8)

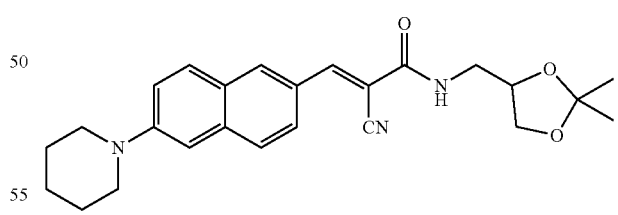

6-(Piperidin-1-yl)-2-naphthaldehyde (A6, 12 mg, 0.05 mmol) and 2-cyano-N-((2,2-dimethyl-1,3-dioxolan-4-yl)methyl)acetamide (D4, 13 mg, 0.066 mmol) in anhydrous THF (1.5 mL) was added piperidine (0.005 mmol) and the resulting mixture refluxed for 12 hours. The reaction was then concentrated under reduced pressure to an oil, which was purified via silica gel chromatography (5% MeOH/DCM) to obtain (E)-2-cyano-N-((2,2-dimethyl-1,3-dioxolan-4-yl)methyl)-3-(6-(piperidin-1-yl)naphthalen-2-yl)acrylamide D8 as a red solid in 72% yield.

Step 4: Preparation of (E)-2-cyano-N-(2,3-dihydroxypropyl)-3-(6-(piperidin-1-yl)naphthalen-2-yl)acrylamide (Compound 5)

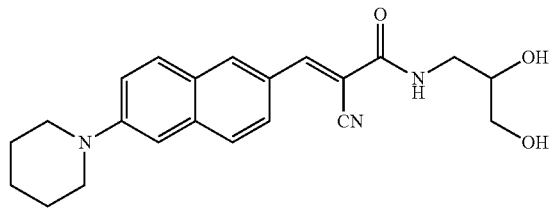 [SMILES: N#C/C(=C\c1ccc2cc(N3CCCCC3)ccc2c1)C(=O)NCC(O)CO]

(E)-2-cyano-N-((2,2-dimethyl-1,3-dioxolan-4-yl)methyl)-3-(6-(piperidin-1-yl)naphthalen-2-yl)acrylamide (D8, 5 mg, 0.012 mmol) was hydrolyzed with 1 N hydrochloric acid (HCl) in MeOH (3 mL) via reflux for 12 hours. The reaction was then concentrated under reduced pressure and the crude residue dissolved in a mixture of 1:2 MeOH:dimethylsulfoxide (DMSO). The solution was then purified by preparative reverse-phase high-performance liquid chromatography (RP-HPLC) (grad. 5-90% acetonitrile in water, 20 min.) to afford (E)-2-cyano-N-(2,3-dihydroxypropyl)-3-(6-(piperidin-1-yl)naphthalen-2-yl)acrylamide as a red solid in 33% yield. $^1$H NMR (300 MHz, CD$_3$OD) δ 8.47 (s, 1H), 8.37 (s, 1H), 8.19 (dd, J=1.9, 1.8 Hz, 1H), 7.91 (d, J=9.1 Hz, 1H), 7.83 (d, J=8.6 Hz, 1H), 7.50 (dd, J=2.3, 2.2 Hz, 1H), 7.37 (d, J=2.0 Hz, 1H), 4.38 (d, J=5.3 Hz, 2H), 4.21-4.15 (m, 2H), 3.89-3.83 (m, 1H), 3.58-3.50 (m, 4H), 1.82-1.75 (m, 6H). HRMS (ESI-TOF-MS): m/z calc. for $C_{22}H_{26}N_3O_3^+$: 380.1969; found: 380.1988.

Example 5: 2-(2-(2-(2-methoxyethoxy)ethoxy)ethoxy)-4-(6-(piperidin-1-yl)naphthalen-2-yl)nicotinonitrile (Compound 17)

Figure 9:
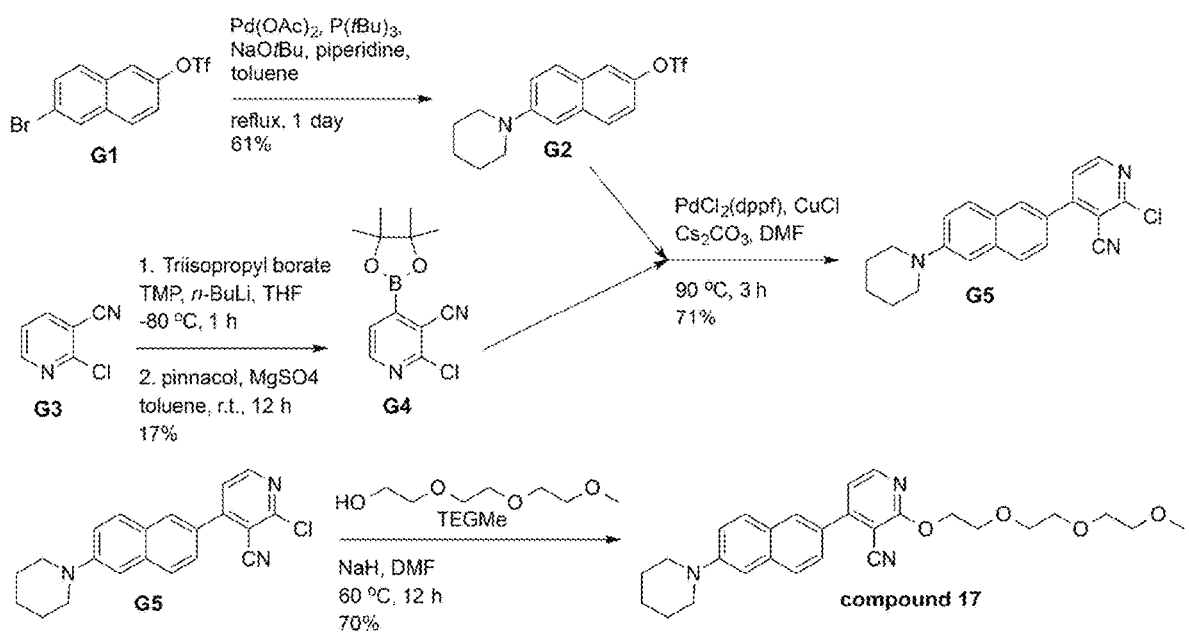
FIG. 9 Shows a synthetic strategy towards the synthesis of compound 17.
Figure 10:
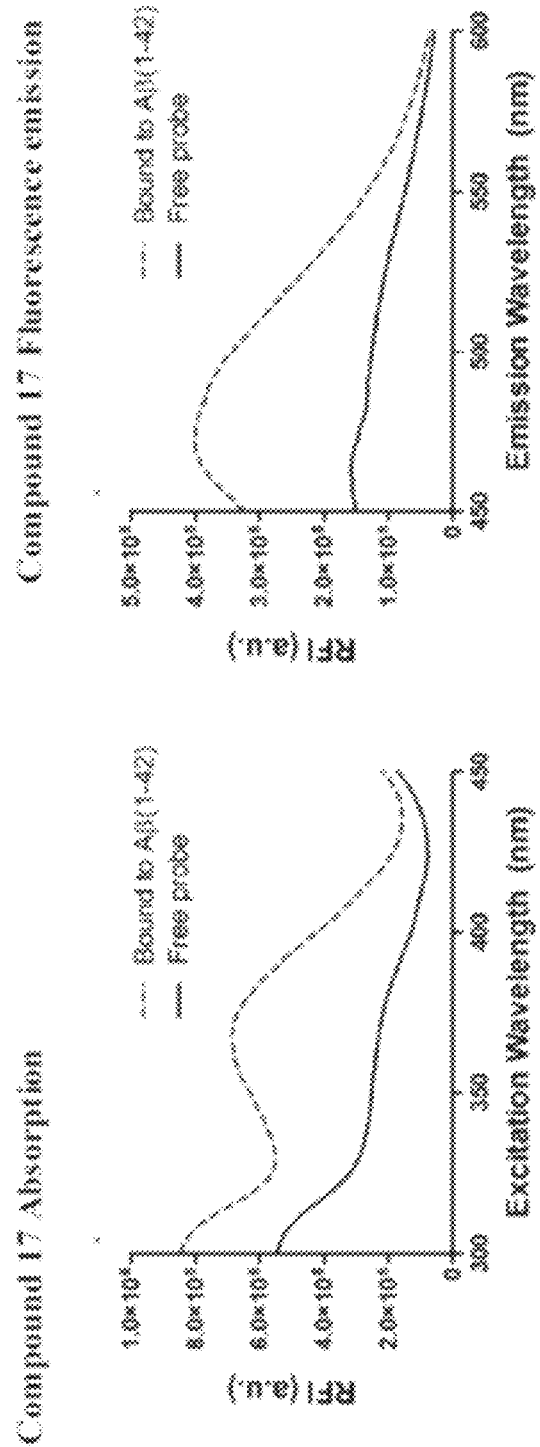
FIG. 10 Shows the fluorescence excitation and emission profiles of compound 17, measured using 4 μM compound 17 and 5 μM Aβ (1-42) in 5% DMSO in water.

See FIG. 9 for a synthetic scheme

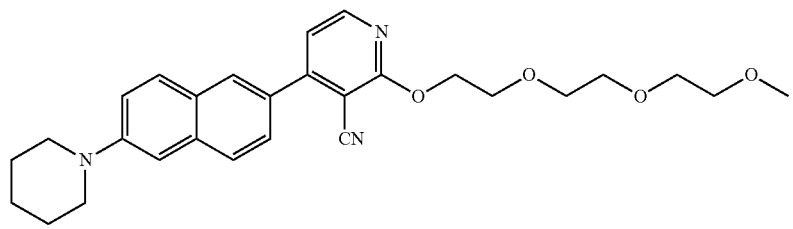 [SMILES: COCCOCCOCCOc1nccc(-c2ccc3cc(N4CCCCC4)ccc3c2)c1C#N]

Step 1: Preparation of 6-(piperidin-1-yl)-naphthalen-2-yl trifluoromethanesulfonate (G2)

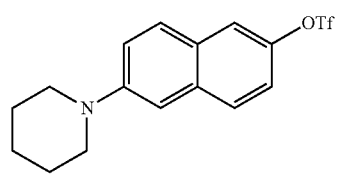 [SMILES: O=S(=O)(Oc1ccc2cc(N3CCCCC3)ccc2c1)C(F)(F)F]

6-Bromonaphthalen-2-yl trifluoromethanesulfonate G1 (500 mg, 1.41 mmol), palladium (II) acetate (16 mg, 0.05 mmol), and sodium tert-butoxide (176 mg, 1.83 mmol) were dissolved in degassed toluene (13 mL) under argon and let stir for 30 minutes at r.t., upon which tri-t-butyl phosphine (0.1 mmol) was added dropwise and the solution let stir an additional 10 minutes. Piperidine (0.17 mL, 1.69 mmol) was then added dropwise and the reaction refluxed at 110° C. for three days. The reaction was then cooled, diluted with DCM, filtered through celite, and concentrated under reduced pressure to obtain a red oil which was purified by silica gel chromatography (0-8% EtOAc/hexanes) to obtain 6-(piperidin-1-yl)-naphthalen-2-yl trifluoromethanesulfonate G2 as a white solid in 61% yield.

Step 2: Preparation of 2-chloro-4-(4,4,5,5-tetramethyl-1,3,2-dioxaborolan-2-yl)nicotinonitrile (G4)

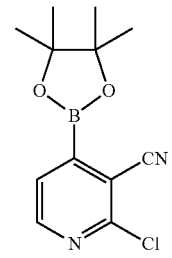 [SMILES: CC1(C)OB(c2ccnc(Cl)c2C#N)OC1(C)C]

2,2,6,6-Tetramethyl-piperidine (TMP) (1.07 g, 7.58 mmol) was dissolved in anhydrous THF (14 mL) and cooled to −78° C. under argon, upon which n-butyllithium (n-BuLi) (7.22 mmol) was added dropwise over 15 minutes with stir. A solution of 2-chloronicotinonitrile G3 (500 mg, 3.609 mmol) in anhydrous THF (7.3 mL) was then added dropwise with stir over 15 minutes. Finally, a solution of triisopropyl borate (1.43 g, 7.58 mmol) in anhydrous THF (3.6 mL) was added dropwise over 15 minutes. The reaction was let stir for 30 minutes, which was then warmed to r.t. and quenched with water (50 mL) and slightly acidified with hydrochloric acid (HCl). The mixture was then extracted with EtOAc and the organic layers dried and concentrated to obtain the boronic acid.

The boronic acid (26 mg, 0.143 mmol), pinnacol (17 mg, 0.143 mmol), and magnesium sulfate (100 mg, 0.83 mmol) were dissolved in anhydrous toluene (1 mL) and the reaction let stir for 12 hours, upon which it was filtered and the resulting solution washed with brine and concentrated under reduced pressure to obtain 2-chloro-4-(4,4,5,5-tetramethyl-1,3,2-dioxaborolan-2-yl)nicotinonitrile G4 in 17% yield.

Step 3: Preparation of 2-chloro-4-(6-(piperidin-1-yl)naphthalen-2-yl)nicotinonitrile (G5)

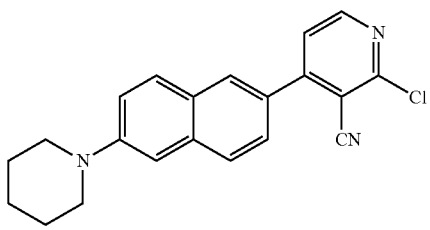 [SMILES: N#Cc1c(-c2ccc3cc(N4CCCCC4)ccc3c2)ccnc1Cl]

2-Chloro-4-(4,4,5,5-tetramethyl-1,3,2-dioxaborolan-2-yl)nicotinonitrile G4 (25 mg, 0.094 mmol), 6-(piperidin-1-yl)-naphthalen-2-yl trifluoromethanesulfonate G2 (17 mg, 0.047 mmol), [1,1'-Bis(diphenylphosphino)ferrocene]dichloropalladium(II) (PdCl$_2$(dppf)) (3.4 mg, 0.005 mmol), copper(I) chloride (5 mg, 0.05 mmol), and cesium carbonate (31 mg, 0.094 mmol) were dissolved in anhydrous DMF (0.5 mL) and heated to 90° C. for 3 hours at standard pressure. The reaction was then diluted with DCM and water, and extracted with DCM. The organic layers were washed with water and brine, dried, and concentrated under reduced pressure to obtain a crude oil which was purified by silica gel chromatography (0-10% EtOAc/hexanes) to obtain 2-chloro-4-(6-(piperidin-1-yl)naphthalen-2-yl)nicotinonitrile G5 in 71% yield.

Step 4: Preparation of 2-(2-(2-(2-methoxyethoxy)ethoxy)ethoxy)-4-(6-(piperidin-1-yl)naphthalen-2-yl)nicotinonitrile (Compound 17)

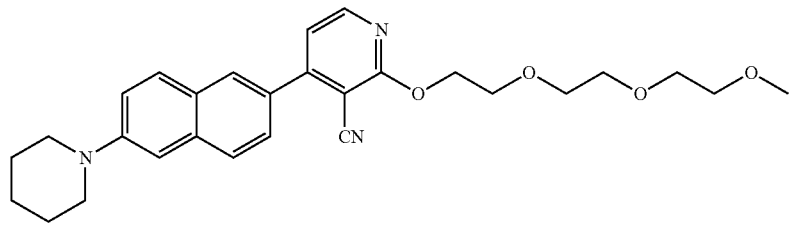 [SMILES: COCCOCCOCCOc1nccc(-c2ccc3cc(N4CCCCC4)ccc3c2)c1C#N]

Triethylene glycol monomethyl ether (TEGMe) (25 mg, 0.14 mmol) was stirred with anhydrous DMF (0.025 mL) was cooled to 0° C. and sodium hydride (1 mg, 0.04 mmol) added. A solution of 2-chloro-4-(6-(piperidin-1-yl)naphthalen-2-yl)nicotinonitrile G5 (5 mg, 0.014 mmol) in anhydrous DMF (0.04 mL) was then added slowly. The reaction was headed to 60° C. for 12 hours, upon which it was removed and concentrated under reduced pressure. The residue was then purified by preparative thin-layer chromatography (0-5% MeOH/EtOAc) to obtain 2-(2-(2-(2-methoxyethoxy)ethoxy)ethoxy)-4-(6-(piperidin-1-yl)naphthalen-2-yl)nicotinonitrile as a dark-yellow oil in 70% yield. R$_f$=0.40 (5% MeOH/EtOAc); $^1$H NMR (500 MHz, CDCl$_3$) δ 8.29-8.30 (d, J=1H), 7.98 (s, 1H), 7.77 (s, 2H), 7.61 (s, 1H), 7.33-7.34 (d, 0.1=Hz, 1H), 7.11-7.12 (d, 2H), 4.63-4.65 (t, 2H), 3.93-3.95 (m, 2H), 3.66-3.70 (m, 4H), 3.54-3.56 (m, 2H), 3.37 (s, 3H), 3.32 (bs, 4H), 1.76 (bs, 4H), 1.64 (bs, 2H); $^{13}$C (125 MHz, CDCl$_3$) δ 165.16, 155.89, 150.38, 132.71, 129.03, 128.80, 128.51, 128.29, 126.52, 125.23, 123.67, 121.34, 117.61, 115.19, 109.43, 95.41, 72.03, 71.13, 7084, 70.70, 69.29, 67.14, 59.20, 53.07, 32.08, 29.83; HRMS calcd for C$_{28}$H$_{33}$N$_3$O$_4$Na [M+Na]$^+$ 498.2361, found 498.2363 by ESI.

Example 6: 4-(6-(piperidin-1-yl)naphthalen-2-yl)nicotinonitrile (Compound 18)

Figure 11:
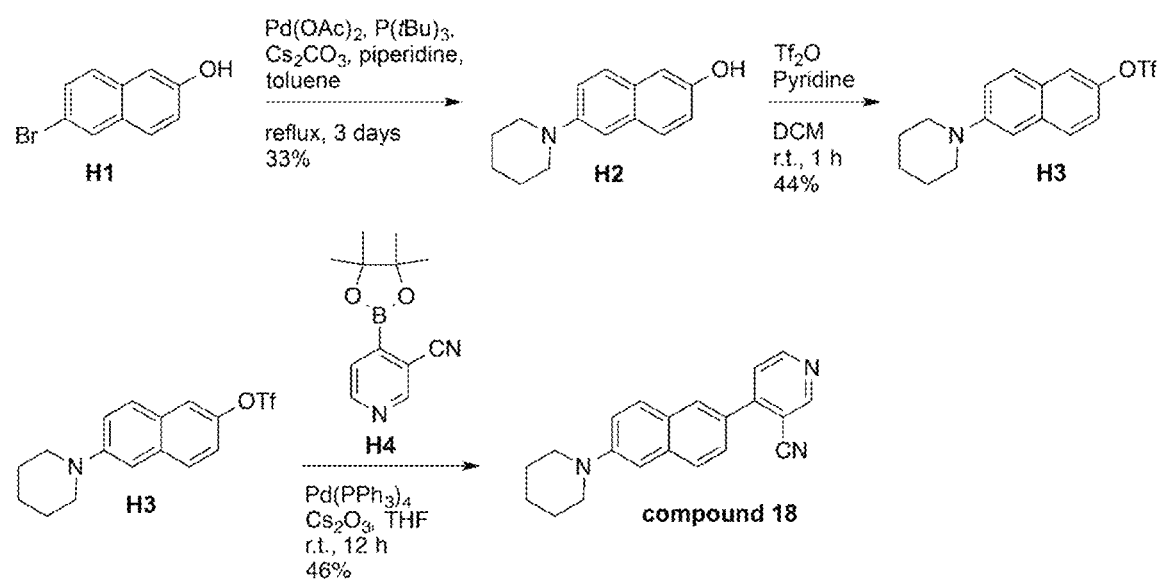
FIG. 11 Shows a synthetic strategy towards the synthesis of compound 18.
Figure 12:
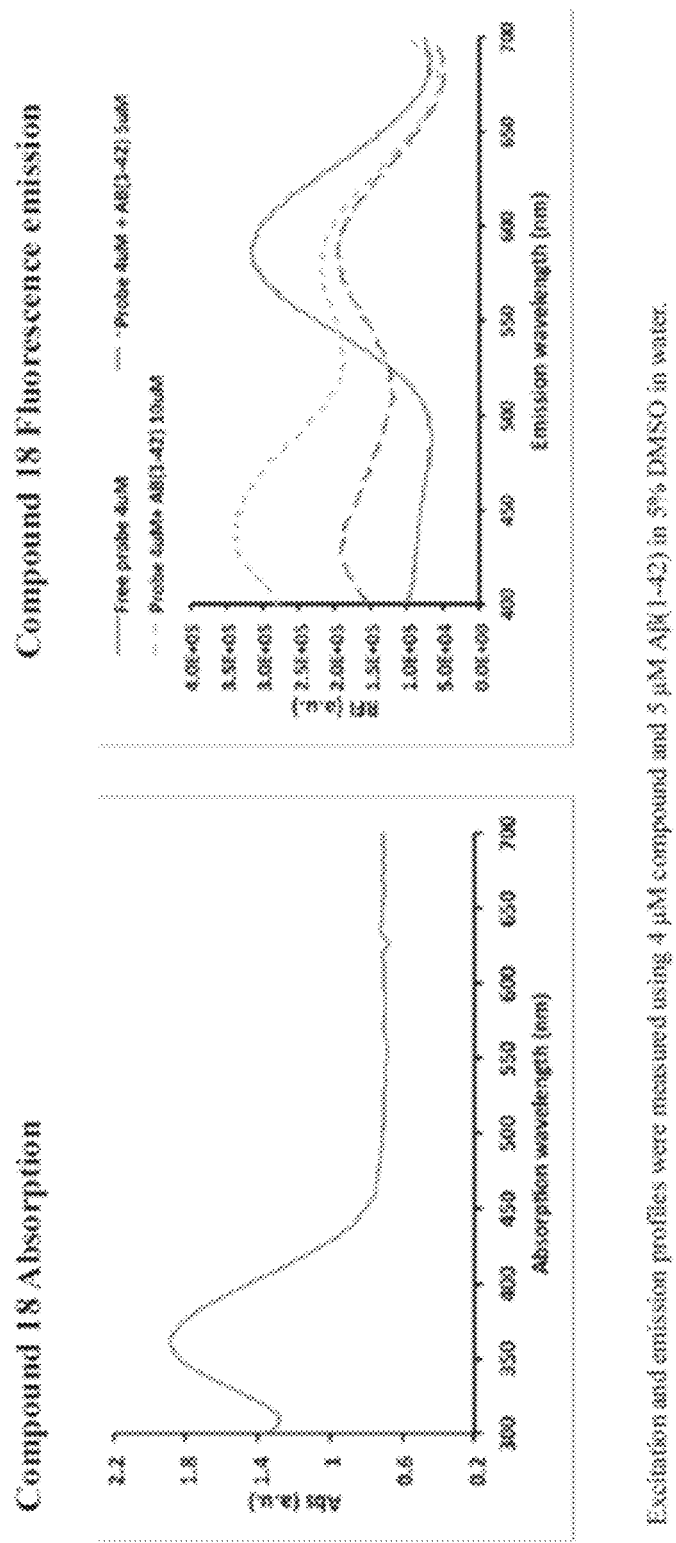
FIG. 12 Shows the fluorescence excitation and emission profiles of compound 18, measured using 4 μM compound 1 and 5 μM or 10 μM Aβ (1-42) in 5% DMSO in water.

See FIG. 11 for a synthetic scheme.

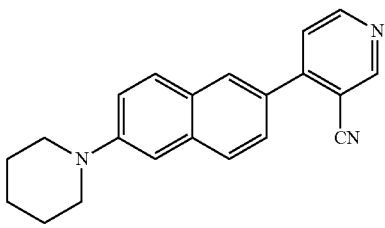 [SMILES: N#Cc1cnccc1-c1ccc2cc(N3CCCCC3)ccc2c1]

Step 1: Preparation of 6-(piperidin-1-yl)naphthalen-2-ol (H2)

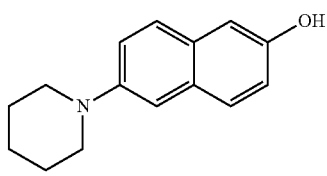 [SMILES: Oc1ccc2cc(N3CCCCC3)ccc2c1]

6-Bromonaphthalen-2-ol (100 mg, 0.45 mmol), palladium (II) acetate (11.2 mg, 0.05 mmol), and cesium carbonate (234 mg, 0.72 mmol) were added to dry, degassed toluene (3 mL) under argon and let stir for 30 minutes at r.t., upon which tri-t-butyl phosphine (0.2 mmol) was added dropwise and the solution let stir an additional 10 minutes. Piperidine (0.123 mL, 1.34 mmol) was then added dropwise and the reaction refluxed at 110° C. for three days. The reaction was then cooled, diluted with DCM, filtered, and concentrated under reduced pressure to obtain a red oil which was purified by silica gel chromatography (10% DCM/hexanes) to obtain the 6-(piperidin-1-yl)-naphthalen-2-ol H2 as a white solid in 33% yield.

Step 2: Preparation of 6-(piperidin-1-yl)-naphthalen-2-yl trifluoromethanesulfonate (H3)

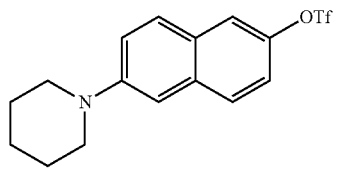 [SMILES: O=S(=O)(Oc1ccc2cc(N3CCCCC3)ccc2c1)C(F)(F)F]

6-(Piperidin-1-yl)-naphthalen-2-ol (H2, 23 mg, 0.01 mmol) was dissolved in DCM (2 mL) and pyridine (0.05 mL) was added and the reaction cooled to 0° C. Trifluoromethanesulfonic anhydride (Tf$_2$O) (33.8 mg, 0.12 mmol) was then added dropwise and the resulting mixture stirred at r.t. for 1 hour, upon which it was concentrated under reduced pressure and the crude purified by silica gel chromatography (5% MeOH/DCM) to obtain 6-(piperidin-1-yl)-naphthalen-2-yl trifluoromethanesulfonate H3 as a white solid in 44% yield.

Step 3: Preparation of 4-(6-(piperidin-1-yl)naphthalen-2-yl)nicotinonitrile (Compound 18)

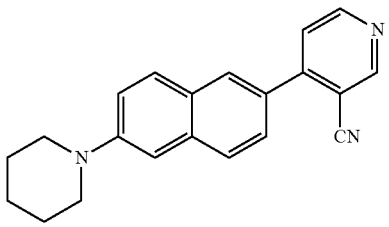 [SMILES: N#Cc1cnccc1-c1ccc2cc(N3CCCCC3)ccc2c1]

6-(Piperidin-1-yl)-naphthalen-2-yl trifluoromethanesulfonate (H3, 13.5 mg, 0.038 mmol), 3-cyanopyridine-4-boronic acid pinacol ester (from Example A5, Step 2, 24 mg, 0.11 mmol), tetrakis(triphenylphosphine)palladium(0) (25.4 mg, 0.022 mmol), and cesium carbonate (40 mg, 0.12 mmol) were added to degassed anhydrous THF (6 mL) and the reaction refluxed for 12 hours. The mixture was then cooled to r.t., diluted with DCM, filtered, and concentrated under reduced pressure to obtain the crude oil, which was then purified by silica gel chromatography (4% acetone/DCM) to afford 4-(6-(piperidin-1-yl)naphthalen-2-yl)nicotinonitrile as a yellow solid in 46% yield. $^1$H NMR (400 MHz, CDCl$_3$) δ 8.96 (s, 1H), 8.80 (s, 1H), 8.02 (s, 1H), 7.82 (s, 2H), 7.60 (dd, J=24.4, 6.6 Hz, 2H), 7.37 (s, 1H), 7.14 (s, 1H), 3.35 (s, 4H), 1.78 (s, 4H), 1.66 (s, 2H). MS (ESI): m/z calc. for C$_{21}$H$_{19}$N$_3$: 313.16; found: 314.41. [M+H]$^+$. HRMS (ESI-TOF-MS): m/z calc. for C$_{21}$H$_{20}$N$_3{}^+$: 314.1652; found: 314.1664.

Figure 14:
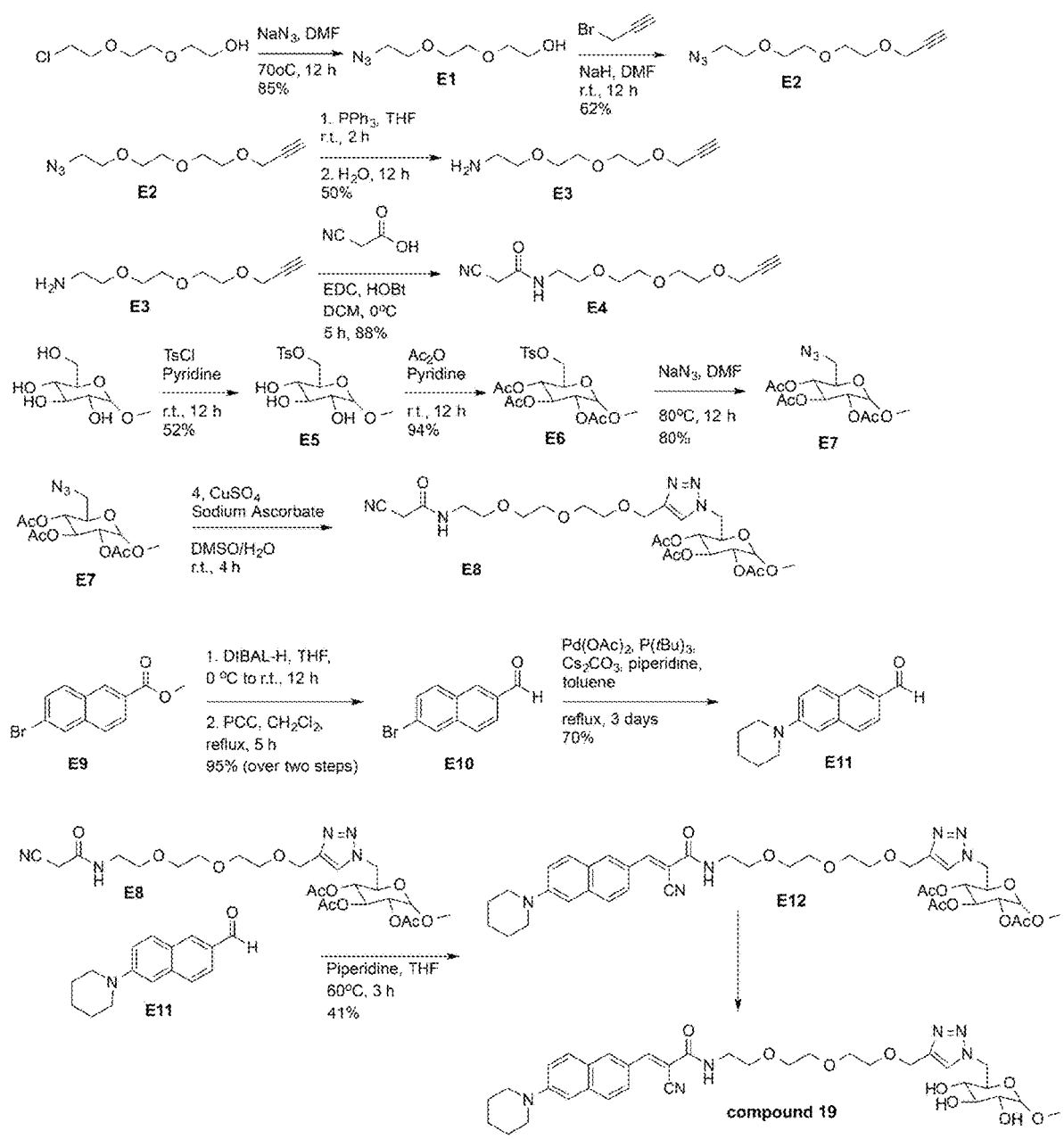
FIG. 14 Shows a synthetic strategy towards the synthesis of compound 19.
Figure 15A:
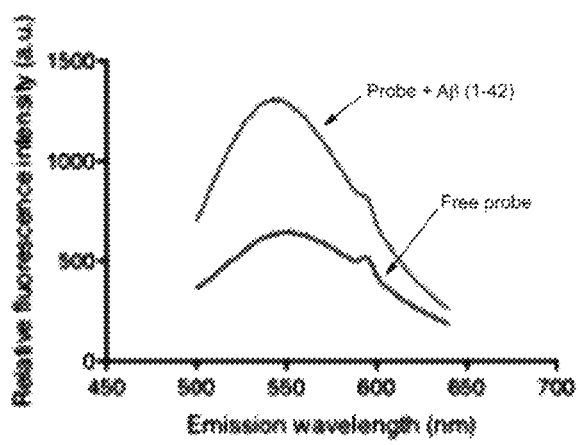
FIG. 15A Shows the emission profiles of compound 19, measured using 4 μM compound 19 and 5 μM Aβ (1-42) in 5% DMSO in water.
Figure 15B:
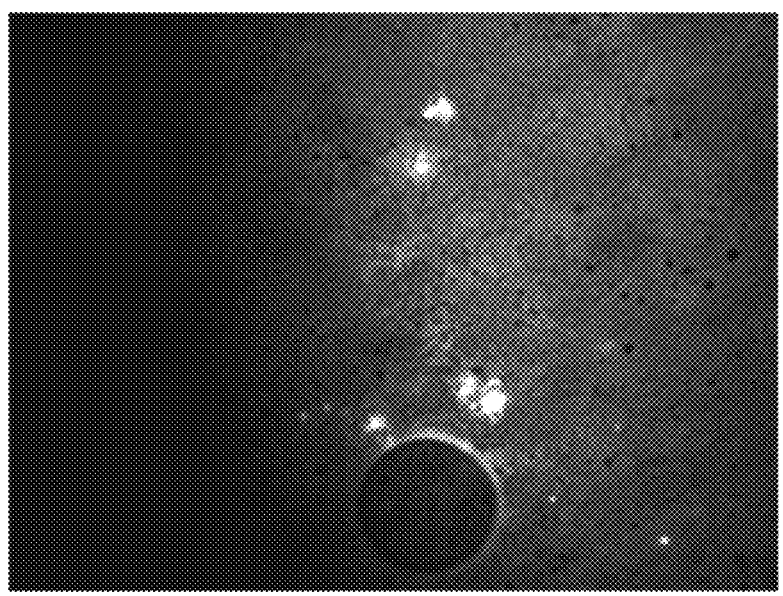
FIG. 15B Shows staining of amyloid deposits in murine AD neuronal tissue by compound 19.

Example 7: (E)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide See FIG. 14 for a synthetic scheme.

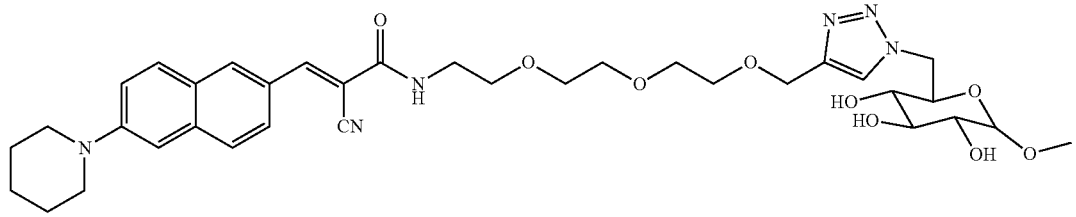 [SMILES: COC1OC(Cn2cc(COCCOCCOCCNC(=O)/C(C#N)=C/c3ccc4cc(N5CCCCC5)ccc4c3)nn2)C(O)C(O)C1O]

Step 1: Preparation of 2-(2-(2-azidoethoxy)ethoxy)ethanol (E1)

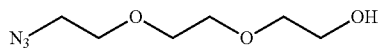

2-[2-(2-Chloroethoxy)ethoxy]ethanol (300 mg, 1.8 mmol), NaN$_3$ (350 mg, 5.4 mmol) and TBAI (66.2 mg, 0.18 mmol) were added to DMF (4 mL). The mixture was heated to 70° C. and stirred under N$_2$ overnight. Solvent was removed under reduced pressure and the product was purified via column chromatography (EtOAc:hexane=1:1) to afford 2-(2-(2-azidoethoxy)ethoxy)ethanol E1 (268 mg, 85%)

Step 2: Preparation of 3-(2-(2-(2-azidoethoxy)ethoxy)ethoxy)prop-1-yne (E2)

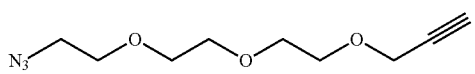

2-(2-(2-Azidoethoxy)ethoxy)ethanol (E1, 140 mg, 0.8 mmol), propargyl bromide (190 mg, 1.6 mmol) and NaH (23 mg, 0.095 mmol) were added to DMF (2 mL). The mixture was stirred at room temperature overnight. Solvent was removed under reduced pressure and the product was purified via column chromatography (EtOAc:hexane=1:4) to afford 3-(2-(2-(2-azidoethoxy)ethoxy)ethoxy)prop-1-yne E2 (106 mg, 62%).

Step 3: Preparation of 2-(2-(2-(prop-2-ynyloxy)ethoxy)ethoxy)ethanamine (E3)

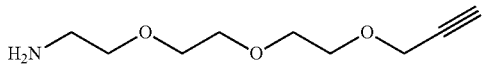

3-(2-(2-(2-Azidoethoxy)ethoxy)ethoxy)prop-1-yne (E2, 30 mg, 0.14 mmol) and Ph$_3$P (55 mg, 0.21 mmol) were added to THF (2 mL). The mixture was stirred at room temperature for 2 h. H$_2$O (1 mL) was added and the reaction was stirred at room temperature overnight. Solvent was removed under reduced pressure and the product was purified via column chromatography (CH$_2$Cl$_2$:MeOH:TEA=100:2:1) to afford 2-(2-(2-(prop-2-ynyloxy)ethoxy)ethoxy)ethanamine E3 (13 mg, 50%).

Step 4: Preparation of 2-cyano-N-(2-(2-(2-(prop-2-ynyloxy)ethoxy)ethoxy)ethyl)acetamide

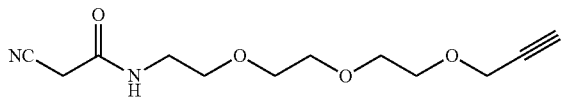 [SMILES: C#CCOCCOCCOCCNC(=O)CC#N]

A mixture of cyanoacetic acid (10 mg, 0.1 mmol), 2-(2-(2-(prop-2-ynyloxy)ethoxy)ethoxy)ethanamine (E3, 30 mg, 0.16 mmol), EDC (30 mg, 0.2 mmol), HOBt (27 mg, 0.2 mmol) and CH$_2$Cl$_2$ (2 mL) was stirred and cooled to 0° C. The mixture was allowed to warm up to room temperature and stirred for 5 h. The solution was concentrated under reduced pressure and the product was purified via column chromatography (EtOAc:MeOH=50:1) to afford 2-cyano-N-(2-(2-(2-(prop-2-ynyloxy)ethoxy)ethoxy)ethyl)acetamide E4 (22 mg, 88%).

Step 5: Preparation of (3,4,5-trihydroxy-6-methoxytetrahydro-2H-pyran-2-yl)methyl 4-methylbenzenesulfonate (E5)

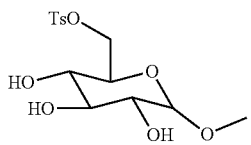 [SMILES: COC1OC(COS(=O)(=O)c2ccc(C)cc2)C(O)C(O)C1O]

Methyl α-D-glucopyranoside (0.3 g, 1.56 mmol) was dissolved in pyridine (3 mL) and cooled to 0° C. under argon. p-Toluenesulfonyl chloride (0.3 g, 1.56 mmol) was added and the solution was stirred overnight. The mixture was then concentrated under reduced pressure and purified via column chromatography (EtOAc) to afford (3,4,5-trihydroxy-6-methoxytetrahydro-2H-pyran-2-yl)methyl 4-methylbenzenesulfonate E5 (0.28 g, 52%).

Step 6: Preparation of 2-methoxy-6-(tosyloxymethyl)tetrahydro-2H-pyran-3,4,5-triyl triacetate (E6)

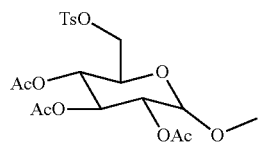 [SMILES: COC1OC(COS(=O)(=O)c2ccc(C)cc2)C(OC(C)=O)C(OC(C)=O)C1OC(C)=O]

To a solution of (3,4,5-trihydroxy-6-methoxytetrahydro-2H-pyran-2-yl)methyl 4-methylbenzenesulfonate (E5, 0.6 g, 1.72 mmol) in dry pyridine (4 mL) was added acetic anhydride (2 mL), and the mixture was stirred at room temperature overnight. Upon completion, MeOH was added and then concentrated. The mixture was then dissolved in CH$_2$Cl$_2$ and washed with saturated solution of sodium bicarbonate and brine, dried over MgSO$_4$ and concentrated under reduced pressure to afford 2-methoxy-6-(tosyloxymethyl)tetrahydro-2H-pyran-3,4,5-triyl triacetate E6 (0.77 g, 94%).

Step 7: Preparation of 2-(azidomethyl)-6-methoxytetrahydro-2H-pyran-3,4,5-triyl triacetate (E7)

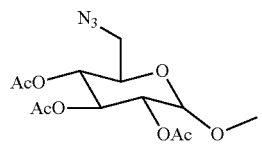 [SMILES: COC1OC(CN=[N+]=[N-])C(OC(C)=O)C(OC(C)=O)C1OC(C)=O]

To a solution of 2-methoxy-6-(tosyloxymethyl)tetrahydro-2H-pyran-3,4,5-triyl triacetate (E6, 1.3 g, 2.7 mmol) in dry DMF (5 mL) was added sodium azide (0.88 g, 13.5 mmol) and the mixture was heated at 80° C. overnight. The solvent was evaporated, and the residue was added CH$_2$Cl$_2$, filtered, concentrated under reduced pressure and purified via column chromatography (EtOAc:hexane=1:10) to afford 2-(azidomethyl)-6-methoxytetrahydro-2H-pyran-3,4,5-triyl triacetate E7 (0.75 g, 80%)

Step 8: Preparation of 2-((4-(13-cyano-12-oxo-2,5,8-trioxa-11-azatridecyl)-1H-1,2,3-triazol-1-yl)methyl)-6-methoxytetrahydro-2H-pyran-3,4,5-triyl triacetate (E8)

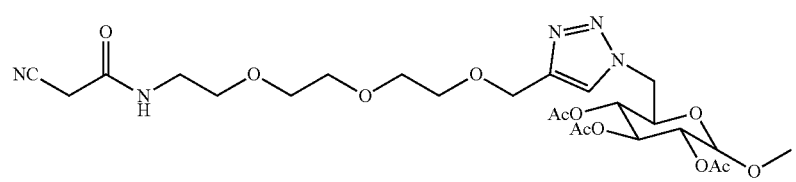 [SMILES: COC1OC(Cn2cc(COCCOCCOCCNC(=O)CC#N)nn2)C(OC(C)=O)C(OC(C)=O)C1OC(C)=O]

2-(Azidomethyl)-6-methoxytetrahydro-2H-pyran-3,4,5-triyl triacetate (E7, 42 mg, 0.12 mmol) and 2-cyano-N-(2-(2-(2-(prop-2-ynyloxy)ethoxy)ethoxy)ethyl)acetamide (E4, 30 mg, 0.12 mmol) were dissolved in H₂O/DMSO (1:2, 3 mL). Sodium ascorbate (20 mg, 0.1 mmol) and CuSO₄ (5 mg, 0.03 mmol) were added, and the solution was stirred for 4 h. After the reaction, the solvents were removed under reduced pressure and the residue was extracted with EtOAc. The organic phase was dried, filtered and purified by column chromatography (EtOAc:MeOH=20:1) to afford 2-((4-(13-cyano-12-oxo-2,5,8-trioxa-11-azatridecyl)-1H-1,2,3-triazol-1-yl)methyl)-6-methoxytetrahydro-2H-pyran-3,4,5-triyl triacetate E8 (50 mg, 70%).

Step 9: Preparation of (E)-2-((4-(13-cyano-12-oxo-14-(6-(piperidin-1-yl)naphthalen-2-yl)-2,5,8-trioxa-11-azatetradec-13-enyl)-1H-1,2,3-triazol-1-yl)methyl)-6-methoxytetrahydro-2H-pyran-3,4,5-triyl triacetate (E12)

(E)-2-((4-(13-cyano-12-oxo-14-(6-(piperidin-1-yl)naphthalen-2-yl)-2,5,8-trioxa-11-azatetradec-13-enyl)-1H-1,2,3-triazol-1-yl)methyl)-6-methoxytetrahydro-2H-pyran-3,4,5-triyl triacetate (E12, 33 mg, 0.04 mmol) was dissolved in MeOH (2 mL) and a solution of K₂CO₃ (0.2 M, 0.5 mL) was then added at 0° C. The mixture was stirred at room temperature for 0.5 h. After the reaction, the residue was concentrated under reduced pressure and then purified by preparative reverse-phase high-performance liquid chromatography (RP-HPLC) (grad. 5-90% acetonitrile in water, 30 min.) to afford (E)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide (12 mg, 43%). ¹H NMR (CD₃OD, 500 MHz) δ 8.45 (s, 1H), 8.33 (s, 1H), 8.21 (dd, J=9.0, 4.0 Hz, 1H), 8.18 (d, J=9.0 Hz, 1H), 8.12 (s, 1H),

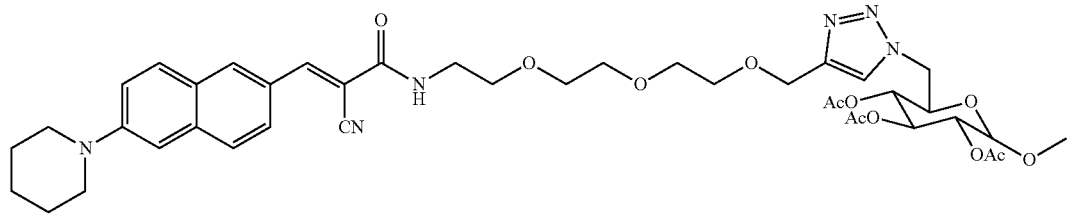 [SMILES: COC1OC(Cn2cc(COCCOCCOCCNC(=O)/C(C#N)=C/c3ccc4cc(N5CCCCC5)ccc4c3)nn2)C(OC(C)=O)C(OC(C)=O)C1OC(C)=O]

The title compound was synthesized as described in Example 1, Step 6, using 2-((4-(13-cyano-12-oxo-2,5,8-trioxa-11-azatridecyl)-1H-1,2,3-triazol-1-yl)methyl)-6-methoxytetrahydro-2H-pyran-3,4,5-triyl triacetate (E8) and 6-(Piperidin-1-yl)-2-naphthaldehyde (A6) as starting materials.

Step 10: (E)-2-cyano-3-(6-(piperidin-1-yl)naphthalen-2-yl)-N-(2-(2-(2-((1-((3,4,5-trihydroxy-6-methoxytetrahydro-2H-pyran-2-yl)methyl)-1H-1,2,3-triazol-4-yl)methoxy)ethoxy)ethoxy)ethyl)acrylamide (Compound 19)

8.07 (d, J=9.0 Hz, 1H), 7.98 (s, 1H), 7.79 (d, J=9.0 Hz, 1H), 4.79 (dd, J=14.0, 2.5 Hz, 1H), 4.63 (s, 2H), 4.60 (d, J=3.5 Hz, 1H), 4.49 (dd, J=14.0, 8.0 Hz, 1H), 3.84-3.80 (m, 1H), 3.73 (t, J=6.0 Hz, 4H), 3.66 (s, 10H), 3.61-3.56 (m, 3H), 3.35 (t, J=6.0 Hz, 1H), 3.11 (s, 3H), 2.06 (brs, 4H), 1.84 (brs, 2H); ¹³C NMR (CD₃OD, 500 MHz) δ 161.9, 150.6, 144.3, 143.1, 135.0, 132.3, 131.7, 130.7, 128.9, 128.8, 126.4, 125.2, 119.4, 118.3, 115.8, 106.0, 99.8, 73.5, 71.9, 71.5, 70.3, 70.2, 70.1, 69.9, 69.3, 68.8, 63.5, 55.7, 54.1, 51.0, 39.9, 23.8, 21.3; MS (ESI): m/z calc. for $C_{35}H_{46}N_6O_9Na^+$: [M+Na]⁺ calcd for 717.33, found 717.44.

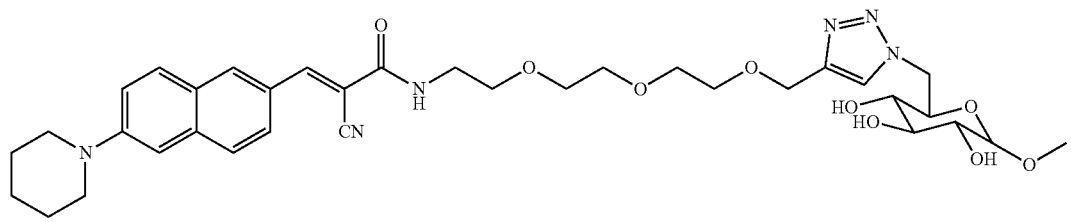 [SMILES: COC1OC(Cn2cc(COCCOCCOCCNC(=O)/C(C#N)=C/c3ccc4cc(N5CCCCC5)ccc4c3)nn2)C(O)C(O)C1O]

Figure 16:
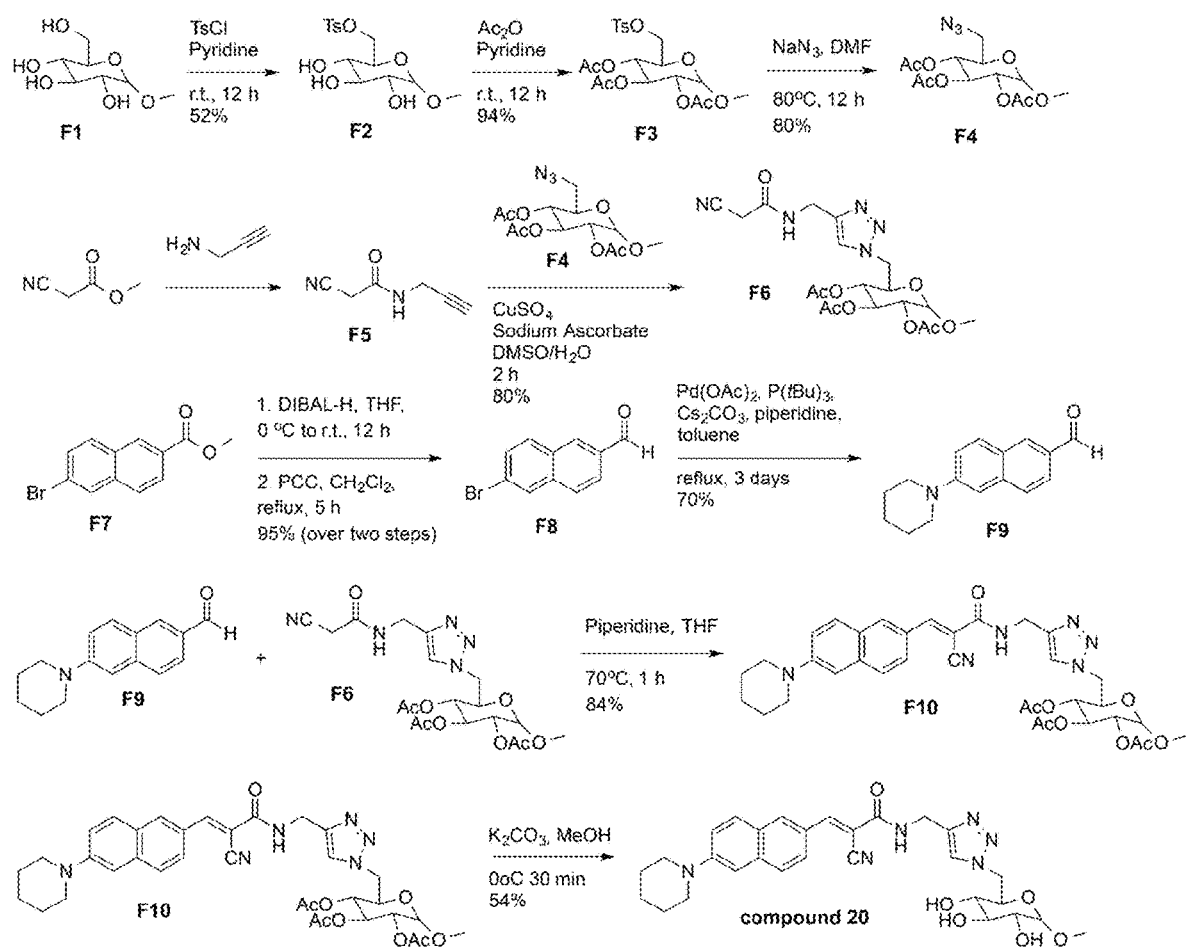
FIG. 16 Shows a synthetic strategy towards the synthesis of compound 20.
Figure 17A:
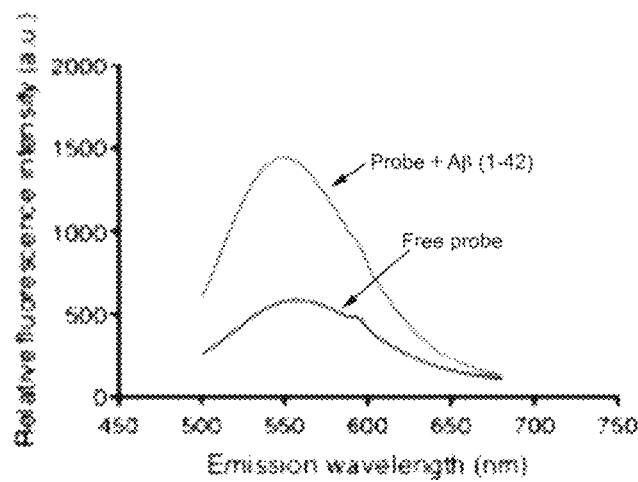
FIG. 17A Shows the emission profiles of compound 20, measured using 4 μM compound 20 and 5 μM Aβ (1-42) in 5% DMSO in water.
Figure 17B:
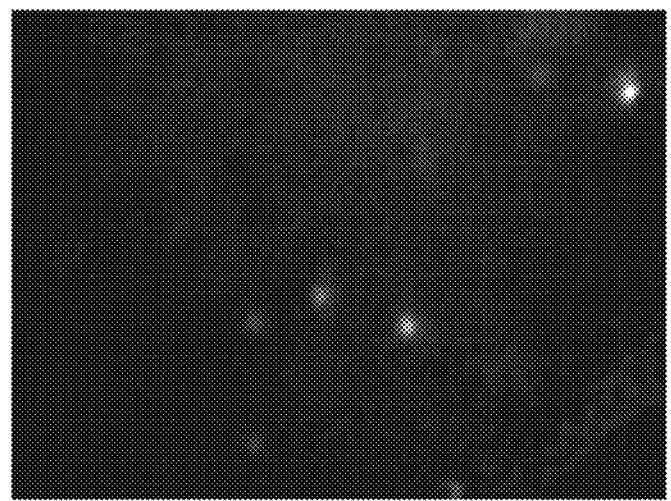
FIG. 17B Shows staining of amyloid deposits in murine AD neuronal tissue by compound 20.

Example 8: (E)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide See FIG. 16 for a synthetic scheme.

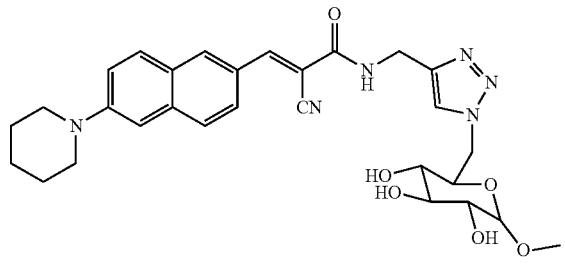 [SMILES: COC1OC(Cn2cc(CNC(=O)/C(C#N)=C/c3ccc4cc(N5CCCCC5)ccc4c3)nn2)C(O)C(O)C1O]

Step 1: Preparation of 2-cyano-N-(prop-2-ynyl)acetamide (F5)

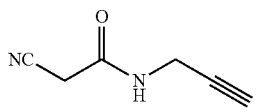

A mixture of methyl cyanoacetate (218 mg, 2.2 mmol) and propargylamine (122 mg, 2.2 mmol) was stirred at room temperature overnight. After the reaction, the residue was purified by column chromatography (EtOAc:hexane=1:1) to afford 2-cyano-N-(prop-2-ynyl)acetamide F5 (220 mg, 82%).

Step 2: Preparation of 2-((4-((2-cyanoacetamido)methyl)-1H-1,2,3-triazol-1-yl)methyl)-6-methoxytetrahydro-2H-pyran-3,4,5-triyl triacetate (F6)

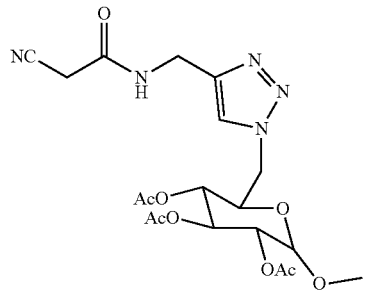 [SMILES: COC1OC(Cn2cc(CNC(=O)CC#N)nn2)C(OC(C)=O)C(OC(C)=O)C1OC(C)=O]

2-(Azidomethyl)-6-methoxytetrahydro-2H-pyran-3,4,5-triyl triacetate (E7, 42 mg, 0.12 mmol) and 2-cyano-N-(prop-2-ynyl)acetamide (F5, 15 mg, 0.12 mmol) were dissolved in H$_2$O/DMSO (1:1, 2 mL). Sodium ascorbate (20 mg, 0.1 mmol) and CuSO$_4$ (5 mg, 0.03 mmol) were added, and the solution was stirred for 2 h. After the reaction, the solvents were removed under reduced pressure and the residue was extracted with EtOAc. The organic phase was dried, filtered and purified by column chromatography (EtOAc:MeOH=30:1) to afford 2-((4-((2-cyanoacetamido)methyl)-1H-1,2,3-triazol-1-yl)methyl)-6-methoxytetrahydro-2H-pyran-3,4,5-triyl triacetate F6 (45 mg, 80%)

Step 3: Preparation of (E)-2-((4-((2-cyano-3-(6-(piperidin-1-yl)naphthalen-2-yl)acrylamido)methyl)-1H-1,2,3-triazol-1-yl)methyl)-6-methoxytetrahydro-2H-pyran-3,4,5-triyl triacetate (F10)

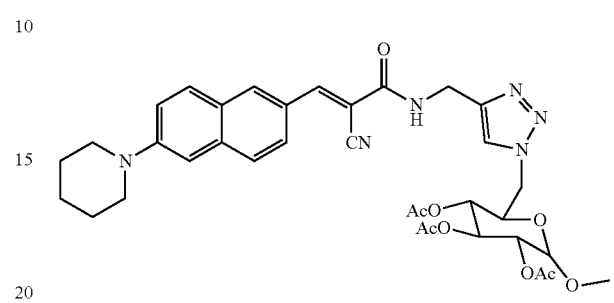

To a round bottom flask containing a solution of 6-(Piperidin-1-yl)-2-naphthaldehyde (A6, 10 mg, 0.042 mmol) and 2-((4-((2-cyanoacetamido)methyl)-1H-1,2,3-triazol-1-yl)methyl)-6-methoxytetrahydro-2H-pyran-3,4,5-triyl triacetate (F6, 20 mg, 0.042 mmol) in THF (2.0 mL), piperidine (50 µL) was added and the mixture refluxed 1 h. The crude mixture was concentrated under reduced pressure and the product was purified via flash column chromatography (EtOAc:CH$_2$Cl$_2$=10:1) to afford (E)-2-((4-((2-cyano-3-(6-(piperidin-1-yl)naphthalen-2-yl)acrylamido)methyl)-1H-1,2,3-triazol-1-yl)methyl)-6-methoxytetrahydro-2H-pyran-3,4,5-triyl triacetate F10 (18 mg, 62%).

Step 4: Preparation of (E)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide (Compound 20)

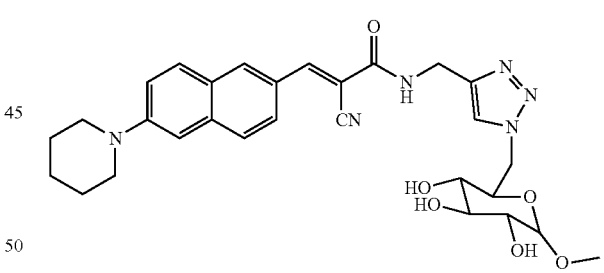

(E)-2-((4-((2-cyano-3-(6-(piperidin-1-yl)naphthalen-2-yl)acrylamido)methyl)-1H-1,2,3-triazol-1-yl)methyl)-6-methoxytetrahydro-2H-pyran-3,4,5-triyl triacetate (F10, 10 mg, 0.015 mmol) was dissolved in MeOH (2 mL) and a solution of K$_2$CO$_3$ (0.3 M, 0.2 mL) was then added at 0° C. The mixture was stirred at room temperature for 0.5 h. After the reaction, the residue was concentrated under reduced pressure and then purified by preparative reverse-phase high-performance liquid chromatography (RP-HPLC) (grad. 5-90% acetonitrile in water, 30 min.) to afford (E)-2-cyano-3-(6-(piperidin-1-yl)naphthalen-2-yl)-N-((1-((3,4,5-trihydroxy-6-methoxytetrahydro-2H-pyran-2-yl)methyl)-1H-1,2,3-triazol-4-yl)methyl)acrylamide (4.5 mg, 54%). 1H NMR (CD$_3$OD, 500 MHz) δ 8.40 (s, 1H), 8.33 (s, 1H), 8.19 (dd, J=8.5, 2.0 Hz, 1H), 8.08 (d, J=9.0 Hz, 1H), 7.98 (d, J=9.0

Hz, 2H), 7.83 (s, 1H), 7.66 (dd, J=9.0, 2.0 Hz, 1H), 4.85 (d, J=2.0 Hz, 1H), 4.82 (d, J=2.0 Hz, 1H), 4.62 (s, 3H), 4.50 (dd, J=14, 8.5 Hz, 1H), 3.84-3.80 (m, 1H), 3.64 (t, J=5.5 Hz, 4H), 3.60 (t, J=9.0 Hz, 1H), 3.36 (dd, J=9.5, 4.0 Hz, 1H), 3.14 (s, 3H), 1.96 (brs, 4H), 1.79 (brs, 2H); $^{13}$C NMR (CD$_3$OD, 500 MHz) δ 163.7, 152.9, 145.9, 137.6, 134.3, 134.3, 132.2, 130.7, 129.7, 129.3, 127.1, 125.8, 120.8, 117.5, 114.9, 104.9, 101.3, 74.9, 73.3, 72.9, 71.8, 71.7, 55.7, 55.6, 53.9, 52.5, 36.5, 25.9, 24.1; MS (ESI): m/z calc. for $C_{29}H_{35}N_6O_6^+$: [M+H]$^+$ calcd for 563.26, found 563.35.

Example 9: In Vitro Amyloid Binding and Tissue Staining Studies

Figure 2A:
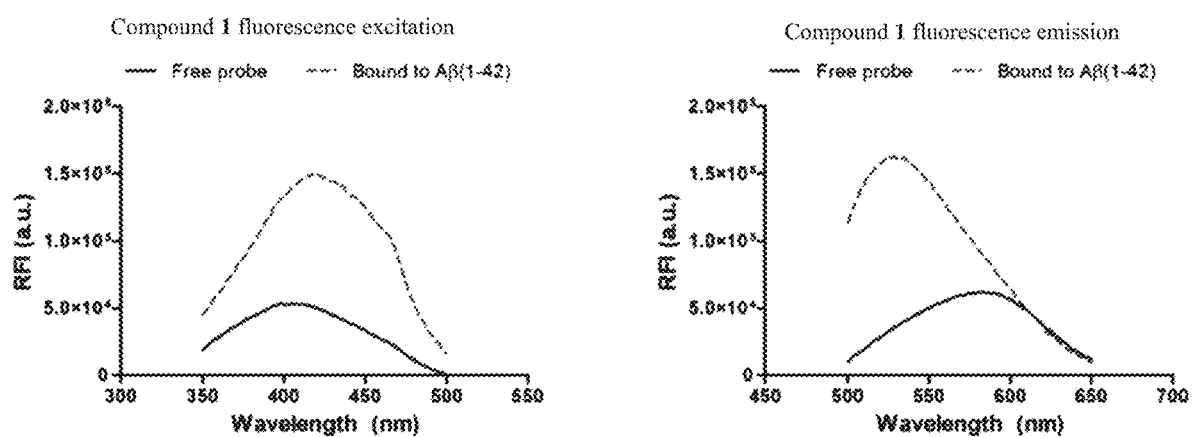
FIG. 2A Shows the fluorescence excitation and emission profiles of compound 1, measured using 4 µM compound 1 and 5 µM Aβ (1-42) in 5% DMSO in water FIG. 2B Shows a plot of fluorescence intensity versus concentration of compound 1 in the presence of aggregated Aβ(1-42) peptide.
Figure 2B:
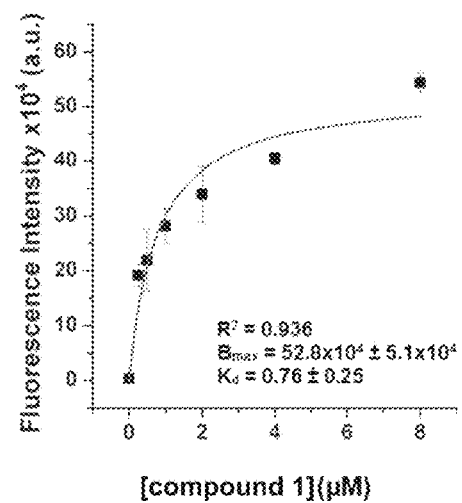
Figure 13A:
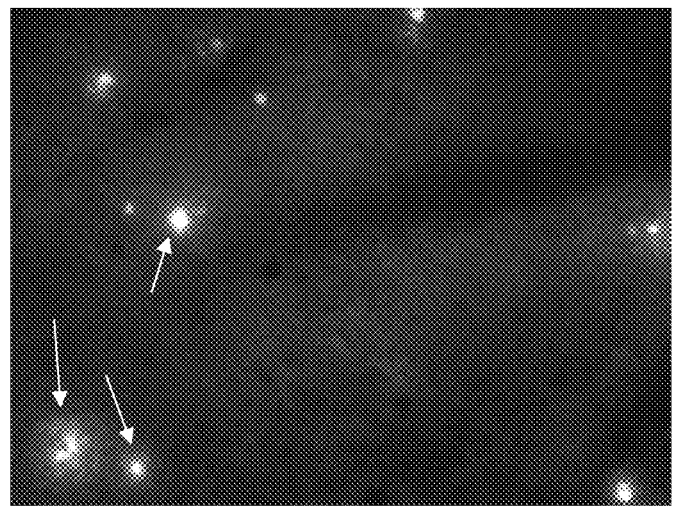
FIG. 13A Shows representative fluorescence micrographs showing the fluorescence labeling of amyloid deposits in hippocampal brain sections from a mouse model for Alzheimer's disease using compound 1.
Figure 13B:
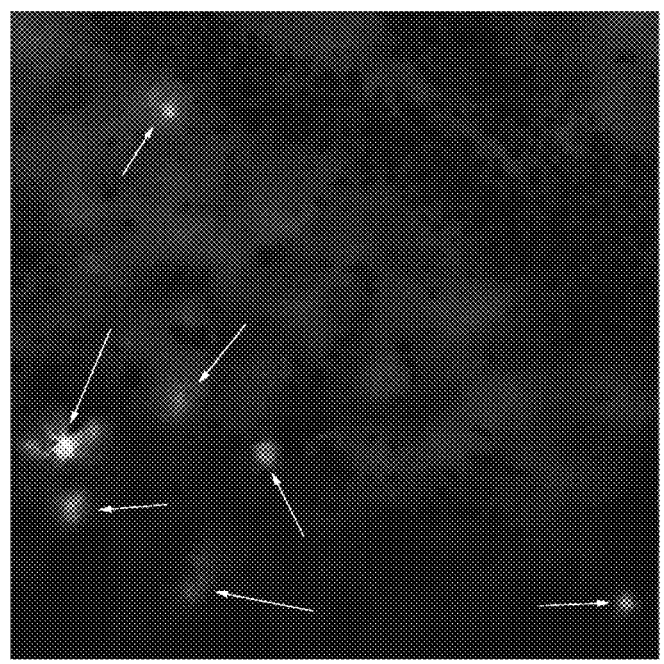
FIG. 13B Shows representative fluorescence micrographs showing the fluorescence labeling of amyloid deposits in hippocampal brain sections from a mouse model for Alzheimer's disease using compound 2.

Extensive in vitro work demonstrate that Compound 1 (FIG. 13A) displays privileged properties in terms of an ability to bind selectively to amyloids and emit a characteristic fluorescence upon binding to Alzheimer's related amyloids. FIG. 2A and FIG. 2B show the absorbance and emission profile of compound 1 free in solution (solid line) and bound (dashed line) to aggregated Alzheimer's-related peptide (Aβ42). FIG. 2C shows a plot of fluorescence intensity versus concentration of compound 1 in the presence of aggregated Aβ(1-42) peptide. Aggregated Aβ(1-42) at a final concentration of 10 µM (based on the molecular weight of monomer) was mixed with increasing concentration of compound 1 (0, 0.25, 0.5, 1, 2, 4, 8 µM) in 5% DMSO in PBS. The $K_d$ was determined by fitting data to a one-site specific binding algorithm: $Y=B_{mx} \cdot X/(K_d+X)$, where X is the concentration of the probe, Y is the specific binding fluorescence intensity, and $B_{max}$ corresponds to the apparent maximal observable fluorescence upon binding of probes to aggregated Aβ(1-42) peptide.

Figure 18:
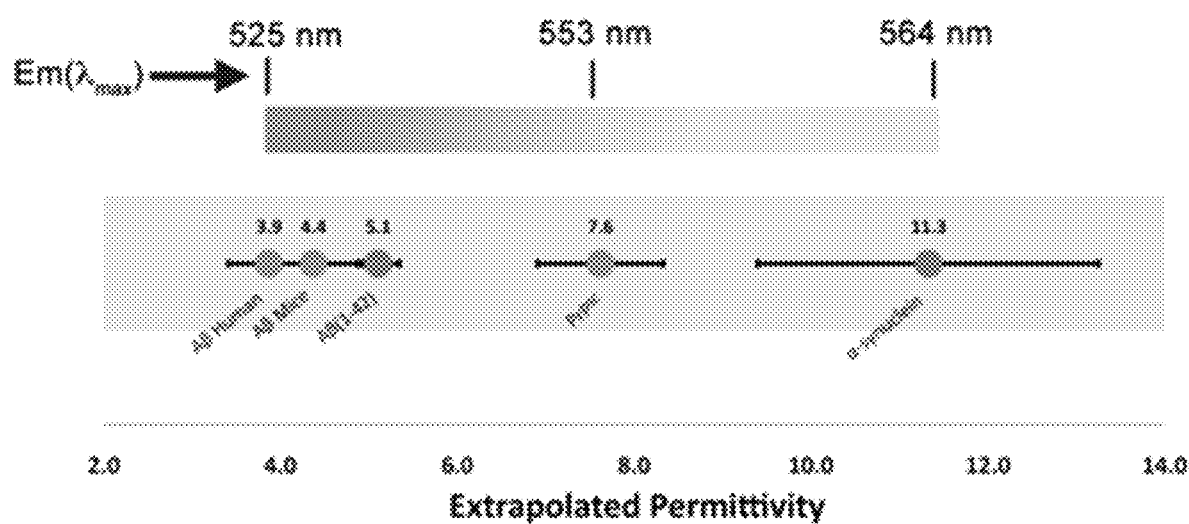
FIG. 18 Shows extrapolated permittivity values ($\varepsilon_o$) of Amyloid-β, α-synuclein, or prion proteins using the solvatochromic properties of compound 1.

In order to test whether Compound 1 could discriminate amyloids based on disease origin, the spectroscopic properties of Compound 1 when bound to amyloids derived from amyloid-β (associated with Alzheimer's disease), PrP (associated with CJD), and α-synuclein (associated with Parkinson's disease) were examined. FIG. 18 shows that Compound 1 can distinguish between amyloids of different disease origin based on color of emission. These results demonstrate the potential specificity that Compound 1 can have for conclusively identifying amyloid deposits from AD patients versus any other disease origin.

Example 10: Stability and Solubility Studies for Compound 1

Figure 19A:
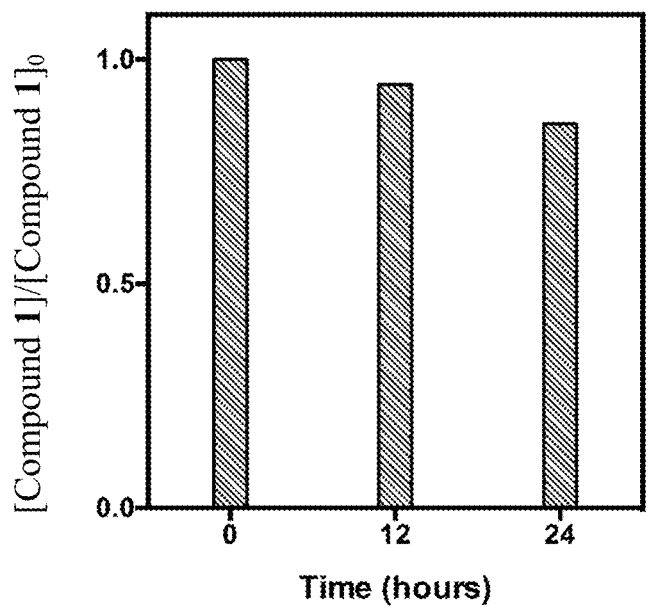
FIG. 19A Shows hydrolysis data of Compound 1 in PBS.

The rate of hydrolytic decomposition of Compound 1 in PBS (with 5% DMSO to aid in solubility) at 25° C. by HPLC was examined. FIG. 19A shows the relative abundance of Compound 1 over a 24 hour period. These studies reveal that Compound 1 has a $t_{1/2}$ for hydrolysis of ~150 hours. For comparison, ANCA-11 ((E)-2-(2-(2-methoxyethoxy)ethoxy)ethyl 2-cyano-3-(6-(piperidin-1-yl)naphthalen-2-yl) acrylate) exhibited a $t_{1/2}$ for hydrolysis of ~11 hours under the same conditions. In certain in vivo environments (especially at high or low pH or in the presence of esterases), ANCA-11 is expected to decompose very rapidly due to the poor stability of its ester functionality. The amide functionality in Compound 1 alleviates the problem of hydrolytic instability inherent to ANCA-11.

Some initial solubility studies have been carried out on Compound 1 (table 1). Compound 1 was soluble at a concentration of >5 mg/mL in all oils tested (Castor Oil (Ricinus Oil), Castor Oil (Ethyoxylated), corn oil, cotton seed oil, sesame oil, soyabean oil, and peanut oil).

TABLE 1

Solubility studies on Compound 1

| Solvent System | Solubility (mg/mL) |
| --- | --- |
| Soybean Oil | 2.0 |
| Sesame Oil | 2.0 |
| Castor Oil | <0.01 |
| Peanut Oil | 1.7 |
| Corn Oil | 1.3 |
| Cotton Seed Oil | 2.0 |
| PEG400 | 20.0 |
| Cremophor EL | <0.01 |
| Isopropyl Myristate | 6.0 |
| Isopropyl Palmitate | 5.0 |
| Medium Chain Triglycerides | 6.0 |
| Tetraglycol | 11.0 |
| Tricapylin | 20.0 |
| 5% beta-cyclodextrin | 0.8 |
| 10% beta-cyclodextrin | 1.8 |
| 20% beta-cyclodextrin | 3.33 |

Additionally the solubility was tested in water miscible solvents such as Benzyl alcohol, PEG 400, Ethylene Glycol, Polysorbate 20, Diethylene Glycol Monoethyl ether, 10% aqueous Poloxamer-188, Glycerol, 10% aqueous Poloxamer-407, Poloxamer 124. Compound 1 was very soluble in alcohols such as benzyl alcohol, propylene glycol, polysorbates and PEGs to a concentration of >5 mg/mL. For the others listed, the solubility was 2-3 mg/ml.

Additionally the solubility was tested in Surfactants such as: Tween 20, Tween 80, ethyl oleate, isopropyl myristate, Neobee M-5. In these solvents, Compound 1 was very well soluble to a concentration of >5 mg/mL.

Figure 19B:
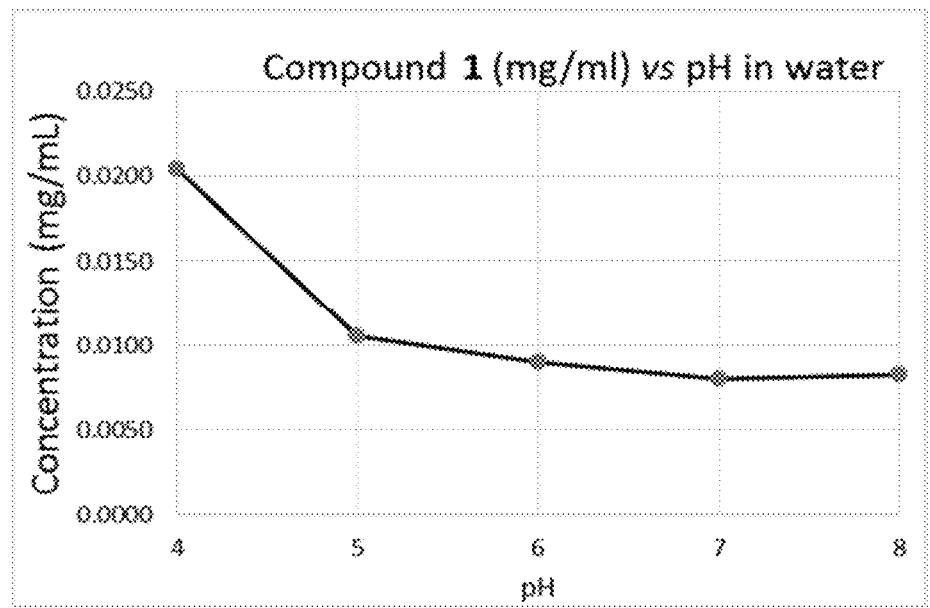
FIG. 19B Shows a solubility vs. pH graph of Compound 1 in water.

The solubility of Compound 1 in water increased as the pH was lowered to a pH<5 (See FIG. 19B).

These data are crucial to help with developing a suitable formulation for IV or topical administration of the probe for retinal imaging of amyloid in AD patients.

Figure 19C:
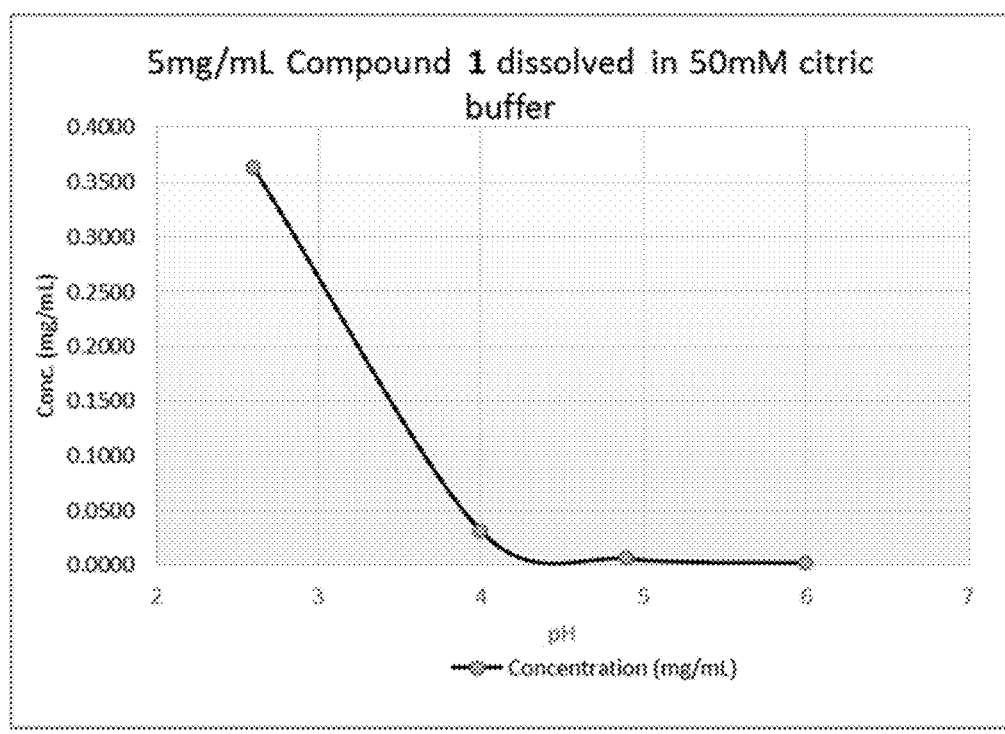
FIG. 19C Shows a solubility vs. pH graph of Compound 1 in 50 mM citric acid.

Compound 1 Solubility in Various Acids:

Solubility of Compound 1 was tested in HCl, acetic, citric, succinic, and lactic acid buffer (20-50 mM) and at pH 2-6. At lower pH and higher buffer concentration, the solubility increased up to 350 µg/mL vs water which is 3 µg/mL, representing a 100 fold increase. A representative example is shown in FIG. 19C for citric acid buffer.

Table 2 shows that at lower pH and higher acidic buffer strength, the solubility of Compound 1 can be increased to more than 6 mg/mL. The HCl salt of Compound 1 is more soluble than the base in water and phosphate buffer. Phosphate buffer tends to decrease the solubility of the HCl salt.

TABLE 2

| Sample | Conc (mg/mL) |
| --- | --- |
| Compound 1 in H$_2$O | 0.0031 |
| Compound 1 in 10 mM phosphate buffer, pH 7.4 | 0.0074 |
| Compound 1 HCl salt in water | 1.9612 |
| Compound 1 HCl salt in 10 mM phos buffer, pH 7.4 | 0.1686 |
| Compound 1 in 10 mM HCl (pH 2.5) | 1.6299 |
| Compound 1 in 10% aq. acetic acid (pH 3.4) | 2.8526 |
| Compound 1 in 10% aq. citric acid (pH 3.4) | 6.5916 |

Example 11: Salt of Compound 1 Preparation and Stability

Figure 24A:
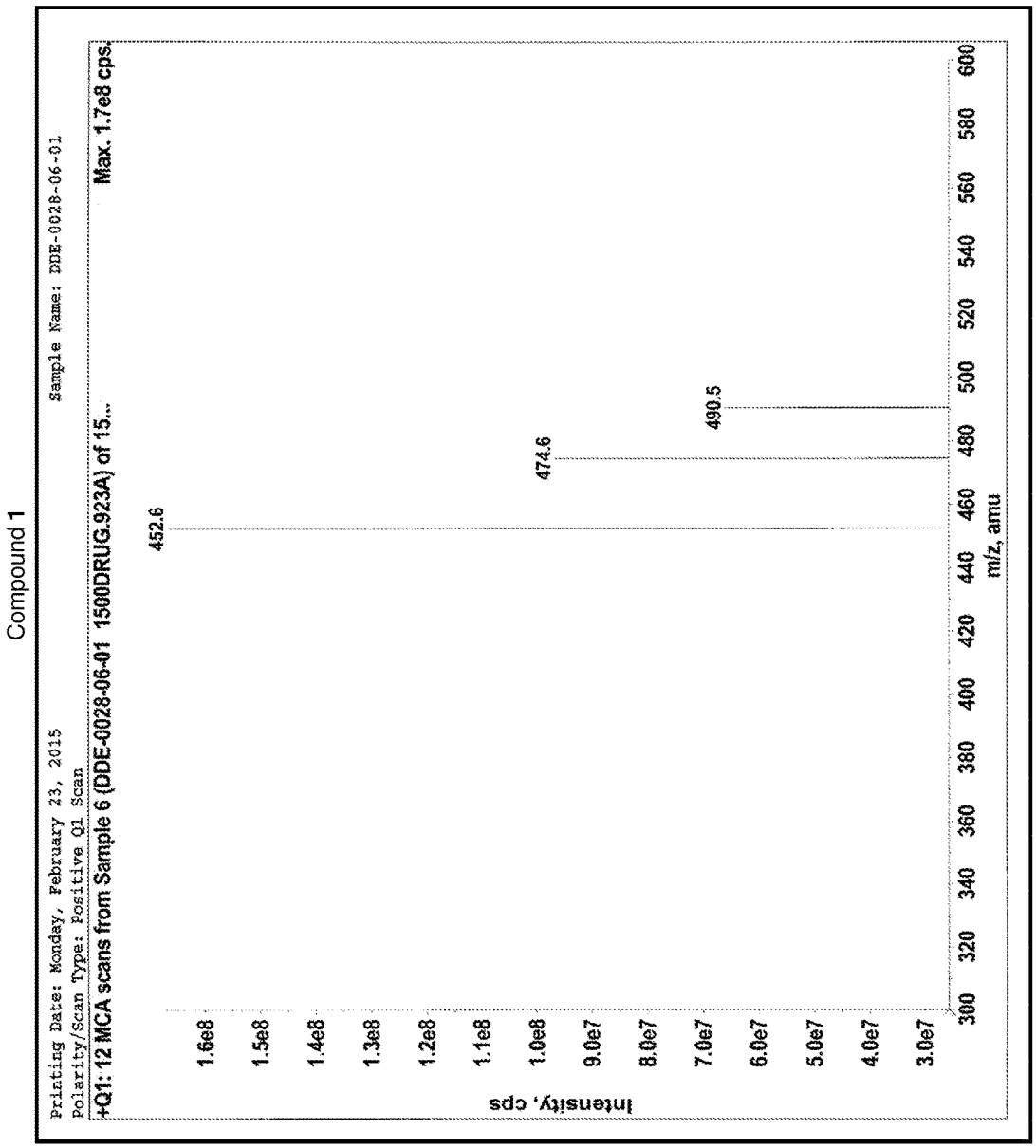
FIG. 24A Shows the Mass Analysis of Compound 1 vs Compound 1-HCl salt.
Figure 24A:
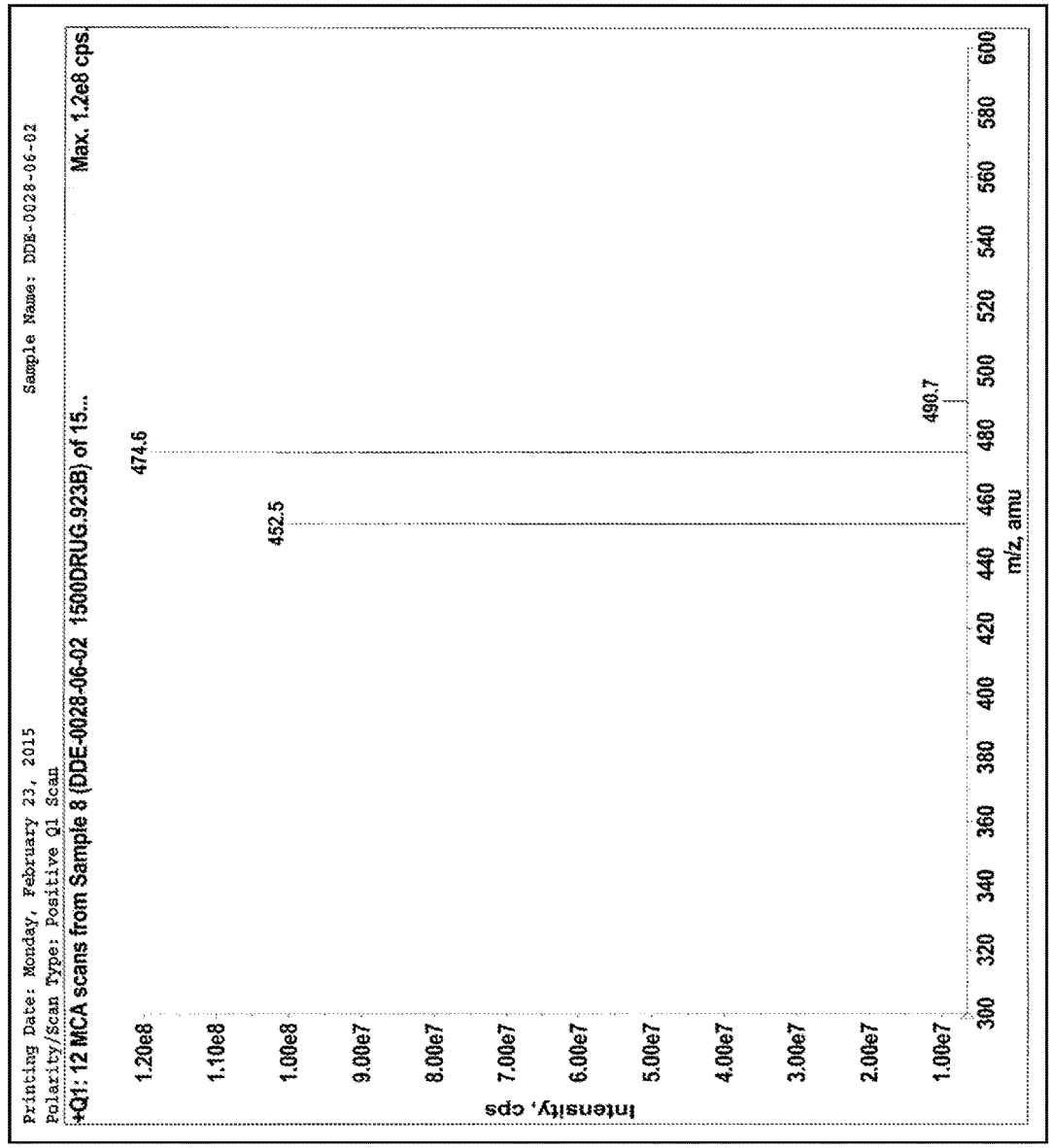
Figure 24B:
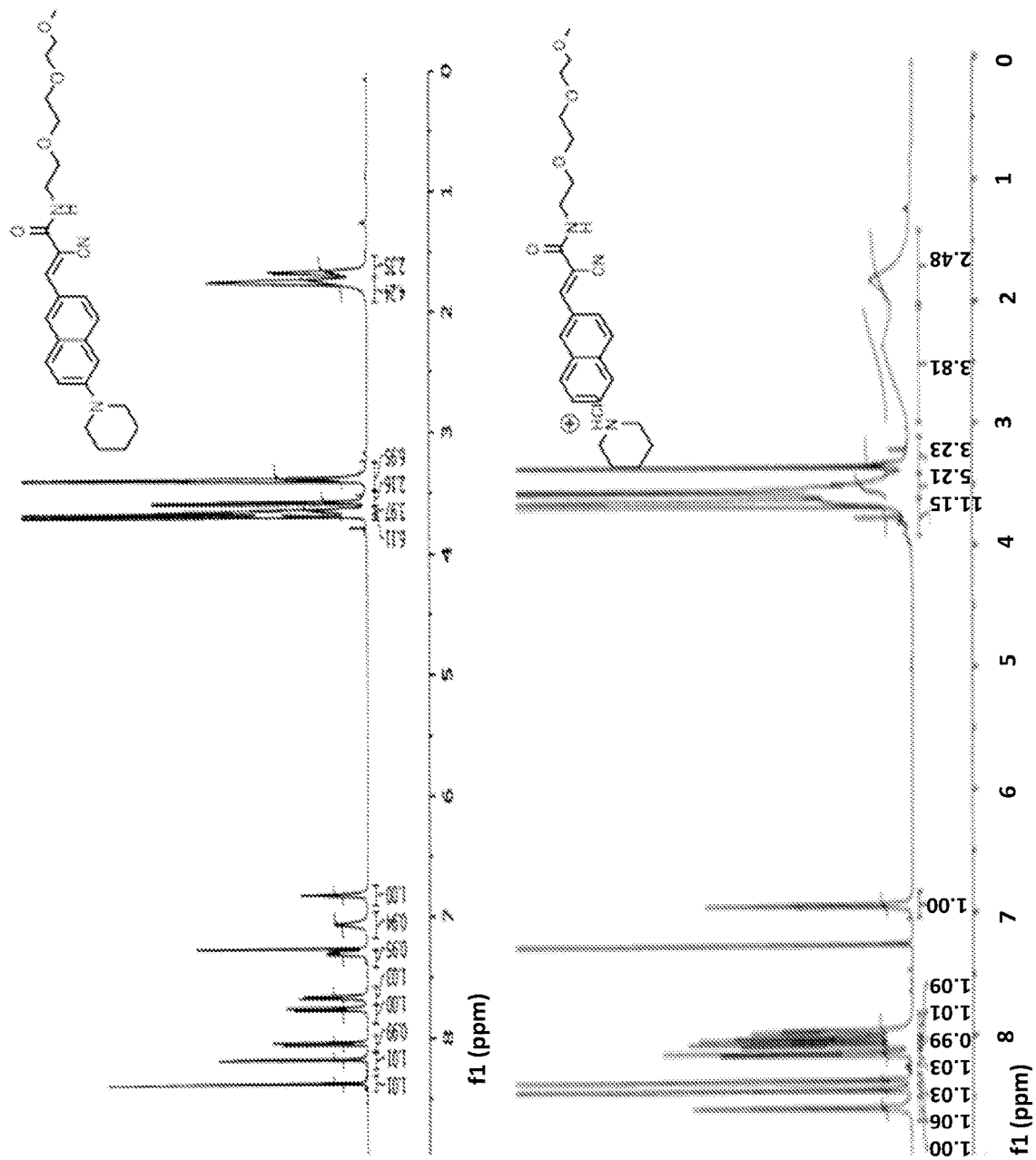
FIG. 24B Shows the $^1$H-NMR analysis of Compound 1 vs Compound 1-HCl salt.

Preparation of the HCl Salt:

Compound 1 dissolved and stirred in 3 molar equivalents of methanolic HCl at 0° C. for 4 hrs at 27° C. Methanol was removed and the solid was triturated with dry ethyl ether (5×10 mL) and dried in high vacuum overnight. Structure and purity was determined by analytical HPLC (comparing retention time to base), proton NMR, and mass spectrometric analysis. Mass Analysis of Compound 1 vs Compound 1-HCl salt: (ES, m/z): [M+H]$^+$ 452 (FIG. 24A). $^1$H-NMR-(500 MHz, CDCl$_3$) analysis of Compound 1 HCl salt: Proton NMR confirmed the protonation of piperazine by analyzing the shifts in the NMR spectrum.

Compound 1. $^1$H NMR (500 MHz, CDCl$_3$) δ 8.33 (s, 1H), 8.11 (s, 1H), 8.00-8.02 (dd, J=8.5 Hz, 1.5 Hz, 1H), 7.69-7.71 (d, J=9.5 Hz, 1H), 7.60-7.62 (d, J=8.5 Hz, 1H), 7.24-7.26 (m, 1H), 7.01 (bs, 1H), 6.84 (m, 1H), 3.64-3.66 (m, 6H), 3.62-3.63 (m, 4H), 3.54-3.55 (m, 2H), 3.35 (s, 3H), 3.12-3.34 (m, 4H), 1.69 (m, 4H), 1.61-1.62 (m, 2H)

Compound 1-HCl: $^1$H-NMR (500 MHz, CDCl$_3$): δ 8.59 (s, 1H), 8.44 (s, 1H), 8.37 (s, 1H), 8.15 (d, J=8.5 Hz, 1H), 8.07 (d, J=8.5 Hz, 1H), 8.02 (d, J=9 Hz, 1H), 7.96 (d, J=8.5 Hz, 1H), 6.94-6.95 (m, 1H), 3.64-3.68 (m, 11H), 3.55-3.57 (m, 5H), 3.36 (s, 3H), 2.37 (bd. s, 4H), 1.83 (bd, m, 2H)

Preparation of the Citrate Salt:

Compound 1 was dissolved in ethanol to which 1.2 molar equivalents of citric acid was added. The mixture was sonicated for dissolution, stirred at room temperature for 2 hrs and cooled to −4° C. The precipitate was filtered, washed with cold ethyl ether and dried under high vacuum. The sample was analyzed by analytical HPLC and retention time was confirmed to be that of parent, establishing the identity of the salt.

Solubility of the Citrate Salt

Solubility of citrate salt is 0.25 mg/ml, an increase of 140 fold versus water at pH 3.5. By comparison, the HCl salt of Compound 1 has a water solubility of 1.96 mg/ml.

Example 12: Ex Vivo Studies

Transgenic mice (J20) that overexpress the Swedish and Indiana mutant forms of amyloid precursor protein (APP) and produce human beta-amyloid served as a convenient murine model of Alzheimer's disease pathogenesis. Six J20 mice (and six wt littermate controls), bred and aged to 21 months, were dosed systemically (through the tail vein) with compound 1 (Test formulation: 100-150 µL of a 500 µM solution of compound 1 in 80% Propylene glycol/20% DMSO for in vivo injection) or vehicle alone. After injection, all mice were allowed to run free in the cage for 30 minutes. Mice were then sacrificed and the retinal tissue was harvested and visualized for compound 1 staining.

For ex vivo analysis of retina, the eyes of J20 or wt mice injected with compound 1 or vehicle alone were removed from the mice within 1 minute of sacrifice and put on ice. The eyes were then dissected to remove the retina within 1 hour of sacrifice. Retina were then subjected to a short 5 minute methanol dehydration/fixation step, and then incubated with DAPI (nuclear stain), red fluorescent lectin (vascular stain), and an anti-Aβ antibody (followed by a fluorescently labelled secondary antibody). The retina were then flat mounted onto a glass coverslip and imaged via confocal microscopy.

Figure 20A:
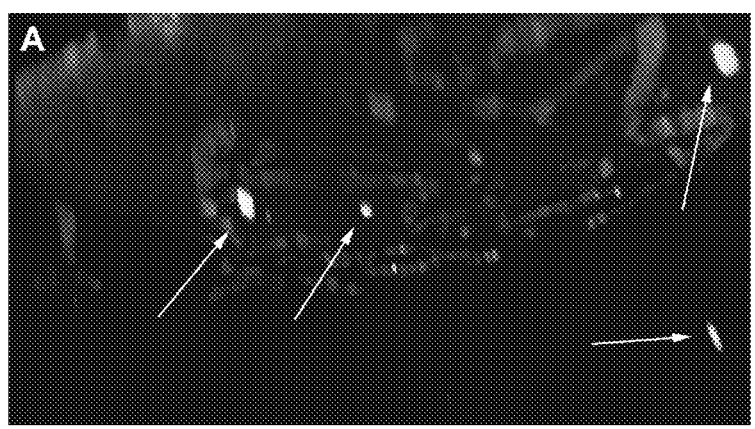
FIG. 20A Shows a 3D rendering assembled from consecutive Z-stack slices of fluorescence confocal micrographs of flat-mounted, whole retinal tissue from a J20 tg mice injected in vivo with compound 1. Cross-sectional image of the retina from a J20 mouse showing the bright objects stained with compound 1.
Figure 20B:
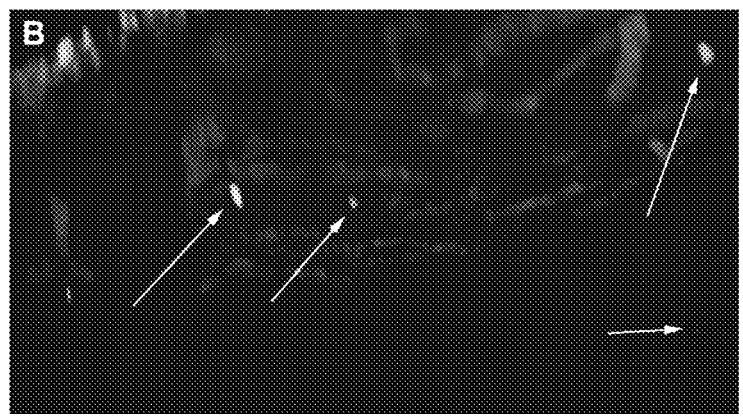
FIG. 20B Shows a 3D rendering assembled from consecutive Z-stack slices of fluorescence confocal micrographs of flat-mounted, whole retinal tissue from a J20 tg mice injected in vivo with compound 1, only showing the bright objects stained with an anti-Aβ arrows.

FIG. 20A and FIG. 20B show a 3D z-stack reconstruction of the retina of a J20 mouse injected with compound 1 30 minutes prior to sacrifice. The white arrows in FIG. 20A highlights several bright objects within the neuronal layers of the retina that are stained with compound 1. Amyloid deposits in the retina of tg mice and humans with AD have been reported to develop within the neuronal layers as a function of disease progression (*Neuroimage* 2011, 54, S204-S217). FIG. 20B is an image of the same retina shown in FIG. 20A, but highlighting only the location (white arrows) of the amyloid deposits stained by the anti-Aβ antibody (followed by a fluorescently labelled secondary antibody). The anti-Aβ antibody (highlighted by the white arrows in FIG. 20B) and compound 1 (highlighted by the white arrows in FIG. 20A) co-localize in the retina, providing very strong evidence that compound 1 can cross the blood-retina barrier and specifically stain amyloids in the retina after in vivo systemic administration.

Example 13: Imaging of Amyloid Deposits in Live Animals

In addition to the visualization of amyloid deposits through the harvesting of tissues and ex vivo imaging, recent efforts have shown the ability to image amyloid deposits in live animals. Three transgenic AD mice (hAPP/PS1, J20, and 5XFAD) mice have been bred and aged for imaging. While these AD tg mouse models age, an animal model of CJD, that has a much shorter timeline for amyloid deposit accumulation, has been investigated for live imaging of retinal amyloid accumulation after IP administration of Compound 1. Mice were anesthetized with ketamine and placed on a stage afixed with a 37° C. heating pad. The retina were imaged via bright field and fluorescence using a Phoenix Laboratory Micron IV rodent retinal microscope to establish a baseline image.

Mice inoculated with GPI-anchorless strain of PrP served as an initial convenient animal model for Creutzfeldt-Jakobs Disease, and has been investigated for live imaging of retinal amyloid accumulation after IP administration of compound 1. For this demonstration, compound 1, dosed via intraperitoneal injection (Formulation: 200 µL of a 10 mg/mL solution of compound 1 in 20% DMSO/80% propylene glycol), allowed for the visualization of amyloid deposits in the retina.

Figures 21A, 21B:
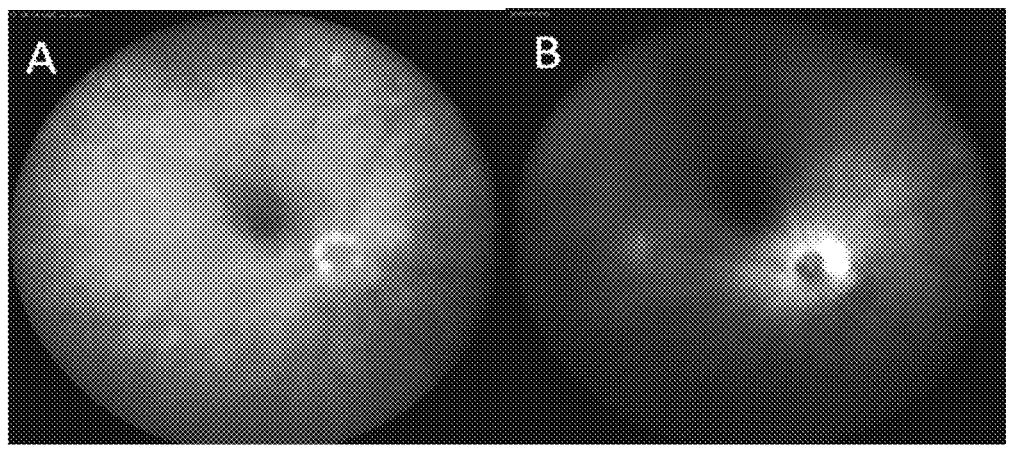
FIG. 21A Shows a bright field retinal image of the retina of an anesthetized wt mouse (pre-injection with compound 1).
FIG. 21B Shows a bright field retinal image of the retina of an anesthetized prion-inoculated mouse (pre-injection with compound 1)
Figures 21C, 21D:
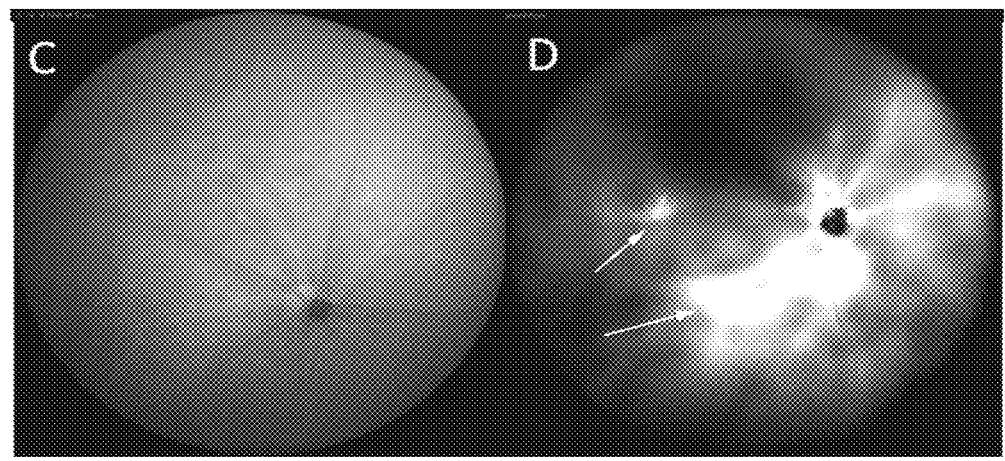
FIG. 21C Shows a bright field retinal image of the retina of wt mouse post-injection with compound 1.
FIG. 21D Shows a bright field retinal image of the retina of Prion-inoculated mouse post-injection with compound 1.

FIG. 21A shows a bright field image of the retina of an anesthetized wt mouse. FIG. 21B shows a bright field image of the retina of an anesthetized prion-infected (156 days post infection with GPI-anchorless PrP) mouse (*J. Virol.*, 2011, 85, 1484-1494). The bright field images of the two different mice shown in FIG. 21A and FIG. 21B are not sufficiently different as to distinguish a healthy versus diseased mouse (the dark area within each image is an artifact of the objectives on the rodent microscope [Phoenix labs Micron IV rodent retinal microscope] used to obtain these live mouse retinal images). FIG. 21C shows a fluorescence image of the retina of the wt mouse (same mouse retina shown in FIG. 21A) immediately after IP injection with compound 1. The dull background fluorescence observable in FIG. 21C, as well as the slightly brighter green fluorescence seen in the retinal vasculature, demonstrates that compound 1 immediately accumulates in the blood and in the retinal tissue after IP injection. This dull background fluorescence is expected to fade over time as compound 1 is cleared from the mouse. FIG. 21D shows a fluorescence image of the retina of the prion-infected mouse (same mouse retina shown in FIG. 21B) immediately after IP injection with compound 1. FIG. 21D reveals very bright objects (due to staining with compound 1) located throughout the retina (highlighted with white arrows). These objects are consistent with prion amyloid deposits that have previously been reported to accumulate in the retina of mice inoculated with GPI-anchorless PrP (*J. Virol.*, 2011, 85, 1484-1494).

Figure 22A:
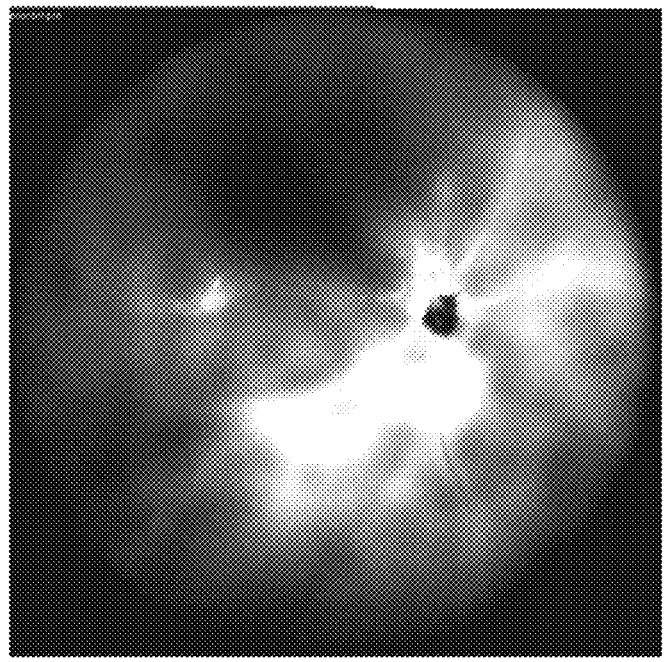
FIG. 22A and FIG. 22B Shows a comparison of in vivo and ex vivo imaging of the retina of a prion-infected mouse injected IP with Compound 1.
Figure 22B:
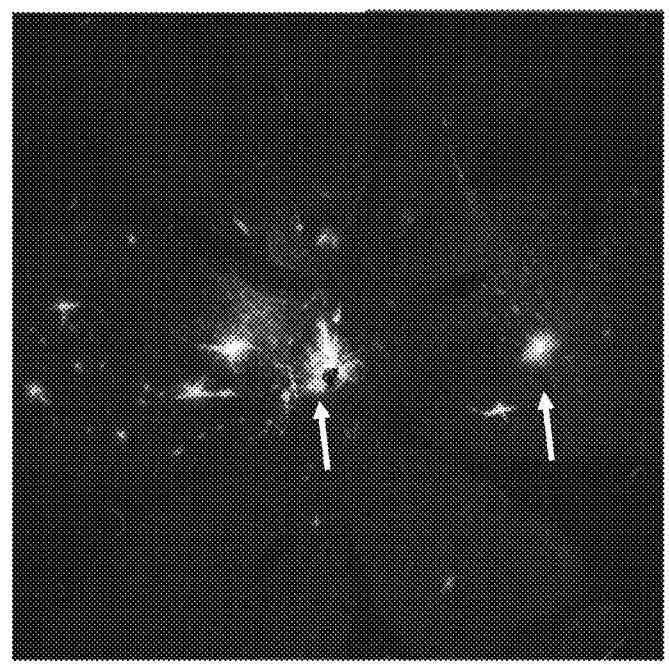

FIG. 22A and FIG. 22B show a comparison of the fluorescence image of the retina of a living prion-infected mouse injected with Compound 1 and the retina of same mouse after sacrifice, removal of the retina, and examination ex vivo by confocal microscopy. FIG. 22A is the same as FIG. 21D. FIG. 22B reveals many bright fluorescent objects (highlighted with white arrows) stained in vivo with Compound 1. No further processing (i.e., no further staining with Compound 1) was performed on the retinal tissue to obtain the fluorescence image in FIG. 22B. Taken together, the results shown in FIGS. 21A-D and FIGS. 22A-B provide strong evidence that Compound 1 can quickly and readily be used for in vivo retina imaging of amyloid deposits as an indicator of disease.

Figure 23:
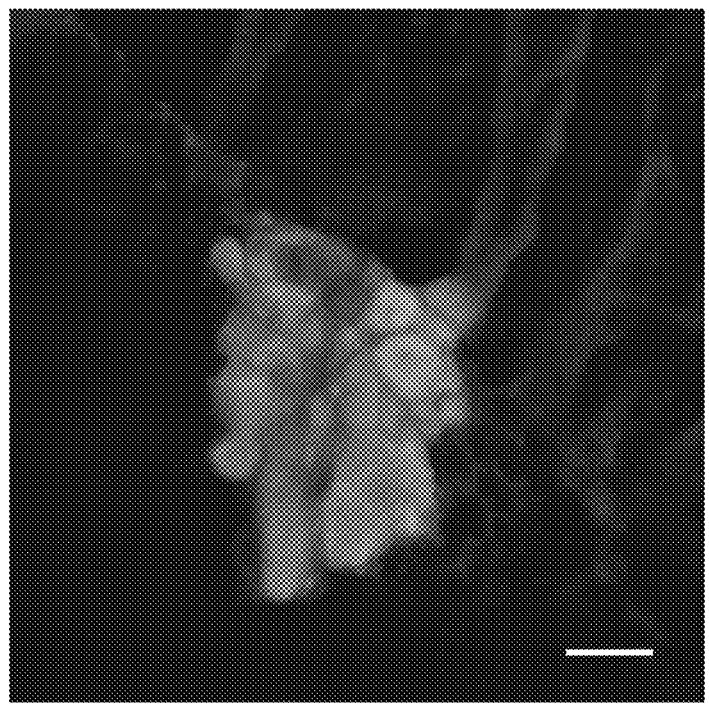
FIG. 23 Shows the true color fluorescence micrograph of a prion plaque deposited in the neuronal layers of the retina of a prion-inoculated mouse (156 days) and stained in vivo with Compound 1. Scale bar=50 μm.

FIG. 23 shows a magnified, true color micrograph of an individual prion plaque from the same eye shown in FIG. 22. Spectroscopic inspection of Compound 1 bound to this amyloid deposit revealed $\lambda_{max}$ (Em)=554 nm, which precisely matched the emission wavelength of Compound 1 bound to prion plaques found in the brain. This result demonstrates that the spectroscopic specificity of Compound 1 for identifying and discriminating amyloid deposits from different disease origins can be achieved in the retina in an analogous manner as has been demonstrated in other parts of the brain.

What is claimed is:

1. A compound of Formula (Ic), a pharmaceutically acceptable salt thereof, or a solvate thereof:

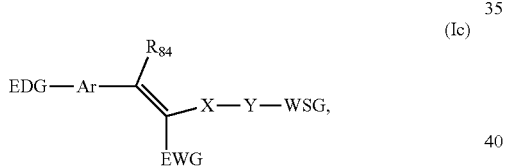

(Ic)

wherein:
EDG is heterocycloalkyl of no more than 10 carbon atoms optionally substituted with one or more $R_{17}$;
each R17 is independently halogen, —$OR_{18}$, —$NR_{19}R_{20}$, $C_1$-$C_{10}$ alkyl, or $C_1$-$C_{10}$ heteroalkyl;
each of $R_{18}$, $R_{19}$, and $R_{20}$ is independently hydrogen, $C_1$-$C_{10}$ alkyl, $C_1$-$C_{10}$ heteroalkyl, or cycloalkyl of no more than 10 carbon atoms, each of which except for hydrogen is optionally substituted with one or more $R_{21}$;
each $R_{21}$ is independently halogen, —$OR_{22}$, —$NR_{23}R_{24}$, $C_1$-$C_{10}$ alkyl, $C_1$-$C_{10}$ heteroalkyl, cycloalkyl of no more than 10 carbon atoms, heterocycloalkyl of no more than 10 carbon atoms, aryl of no more than 10 carbon atoms, or heteroaryl of no more than 10 carbon atoms;
each of $R_{22}$, $R_{23}$, and $R_{24}$ is independently hydrogen or $C_1$-$C_{10}$ alkyl;
Ar is naphthyl optionally substituted with one or more $R_1$;
each $R_1$ is independently halogen, —$OR_2$, —$NR_3R_4$, $C_1$-$C_{10}$ alkyl, or $C_1$-$C_{10}$ heteroalkyl,
each of $R_2$, $R_3$, and $R_4$ is independently hydrogen, $C_1$-$C_{10}$ alkyl, or $C_1$-$C_{10}$ heteroalkyl;
$R_{84}$ is hydrogen or $C_1$-$C_{10}$ alkyl;
EWG is —CN;
WSG is

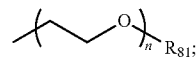

n is an integer from 2 to 10;
$R_{81}$ is hydrogen;
X is C=O; and
Y is NH.

2. The compound of claim 1, wherein EDG is:

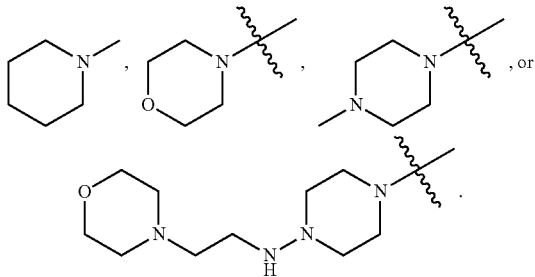

3. The compound claim 1, wherein EDG is heterocycloalkyl having 6 ring atoms.
4. The compound of claim 1, wherein EDG is unsubstituted.
5. The compound claim 1, wherein EDG is

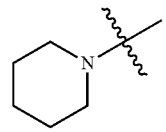

6. The compound of claim 1, wherein n is 3.
7. The compound of claim 1, wherein $R_{84}$ is hydrogen.
8. The compound of claim 1, wherein $R_{84}$ is methyl.
9. The compound of claim 1, wherein Ar is

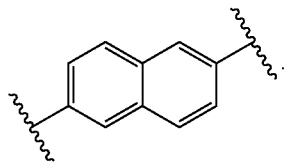 [SMILES: *c1ccc2cc(*)ccc2c1]

10. A pharmaceutical composition comprising the compound of claim 1, the pharmaceutically acceptable salt thereof, or the solvate thereof, and a pharmaceutically acceptable excipient.

11. The pharmaceutical composition of claim 10, wherein the pharmaceutically acceptable excipient is ethanol, dimethyl sulfoxide, polyethylene glycol, polypropylene glycol, aqueous acetate buffer, aqueous citrate buffer, aqueous phosphate buffer, aqueous carbonate buffer, a cyclodextrin, corn oil, vitamin E, a polysorbate, polyethyleneglycol-15 hydroxystearate, a bile acid, or a combination of two or more thereof.

12. A method for monitoring response to a treatment of a patient having a disease or condition characterized by amyloid deposit in a body part or a body area of the patient, the method comprising:

(i) forming a detectable complex in the body part or the body area following the treatment by contacting an effective amount of the compound of claim 1, the pharmaceutically acceptable salt thereof, or the solvate thereof, or a pharmaceutical composition thereof, with the amyloid deposit; and (ii) detecting the detectable complex, wherein a decrease of detectable complex as compared to before treatment indicates that the patient is responsive to treatment.

13. The method of claim 12, in which the amyloid deposit comprises an amyloid or amyloid like protein, wherein the amyloid or amyloid like protein is Aβ peptide, prion peptide, alpha-synuclein, or superoxide dismutase.

14. The method of claim 13, wherein the amyloid or amyloid like protein is beta amyloid (1-42) (Aβ(1-42)).

15. The method of claim 12, wherein the disease or condition is Alzheimer's disease, Parkinson's disease, Huntington's disease, amyotrophic lateral sclerosis, Lewy body dementia, or Down's syndrome.

16. The method of claim 12, wherein the disease or condition is a prion disease.

17. The method of claim 12, wherein the disease or condition is Creutzfeldt-Jakob disease.

18. A method for monitoring the response of a patient having a disease or condition characterized by amyloid deposit to a treatment, the method comprising (i) forming a detectable complex following the treatment by contacting an effective amount of a compound of the formula:

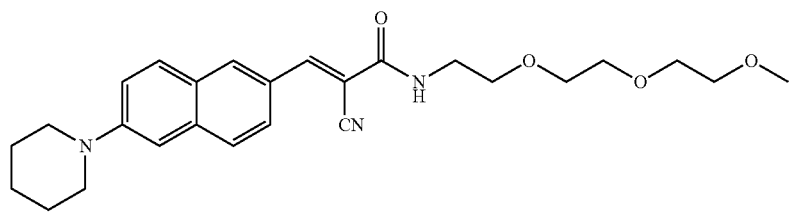 [SMILES: COCCOCCOCCNC(=O)/C(C#N)=C/c1ccc2cc(N3CCCCC3)ccc2c1]

or a pharmaceutically acceptable salt thereof, or a solvate thereof, or a pharmaceutical composition thereof, with a sample, a body part, or a body area of the patient; and (ii) detecting the formation of the detectable complex, wherein a decrease of detectable complex as compared to before the treatment indicates that the patient is responsive to the treatment;

wherein the disease or condition is selected from the group consisting of Alzheimer's disease, Parkinson's disease, Huntington's disease, amyotrophic lateral sclerosis, Lewy body dementia, Down's syndrome, and Creutzfeldt-Jakob disease.

19. A method of detecting an amyloid or amyloid like protein, the method comprising (i) contacting the compound of formula (Ic), a pharmaceutically acceptable salt thereof, or a solvate thereof with a sample potentially comprising the amyloid or amyloid like protein, wherein in presence of an amyloid or amyloid like protein the compound forms a detectable complex; and (ii) detecting the formation of the detectable complex such that the presence or absence of the detectable complex correlates with the presence or absence of the amyloid or amyloid like protein;

wherein the compound of Formula (Ic) is:

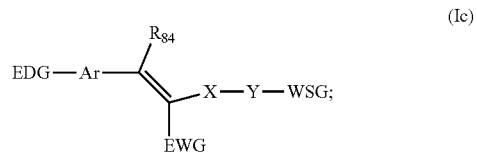

wherein

EDG is heterocycloalkyl of no more than 10 carbons optionally substituted with one or more $R_{17}$;

wherein each $R_{17}$ is independently halogen, —$OR_{18}$, —$NR_{19}R_{20}$, $C_1$-$C_{10}$ alkyl, or $C_1$-$C_{10}$ heteroalkyl;

each of $R_{18}$, $R_{19}$, and $R_{20}$ is independently hydrogen, $C_1$-$C_{10}$ alkyl, $C_1$-$C_{10}$ heteroalkyl, or cycloalkyl of no more than 10 carbon atoms, each of which except for hydrogen is optionally substituted with one or more $R_{21}$;

each $R_{21}$ is independently halogen, —$OR_{22}$, —$NR_{23}R_{24}$, $C_1$-$C_{10}$ alkyl, $C_1$-$C_{10}$ heteroalkyl, cycloalkyl of no more than 10 carbon atoms, heterocycloalkyl of no more than 10 carbon atoms, aryl of no more than 10 carbon atoms, or heteroaryl of no more than 10 carbon atoms;

each of $R_{22}$, $R_{23}$, and $R_{24}$ is independently hydrogen or $C_1$-$C_{10}$ alkyl;

Ar is aryl of no more than 14 carbon atoms optionally substituted with one or more $R_1$;

each $R_1$ is independently halogen, —$OR_2$, —$NR_3R_4$, $C_1$-$C_{10}$ alkyl, or $C_1$-$C_{10}$ heteroalkyl, each of $R_2$, $R_3$, and $R_4$ is independently hydrogen, $C_1$-$C_{10}$ alkyl, or $C_1$-$C_{10}$ heteroalkyl;

$R_{84}$ is hydrogen or $C_1$-$C_{10}$ alkyl;

EWG is halogen, —CN, —$NO_2$, or methyl;

WSG is:

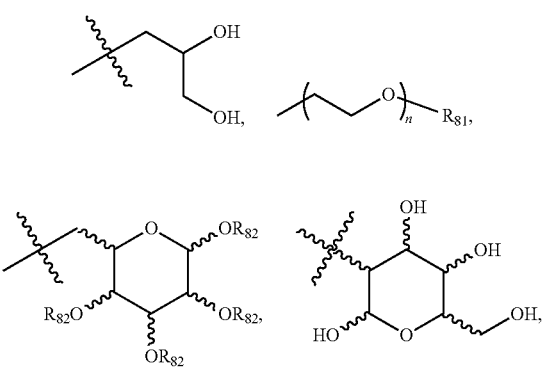

-continued

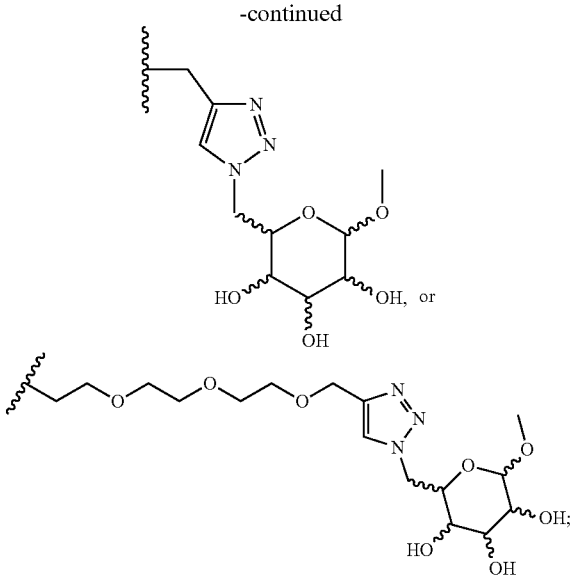

n is an integer from 2 to 50, $R_{81}$ is hydrogen, a $C_1$-$C_{10}$ alkyl, a $C_2$-$C_{10}$ alkenyl, or a $C_2$-$C_{10}$ alkynyl, wherein the alkyl, alkenyl, or alkynyl is optionally substituted with one or more $C_1$-$C_{10}$ alkyl, $C_1$-$C_{10}$ heteroalkyl, cycloalkyl of no more than 10 carbon atoms, heterocycloalkyl of no more than 10 carbon atoms, aryl of no more than 10 carbon atoms, or heteroaryl of no more than 10 carbon atoms;

each $R_{82}$ is independently hydrogen or $C_1$-$C_{10}$ alkyl;

X is C=O or $SO_2$; and

Y is NH or S;

wherein the sample is from a patient having a disease or condition selected from the group consisting of Alzheimer's disease, Parkinson's disease, Huntington's disease, amyotrophic lateral sclerosis, Lewy body dementia, Down's syndrome, and Creutzfeldt-Jakob disease.

20. The method of claim 19, wherein the disease or condition is Alzheimer's disease.

* * * * *